(12) United States Patent
Mathews et al.

(10) Patent No.: US 8,865,623 B2
(45) Date of Patent: Oct. 21, 2014

(54) HERBICIDALLY ACTIVE CYCLIC DIONES AND DERIVATIVES THEREOF, PROCESSES FOR THEIR PREPARATION, COMPOSITIONS, AND METHOD OF CONTROLLING WEEDS

(75) Inventors: Christopher John Mathews, Bracknell (GB); John Finney, Bracknell (GB); James Nicholas Scutt, Bracknell (GB); Louisa Robinson, Bracknell (GB); John Stephen Delaney, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 33 days.

(21) Appl. No.: 13/144,705

(22) PCT Filed: Jan. 6, 2010

(86) PCT No.: PCT/EP2010/050074
§ 371 (c)(1), (2), (4) Date: Oct. 14, 2011

(87) PCT Pub. No.: WO2010/081755
PCT Pub. Date: Jul. 22, 2010

(65) Prior Publication Data
US 2012/0021907 A1   Jan. 26, 2012

(30) Foreign Application Priority Data

Jan. 15, 2009   (GB) .................................. 0900641.2

(51) Int. Cl.

| | | |
|---|---|---|
| *C07D 309/10* | (2006.01) | |
| *C07C 49/753* | (2006.01) | |
| *A01N 43/78* | (2006.01) | |
| *A01N 43/16* | (2006.01) | |
| *A01N 43/707* | (2006.01) | |
| *A01N 43/54* | (2006.01) | |
| *A01N 43/40* | (2006.01) | |

(Continued)

(52) U.S. Cl.
CPC .............. *C07D 309/10* (2013.01); *A01N 43/78* (2013.01); *C07C 255/54* (2013.01); *C07C 205/38* (2013.01); *C07D 409/10* (2013.01); *C07D 493/10* (2013.01); *C07C 309/66* (2013.01); *C07D 309/32* (2013.01); *C07D 405/10* (2013.01); *A01N 43/40* (2013.01); *A01N 43/54* (2013.01); *C07D 407/04* (2013.01); *A01N 43/60* (2013.01); *A01N 43/90* (2013.01); *C07C 49/753* (2013.01); *C07C 2102/42* (2013.01); *C07C 2102/50* (2013.01); *C07D 311/96* (2013.01); *A01N 43/707* (2013.01); *A01N 43/42* (2013.01); *C07C 2101/14* (2013.01); *C07D 413/10* (2013.01); *C07D 417/10* (2013.01); *A01N 35/06* (2013.01); *A01N 43/16* (2013.01); *C07C 2101/02* (2013.01); *C07C 2101/16* (2013.01); *C07C 2102/44* (2013.01)
USPC ........... 504/121; 504/124; 504/128; 504/137; 504/238; 504/241; 504/242; 504/267; 504/270; 504/292; 504/348; 544/183; 544/236; 544/238; 544/278; 544/318; 544/354; 546/282.1; 548/170; 548/221; 549/331; 549/417; 568/315; 568/327; 568/329

(58) Field of Classification Search
USPC ......... 504/121, 124, 128, 137, 238, 241, 242, 504/267, 270, 292, 348; 544/183, 236, 238, 544/278, 318, 354; 546/282.1; 548/170, 548/221; 549/331, 417; 568/315, 327, 329
See application file for complete search history.

(56) References Cited

U.S. PATENT DOCUMENTS

| | | | |
|---|---|---|---|
| 4,175,135 | A | 11/1979 | Haines |
| 4,209,532 | A | 6/1980 | Wheeler |

(Continued)

FOREIGN PATENT DOCUMENTS

| | | |
|---|---|---|
| CA | 2322158 A1 | 8/2000 |
| CA | 2325526 A1 | 9/2000 |

(Continued)

OTHER PUBLICATIONS

Muehlebach et al., "Discovery and SAR of pinoxaden: a new broad spectrum, postemergence cereal herbicide," in Pesticide Chemistry. Crop Protection, Public Health, Environmental Safety, ed. H. Ohkawa et al., Jun. 2007, Wiley-VCH Verlag, Weinheim, pp. 101-110.

(Continued)

*Primary Examiner* — Kristin Vajda
*Assistant Examiner* — Valerie Rodriguez-Garcia
(74) *Attorney, Agent, or Firm* — R. Kody Jones

(57) ABSTRACT

Compounds of formula (I), wherein the substituents are as defined in claim 1, are suitable for use as herbicides.

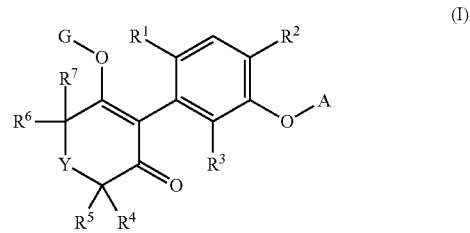

46 Claims, No Drawings

(51) Int. Cl.

| | |
|---|---|
| C07D 413/10 | (2006.01) |
| C07D 407/04 | (2006.01) |
| A01N 43/90 | (2006.01) |
| C07C 309/66 | (2006.01) |
| C07D 311/96 | (2006.01) |
| C07C 255/54 | (2006.01) |
| C07C 205/38 | (2006.01) |
| C07D 409/10 | (2006.01) |
| C07D 493/10 | (2006.01) |
| C07D 309/32 | (2006.01) |
| C07D 405/10 | (2006.01) |
| A01N 43/60 | (2006.01) |
| A01N 43/42 | (2006.01) |
| C07D 417/10 | (2006.01) |
| A01N 35/06 | (2006.01) |

(56) References Cited

U.S. PATENT DOCUMENTS

| | | | |
|---|---|---|---|
| 4,409,153 | A | 10/1983 | Hodakowski |
| 4,489,012 | A | 12/1984 | Hodakowski |
| 4,526,723 | A | 7/1985 | Wheeler et al. |
| 4,659,372 | A | 4/1987 | Wheeler |
| 5,502,048 | A * | 3/1996 | Chapdelaine et al. .......... 514/63 |
| 5,801,120 | A | 9/1998 | Lee et al. |
| 6,251,833 | B1 | 6/2001 | Erdelen et al. |
| 6,458,965 | B1 | 10/2002 | Lieb et al. |
| 6,894,005 | B1 | 5/2005 | Maetzke et al. |
| 8,058,210 | B2 | 11/2011 | Lieb et al. |
| 8,084,649 | B2 | 12/2011 | Muehlebach et al. |
| 2003/0216260 | A1 | 11/2003 | Ruther et al. |
| 2006/0166829 | A1 | 7/2006 | Fischer et al. |
| 2010/0113270 | A1 | 5/2010 | Mathews et al. |
| 2010/0210466 | A1 | 8/2010 | Muehlebach et al. |
| 2010/0216638 | A1 | 8/2010 | Mathews et al. |
| 2010/0279868 | A1 | 11/2010 | Jeanmart et al. |
| 2012/0021909 | A1 | 1/2012 | Mathews et al. |
| 2012/0040826 | A1 | 2/2012 | Jeanmart et al. |

FOREIGN PATENT DOCUMENTS

| | | |
|---|---|---|
| CA | 2382432 A1 | 2/2002 |
| CA | 2382435 A1 | 2/2002 |
| CA | 2456776 A1 | 2/2004 |
| DE | 2813341 C2 | 4/1983 |
| WO | WO 92/16510 A1 | 10/1992 |
| WO | WO 96/11574 A1 | 4/1996 |
| WO | WO96/21652 A1 | 7/1996 |
| WO | WO99/43649 A1 | 9/1999 |
| WO | WO 99/47525 A1 | 9/1999 |
| WO | WO99/48869 A1 | 9/1999 |
| WO | WO 00/37437 A1 | 6/2000 |
| WO | WO01/17972 A2 | 3/2001 |
| WO | WO 01/17973 A2 | 3/2001 |
| WO | WO01/74770 A1 | 10/2001 |
| WO | WO03/013249 A1 | 2/2003 |
| WO | WO98/39281 A1 | 12/2004 |
| WO | WO2004/111042 A1 | 12/2004 |
| WO | WO 2005/123667 A1 | 12/2005 |
| WO | WO 2006/034315 A2 | 3/2006 |
| WO | WO 2006/034446 A2 | 3/2006 |
| WO | 2008071405 | 6/2008 |
| WO | WO2008/071405 A1 | 6/2008 |
| WO | WO2008/110307 A1 | 9/2008 |
| WO | WO2008/110308 A2 | 9/2008 |
| WO | 2008145336 | 12/2008 |
| WO | WO2008/145336 A1 | 12/2008 |
| WO | WO2009/000533 A1 | 12/2008 |
| WO | WO2009/015877 A1 | 2/2009 |
| WO | WO2009/019015 A1 | 2/2009 |
| WO | WO2009/074314 A1 | 6/2009 |
| WO | WO2010/089210 A1 | 8/2010 |
| WO | WO2010/089211 A1 | 8/2010 |
| WO | WO2010/102848 A1 | 9/2010 |

OTHER PUBLICATIONS

Wenger, J. and Nidermann, T., Chapter 9: Acetyl-CoA Carboxylase Inhibitors', in Modern Crop Protection Compounds, ed. W. Kraemer et al., Wiley-VCH Verlag, Weinheim, 2007, pp. 335-357.

Wenger, et al., "Chapter 11: Acetyl-CoA Carboxylase Inhibitors", in Modern Crop Protection Compounds, Second Edition, ed. W. Kraemer et al., Wiley-VCH Verlag, Weinheim, available online Jan. 2012, pp. 447-477.

* cited by examiner

HERBICIDALLY ACTIVE CYCLIC DIONES AND DERIVATIVES THEREOF, PROCESSES FOR THEIR PREPARATION, COMPOSITIONS, AND METHOD OF CONTROLLING WEEDS

This application is a 371 of International Application No. PCT/EP2010/050074 filed Jan. 6, 2010, which claims priority to GB 0900641.2 filed Jan. 15, 2009, the contents of which are incorporated herein by reference.

The present invention relates to novel, herbicidally active cyclic diones, and derivatives thereof, to processes for their preparation, to compositions comprising those compounds, and to their use in controlling weeds, especially in crops of useful plants, or in inhibiting undesired plant growth.

Cyclic diones having herbicidal action are described, for example, in WO08/071,405 and WO08/145,336.

Novel cyclic diones, and derivatives thereof, having herbicidal and growth-inhibiting properties have now been found.

The present invention accordingly relates to compounds of formula I

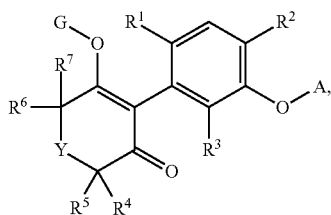

wherein
A is a mono- or bicyclic aryl or heteroaryl which contains a heteroatom selected from nitrogen, oxygen and sulfur, and which is unsubstituted or substituted,
$R^1$ is methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy,
$R^2$ and $R^3$ are independently of each other hydrogen, methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy,
$R^4$, $R^5$, $R^6$ and $R^7$ are independently of each other hydrogen, $C_1$-$C_6$alkyl, $C_1$-$C_6$alkyl substituted by $C_1$-$C_4$alkoxy or halogen, $C_2$-$C_6$ alkenyl, $C_2$-$C_6$ alkenyl substituted by $C_1$-$C_4$alkoxy or halogen, $C_2$-$C_6$alkynyl, $C_2$-$C_6$alkynyl substituted by $C_1$-$C_4$alkoxy or halogen, $C_3$-$C_7$cycloalkyl, $C_3$-$C_7$cycloalkyl substituted by $C_1$-$C_4$alkyl or $C_1$-$C_4$alkoxy, $C_5$-$C_7$cycloalkenyl, $C_5$-$C_7$cycloalkenyl substituted by $C_1$-$C_4$alkyl or $C_1$-$C_4$alkoxy, heterocyclyl or heterocyclyl substituted by $C_1$-$C_4$alkyl or $C_1$-$C_4$alkoxy, or
$R^4$ and $R^5$, or $R^6$ and $R^7$, together with the atoms to which they are bonded, form a 5- to 8-membered spiro-carbocyclyl or spiro-heterocyclyl, which contains one or two heteroatoms selected from nitrogen, oxygen or sulfur, or
$R^5$ and $R^6$, together with the atoms to which they are bonded, form a 5- to 8-membered carbocyclyl or heterocyclyl, which contains one or two heteroatoms selected from nitrogen, oxygen or sulfur,
Y is O, S(O)$_n$, C=O, $CR^8R^9$ or $CR^{10}R^{11}CR^{12}R^{13}$,
n is 0, 1 or 2,
$R^8$ and $R^9$ are independently of each other hydrogen, $C_1$-$C_6$alkyl, $C_1$-$C_6$alkyl substituted by $C_1$-$C_4$alkoxy or halogen, $C_2$-$C_6$ alkenyl, $C_2$-$C_6$ alkenyl substituted by $C_1$-$C_4$alkoxy or halogen, $C_2$-$C_6$alkynyl, $C_2$-$C_6$alkynyl substituted by $C_1$-$C_4$alkoxy or halogen, $C_3$-$C_7$cycloalkyl, $C_3$-$C_7$cycloalkyl substituted by $C_1$-$C_4$alkyl or $C_1$-$C_4$alkoxy, $C_5$-$C_7$cycloalkenyl, $C_5$-$C_7$cycloalkenyl substituted by $C_1$-$C_4$alkyl or $C_1$-$C_4$alkoxy, heterocyclyl or heterocyclyl substituted by $C_1$-$C_4$alkyl or $C_1$-$C_4$alkoxy, or
$R^8$ and $R^9$, together with the atoms to which they are bonded, form a 5- to 8-membered spiro-carbocyclyl or spiro-heterocyclyl, which contains one or two heteroatoms selected from nitrogen, oxygen or sulfur, and
$R^{10}$, $R^{11}$, $R^{12}$ and $R^{13}$ are independently of each other hydrogen, $C_1$-$C_6$alkyl or $C_1$-$C_6$alkoxy, and
G is hydrogen or an agriculturally acceptable metal, sulfonium, ammonium or latentiating group.

In the substituent definitions of the compounds of the formula I, each alkyl moiety either alone or as part of a larger group (such as alkoxy, alkylthio, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, isopropyl, n-butyl, sec-butyl, isobutyl, tert-butyl or neopentyl. The alkyl groups are suitably $C_1$-$C_6$alkyl groups, but are preferably $C_1$-$C_4$alkyl or $C_1$-$C_3$alkyl groups, and, more preferably, $C_1$-$C_2$alkyl groups.

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkylinylalkenyl are included in these terms.

Halogen is fluorine, chlorine, bromine or iodine.

Haloalkyl groups are alkyl groups which are substituted with one or more of the same or different halogen atoms and are, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

In the context of the present specification the term "aryl" refers to ring systems which may be mono- or bicyclic. Examples of such rings include phenyl and naphthyl. A preferred aryl group is phenyl.

The term "heteroaryl" preferably refers to an aromatic ring system containing at least one heteroatom and consisting either of a single ring or of two fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

The term "heterocyclyl" preferably refers to a non-aromatic preferably monocyclic or bicyclic ring systems containing up to 7 atoms including one or more (preferably one or two) heteroatoms selected from O, S and N. Examples of such rings include tetrahydropyran, 1,3-dioxolane, oxetane, tetrahydrofuran, morpholine, thiomorpholine and piperazine.

Cycloalkyl includes preferably cyclopropyl, cyclobutyl, cyclopentyl and cyclohexyl. Cycloalkylalkyl is preferentially cyclopropylmethyl. Cycloalkenyl includes preferably cyclopentenyl and cyclohexenyl.

Carbocyclic rings include aryl, cycloalkyl or carbocyclic groups, and cycloalkenyl groups.

When present, the optional substituents on aryl, heteroaryl and carbocycles are preferably selected independently, from halogen, nitro, cyano, rhodano, isothiocyanato, $C_1$-$C_6$alkyl, $C_1$-$C_6$haloalkyl, $C_1$-$C_6$alkoxy($C_1$-$C_6$) alkyl, $C_2$-$C_6$alkenyl, $C_2$-$C_6$haloalkenyl, $C_2$-$C_6$alkynyl, $C_3$-$C_7$cycloalkyl (itself optionally substituted with $C_1$-$C_6$alkyl or halogen), $C_{5-7}$cycloalkenyl (itself optionally substituted with $C_1$-$C_6$alkyl or halogen), hydroxy, $C_1$-$C_{10}$alkoxy, $C_1$-$C_{10}$alkoxy($C_1$-$C_{10}$) alkoxy, tri($C_1$-$C_4$)alkylsilyl($C_1$-$C_6$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted with halogen or $C_1$-$C_6$alkyl), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio, $C_3$-$C_7$cycloalkylthio (where the cycloalkyl group is optionally substituted with $C_1$-$C_6$alkyl or halogen), tri($C_1$-$C_4$)-alkylsilyl($C_1$-$C_6$)alkylthio, arylthio, $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl, tri($C_1$-$C_4$)alkylsilyl, aryldi($C_1$-$C_4$)alkylsilyl, $C_1$-$C_4$alkyldiarylsilyl, triarylsilyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$alkyl)-aminocarbonyl, N—($C_1$-$C_3$ alkyl)-N—($C_1$-$C_3$alkoxy)aminocarbonyl, $C_1$-$C_6$alkylcarbonyloxy, arylcarbonyloxy, di($C_1$-$C_6$)alkylaminocarbonyloxy, aryl (itself optionally substituted with $C_1$-$C_6$alkyl or halogen), heteroaryl (itself optionally substituted with $C_1$-$C_6$alkyl or halogen), heterocyclyl (itself optionally substituted with $C_1$-$C_6$alkyl or halogen), aryloxy (where the aryl group is optionally substituted with $C_1$-$C_6$alkyl or halogen), heteroaryloxy (where the heteroaryl group is optionally substituted with $C_1$-$C_6$alkyl or halogen), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, arylcarbonyl, (where the aryl group is itself optionally substituted with halogen or $C_1$-$C_6$alkyl) or two adjacent positions on an aryl or heteroaryl system may be cyclised to form a 5, 6 or 7 membered carbocyclic or heterocyclic ring, itself optionally substituted with halogen or $C_1$-$C_6$alkyl. Further substituents for aryl or heteroaryl include arylcarbonylamino (where the aryl group is substituted by $C_1$-$C_6$alkyl or halogen), ($C_1$-$C_6$)alkoxycarbonylamino, ($C_1$-$C_6$)alkoxycarbonyl-N—($C_1$-$C_6$)alkylamino, aryloxycarbonylamino (where the aryl group is substituted by $C_1$-$C_6$alkyl or halogen), aryloxycarbonyl-N—($C_1$-$C_6$)alkylamino, (where the aryl group is substituted by $C_1$-$C_6$alkyl or halogen), arylsulphonylamino (where the aryl group is substituted by $C_1$-$C_6$alkyl or halogen), arylsulphonyl-N—($C_1$-$C_6$)alkylamino (where the aryl group is substituted by $C_1$-$C_6$alkyl or halogen), aryl-N—($C_1$-$C_6$)alkylamino (where the aryl group is substituted by $C_1$-$C_6$alkyl or halogen), arylamino (where the aryl group is substituted by $C_1$-$C_6$alkyl or halogen), heteroaryl amino (where the heteroaryl group is substituted by $C_1$-$C_6$alkyl or halogen), heterocyclylamino (where the heterocyclyl group is substituted by $C_1$-$C_6$alkyl or halogen), aminocarbonylamino, $C_1$-$C_6$alkylaminocarbonylamino, di($C_1$-$C_6$)alkylaminocarbonylamino, arylaminocarbonylamino where the aryl group is substituted by $C_1$-$C_6$alkyl or halogen), aryl-N—($C_1$-$C_6$)alkylaminocarbonylamino where the aryl group is substituted by $C_1$-$C_6$alkyl or halogen), $C_1$-$C_6$alkylaminocarbonyl-N—($C_1$-$C_6$)alkylamino, di($C_1$-$C_6$)alkylaminocarbonyl-N—($C_1$-$C_6$)alkylamino, arylaminocarbonyl-N—($C_1$-$C_6$)alkylamino where the aryl group is substituted by $C_1$-$C_6$alkyl or halogen) and aryl-N—($C_1$-$C_6$) alkylaminocarbonyl-N—($C_1$-$C_6$)alkylamino where the aryl group is substituted by $C_1$-$C_6$alkyl or halogen).

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine.

Preferred quaternary ammonium bases suitable for salt formation correspond, for example, to the formula $[N(R_aR_bR_cR_d)]OH$, wherein $R_a$, $R_b$, $R_c$ and $R_d$ are each independently of the others hydrogen, $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula $[SR_eR_fR_g]OH$, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates which may be formed during the salt formation.

The latentiating groups G are selected to allow its removal by one or a combination of biochemical, chemical or physical processes to afford compounds of formula I where G is H before, during or following application to the treated area or plants. Examples of these processes include enzymatic cleavage, chemical hydrolysis and photolysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

The latentiating group G is preferably selected from the groups $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—N($R^c$)—$R^d$, —$SO_2$—$R^e$, —$P(X^e)(R^f)$—$R^g$ or $CH_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$—($C_1$-$C_5$)oxyalkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$-trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$) alkyl, $C_1$-$C_5$alkylsulfinyl($C_1$-$C_5$)alkyl, $C_1$-$C_5$alkylsulfonyl ($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl ($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro or $C_3$-$C_7$cycloalkylamino, di-$C_3$-$C_7$cycloalkylamino or $C_3$-$C_7$cycloalkoxy or $R^c$ and $R^d$ may join together to form a 3-7 membered ring, optionally containing one heteroatom selected from O or S, $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$) alkyl, $C_1$-$C_5$alkylsulfinyl($C_1$-$C_5$)alkyl, $C_1$-$C_5$alkylsulfonyl ($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino, $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di$C_3$-$C_7$cycloalkylamino or $C_3$-$C_7$cycloalkoxy, $C_1$-$C_{10}$haloalkoxy, $C_1$-$C_5$alkylamino or $C_2$-$C_8$dialkylamino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$-aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy($C_1$-$C_5$)alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy($C_1$-$C_5$)alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

It is preferred that G is hydrogen, an alkali metal or alkaline earth metal, where hydrogen is especially preferred.

Depending on the nature of the substituents, compounds of formula I may exist in different isomeric forms. For example, when G is hydrogen and $R^4$ and $R^5$ are different from $R^6$ and $R^7$, compounds of formula I may exist in different tautomeric forms:

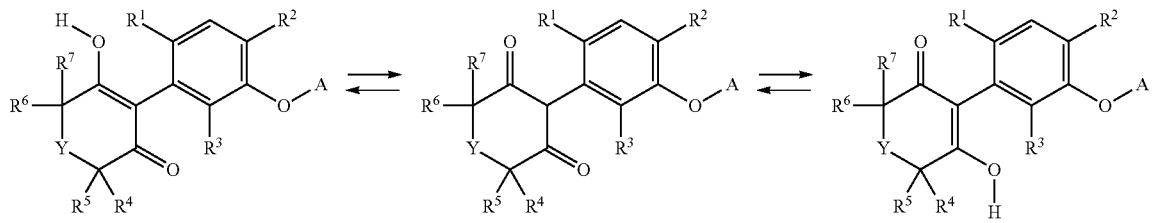

This invention covers all such isomers and tautomers and mixtures thereof in all proportions. Also, when substituents contain double bonds, cis- and trans-isomers can exist. These isomers, too, are within the scope of the claimed compounds of the formula I.

Preferably, in the compounds of formula I, A is phenyl, naphthyl, a 5- or 6-membered heteroaryl or a bicyclic 8- to 10-membered heteroaryl.

Preferably, in the compounds of formula I, A is substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro, cyano, $C_3$-$C_6$cycloalkyl, $C_1$-$C_3$alkylcarbonyl, $C_1$-$C_4$alkoxycarbonyl, aminocarbonyl, $C_1$-$C_3$alkylaminocarbonyl, di-$C_1$-$C_3$alkylaminocarbonyl, $C_1$-$C_3$alkylaminocarbonyloxy, di-$C_1$-$C_3$alkylaminocarbonyloxy, aminothiocarbonyl, $C_1$-$C_3$alkylaminothiocarbonyl, di$C_1$-$C_3$alkylaminothiocarbonyl, $C_1$-$C_4$alkylcarbonylamino, $C_3$-$C_6$cycloalkylcarbonylamino, $C_1$-$C_4$alkoxycarbonylamino, $C_1$-$C_4$alkylthiocarbonylamino, $C_1$-$C_3$alkoxy$C_1$-$C_3$alkyl, $C_1$-$C_6$alkylthio$C_1$-$C_6$alkyl, $C_1$-$C_6$alkylsulfinyl$C_1$-$C_6$alkyl, $C_1$-$C_6$alkylsulfonyl$C_1$-$C_6$alkyl, $C_1$-$C_3$alkylsulfonyloxy, $C_1$-$C_3$haloalkylsulfonyloxy or di$C_1$-$C_6$alkylaminosulfonyl, or 2 substituents on adjacent carbon atoms of A together form a $C_3$-$C_4$alkylene, wherein 1 or 2 methylene groups are optionally substituted by halogen, or wherein 1 or 2 of these methylene groups are replaced by oxygen.

More preferably, A is phenyl, naphthyl, pyridyl, pyrazinyl, pyrimidinyl, pyridazinyl, benzothiazolyl, benzoxazolyl, cinnolinyl, quinolinyl, quinazolinyl, quinoxalinyl or benzotriazinyl in each case substituted by halogen, methyl, ethyl, trifluoromethyl, methoxy, difluoromethoxy, trifluoromethoxy, nitro or cyano.

Preferably, $R^1$ is methyl, ethyl, n-propyl, cyclopropyl, halogen or $C_1$-$C_2$haloalkoxy.

Preferably, $R^2$ and $R^3$ are independently of each other hydrogen, methyl or halogen, especially hydrogen.

Preferably, $R^4$, $R^5$, $R^6$ and $R^7$ are independently of each other hydrogen or $C_1$-$C_6$alkyl, or $R^4$ and $R^5$, or $R^6$ and $R^7$, together with the atoms to which they are bonded form a spiro-tetrahydropyranyl or spiro-tetrahydrofuranyl, or $R^5$ and $R^6$ together with the atoms to which they are bonded form a 6- or 7-membered carbocyclyl.

Preferably, Y is O or $CR^8R^9$, where $R^8$ and $R^9$ are as defined above.

Preferably, $R^8$ and $R^9$ are independently of each other hydrogen or methyl, or $R^8$ and $R^9$ together with the atoms to which they are bonded form a spiro-tetrahydropyranyl or a spiro-tetrahydrofuranyl.

Preferably, G is hydrogen, a group —C($X^a$)—$R^a$ or —C($X^b$)—$X^c$—$R^b$, where the meanings of $X^a$, $R^a$, $X^b$, $X^c$ and $R^b$ are as defined above, and particularly hydrogen.

In a particularly preferred group of compounds of formula I A is phenyl, naphthyl, pyridyl, pyrazinyl, pyrimidinyl, pyridazinyl, benzothiazolyl, benzoxazolyl, cinnolinyl, quinolinyl, quinazolinyl, quinoxalinyl or benzotriazinyl, in each case substituted by halogen, methyl, trifluoromethyl, nitro or cyano, $R^1$ is ethyl, $R^2$ and $R^3$ are hydrogen, $R^4$ to $R^7$ are hydrogen or methyl or $R^5$ and $R^6$, together with the atoms to which they are bonded, form a 6- or 7-membered carbocyclyl, Y is O or $CR^8R^9$, wherein $R^8$ and $R^9$ are independently of each other hydrogen or methyl, or $R^8$ and $R^9$ together with the atoms to which they are bonded form a spiro-tetrahydropyranyl or a spiro-tetrahydrofuranyl, and G is hydrogen.

In another particularly preferred group of compounds of formula (I), $R^1$ is methyl, ethyl or cyclopropyl, $R^2$ and $R^3$ are hydrogen, $R^4$, $R^5$, $R^6$ and $R^7$ are independently of each other hydrogen or methyl, or $R^4$ and $R^5$, or $R^6$ and $R^7$, together with the atoms to which they are bonded form a spiro-tetrahydropyranyl or spiro-tetrahydrofuranyl, or $R^5$ and $R^6$ together with the atoms to which they are bonded form a 6- or 7-membered carbocyclyl, Y is O or $CR^8R^9$, where $R^8$ and $R^9$ are independently of each other hydrogen or methyl, or $R^8$ and $R^9$ together with the atoms to which they are bonded form a spiro-tetrahydropyranyl or a spiro-tetrahydrofuranyl, G is hydrogen and A is phenyl, naphthyl, pyridyl, pyrazinyl, pyrimidinyl, pyridazinyl, benzothiazolyl, benzoxazolyl, quinolinyl or quinoxalinyl, in each case unsubstituted or substituted by hydroxyl, methoxy, ethoxy, fluoro, chloro, bromo, iodo, methyl, trifluoromethyl, amino, formyl, nitro or cyano.

A compound of formula I wherein Q is $Q_1$ and G is $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), $C_3$-$C_8$alkenyl, $C_3$-$C_8$haloalkenyl, $C_3$-$C_8$alkynyl, C($X^a$)—$R^a$, C($X^b$)—$X^c$—$R^b$, C($X^d$)—N($R^c$)—$R^d$, —$SO_2$—$R^e$, —P($X^e$)($R^f$)—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of formula (A), which is a compound of formula I wherein G is H, with a reagent G-Z, wherein G-Z is an alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$alkyl sulfonate, or a di($C_1$-$C_8$alkyl) sulfate, or with a $C_3$-$C_8$alkenyl halide, or with a $C_3$-$C_8$alkynyl halide, or with an acylating agent such as a carboxylic acid, HO—C($X^a$)$R^a$, wherein $X^a$ is oxygen, an acid chloride, Cl—C($X^a$)$R^a$, wherein $X^a$ is oxygen, or acid anhydride, $[R^aC(X^a)]_2O$, wherein $X^a$ is oxygen, or an isocyanate, $R^c$N═C═O, or a carbamoyl chloride, Cl—C($X^d$)—N($R^c$)—$R^d$ (wherein $X^d$ is oxygen and with the proviso that neither $R^c$ or $R^d$ is hydrogen), or a thiocarbamoyl chloride Cl—($X^d$)—N($R^c$)—$R^d$ (wherein $X^d$ is sulfur and with the proviso that neither $R^c$ or $R^d$ is hydrogen) or a chloroformate, Cl—C($X^b$)—$X^c$—$R^b$, (wherein $X^b$ and $X^c$ are oxygen), or a chlorothioformate Cl—C($X^b$)—$X^c$—$R^b$ (wherein $X^b$ is oxygen and $X^c$ is sulfur), or a chlorodithioformate Cl—C($X^b$)—$X^c$—$R^b$, (wherein $X^b$ and $X^c$ are sulfur), or an isothiocyanate, $R^c$N═C═S, or by sequential treatment with carbon disulfide and an alkylating agent, or with a phosphorylating agent such as a phosphoryl chloride, Cl—P($X^e$)($R^f$)—$R^g$ or with a sulfonylating agent such as a sulfonyl chloride Cl—$SO_2$—$R^e$, preferably in the presence of at least one equivalent of base.

Where substituents $R^4$ and $R^5$ are not equal to substituents $R^6$ and $R^7$, these reactions may produce, in addition to a compound of formula I, a second compound of formula $I_A$.

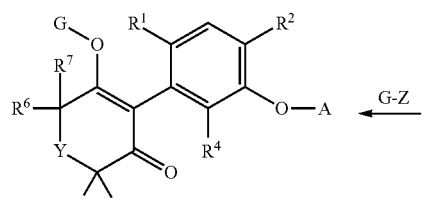 Formula I

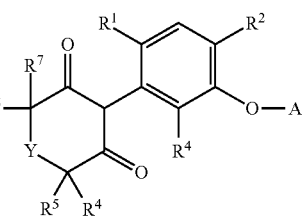 Formula (A)

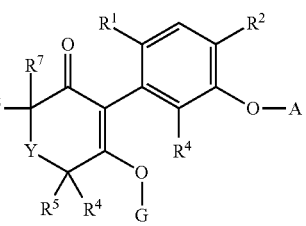 Formula $I_A$

This invention covers both a compound of formula I and a compound of formula $I_A$, together with mixtures of these compounds in any ratio.

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected by procedures similar to those described, for example, by R. Haines, U.S. Pat. No. 4,175,135, and by T. Wheeler, U.S. Pat. No. 4,422,870, U.S. Pat. No. 4,659,372 and U.S. Pat. No. 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]-octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A), may be achieved using an alkyl or aryl sulfonyl halide, preferably in the presence of at least one equivalent of base, for example by the procedure of C. Kowalski and K. Fields, J. Org. Chem., (1981), 46, 197-201.

Compounds of formula (A), wherein Y is $S(O)_n$ and n is 1 or 2 may be prepared from compounds of formula (A) wherein Y is S by oxidation, according to a procedure analogous to that of E. Fehnel and A. Paul, J. Am. Chem. Soc., (1955), 77, 4241-4244.

A compound of formula (A), wherein Y is O, S, C=O or $CR^{12}R^{13}$ may be prepared via the cyclisation of a compound of formula (B), preferably in the presence of an acid or base, and optionally in the presence of a suitable solvent, by analogous methods to those described by T. Wheeler, U.S. Pat. No. 4,209,532. The compounds of the formula (B) have been particularly designed as intermediates in the synthesis of the compounds of the formula I. Compounds of formula (B) wherein R is hydrogen or $C_1$-$C_4$alkyl, (especially methyl, ethyl and tert-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

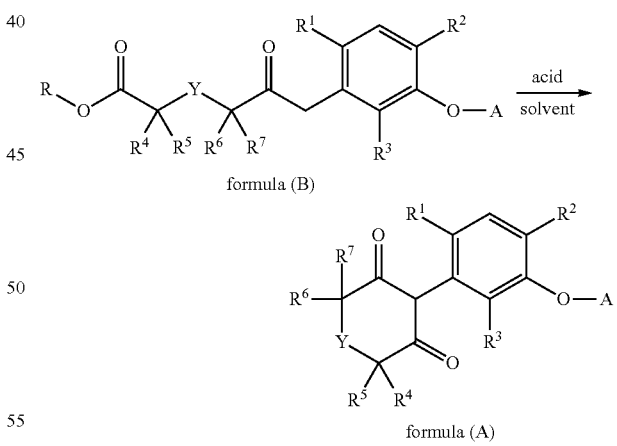

formula (B)

formula (A)

A compound of formula (B) wherein R is alkyl (preferably methyl or ethyl) may be cyclised under acidic or basic conditions, preferably under basic conditions in the presence of at least one equivalent of a strong base such as potassium tert-butoxide, lithium diisopropylamide, sodium bis(trimethylsilyl)amide or sodium hydride and in a solvent such as tetrahydrofuran, toluene, dimethylsulfoxide or N,N-dimethylformamide.

A compound of formula (B), wherein R is H may be esterified to a compound of formula (B), wherein R is alkyl, under known conditions (for example by treatment with an alcohol, R—OH, in the presence of an acid catalyst).

A compound of formula (B), wherein R is H may be prepared by hydrolysis of a compound of formula (C) wherein R is H or alkyl and R' is alkyl (preferably methyl or ethyl), followed by acidification of the reaction mixture to effect decarboxylation, by similar processes to those described by, for example, T. Wheeler, U.S. Pat. No. 4,209,532. Alternatively, a compound of formula (B), wherein R is alkyl (preferably methyl) may be prepared from a compound of formula (C), wherein R is alkyl (preferably methyl), through a Krapcho decarboxylation procedure under known conditions using known reagents (see for example G. Quallich, P. Morrissey, Synthesis, (1993), (1), 51-53).

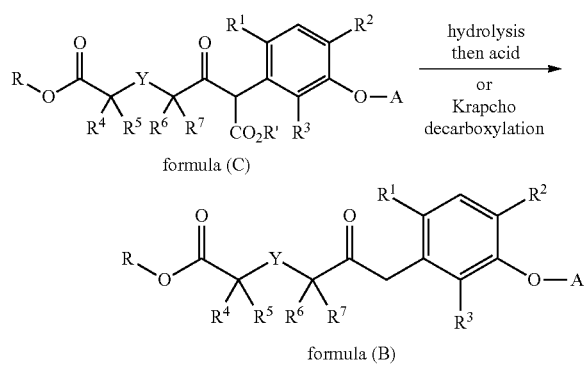

A compound of formula (C) wherein R is alkyl may be prepared by treating a compound of formula (D) with a suitable carboxylic acid chloride of formula (E) wherein R is alkyl under basic conditions. Suitable bases include potassium tert-butoxide, sodium bis(trimethylsilyl)amide and lithium diisopropylamide and the reaction is preferably conducted in a suitable solvent (such as tetrahydrofuran or toluene) at a temperature of between −80° C. and 30° C.:

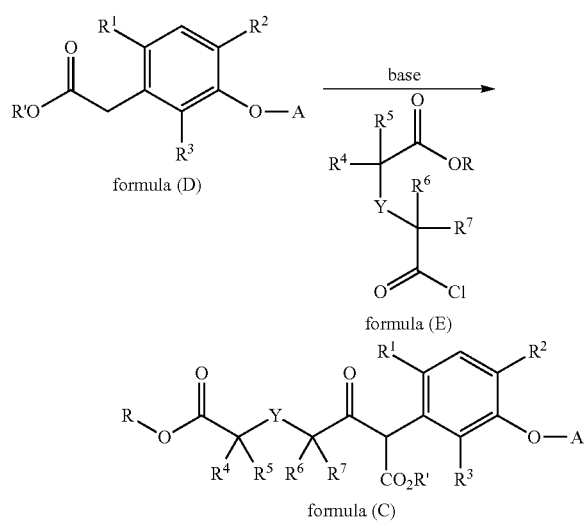

Alternatively, a compound of formula (C), wherein R is H, may be prepared by treating a compound of formula (D) with a suitable base (such as potassium tert-butoxide, sodium bis (trimethylsilyl)amide and lithium diisopropylamide) in a suitable solvent (such as tetrahydrofuran or toluene) at a suitable temperature (between −80° C. and 30° C.) and reacting the resulting anion with a suitable anhydride of formula (F):

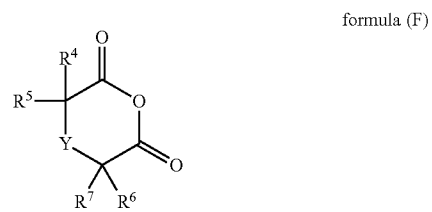

Compounds of formula (E) and formula (F) are known, or may be made by similar methods from commercially available starting materials (see, for example C. Rouvier, Tetrahedron Lett., (1984), 25 (39), 4371-4374; D. Walba and M. Wand, Tetrahedron Lett., (1982), 23 (48), 4995-4998; T. Terasawa and T. Okada, J. Org. Chem., (1977), 42 (7), 1163-1169 and G. Bennett, W. Houlihan, R. Mason, and R. Engstrom, J. Med. Chem., (1976), 19 (5), 709-714; J. Cason, Org. Synth. Coll. Vol. IV, (1963), 630-633).

Compounds of formula (D) are known (see, for example, H. Ishibashi et al., Chem. Pharm. Bull., (1991), 39 (11), 2878-2882; R. Kirsten et al., EP338306 A2; W. Marshall, U.S. Pat. No. 3,649,679) or may be made by similar methods from known compounds.

In a further approach, a compound of formula (A) may be prepared by reacting a compound of formula (G) with an aryllead tricarboxylate, in the presence of a suitable ligand and in a suitable solvent. Similar reactions are described in the literature (for example see, M. Muehlebach et al., WO08/071,405; J. Pinhey, B. Rowe, Aust. J. Chem., (1979), 32, 1561-6; J. Morgan, J. Pinhey, J. Chem. Soc. Perkin Trans. 1, (1990), 3, 715-20). Preferably the aryllead tricarboxylate is an aryllead triacetate of formula (H). Preferably the ligand is a nitrogen containing heterocycle such as N,N-dimethylaminopyridine, 1,10-phenanthroline pyridine, bipyridine, or imidazole, and one to ten equivalents of ligand with respect to a compound of formula (J) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.).

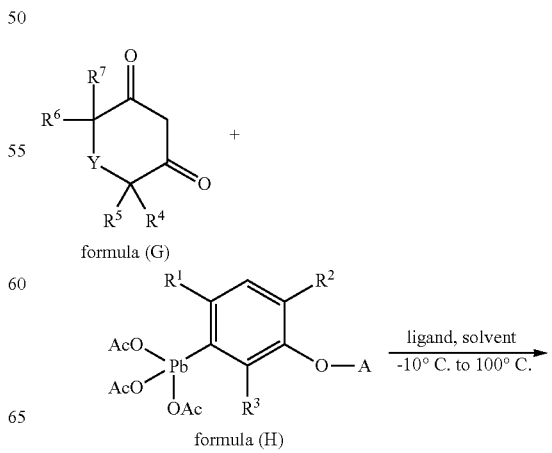

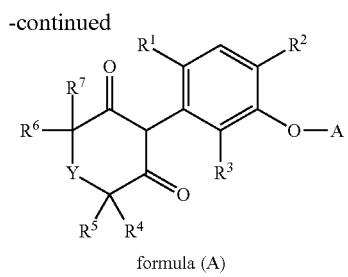

formula (A)

Compounds of formula (G), wherein Y is O, are known compounds or may be prepared by routes analogous to those described in the literature (see, for example, M. Muehlebach et al., WO08/071,405; M. Morgan and E. Heyningen, J. Am. Chem Soc., (1957), 79, 422-424; I. Korobitsyna and K. Pivnitskii, Russian Journal of General Chemistry, (1960), 30, 4016-4023; T. Terasawa, and T. Okada, J. Org. Chem., (1977), 42 (7), 1163-1169; R. Anderson et al. U.S. Pat. No. 5,089, 046; R. Altenbach, K. Agrios, I. Drizin and W. Carroll, Synth. Commun., (2004), 34 (4) 557-565; R. Beaudegnies et al., WO2005/123667; W. Li, G. Wayne, J. Lallaman, S. Chang, and S. Wittenberger, J. Org. Chem. (2006), 71, 1725-1727; R. Altenbach, M. Brune, S. Buckner, M. Coghlan, A. Daza, A. Fabiyi, M. Gopalakrishnan, R. Henry, A. Khilevich, M. Kort, I. Milicic, V. Scott, J. Smith, K. Whiteaker, and W. Carroll, J. Med. Chem, (2006), 49(23), 6869-6887; Carroll et al., WO 2001/083484 A1; J. K. Crandall, W. W. Conover, J. Org. Chem. (1978), 43(18), 3533-5; I. K. Korobitsyna, O. P. Studzinskii, Chemistry of Heterocyclic Compounds (1966), (6), 848-854). Compounds of formula (G), wherein Y is S, are known compounds or may be prepared by routes analogous to those described in the literature (see, for example, E. Fehnel and A. Paul, J. Am. Chem Soc., (1955), 77, 4241-4244; E. Er and P. Margaretha, Helvetica Chimica Acta (1992), 75(7), 2265-69; H. Gayer et al., DE 3318648 A1). Compounds of formula (G), wherein Y is C=O, are known compounds or may be prepared by routes analogous to those described in the literature (see, for example, R. Götz and N. Götz, WO2001/060776 R. Götz et al. WO 2000/075095; M. Benbakkar et al., Synth. Commun. (1989) 19(18) 3241-3247; A. Jain and T. Seshadri, Proc. Indian Acad. Sci. Sect. A, (1955), 42, 279); N. Ahmad et al., J. Org. Chem., (2007), 72(13), 4803-4815); F. Effenberger et al., Chem. Ber., (1986), 119, 3394-3404 and references therein). Compounds of formula (G), wherein Y is $CR^{12}R^{13}$ are known compounds of may be prepared by routes analogous to those described in the literature (see for example, M. Muehlebach et al., WO08/110,307; M. Muehlebach et al., WO08/110,308; S. Spessard and B. Stoltz, Organic Letters, (2002), Vol. 4, No. 11, 1943-1946; F. Effenberger et al., Chem. Ber., (1984), 117, 3280-3296; W. Childers et al., Tetrahedron Lett., (2006), 2217-2218; W. Childers et al., US2006/0004108; H. Schneider and C. Luethy, EP1352890; D. Jackson, A. Edmunds, M. Bowden and B. Brockbank, WO2005/105745 and WO2005/105717; R. Beaudegnies, C. Luethy, A. Edmunds, J. Schaetzer and S. Wendeborn, WO2005/123667; J-C. Beloeil, J-Y. Lallemand, T. Prange, Tetrahedron, (1986), Vol. 42. No. 13, 3491-3502; G. Stork and R. Danheiser, J. Org. Chem., (1973), 38 (9), 1775-1776; H. Favre et al., Can. J. Chem. (1956), 34 1329-39; R. Shriner and H. Todd, Org. Synth. Coll. Vol. II, (1943), 200-202).

A compound of formula (H) may be prepared from a compound of formula (I) by treatment with lead tetraacetate in a suitable solvent (for example chloroform) at 25° C. to 100° C. (preferably 25-50° C.), and optionally in the presence of a catalyst such as mercury diacetate, according to procedures described in the literature (for example see, K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1; (1990), 3, 715-720).

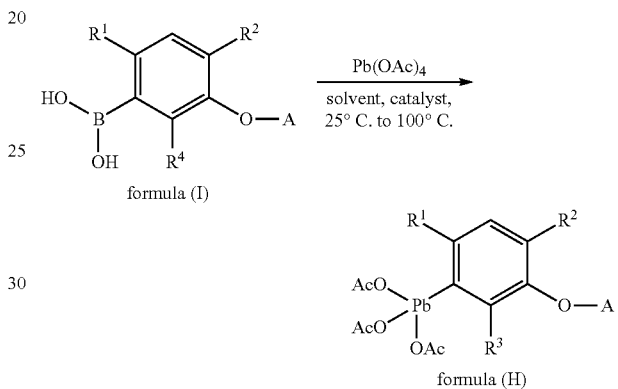

formula (I)

formula (H)

An aryl boronic acid of formula (I) may be prepared from an aryl halide of formula (J), wherein Hal is bromine or iodine by known methods (see, for example, W. Thompson and J. Gaudino, J. Org. Chem, (1984), 49, 5237-5243 and R. Hawkins et al., J. Am. Chem. Soc., (1960), 82, 3053-3059). Thus an aryl halide of formula (J) may be treated with an alkyl lithium or alkyl magnesium halide at low temperature, and the aryl magnesium or aryl lithium reagent obtained is allowed to react with a trialkyl borate, $B(OR'')_3$, preferably trimethylborate, to give an aryl dialkylboronate which may be hydrolysed to the desired boronic acid of formula (I) under acidic conditions. Alternatively the same overall transformation of compound (J) to compound (I) may be achieved through a palladium-catalysed borylation reaction under known conditions using known reagents (see for example T. Ishiyama, M. Murata, N. Miyaura, J. Org. Chem. (1995), 60, 7508-7501; and K. L. Billingsley, T. E. Barder, S. L. Buchwald, Angew. Chem. Int. Ed. (2007), 46, 5359-5363), followed by hydrolysis of the intermediate boronate ester.

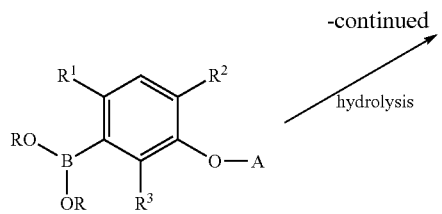

Aryl halides of formula (J) are known compounds or may be made by known methods from known compounds (See, for example, R. Clark, J. Agric. Food Chem., (1996), 44 (11), 3643-3652; T. Okamato and J. Bunnett, J. Am. Chem. Soc., (1956), 78, 5357-5362; H. Scarborough and J. Sweeten, J. Chem. Soc., (1934), 52-56).

In a further approach, a compound of formula (A) may be prepared by cross-coupling an aryl halide of formula (K), wherein Hal is bromine or iodine, with a phenol, A-OH, in the presence of a suitable catalyst, optionally a suitable ligand or additive, a suitable base and a suitable solvent, under conditions similar to those described, for example, by S. Hu et al., J. Org. Chem., (2008), 73, 7814-7817; P. Chan et al., Tetrahedron Lett., (2008), 49, 2018-2022); R. Hosseinzadeh et al., Synthetic Commun., (2008) 38, 3023-3031; S. Buchwald et al., J. Am. Chem. Soc., (2006), 128, 10694-10695; H. Rao et al., Chem. Eur. J., (2006), 12, 3636-3646; M. Taillefer et al., Adv. Synth. Catal. (2006), 348, 499-505; M. Beller et al., Tetrahedron Lett., (2005), 46 (18), 3237-3240; M. Taillefer et al., Org. Lett. (2004), 6 (6), 913; D. Ma and Q. Cai, Org. Lett. (2003), 5 (21), 3799-3802; J. Song et al., Org. Lett. (2002), 4 (9), 1623-1626; R. Venkataraman et al., Org. Lett. (2001), 3 (26), 4315-4317; S. Buchwald et al., J. Am. Chem. Soc. (1999), 121, 4369-4378; S. Buchwald et al., J. Am. Chem. Soc., (1997), 119, 10539-10540; G. Mann and J. Hartwig, Tetrahedron Lett., (1997), 38 (46), 8005-8008.

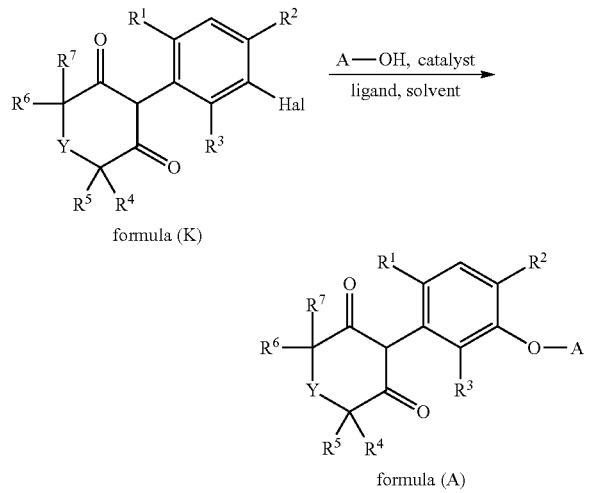

Suitable catalysts include palladium and copper catalysts such as palladium(II) acetate, bis(dibenzylideneacetone)palladium(II), copper powder, copper(II) acetate, copper(I) chloride, copper(I) bromide, copper(II) bromide, copper(I) iodide, copper(I) oxide, copper(II) sulfate, copper(I) trifluoromethanesulfonate and copper(II) trifluoromethanesulfonate. Optionally the catalysts are used in conjunction with appropriate ligands or additives, such as N-methylglycine N,N-dimethylglycine, 1-butylimidazole, ethyl acetate, ethylene glycol diacetate, 8-hydroxyquinoline, L-proline, 1-naphthoic acid, triphenylphosphine, 1,1'-bis(diphenylphosphino)ferrocene, salicylaldoxime, 2-(N,N-dimethylamino)-2'-di-tert-butylphosphinobiphenyl, neocuproine, pyrrolidine-2-phosphonic acid phenyl monoester, 2,2,6,6-tetramethylheptane-3,5-dione, tetrabutylammonium bromide, 2,2-bipyridine or 1,10-phenanthroline. Suitable bases are cesium carbonate, cesium fluoride, potassium fluoride, potassium phosphate and sodium hydroxide. Suitable solvents are acetonitrile, N,N-dimethylformamide, 1,4-dioxane or toluene, or mixed solvent systems such as toluene/tetrahydrofuran and 1,4-dioxane/water.

The use of copper(I) iodide and copper(II) trifluoromethanesulfonate catalysts is preferred.

A compound of formula (K) may be prepared according to procedures described by M. Muehlebach et al., WO08/071,405. For example, a compound of formula (K) may be prepared from a compound of formula (G) by reaction with a compound of formula (L) under conditions similar to those used for the preparation of a compound of formula (A) from a compound of formula (G).

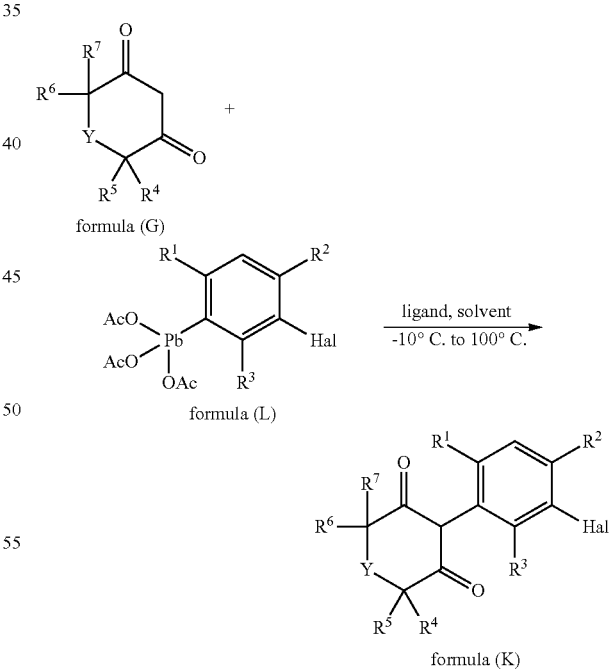

In a further approach, a compound of formula (A) may be prepared by reacting a compound of formula (M) with an aryl halide of formula A-Hal, wherein Hal represents fluorine, chlorine, bromine or iodine. When A-Hal is an aryl bromide or aryl iodide, the reaction may be effected using suitable copper or palladium catalysts under conditions described previously for the preparation of a compound of formula (A) from a compound of formula (K).

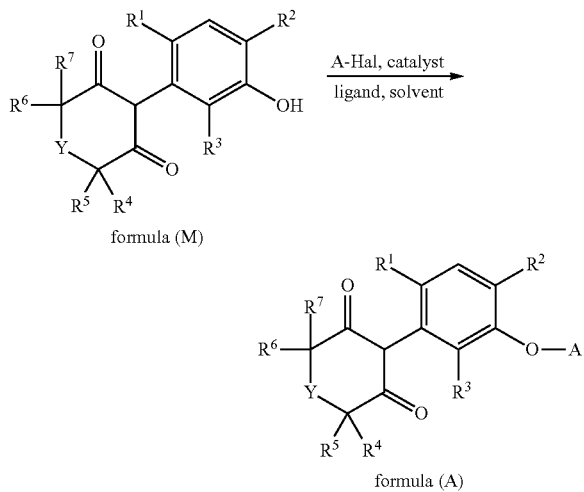

formula (M)

formula (A)

Alternatively, when A-Hal is a suitably electron-deficient aryl halide (for example an aryl fluororide or aryl chloride additionally bearing one or more electron-withdrawing substituents such as trifluoromethyl, nitro or cyano), or a suitable heteroaryl halide (for example a halopyridine, halopyrimidine, or other electron-deficient heteroaryl halide) the reaction may be effected in the presence of a suitable base such as potassium carbonate or cesium carbonate, without the need for a catalyst and a ligand.

A compound of formula (M) may be prepared from a compound of formula (K). In one approach, a compound of formula (K) is deprotonated with a base (such as a Grignard reagent or alkyllithium reagent), and then treated with an alkyllithium reagent to effect metal-halogen exchange. The resulting organometallic species may then be converted into a compound of formula (M) either by treatment with a trialkylborate such as trimethyl borate followed by oxidation (for example by hydrogen peroxide, N-methyl morpholine N-oxide or oxone) as described, for example by G. Prakash et al., J. Org. Chem., (2001), 66 (2), 633-634; J-P Gotteland and S Halazy, Synlett. (1995), 931-932; K. Webb and D. Levy, Tetrahedron Lett., (1995), 36 (29), 5117-5118. In an alternative approach, a compound of formula (M) may be prepared from a compound of formula (K) by treatment with an aqueous solution of an alkali metal hydroxide in the presence of a suitable catalyst and a suitable ligand, according to known procedures. For example, a compound of formula (M) may be prepared by treating a compound of formula (K) with potassium hydroxide in the presence of a palladium catalyst (for example bis(dibenzylidene-acetone)palladium(II), and in the presence of a suitable phosphine ligand such as 2-(di-tert-butylphosphino)-2',4',6'-triisopropylbiphenyl and 2-(di-tert-butylphosphino)-3,4,5,6-tetramethyl-2',4',6'-triisopropylbiphenyl, under conditions described, for example, by S. Buchwald et al., J. Am. Chem. Soc., (2006), 128, 10694-10695. Alternatively, a compound of formula (M) may be prepared by treating a compound of formula (K) treatment with an aqueous solution of sodium hydroxide in the presence of a suitable copper catalyst (for example copper(I) iodide) and a suitable ligand (such as L-proline), under conditions described, for example, by C. Kormos and N. Leadbeater, Tetrahedron (2006), 62 (19), 4728-4732.

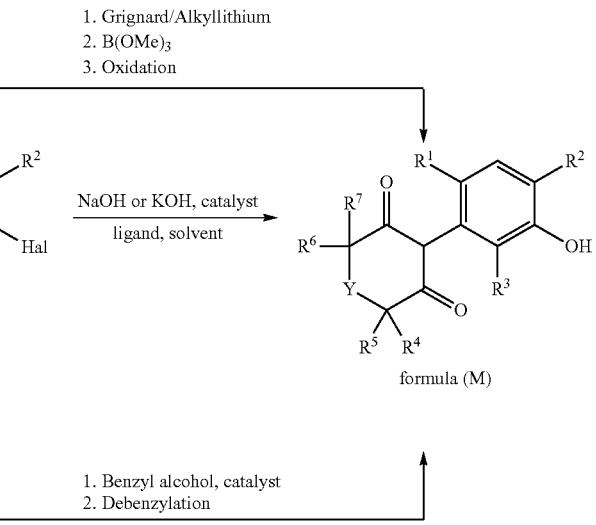

In a third approach to a compound of formula (M) a compound of formula (K) may be treated with a benzyl alcohol in the presence of a suitable copper catalyst, followed by debenzylation under known conditions (for example by catalytic hydrogenolysis).

The compounds of the formula (M) are novel and have been especially designed as intermediates for the synthesis of the compounds of formula I.

In an alternative approach, a compound of formula (A) may be prepared by the reaction of a compound of formula (N), wherein Ar is an aryl moiety (preferably phenyl) with an arylboronic acid of formula (I) in the presence of a suitable palladium catalyst, a suitable base, an optionally in the presence of a suitable ligand or additive, and in a suitable solvent.

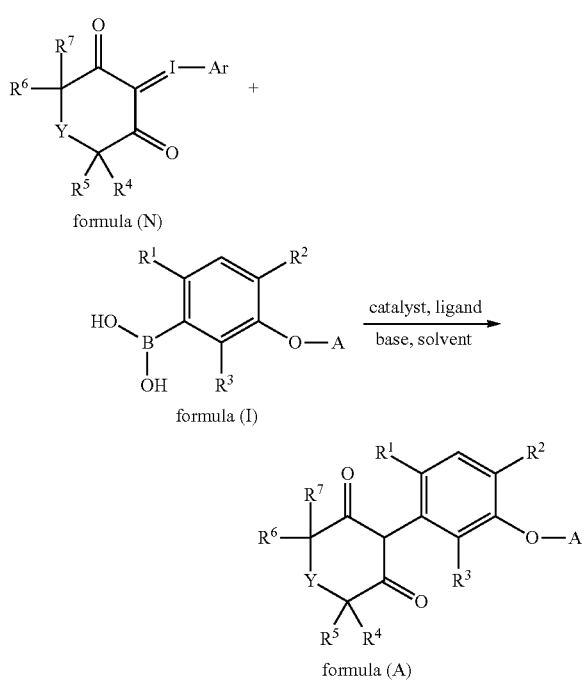

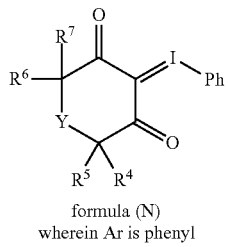

formula (N)
wherein Ar is phenyl

Suitable palladium catalysts include, for example palladium(II) dihalides, palladium(II) acetate and palladium(II) sulfate, and is preferably palladium(II) acetate. Suitable ligands include triphenylphosphine, tricyclopentylphosphine, tricyclohexylphosphine, 2-dicyclo-hexylphosphino-2',6'-dimethoxybiphenyl, 2-dicyclohexylphosphino-2',4',6'-triisopropyl-biphenyl, 1,1'-bis(diphenyl-phosphino)ferrocene and 1,2-bis(diphenylphosphino)ethane. The reaction may also be carried out in the presence of other additives, such as tetraalkylammonium salts, for example, tetrabutylammonium bromide. Suitable bases include alkali metal hydroxides, especially lithium hydroxide. A suitable solvent is aqueous 1,2-dimethoxyethane.

A compound of Formula (N), wherein Ar is phenyl, may be prepared from a compound of Formula (G) by treatment with a hypervalent iodine reagent such as a (diacetoxy)iodobenzene or iodosylbenzene and a base such as aqueous sodium carbonate, lithium hydroxide or sodium hydroxide in a solvent such as water or an aqueous alcohol such as aqueous ethanol according to the procedures of K. Schank and C. Lick, Synthesis (1983), 392; R. Moriarty et al, J. Am. Chem. Soc, (1985), 107, 1375, or of Z. Yang et al., Org. Lett., (2002), 4 (19), 3333:

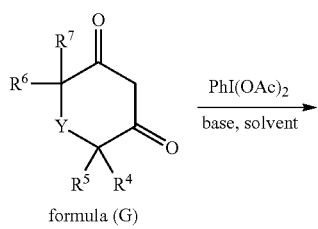

In a further approach, a compound of formula I may be prepared by reacting a compound of formula (O) (wherein G is preferably $C_{1-4}$ alkyl, and Hal is a halogen, preferably bromine or iodine), with an arylboronic acid of formula (I) in the presence of a suitable palladium catalyst (for example 0.001-50% palladium(II) acetate with respect to compound (O)) and a base (for example 1 to 10 equivalents potassium phosphate with respect to compound (O)) and preferably in the presence of a suitable ligand (for example 0.001-50% (2-dicyclohexylphosphino)-2',6'-dimethoxybiphenyl with respect to compound (U)), and in a suitable solvent (for example toluene), preferably between 25° C. and 200° C. Similar couplings are known in the literature (see for example, Y. Song, B. Kim and J.-N. Heo, Tetrahedron Letters (2005), 46 (36), 5987-5990).

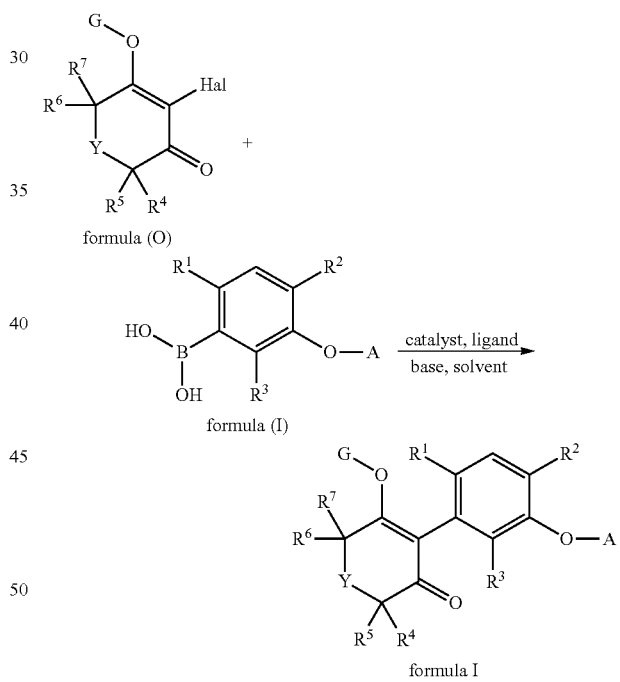

A compound of formula (O) may be prepared by halogenating a compound of formula (G), followed by reaction of the resulting halide of formula (O) with a $C_1$-$C_4$alkyl halide or tri-$C_1$-$C_4$-alkylorthoformate under known conditions, for example by the procedures of R. Shepherd and A. White (J. Chem. Soc. Perkin Trans. 1 (1987), 2153-2155) and Y.-L. Lin et al. (Bioorg. Med. Chem. (2002), 10, 685-690). Alternatively, a compound of formula (O) may be prepared by reacting a compound of formula (G) with a $C_1$-$C_4$alkyl halide or a tri-$C_1$-$C_4$-alkylorthoformate, and halogenating the resulting enone of formula (R) under known conditions (see for example Y. Song, B. Kim and J.-N. Heo, Tetrahedron Letters (2005), 46(36), 5987-5990).

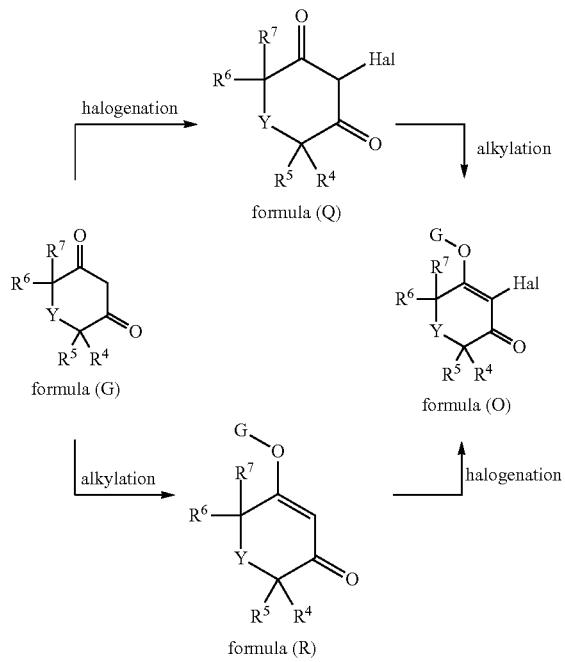

In a further approach, a compound of formula (A) may be prepared by reacting a compound of formula (G) with a compound of formula (J) in the presence of a suitable palladium catalyst (for example 0.001-50% palladium(II) acetate with respect to compound (G)) and a base (for example 1 to 10 equivalents potassium phosphate with respect to compound (G)) and preferably in the presence of a suitable ligand (for example 0.001-50% (2-dicyclohexylphosphino)-2',4',6'-triisopropylbiphenyl with respect to compound (G)), and in a suitable solvent (for example dioxane), preferably between 25° C. and 200° C. and optionally under microwave heating.

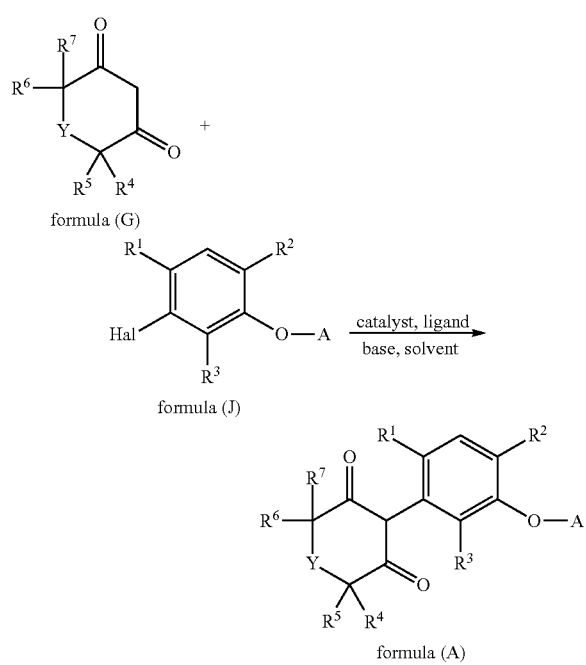

Similar couplings are known in the literature (see for example, S. Buchwald et al., J. Am. Chem. Soc. (2000), 122, 1360-1370; B. Hong et al. WO 2005/000233). Alternatively, a compound of formula (A) may be prepared by reacting a compound of formula (J) with a compound of formula (M) in the presence of a suitable copper catalyst (for example 0.001-50% copper(I) iodide with respect to compound (J)) and a base (for example 1 to 10 equivalents cesium carbonate with respect to compound (J)) and preferably in the presence of a suitable ligand (for example 0.001-50% L-proline with respect to compound (J)), and in a suitable solvent (for example dimethylsulfoxide), preferably between 25° C. and 200° C. Similar couplings are known in the literature (see for example, Y. Jiang et al., Synlett, (2005), 18, 2731-2734, and X. Xie et al., Organic Letters (2005), 7(21), 4693-4695).

The compounds of formula I according to the invention can be used as crop protection agents in unmodified form, as obtained in the synthesis, but they are generally formulated into crop protection compositions in a variety of ways using formulation adjuvants, such as carriers, solvents and surface-active substances. The formulations can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or microrods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means.

Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc.

Other suitable matrix materials for slow release formulations are starch, stearin, lignin.

The formulation adjuvants suitable for the preparation of the compositions according to the invention are known per se.

As liquid carriers there may be used: water, aromatic solvents such as toluene, m-xylene, o-xylene, p-xylene and mixtures thereof, cumene, aromatic hydrocarbon blends with boiling ranges between 140 and 320° C. known under various trademarks like Solvesso®, Shellsol A®, Caromax®, Hydrosol®, paraffinic and isoparaffinic carriers such as paraffin oils, mineral oils, dearomatized hydrocarbon solvents with boiling ranges between 50 and 320° C. known for instance under the trademark Exxsol®, non-dearomatized hydrocarbon solvents with boiling ranges between 100 and 320° C. known under the tradename Varsol®, isoparaffinic solvents with boiling ranges between 100 and 320° C. known under tradenames like Isopar® or Shellsol T®, hydrocarbons such as cyclohexane, tetrahydronaphthalene (tetralin), decahydronaphthalene, alpha-pinene, d-limonene, hexadecane, isooctane, ester solvents such as ethyl acetate, n/i-butyl acetate, amyl acetate, i-bornyl acetate, 2-ethylhexyl acetate, $C_6$-$C_{18}$ alkyl esters of acetic acid known under the tradename Exxate®, lactic acid ethylester, lactic acid propylester, lactic acid butylester, benzyl benzoate, benzyl lactate, dipropyleneglycol dibenzoate, dialkyl esters of succinic, maleic and fumaric acid and polar solvents like N-methylpyrrolidone, N-ethyl pyrrolidone, $C_3$-$C_{18}$-alkyl pyrrolidones, gamma-butyrolactone, dimethylsulfoxide, N,N-dimethyl-formamide, N,N-dimethylacetamide, N,N-dimethyllactamide, $C_4$-$C_{18}$ fatty acid dimethylamides, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, butylene carbonate, alcoholic solvents and diluents such as methanol, ethanol, propanol, n/iso-butanol, n/iso-pentanol, 2-ethyl hexanol, n-octanol, tetrahydrofurfuryl alkohol, 2-methyl-2,4-pentanediol, 4-hydroxy-4-methyl-2-pentanon, cyclohexanol, benzyl alcohol, ethylene glycol, ethylene glycol butyl ether, ethylene glycol methyl ether, diethylene glycol, diethylene glycol butyl ether, diethylene glycol ethyl ether, diethylene glycol methyl ether, propylene glycol, dipropylene glycol, dipropylene glycol methyl ether and other similar glycol ether solvents based on ethylene glycol, propylene glycol and butylene glycol feedstocks, triethylene glycol, polyethylene glycol (PEG 400), polypropylenglycols with molecular masses of 400-4000, glycerol, glycerol acetate, glycerol diacetate, glycerol triacetate, 1,4-dioxane, diethylene glycol abietate, chlorobenzene, chlorotoluene, fatty acid esters such as methyl octanoate, isopropyl myristate, methyl laurate, methyl oleate, mixture of $C_8$-$C_{10}$ fatty acid methyl esters, rape seed oil methyl and ethyl esters, soy bean oil methyl and ethyl esters, vegetable oils, fatty acids such as oleic acid, linoleic acid, linolenic acid, esters of phosphoric and phosphonic acid such as triethyl phosphate, $C_3$-$C_{18}$-tris-alkyl phosphates, alkylaryl phosphates, bis-octyl-octyl phosphonates.

Water is generally the carrier of choice for the dilution of the concentrates.

Suitable solid carriers are, for example, talc, titanium dioxide, pyrophyllite clay, silica (fumed or precipitated silica and optionally functionalised or treated, for instance silanised), attapulgite clay, kieselguhr, limestone, calcium carbonate, bentonite, calcium montmorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations, especially in those formulations which can be diluted with a carrier prior to use. Surface-active substances may be anionic, cationic, amphoteric, non-ionic or polymeric and they may be used as emulsifying, wetting, dispersing or suspending agents or for other purposes. Typical surface-active substances include, for example, salts of alkyl sulfates, such as diethanolammonium lauryl sulfate; Sodium lauryl sulfate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, antifoams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, compatibility agents and solubilisers and also liquid and solid fertilisers.

The formulations may also comprise additional active substances, for example further herbicides, herbicide safeners, plant growth regulators, fungicides or insecticides.

The compositions according to the invention can additionally include an additive (commonly referred to as an adjuvant), comprising a mineral oil, an oil of vegetable or animal origin, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsifiable vegetable oil, such as AMIGO® (Loveland Products Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is AGNIQUE ME 18 RD-F® (Cognis). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic, cationic or amphoteric surfactants. Examples of suitable anionic, non-ionic, cationic or amphoteric surfactants are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total additive is generally from 1 to 50% by weight. Examples of oil additives that consist of mixtures of oils or mineral oils or derivatives thereof with surfactants are TURBOCHARGE®, ADIGOR® (both (Syngenta Crop Protection AG), ACTIPRON® (BP Oil UK Limited), AGRI-DEX® (Helena Chemical Company).

The said surface-active substances may also be used in the formulations alone, that is to say without oil additives.

Furthermore, the addition of an organic solvent to the oil additive/surfactant mixture can contribute to a further enhancement of action. Suitable solvents are, for example, SOLVESSO® and AROMATIC® solvents (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF). Further oil additives that are preferred according to the invention are SCORE® and ADIGOR® (both Syngenta Crop Protection AG).

In addition to the oil additives listed above, in order to enhance the activity of the compositions according to the invention it is also possible for formulations of alkylpyrrolidones, (e.g. AGRIMAX® from ISP) to be added to the spray mixture. Formulations of synthetic lattices, such as, for example, polyacrylamide, polyvinyl compounds or poly-1-p-menthene (e.g. BOND®, COURIER® or EMERALD®) can also be used.

Such adjuvant oils as described in the preceding paragraphs may be employed as the carrier liquid in which an active compound is dissolved, emulsified or dispersed as appropriate to the physical form of the active compound.

The pesticidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1-2000 g/ha, preferably 1-1000 g/ha and most preferably at 1-500 g/ha.

Preferred formulations have especially the following representative compositions: (%=percent by weight):
Emulsifiable Concentrates:
active ingredient: 1 to 95%, preferably 60 to 90%
surface-active agents: 1 to 30%, preferably 5 to 20%
solvents as liquid carrier: 1 to 80%, preferably 1 to 35%
Dusts:
active ingredient: 0.1 to 10%, preferably 0.1 to 5%
solid carriers: 99.9 to 90%, preferably 99.9 to 99%
Suspension Concentrates:
active ingredient: 5 to 75%, preferably 10 to 50%
water: 94 to 24%, preferably 88 to 30%
surface-active agents: 1 to 40%, preferably 2 to 30%
Wettable Powders:
active ingredient: 0.5 to 90%, preferably 1 to 80%
surface-active agents: 0.5 to 20%, preferably 1 to 15
solid carriers: 5 to 95%, preferably 15 to 90%
Granules:
active ingredient: 0.1 to 30%, preferably 0.1 to 15%
solid carriers: 99.5 to 70%, preferably 97 to 85%
Waterdispersible Granules:
active ingredient: 1 to 90%, preferably 10 to 80%
surface-active agents: 0.5 to 80%, preferably 5 to 30%
solid carriers: 90 to 10%, preferably 70 to 30%

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | 10% | — | 20% |
| arom. hydrocarbon mixture $C_9$-$C_{12}$ | 85% | 68% | 65% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | 40% | 50% | — | |

-continued

| F2. Solutions | a) | b) | c) | d) |
|---|---|---|---|---|
| polyethylene glycol MW 400 | 20% | 10% | — | — |
| NMP | — | — | 50% | 10% |
| arom. hydrocarbon mixture $C_9$-$C_{12}$ | 35% | 30% | — | — |

The solutions are suitable for application undiluted or after dilution with water.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly dispersed silica | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruded granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Water-dispersible granules | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | |
| Sodium sulfate | | 4% | 5% | |
| kaolin | 48% | 30% | 30% | |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-Benzisothiazolin-3-on | 0.1% | 0.1% | 0.1% | 0.1% |
| silicone oil emulsion | 0.7% | 0.7% | 0.7% | 0.7% |
| water | 87% | 79% | 62% | 38% |

The finely ground active ingredient is intimately mixed with the adjuvants, yielding a suspension concentrate from which suspensions of any desired concentration can be prepared by dilution with water.

Crops of useful plants in which the compositions according to the invention can be used include especially cereals, in particular wheat and barley, rice, corn, rape, sugarbeet, sugarcane, soybean, cotton, sunflower, peanut and plantation crops.

The term "crops" is to be understood as also including crops that have been rendered tolerant to herbicides or classes of herbicides (for example ALS, GS, EPSPS, PPO and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*. Control of monocotyledonous weeds, in particular *Agrostis, Avena, Setaria, Lolium, Echinochloa, Bromus, Alopecurus* and *Sorghum* is very extensive.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with further herbicides. Preferably, in these mixtures, the compound of the formula I is one of those compounds listed in Tables 1 to 57 below. The following mixtures of the compound of formula I are especially important:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chloroflurenol, compound of formula I+chloroflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorothal, compound of formula I+chlorothal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydime, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichloroprop, compound of formula I+dichloroprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fenoxasulfone (CAS RN 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+fluorenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS RN 212201-70-2), compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlore, compound of formula I+metazosulfuron (NC-620, CAS RN 868680-84-6), compound of formula I+methabenzthiazuron, compound of formula I+methylarsonic acid, compound of formula I+methyldymron, compound of formula I+methyl isothiocyanate, compound of formula I+metobenzuron, compound of formula I+metolachlore, compound of formula I+S-metolachlore, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS RN 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumetone, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS RN 335104-84-2), compound of formula I+topramezone (CAS RN 210631-68-8), compound of formula I+4-hydroxy-3-[[4[(2-methoxyethoxy)methyl]-6-(trifluoromethyl)-3-pyridinyl]carbonyl]-bicyclo[3.2.1]oct-3-en-2-one (CAS RN 352010-68-5), and compound of formula I+4-hydroxy-3-[[2-(3-methoxypropyl)-6-(difluoromethyl)-3-pyridinyl]carbonyl]-bicyclo[3.2.1]oct-3-en-2-one.

The mixing partners for the compound of formula I may also be in the form of esters or salts, as mentioned e.g. in The Pesticide Manual, 12th Edition (BCPC) 2000.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+dicamba, compound of formula I+dichlobenil, compound of formula I+dichloroprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+fluorochloridone, compound of formula I+fluoroxypyr, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIN-485), compound of formula I+pyroxsulam compound of formula I+sulfosulfuron, compound of formula I+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+tri-allate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, where the mixtures comprising a compound of formula (I)+amidosulfuron, compound of formula (I)+aminopyralid, compound of formula (I)+beflubutamid, compound of formula (I)+bromoxynil, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, 2,4-D, compound of formula (I)+dicamba, compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluoroxypyr, compound of formula (I)+flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIN-485), compound of formula (I)+pyroxsulam, compound of formula (I)+sulfosulfuron, compound of formula (I)+thifensulfuron, compound of formula (I)+thifensulfuron-methyl, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl and compound of formula (I)+tritosulfuron are particularly preferred.

For applications in rice, the following mixtures are preferred: compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+butachlor, compound of formula (I)+cafenstrole, compound of formula (I)+cinosulfuron, compound of formula (I)+clomazone, compound of formula (I)+clomeprop, compound of formula (I)+cyclosulfamuron, compound of formula (I)+cyhalofop, compound of formula (I)+cyhalofop-butyl, compound of formula (I)+2,4-D, compound of formula (I)+daimuron, compound of formula (I)+dicamba, compound of formula (I)+diquat, compound of formula (I)+diquat dibromide, compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS RN 639826-16-7), compound of formula (I)+fentrazamide, compound of formula (I)+florasulam, compound of formula (I)+glufosinate-ammonium, compound of formula (I)+glyphosate, compound of formula (I)+halosulfuron, compound of formula (I)+halosulfuron-methyl, compound of formula (I)+imazosulfuron, compound of formula I+ipfencarbazone (CAS RN 212201-70-2), compound of formula (I)+MCPA, compound of formula (I)+mefenacet, compound of formula (I)+mesotrione, compound of formula (I)+metamifop, compound of formula I+metazosulfuron (NC-620, CAS RN 868680-84-6), compound of formula (I)+metsulfuron, compound of formula (I)+metsulfuron-methyl, compound of formula (I)+n-methyl glyphosate, compound of formula (I)+orthosulfamuron, compound of formula (I)+oryzalin, compound of formula (I)+oxadiargyl, compound of formula (I)+oxadiazon, compound of formula (I)+paraquat dichloride, compound of formula (I)+pendimethalin, compound of formula (I)+penoxsulam, compound of formula (I)+pretilachlor, compound of formula (I)+profoxydim, compound of formula (I)+propanil, compound of formula I+propyrisulfuron (TH-547, CAS RN 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, where the mixtures comprising a compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+clomazone, compound of formula (I)+clomeprop, compound of formula (I)+cyhalofop, compound of formula (I)+cyhalofop-butyl, compound of formula (I)+2,4-D, compound of formula (I)+daimuron, compound of formula (I)+dicamba, compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS RN 639826-16-7), compound of formula (I)+fentrazamide, compound of formula (I)+florasulam, compound of formula (I)+halosulfuron, compound of formula (I)+halosulfuron-methyl, compound of formula (I)+imazosulfuron, compound of formula I+ipfencarbazone (CAS RN 212201-70-2), compound of formula (I)+MCPA, compound of formula (I)+mefenacet, compound of formula (I)+mesotrione, compound of formula I+metazosulfuron (NC-620, CAS RN 868680-84-6), compound of formula (I)+metsulfuron, compound of formula (I)+metsulfuron-methyl, compound of formula (I)+orthosulfamuron, compound of formula (I)+oxadiargyl, compound of formula (I)+oxadiazon, compound of formula (I)+pendimethalin, compound of formula (I)+penoxsulam, compound of formula (I)+pretilachlor, compound of formula I+propyrisulfuron (TH-547, CAS RN 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl are particularly preferred.

The compounds of formula I according to the invention can also be used in combination with safeners. Preferably, in these mixtures, the compound of the formula I is one of those compounds listed in Tables 1 to 57 below. The following mixtures with safeners, especially, come into consideration: compound of formula I+cloquintocet-mexyl, compound of formula I+cloquintocet acid and salts thereof, compound of formula I+fenchlorazole-ethyl, compound of formula I+fenchlorazole acid and salts thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292. A safening effect can also be observed for the mixtures compound of the formula I+dymron, compound of the formula I+MCPA, compound of the formula I+mecopropand compound of the formula I+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484. Benoxacor, cloquintocet-mexyl, cyprosulfamide, mefenpyr-diethyl and N-(2-methoxybenzoyl)-4-[(methylaminocarbonyl)amino]benzenesulfonamide are especially preferred, where cloquintocet-mexyl is particularly valuable.

The rate of application of safener relative to the herbicide is largely dependent upon the mode of application. In the case of field treatment, generally from 0.001 to 5.0 kg of safener/ha, preferably from 0.001 to 0.5 kg of safener/ha, and generally from 0.001 to 2 kg of herbicide/ha, but preferably from 0.005 to 1 kg/ha, are applied.

The herbicidal compositions according to the invention are suitable for all methods of application customary in agriculture, such as, for example, pre-emergence application, post-emergence application and seed dressing. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field treatment, generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

It is preferred to apply the other herbicide together with one of the safeners mentioned above.

The following Examples illustrate the invention further but do not limit the invention.

PREPARATION EXAMPLES

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table T1 are drawn as an arbitrary single enol tautomer, but it should be inferred that this description covers both the diketone form and any possible enols which could arise through tautomerism. Where more than one tautomer is observed in proton NMR, the data shown are for the mixture of tautomers. Furthermore, some of the compounds shown below are drawn as single enantiomers for the purposes of simplicity, but unless specified as single enantiomers, these structures should be construed as representing a mixture of enantiomers. Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer is the enol form.

Example 1

Preparation of 2-[5-(4-chloro-2-fluorophenoxy)-2-ethylphenyl]cyclohexane-1,3-dione

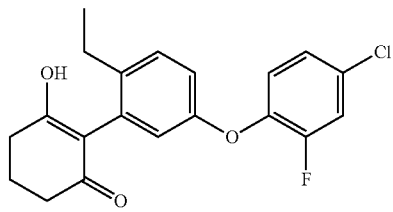 [SMILES: CCc1ccc(Oc2ccc(Cl)cc2F)cc1C1=C(O)CCCC1=O]

Step 1: Preparation of 2-(5-bromo-2-ethylphenyl)cyclohexane-1,3-dione

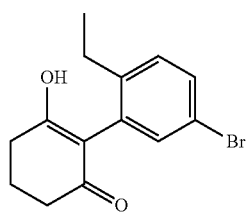 [SMILES: CCc1ccc(Br)cc1C1=C(O)CCCC1=O]

To a solution of 5-bromo-2-ethylphenyllead triacetate (20.00 g, 35.2 mmol) (described in WO08/071,405) in chloroform (100 ml) is added cyclohexane-1,3-dione (3.94 g, 35.2 mmol) and 4-dimethylaminopyridine (22.36 g, 176 mmol). After stirring the reaction at room temperature for 5 minutes toluene (50 ml) is added and the solution is heated at 80° C. for 4 hours. After cooling to room temperature the mixture is allowed to stand overnight, followed by treatment with 2M aqueous hydrochloric acid. Following filtration of the precipitate the biphasic solution is separated, and the aqueous phase is extracted again with dichloromethane (×2). Organic fractions are combined then evaporated under reduced pressure to yield a crude product which is purified by flash column chromatography (10% ethyl acetate/hexane to 70% ethyl acetate/hexane eluant) to afford 2-(5-bromo-2-ethylphenyl)cyclohexane-1,3-dione as a white solid.

Step 2: Preparation of 2-(2-ethyl-5-iodophenyl)cyclohexane-1,3-dione

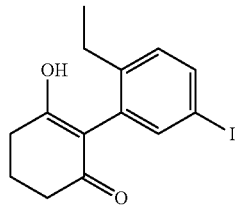 [SMILES: CCc1ccc(I)cc1C1=C(O)CCCC1=O]

To a mixture of 2-(5-bromo-2-ethylphenyl)cyclohexane-1,3-dione (0.917 g, 3.11 mmol), sodium iodide (0.934 g, 6.23 mmol) and hexamethyldisilazane (0.454 g, 3.11 mmol) is added copper (I) iodide (0.030 g, 0.15 mmol) and trans-N,N-dimethyl-1,2-cyclohexane diamine (0.044 g, 0.31 mmol). Degassed dioxane (5 ml) is added and the mixture is purged with nitrogen then heated at 180° C. for 1 hour under microwave irradiation. After cooling to room temperature the reaction mixture is treated with 2M aqueous hydrochloric acid and extracted with dichloromethane. The phases are separated and the aqueous phase is further extracted with dichloromethane. Organic fractions are combined then evaporated under reduced pressure to yield a crude product which is purified by flash column chromatography (10% ethyl acetate/hexane to 70% ethyl acetate/hexane eluant) to afford 2-(2-ethyl-5-iodophenyl)cyclohexane-1,3-dione as a white foam.

Step 3: Preparation of 2-[5-(4-chloro-2-fluorophenoxy)-2-ethylphenyl]cyclohexane-1,3-dione

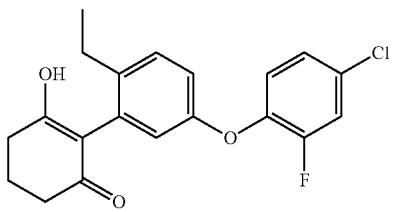 [SMILES: CCc1ccc(Oc2ccc(Cl)cc2F)cc1C1=C(O)CCCC1=O]

To a mixture of 2-(2-ethyl-5-iodophenyl)cyclohexane-1,3-dione (0.250 g, 0.73 mmol), 4-chloro-2-fluorophenol (0.535 g, 3.65 mmol) and cesium carbonate (0.477 g, 1.46 mmol) is added powdered 3 Å molecular sieves (0.300 g) and copper (II) trifluoromethanesulfonate (0.012 g, 0.037 mmol). After degassing with nitrogen anhydrous toluene (4 ml) is added, and the suspension is heated at 160° C. for 1 hour under microwave irradiation. The reaction mixture is acidified with 2M aqueous hydrochloric acid and extracted with dichloromethane (×2). The organic phase is separated then evaporated under reduced pressure to yield a crude product which is purified by preparative reverse-phase HPLC to afford 2-[5-(4-chloro-2-fluoro-phenoxy)-2-ethylphenyl]cyclohexane-1,3-dione.

Example 2

Preparation of 2-[5-(4-chloro-3-fluorophenoxy)-2-ethylphenyl]-5,5-dimethylcyclohexane-1,3-dione

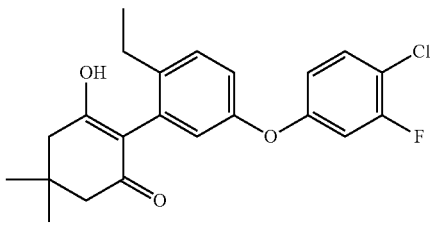 [SMILES: CCc1ccc(Oc2ccc(Cl)c(F)c2)cc1C1=C(O)CC(C)(C)CC1=O]

To a mixture of 2-(5-bromo-2-ethylphenyl)-5,5-dimethylcyclohexane-1,3-dione (0.236 g, 0.73 mmol), cesium carbonate (0.477 g, 1.46 mmol), 4-chloro-3-fluorophenol (0.535 g, 3.65 mmol), copper (II) trifluoromethanesulfonate (0.012 g, 0.04 mmol) and powdered 3 Å molecular sieves (0.300 g) is added anhydrous toluene (4 ml). After purging with nitrogen the reaction mixture is heated at 170° C. for 1 hour under microwave irradiation, then allowed to cool to room temperature. After quenching with 2M aqueous hydrochloric acid the crude product is extracted into dichloromethane (×2) and the phases are separated. Organic solvents are removed in vacuo and the crude product is purified by preparative reverse-phase HPLC to afford 2-[5-(4-chloro-3-fluorophenoxy)-2-ethylphenyl]-5,5-dimethylcyclohexane-1,3-dione as a white solid.

Example 3

Preparation of meso-(1R,5S)-3-[5-(4-chlorophenoxy)-2-ethylphenyl]bicyclo[3.2.1]octane-2,4-dione

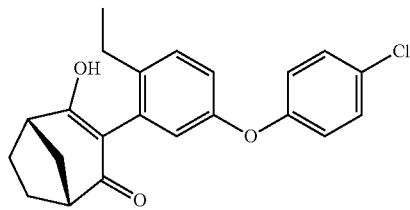 [SMILES: CCc1ccc(Oc2ccc(Cl)cc2)cc1C1=C(O)[C@H]2CC[C@H](C2)C1=O]

Step 1: Preparation of 3-(5-bromo-2-ethylphenyl)bicyclo[3.2.1]octane-2,4-dione

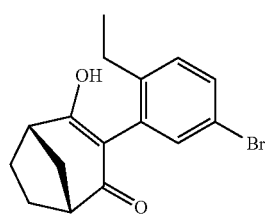 [SMILES: CCc1ccc(Br)cc1C1=C(O)[C@H]2CC[C@H](C2)C1=O]

To a solution of 5-bromo-2-ethylphenyllead triacetate (16.34 g, 28.80 mmol) in chloroform (160 ml) is added bicyclo[3.2.1]octane-2,4-dione (3.61 g, 26.10 mmol) and 4-dimethylaminopyridine (16.63 g, 131 mmol), and the reaction mixture is stirred at room temperature for 5 minutes. Next toluene (40 ml) is added, and the mixture is stirred at 80° C. for 1 hour (pre-heated oil bath). The reaction mixture is allowed to cool to room temperature, quenched with 1M hydrochloric acid, and the organic phase separated. The aqueous phase is further washed with dichloromethane (×2), and again the phases are separated. All organics are combined then evaporated under reduced pressure to give a crude oil, which is purified by flash column chromatography on silica gel (30% to 50% ethyl acetate/iso-hexane eluant ratio, then 10% methanol/dichloromethane eluant ratio). The resulting gum is then recrystalised from dichloromethane/hexane to afford 3-(5-bromo-2-ethylphenyl)bicyclo[3.2.1]octane-2,4-dione as a cream coloured solid.

Step 2: Preparation of meso-(1R,5S)-3-[5-(4-chlorophenoxy)-2-ethylphenyl]bicyclo[3.2.1]octane-2,4-dione

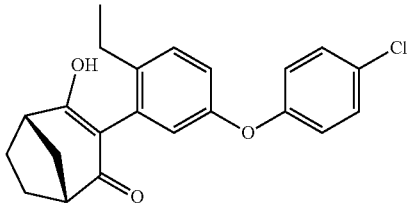 [SMILES: CCc1ccc(Oc2ccc(Cl)cc2)cc1C1=C(O)[C@H]2CC[C@H](C2)C1=O]

To a mixture of 3-(5-bromo-2-ethylphenyl)bicyclo[3.2.1]octane-2,4-dione (0.200 g, 0.62 mmol), caesium carbonate (0.406 g, 1.25 mmol) and 4-chlorophenol (0.400 g, 3.12 mmol) is added copper (II) trifluoromethanesulfonate (0.011 g, 0.03 mmol) and powdered 3 Å molecular sieves (0.300 g). Degassed anhydrous toluene (2 ml) is then added followed by purging with nitrogen then heating at 170° C. for 1 hour under microwave irradiation. After cooling to room temperature the mixture is acidified with 2M aqueous hydrochloric acid and extracted with dichloromethane (×2). The organic phase is separated then concentrated under vacuum. The crude product is then purified by preparative reverse phase HPLC and additionally flash column chromatography (10% ethyl acetate/hexane to 70% ethyl acetate/hexane eluant) to afford meso-(1R,5S)-3-[5-(4-chlorophenoxy)-2-ethylphenyl]bicyclo[3.2.1]octane-2,4-dione as a white solid.

Example 4

Preparation of rac-(1S,5R)-3-[5-(2,4-dichlorophenoxy)-2-ethylphenyl]-1,8,8-trimethylbicyclo[3.2.1]octane-2,4-dione

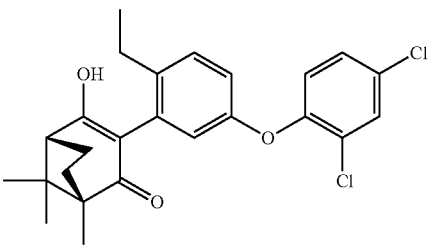 [SMILES: CCc1ccc(Oc2ccc(Cl)cc2Cl)cc1C1=C(O)[C@@H]2CC[C@](C)(C1=O)C2(C)C]

Step 1: Preparation of rac-3-(5-bromo-2-ethylphenyl)-1,8,8-trimethylbicyclo[3.2.1]octane-2,4-dione

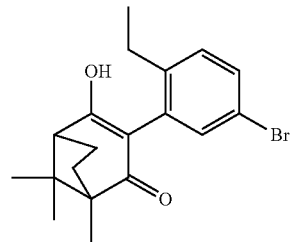 [SMILES: CCc1ccc(Br)cc1C1=C(O)C2CCC(C)(C1=O)C2(C)C]

A solution of 1,8,8-trimethylbicyclo[3.2.1]octane-2,4-dione (0.22 g, 1.22 mmol) (preparation described by H. Favre et al., Can. J. Chem. (1956), 34 1329-39.) in dry chloroform (10 ml) is stirred at room temperature then thoroughly flushed with nitrogen. To this mixture is then added 4-dimethylaminopyridine (0.744 g, 6.15 mmol) and anhydrous toluene (3 ml), followed by heating to 80° C. 5-Bromo-2-ethylphenyl-lead triacetate (0.673 g, 1.18 mmol) is added portionwise over 10 minutes, and the mixture is further heated at this temperature for a further 4 hours then left to stand overnight. 2M hydrochloric acid (10 ml) is added, and the resulting biphasic mixture is filtered to remove any inorganic salts (washing with additional dichloromethane, 10 ml). The organic phase separated, and the aqueous phase is extracted again with dichloromethane (10 ml×2). All organic fractions are combined, dried over magnesium sulfate, filtered and the filtrate concentrated under reduced pressure to give an orange gum. This crude product is purified by flash column chromatography on silica gel (100% to 40% hexane/ethyl acetate eluant ratio) to afford rac-3-(5-bromo-2-ethylphenyl)-1,8,8-trimethylbicyclo[3.2.1]octane-2,4-dione as a colourless gum.

Step 2: Preparation of rac-(1S,5R)-3-[5-(2,4-dichlorophenoxy)-2-ethylphenyl]-1,8,8-trimethylbicyclo[3.2.1]octane-2,4-dione

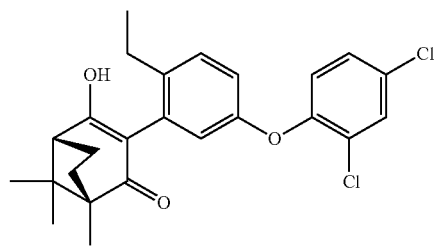 [SMILES: CCc1ccc(Oc2ccc(Cl)cc2Cl)cc1C1=C(O)[C@@H]2CC[C@](C)(C1=O)C2(C)C]

To a mixture of rac-3-(5-bromo-2-ethylphenyl)-1,8,8-trimethylbicyclo[3.2.1]octane-2,4-dione (0.175 g, 0.48 mmol), cesium carbonate (0.314 g, 0.96 mmol) and 2,4-dichlorophenol (0.393 g, 2.41 mmol) is added copper (II) trifluoromethanesulfonate (0.009 g, 0.024 mmol) and powdered 3 Å molecular sieves (0.200 g). Degassed anhydrous toluene (2 ml) is then added, followed by purging with nitrogen and heating at 170° C. for 1 hour under microwave irradiation. After cooling to room temperature the reaction mixture is quenched with 2M aqueous hydrochloric acid and extracted with dichloromethane (×2). The organic phase is separated and concentrated under reduced pressure. The crude product is then purified by preparative reverse phase HPLC to afford rac-(1S,5R)-3-[5-(2,4-dichlorophenoxy)-2-ethylphenyl]-1,8,8-trimethylbicyclo[3.2.1]octane-2,4-dione.

Example 5

Preparation of 4-[2-ethyl-5-(3-fluorophenoxy)phenyl]-2,2,6,6-tetramethylpyran-3,5-dione

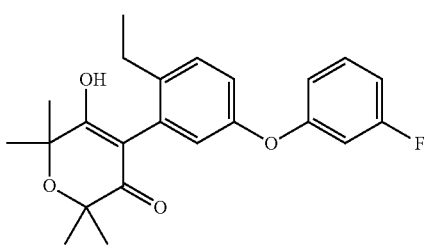 [SMILES: CCc1ccc(Oc2cccc(F)c2)cc1C1=C(O)C(C)(C)OC(C)(C)C1=O]

A mixture of 4-(5-bromo-2-ethylphenyl)-2,2,6,6-tetramethylpyran-3,5-dione (200 mg, 0.57 mmol), 3-fluorophenol (320 mg, 2.83 mmol), cesium carbonate (400 mg, 1.13 mmol), copper(II) trifluoromethanesulfonate (10 mg, 0.03 mmol), and powdered 3 Å molecular sieves (400 mg) in toluene (3.5 ml) is heated to 160° C. under microwave irradiation for 60 minutes. The mixture is cooled to room temperature, poured into 2M aqueous hydrochloric acid, diluted with dichloromethane and filtered through a phase separation cartridge. The organic phase is collected. The solvent is evaporated under reduced pressure and the residue is purified by column chromatography on silica gel to give 4-[2-ethyl-5-(3-fluorophenoxy)phenyl]-2,2,6,6-tetramethylpyran-3,5-dione.

Example 6

Preparation of 4-[5-(4-chlorophenoxy)-2-ethylphenyl]-2,2,6,6-tetramethylpyran-3,5-dione

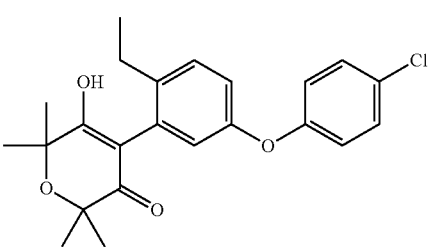 [SMILES: CCc1ccc(Oc2ccc(Cl)cc2)cc1C1=C(O)C(C)(C)OC(C)(C)C1=O]

A mixture of 4-(5-bromo-2-ethylphenyl)-2,2,6,6-tetramethylpyran-3,5-dione (200 mg, 0.57 mmol), 4-chlorophenol (110 mg, 0.86 mmol), copper(I) iodide (109 mg, 0.57 mmol), 1,10-phenanthroline (103 mg, 0.57 mmol) and potassium phosphate (483 mg, 2.28 mmol), in dimethylsulfoxide (3.5 ml) is heated to 200° C. under microwave irradiation for 30 minutes. The mixture is cooled to room temperature, poured into 2M aqueous hydrochloric acid and extracted with dichloromethane. The organic extract is washed with water, dried over anhydrous magnesium sulfate, filtered and the filtrate is evaporated under reduced pressure. The solvent is evaporated under reduced pressure and the residue is purified by column chromatography on silica gel to give 4-[5-(4-chlorophenoxy)-2-ethylphenyl]-2,2,6,6-tetramethylpyran-3,5-dione.

Example 7

Preparation of 4-[5-(3-chloro-4-nitrophenoxy)-2-ethylphenyl]-2,2,6,6-tetramethylpyran-3,5-dione

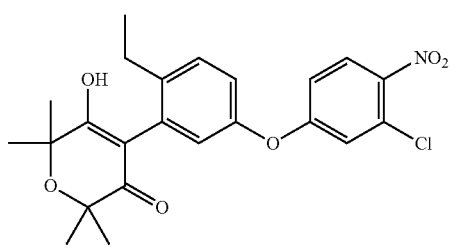 [SMILES: CCc1ccc(Oc2ccc([N+](=O)[O-])c(Cl)c2)cc1C1=C(O)C(C)(C)OC(C)(C)C1=O]

Step 1: Preparation of 4-(2-ethyl-5-hydroxyphenyl)-2,2,6,6-tetramethylpyran-3,5-dione

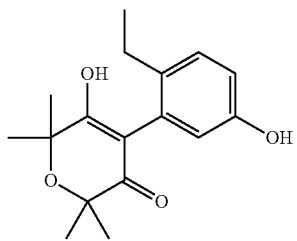 [SMILES: CCc1ccc(O)cc1C1=C(O)C(C)(C)OC(C)(C)C1=O]

A solution of isopropylmagnesium chloride in dry tetrahydrofuran (10.6 ml of a 2 M solution, 21.2 mmol) is added dropwise to a solution of 4-(5-bromo-2-ethylphenyl)-2,2,6,6-tetramethylpyran-3,5-dione (5.0 g, 14.2 mmol) in tetrahydrofuran (60 ml) at 0° C., and once the addition is complete the mixture is stirred for ten minutes, then allowed to warm and stirred for 70 minutes at room temperature. The mixture is then cooled to −78° C. and a solution of n-butyllithium in hexanes (53 ml of a 1.6 M solution, 85.0 mmol) is added dropwise over 20 minutes. The mixture is stirred at −78° C. for 10 minutes, and then the solution is allowed to warm and stirred for 1 hour and 50 minutes at room temperature.

The mixture obtained is added via cannular to a solution of trimethylborate (31.6 ml, 283 mmol) in dry tetrahydrofuran (30 ml) at −78° C., and the mixture stirred for 20 minutes, then allowed to warm to room temperature. A further quantity of dry tetrahydrofuran (20 ml) is added to aid stirring, and the mixture is stirred at room temperature for a further 1 hour and 30 minutes.

The mixture is cooled to 0° C. and a 30% hydrogen peroxide solution (16 ml, 142 mmol) is added cautiously. The mixture stirred for 10 minutes at 0° C., then allowed to warm to room temperature and stirred at for 18 hours.

The mixture is partitioned between dichloromethane and dilute aqueous hydrochloric acid. The aqueous is extracted with dichloromethane and the organic extracts are combined, washed with brine, dried over anhydrous magnesium sulfate, filtered and the filtrate is concentrated under reduced pressure. The residue is purified by column chromatography on silica gel to give 4-(2-ethyl-5-hydroxyphenyl)-2,2,6,6-tetramethylpyran-3,5-dione.

Step 2: Preparation of 4-[5-(3-chloro-4-nitrophenoxy)-2-ethylphenyl]-2,2,6,6-tetramethylpyran-3,5-dione

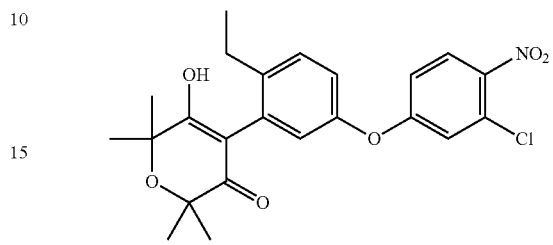

A mixture of 4-(2-ethyl-5-hydroxyphenyl)-2,2,6,6-tetramethylpyran-3,5-dione (100 mg, 0.34 mmol), 2-chloro-4-fluoro-1-nitrobenzene (72 mg, 0.41 mmol), and potassium carbonate (110 mg, 0.69 mmol) in N,N-dimethylformamide (2 ml) is heated to 140° C. under microwave irradiation for 40 minutes. The mixture is cooled to room temperature, poured into 2M aqueous hydrochloric acid and extracted with ethyl acetate. The organic extract is washed with brine, dried over anhydrous magnesium sulfate, filtered and the filtrate is evaporated under reduced pressure. The residue is purified by column chromatography on silica gel to give 4-[5-(3-chloro-4-nitrophenoxy)-2-ethylphenyl]-2,2,6,6-tetramethylpyran-3,5-dione.

Example 8

Preparation of 4-[2-ethyl-5-(6-trifluoromethylpyridin-2-yloxy)phenyl]-2,2,6,6-tetramethylpyran-3,5-dione

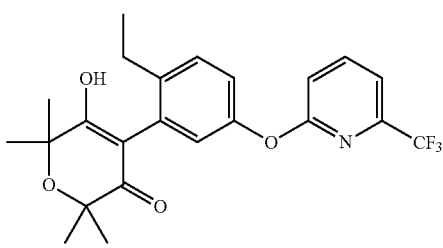 [SMILES: CCc1ccc(Oc2cccc(C(F)(F)F)n2)cc1C1=C(O)C(C)(C)OC(C)(C)C1=O]

Step 1: Alternative preparation of 4-(2-ethyl-5-hydroxyphenyl)-2,2,6,6-tetramethylpyran-3,5-dione

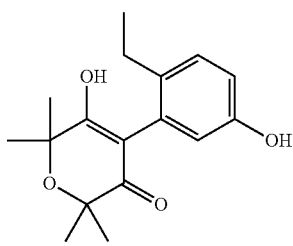 [SMILES: CCc1ccc(O)cc1C1=C(O)C(C)(C)OC(C)(C)C1=O]

A mixture of 4-(5-bromo-2-ethylphenyl)-2,2,6,6-tetramethylpyran-3,5-dione (1.0 g, 2.8 mmol), copper(I) iodide (108 mg, 0.57 mmol) and L-proline (33 mg, 0.28 mmol) in an aqueous solution of sodium hydroxide (8.8 ml of a 1N solution) is heated at 200° C. for 2 hours under microwave irradiation. The mixture is cooled to room temperature, poured into 2M aqueous hydrochloric acid and extracted with ethyl acetate. The organic extract is washed with brine, dried over anhydrous magnesium sulfate, filtered and the filtrate is evaporated under reduced pressure. The solvent is evaporated under reduced pressure and the residue is purified by column chromatography on silica gel to give 4-(2-ethyl-5-hydroxyphenyl)-2,2,6,6-tetramethylpyran-3,5-dione.

Step 2: Preparation of 4-[2-ethyl-5-(6-trifluoromethylpyridin-2-yloxy)phenyl]-2,2,6,6-tetramethylpyran-3,5-dione

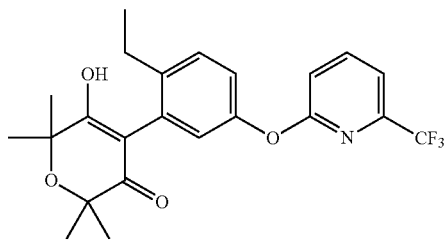 [SMILES: CCc1ccc(Oc2cccc(C(F)(F)F)n2)cc1C1=C(O)C(C)(C)OC(C)(C)C1=O]

A mixture of 4-(2-ethyl-5-hydroxyphenyl)-2,2,6,6-tetramethylpyran-3,5-dione (100 mg, 0.34 mmol), 2-fluoro-6-trifluoromethylpyridine (68 mg, 0.41 mmol), and potassium carbonate (110 mg, 0.69 mmol) in N,N-dimethylformamide (3 ml) is heated to 140° C. under microwave irradiation for 40 minutes. The mixture is cooled to room temperature, poured into 2M aqueous hydrochloric acid, diluted with dichloromethane and filtered through a phase separation cartridge. The organic phase is collected. The solvent is evaporated under reduced pressure and the residue is purified by column chromatography on silica gel to give 4-[2-ethyl-5-(6-trifluoromethylpyridin-2-yloxy)phenyl]-2,2,6,6-tetramethylpyran-3,5-dione.

Example 9

Preparation of 4-[2-ethyl-5-(2-fluoro-4-nitrophenoxy)phenyl]-2,2,6,6-tetramethylpyran-3,5-dione

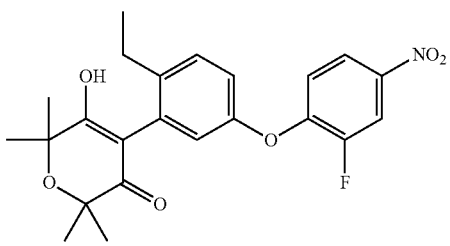 [SMILES: CCc1ccc(Oc2ccc([N+](=O)[O-])cc2F)cc1C1=C(O)C(C)(C)OC(C)(C)C1=O]

A mixture of 4-(2-ethyl-5-hydroxyphenyl)-2,2,6,6-tetramethylpyran-3,5-dione (135 mg, 0.47 mmol), 3,4-difluoro-1-nitrobenzene (90 mg, 0.56 mmol), and potassium carbonate (130 mg, 0.94 mmol) in N,N-dimethylformamide (3 ml) is heated to 80° C. for 3 hours. The mixture is cooled to room temperature, poured into 2M aqueous hydrochloric acid and extracted with ethyl acetate. The organic extract is dried over anhydrous magnesium sulfate, filtered and the filtrate is evaporated under reduced pressure. The residue is purified by column chromatography on silica gel to give 4-[2-ethyl-5-(2-fluoro-4-nitrophenoxy)phenyl]-2,2,6,6-tetramethylpyran-3,5-dione.

Example 10

Preparation of 9-[5-(4-bromo-2-fluorophenoxy)-2-ethylphenyl]-3-oxaspiro[5.5]undecane-8,10-dione

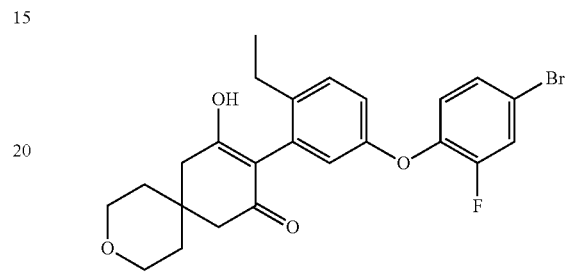

Step 1: Preparation of 9-(5-bromo-2-ethylphenyl)-3-oxaspiro[5.5]undecane-8,10-dione

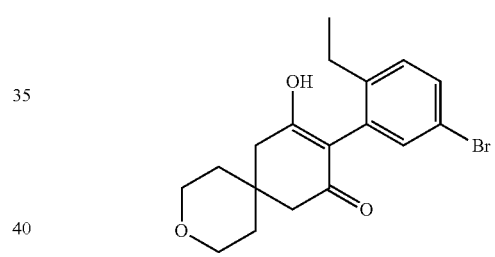

3-oxaspiro[5.5]undecane-8,10-dione (50.0 g, 0.275 mol) is added to a solution of sodium carbonate (58.3 g, 0.55 mol) in a mixture of ethanol (175 ml) and water (700 ml), and the mixture is stirred at room temperature until dissolution is complete, and then the mixture is cooled to 5° C. Iodobenzene diacetate (88.45 g, 0.275 mol) is added portionwise over 15 minutes, and once the addition is complete the mixture is stirred for 15 minutes at 5° C., then the cooling bath is removed and the mixture is stirred and allowed to warm to room temperature for 4 hours. The precipitated iodonium ylide is collected by filtration.

A portion of the iodonium ylide (2.0 g, 5.21 mmol) is added to a mixture of 2-ethyl-5-bromophenylboronic acid (1.43 g, 6.25 mmol), palladium(II) acetate (59 mg, 0.26 mmol) and lithium hydroxide monohydrate (0.656 g, 15.6 mmol) in 1,2-dimethoxyethane (40 ml) and water (10 ml), and the mixture is heated at 50° C. for 6 hours, and then allowed to stand at room temperature overnight. The mixture is filtered through diatomaceous earth, washing the filter cake with water (50 ml) and ethyl acetate (50 ml). The organic phase is discarded. The aqueous phase is acidified to pH2 by addition of concentrated hydrochloric acid, and then extracted with ethyl acetate. The organic extract is dried over anhydrous magnesium sulfate, filtered and the filtrate is evaporated under reduced pressure. The residue is purified by column chromatography on silica gel to give 9-(5-bromo-2-ethylphenyl)-3-oxaspiro[5.5]undecane-8,10-dione.

Step 2: Preparation of 9-[5-(4-bromo-2-fluorophenoxy)-2-ethylphenyl]-3-oxaspiro[5.5]undecane-8,10-dione

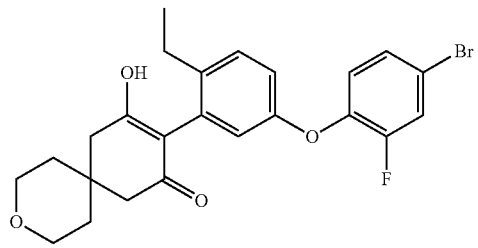 [SMILES: CCc1ccc(Oc2ccc(Br)cc2F)cc1C1=C(O)CC2(CCOCC2)CC1=O]

A mixture of 9-(5-bromo-2-ethylphenyl)-3-oxaspiro[5.5]undecane-8,10-dione (360 mg, 0.99 mmol), 4-bromo-2-fluorophenol (227 mg, 1.19 mmol), cesium carbonate (645 mg, 1.98 mmol), copper(II) trifluoromethanesulfonate (18 mg, 0.05 mmol) and ethyl acetate (50 μl) in toluene (10 ml) is heated under reflux for 19 hours. The mixture is cooled to room temperature, N,N-dimethylformamide (2 ml) and 2M aqueous hydrochloric acid (10 ml) are added, and the mixture is stirred vigorously for 45 minutes. The mixture is extracted with ethyl acetate, and the organic extract is dried over anhydrous magnesium sulfate, filtered and the filtrate is evaporated under reduced pressure. The residue is purified by preparative reverse phase HPLC to give 9-[5-(4-bromo-2-fluorophenoxy)-2-ethylphenyl]-3-oxaspiro[5.5]undecane-8,10-dione.

Example 11

Preparation of 4-[2-cyclopropyl-5-(2,4-dichlorophenoxy)-phenyl]-2,2,6,6-tetramethylpyran-3,5-dione

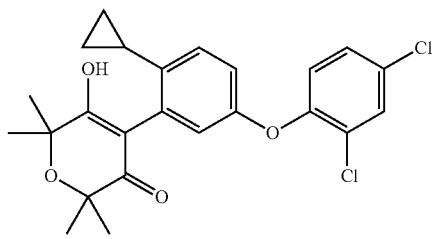 [SMILES: CC1(C)OC(C)(C)C(O)=C(c2cc(Oc3ccc(Cl)cc3Cl)ccc2C2CC2)C1=O]

Step 1: Preparation of 5-bromo-2-cyclopropylbenzaldehyde

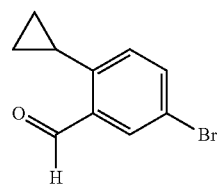 [SMILES: O=Cc1cc(Br)ccc1C1CC1]

To a mixed solution of toluene (2250 ml) and distilled water (250 ml) at 0° C. is added finely ground potassium phosphate tribasic (699.23 g, 3.29 mol) portionwise over 10 minutes. This mixture is then allowed to warm to room temperature, followed by the addition of 2,5-dibromobenzaldehyde (235.0 g, 890 mmol) and cyclopropylboronic acid (68.92 g, 801 mmol). After stirring at room temperature for 50 minutes under a blanket of nitrogen tetrakis(triphenylphosphine)palladium (102.89 g, 89 mmol) is added over 10 minutes, washing residual solid with toluene (50 ml). The reaction mixture is then stirred at 80° C. for 22 hours, followed by cooling to room temperature and addition of distilled water (500 ml). The mixture is filtered through a pad of silica (washing with additional ethyl acetate) and the aqueous phase is extracted with ethyl acetate (2×300 ml). The combined organic extracts are washed with brine (500 ml), dried with anhydrous magnesium sulfate and concentrated under reduced pressure. The residue is purified by chromatography on silica gel (iso-hexane/ethyl acetate as eluant) followed by distillation under reduced pressure to afford 5-bromo-2-cyclopropylbenzaldehyde as a yellow oil.

Step 2: Preparation of 4-[1-(5-bromo-2-cyclopropylphenyl)methylidene]-2,2,5,5-tetramethyldihydrofuran-3-one

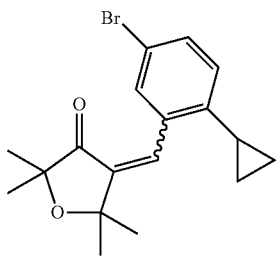 [SMILES: CC1(C)OC(C)(C)C(=Cc2cc(Br)ccc2C2CC2)C1=O]

To an ice-cold suspension of sodium methoxide (40.1 g, 740 mmol) in anhydrous 1,2-dimethoxyethane is added 2,2,5,5-tetramethyldihydrofuran-3-one (94.9 g, 670 mmol), washing with additional dimethoxyethane (120 ml). The reaction mixture is stirred at 0° C. 30 minutes, followed by addition of 5-bromo-2-cyclopropylbenzaldehyde (137.2 g, 610 mM) as a solution in dimethoxyethane (280 mL). After stirring for an additional 3 hours at this temperature the reaction is quenched with water (800 ml) and allowed to warm to room temperature. Diethyl ether (800 ml) is added and the two phases are separated. The aqueous phase is extracted again with diethyl ether (×2), and all organics are washed with brine (800 mL) then dried over magnesium sulfate. After concentration in vacuo the residue is purified by flash chromatography on silica gel (iso-hexane/ethyl acetate as eluant) to afford 4-[1-(5-bromo-2-cyclopropylphenyl)methylidene]-2,2,5,5-tetramethyldihydrofuran-3-one.

Step 3: Preparation of 2-(5-bromo-2-cyclopropylphenyl)-4,4,6,6-tetramethyl-1,5-dioxaspiro[2.4]heptan-7-one

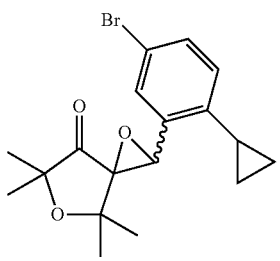 [SMILES: CC1(C)OC(C)(C)C2(OC2c2cc(Br)ccc2C2CC2)C1=O]

To a solution of 4-[1-(5-bromo-2-cyclopropylphenyl)methylidene]-2,2,5,5-tetramethyldihydrofuran-3-one (189 g, 541 mmol) in methanol (2650 ml) at 53° C. is added and 2M aqueous lithium hydroxide (27.1 ml, 54.2 mmol) then 50% aqueous hydrogen peroxide (46.1 ml, 812 mmol). After stirring for 30 minutes at this temperature the solution is cooled to 45° C. and quenched with saturated aqueous sodium thiosulfate. Distilled water (1000 ml) is added and the organic solvents are removed in vacuo. The aqueous phase is then extracted into ethyl acetate (×2) and the combined organic extracts are washed with saturated aqueous sodium hydrogen carbonate (×2), brine (500 mL), then dried over anhydrous magnesium sulfate. Volatile solvents are removed under vacuum to afford 2-(5-bromo-2-cyclopropylphenyl)-4,4,6,6-tetramethyl-1,5-dioxaspiro[2.4]heptan-7-one.

Step 4: Preparation of 4-(5-bromo-2-cyclopropylphenyl)-2,2,6,6-tetramethylpyran-3,5-dione

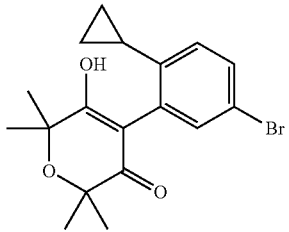 [SMILES: CC1(C)OC(C)(C)C(O)=C(c2cc(Br)ccc2C2CC2)C1=O]

To a suspension of iron (III) chloride (53.0 g, 327 mmol) in anhydrous dichloromethane (1000 ml) at 5° C. is added a second solution of 2-(5-bromo-2-cyclopropylphenyl)-4,4,6,6-tetramethyl-1,5-dioxaspiro[2.4]heptan-7-one (119.1 g, 326 mmol) in anhydrous dichloromethane (400 ml), at such a rate as to maintain an internal temperature below 10° C. After stirring for 15 minutes the reaction is quenched with distilled water (900 ml) and the mixture is allowed to warm to room temperature. The two phases are separated and the aqueous phase is extracted with dichloromethane (×2). Organics are combined and the crude product is extracted into 1M aqueous potassium carbonate, followed by acidification to pH0 with concentrated hydrochloric acid and re-extraction with dichloromethane. All organics are combined then washed with brine and dried over anhydrous magnesium sulfate. Concentration in vacuo then affords 4-(5-bromo-2-cyclopropylphenyl)-2,2,6,6-tetramethylpyran-3,5-dione as a white solid.

Step 5: Preparation of 4-[2-cyclopropyl-5-(2,4-dichlorophenoxy)-phenyl]-2,2,6,6-tetramethylpyran-3,5-dione

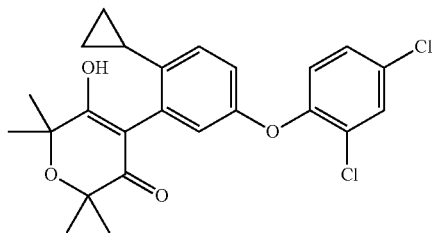 [SMILES: CC1(C)OC(C)(C)C(O)=C(c2cc(Oc3ccc(Cl)cc3Cl)ccc2C2CC2)C1=O]

To a mixture of 4-(5-bromo-2-cyclopropylphenyl)-2,2,6,6-tetramethylpyran-3,5-dione (0.208 g, 0.57 mmol), 2,4-dichlorophenol (473 mg, 2.85 mmol), cesium carbonate (0.400 g, 1.13 mmol), copper (II) trifluoromethanesulfonate (10 mg, 0.03 mmol) and activated (powdered) 5 Å molecular sieves (0.330 g) is added anhydrous toluene (3.5 ml). The mixture is purged with nitrogen then heated at 160° C. for 1 hour under microwave irradiation. After cooling to room temperature the reaction mixture is diluted with dichloromethane and 2M hydrochloric acid, then filtered and the organic phase separated. After concentration in vacuo the residue is purified by preparative reverse phase HPLC to afford 4-[2-cyclopropyl-5-(2,4-dichlorophenoxy)-phenyl]-2,2,6,6-tetramethylpyran-3,5-dione.

Example 12

Preparation of 4-[5-(4-chlorophenoxy)-2-trifluoromethoxyphenyl]-2,2,6,6-tetramethylpyran-3,5-dione

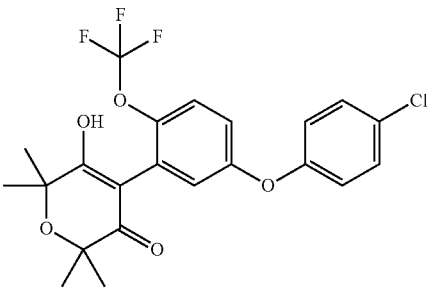 [SMILES: CC1(C)OC(C)(C)C(O)=C(c2cc(Oc3ccc(Cl)cc3)ccc2OC(F)(F)F)C1=O]

Step 1: Preparation of 4-[1-(5-bromo-2-trifluoromethoxyphenyl)-methylidene]-2,2,5,5-tetramethyldihydrofuran-3-one

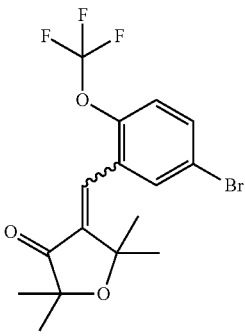 [SMILES: CC1(C)OC(C)(C)C(=Cc2cc(Br)ccc2OC(F)(F)F)C1=O]

To an ice-cold solution of 2,2,5,5-tetramethyldihydrofuran-3-one (2.84 g, 20.00 mmol) in anhydrous 1,2-dimethoxyethane (6 ml) is added sodium methoxide (1.19 g, 22.04 mmol) in one portion. After stirring at this temperature for 5 minutes a solution of 5-bromo-2-trifluoromethoxybenzaldehyde (4.84 g, 18.00 mmol) in 1,2-dimethoxyethane (6 ml) is added dropwise over 10 mins, followed by stirring at 0° C. for a further 1 hour. After warming to room temperature the reaction mixture is diluted with ether and washed with 2M hydrochloric acid (×2). Organic fractions are combined, dried over magnesium sulfate, filtered and the filtrate evaporated in vacuo to afford 4-[1-(5-bromo-2-trifluoromethoxyphenyl)-methylidene]-2,2,5,5-tetramethyldihydrofuran-3-one (7.06 g) as an orange liquid.

Step 2: Preparation of 2-(5-bromo-2-trifluoromethoxyphenyl)-4,4,6,6-tetramethyl-1,5-dioxaspiro[2.4]heptan-7-one

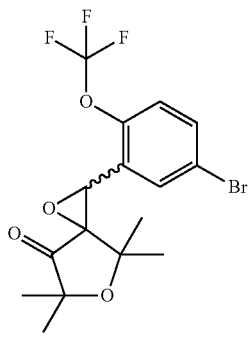 [SMILES: CC1(C)OC(C)(C)C2(OC2c2cc(Br)ccc2OC(F)(F)F)C1=O]

To a solution of 4-[1-(5-bromo-2-trifluoromethoxyphenyl)-methylidene]-2,2,5,5-tetramethyldihydrofuran-3-one (7.06 g, 18.00 mmol) in methanol (300 ml) at 35° C. is added 50% aqueous hydrogen peroxide (1.80 ml, 27.00 mmol), immediately followed by 2M aqueous lithium hydroxide (1.80 ml, 3.60 mmol). After stirring at this temperature for 1 hour the reaction mixture is allowed to cool, then quenched with 10% sodium metabisulfite solution (negative KI-starch indicator test). The reaction mixture is extracted with diethyl ether (×3), then the organic phase is further washed with saturated aqueous sodium bicarbonate (×2) then brine. All organics are combined, dried over magnesium sulfate, filtered and the filtrate concentrated in vacuo to afford 2-(5-bromo-2-trifluoromethoxyphenyl)-4,4,6,6-tetramethyl-1,5-dioxaspiro[2.4]heptan-7-one (6.34 g, 86%) as a yellow oil.

Step 3: Preparation of 4-(5-bromo-2-trifluoromethoxyphenyl)-2,2,6,6-tetramethylpyran-3,5-dione

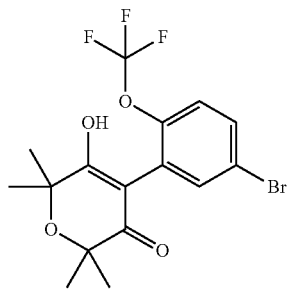 [SMILES: CC1(C)OC(C)(C)C(O)=C(c2cc(Br)ccc2OC(F)(F)F)C1=O]

To an ice-cold solution of concentrated sulphuric acid (10 ml) is added a second solution of 2-(5-bromo-2-trifluoromethoxyphenyl)-4,4,6,6-tetramethyl-1,5-dioxaspiro[2.4]heptan-7-one (6.34 g, 15.00 mmol) in 1,2-dichloroethane (10 ml) dropwise over 5 minutes. This biphasic mixture is stirred vigorously for 2 hours at 0° C., then poured into ice-water, rinsing with a small amount of additional 1,2-dichloroethane/water. This mixture is then concentrated under vacuum to remove all organic solvents, until a free-flowing solid was produced. The solid is filtered, washed with water then iso-hexane, followed by drying under vacuum overnight. The solid is next redissolved in ethyl acetate, dried over magnesium sulfate, filtered and the filtrate concentrated in vacuo to afford 4-(5-bromo-2-trifluoromethoxyphenyl)-2,2,6,6-tetramethylpyran-3,5-dione (4.17 g, 68%).

Step 4: Preparation of 4-[5-(4-chlorophenoxy)-2-trifluoromethoxyphenyl]-2,2,6,6-tetramethylpyran-3,5-dione

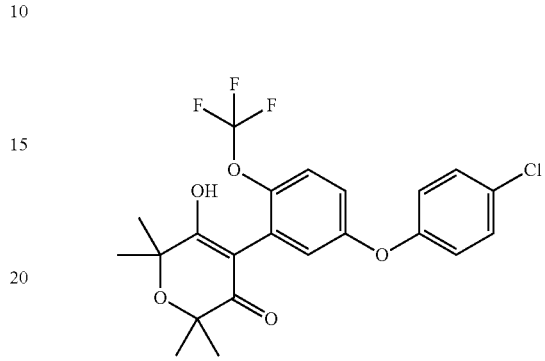

To a mixture of 4-(5-bromo-2-trifluoromethoxyphenyl)-2,2,6,6-tetramethylpyran-3,5-dione (0.254 g, 0.62 mmol), 4-chlorophenol (0.400 g, 3.11 mmol), cesium carbonate (0.440 g, 1.25 mmol), copper (II) trifluoromethanesulfonate (11 mg, 0.03 mmol) and powdered 4 Å molecular sieves (0.40 g) is added anhydrous toluene (3.5 ml). After flushing with nitrogen the mixture is heated at 160° C. for 1 hour under microwave irradiation, then cooled to room temperature and quenched with 2M aqueous hydrochloric acid. The crude product is extracted with dichloromethane (×3), and the organic fractions are combined, washed with brine, dried over magnesium sulfate and concentrated in vacuo. Purification by preparative reverse phase HPLC affords 4-[5-(4-chlorophenoxy)-2-trifluoromethoxyphenyl]-2,2,6,6-tetramethylpyran-3,5-dione as a white powder.

Example 13

Preparation of acetic acid 4-[5-(4-cyano-2-fluorophenoxy)-2-ethylphenyl]-2,2,6,6-tetramethyl-5-oxo-5,6-dihydro-2H-pyran-3-yl ester

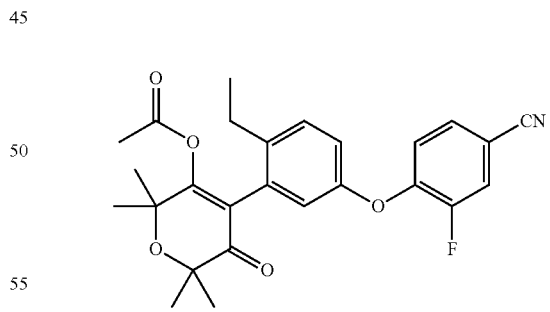

To a solution of 4-[4-ethyl-3-(2,2,6,6-tetramethyl-3,5-dioxotetrahydropyran-4-yl)phenoxy]-3-fluorobenzonitrile (0.130 g, 0.31 mmol) in dichloromethane at 0° C. is added triethylamine (0.133 ml, 0.95 mmol) followed by acetyl chloride (0.067 ml, 0.95 mmol). The mixture is stirred at 0° C. for 60 minutes, then allowed to warm to room temperature and stir for a further 18 hours. After concentration in vacuo the crude product is purified by flash column chromatography on silica gel (iso-hexane/ethyl acetate eluant) to afford 4-[5-(4-cyano-2-fluorophenoxy)-2-ethylphenyl]-2,2,6,6-tetramethyl-5-oxo-5,6-dihydro-2H-pyran-3-yl ester.

Additional compounds in Table T1 below were prepared by similar methods using appropriate starting materials.

TABLE T1

| Compound Number | Structure | $^1$H NMR (CDCl$_3$ unless stated) or other physical data |
|---|---|---|
| A-1 | 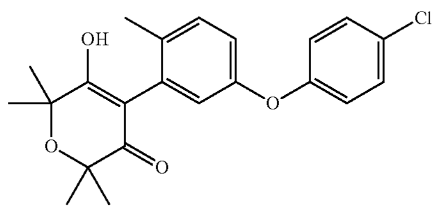 [SMILES: Cc1ccc(Oc2ccc(Cl)cc2)cc1C1=C(O)C(C)(C)OC(C)(C)C1=O] | δ 7.30-7.23 (m, 3H), 6.92-6.97 (m, 3H), 6.79 (d, 1H), 5.59 (br. s, 1H), 2.11 (s, 3H), 1.59 (app. d, 6H), 1.48 (app. d, 6H). |
| A-2 | 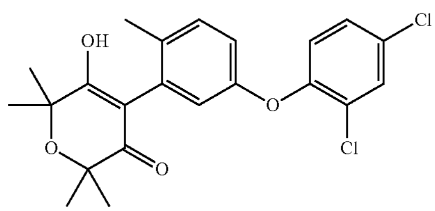 [SMILES: Cc1ccc(Oc2ccc(Cl)cc2Cl)cc1C1=C(O)C(C)(C)OC(C)(C)C1=O] | δ 7.45 (d, 1H), 7.28 (d, 1H), 7.19 (dd, 1H), 6.93 (d, 1H), 6.89 (dd, 1H), 6.79 (d, 1H), 5.62 (br. s, 1H), 2.11 (s, 3H), 1.60 (app. d, 6H), 1.48 (app. d, 6H). |
| A-3 | 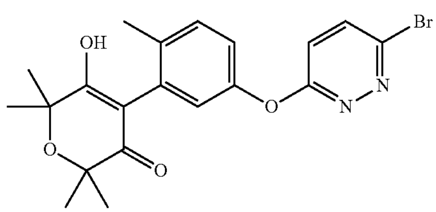 [SMILES: Cc1ccc(Oc2ccc(Br)nn2)cc1C1=C(O)C(C)(C)OC(C)(C)C1=O] | d-DMSO δ 8.02 (d, 1H), 7.40 (d 1H), 7.30 (d, 1H), 7.10 (dd, 1H), 6.80 (m, 1H), 2.05 (s, 3H), 1.30-1.60 (br. d, 12H) |
| A-4 | 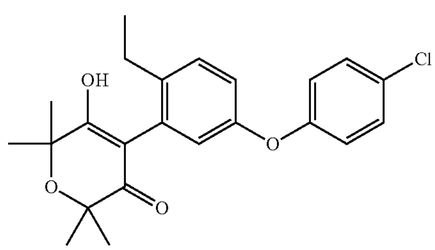 [SMILES: CCc1ccc(Oc2ccc(Cl)cc2)cc1C1=C(O)C(C)(C)OC(C)(C)C1=O] | δ 7.30 (m, 3H), 6.93-6.99 (m, 3H), 6.76 (dd, 1H), 5.57 (br. s, 1H), 2.41 (m, 2H), 1.59 (d, 6H), 1.47 (d, 6H), 1.11 (t, 3H) |
| A-5 | 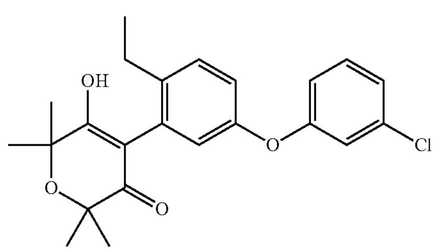 [SMILES: CCc1ccc(Oc2cccc(Cl)c2)cc1C1=C(O)C(C)(C)OC(C)(C)C1=O] | δ 7.32 (dd, 1H), 7.25 (m, 1H), 7.07 (m, 1H), 7.03 (m, 1H), 7.00 (dd, 1H), 6.90 (m, 1H), 6.79 (dd, 1H), 5.65 (br. s, 1H), 2.42 (m, 2H), 1.54 (m, 12H), 1.12 (t, 3H) |
| A-6 | 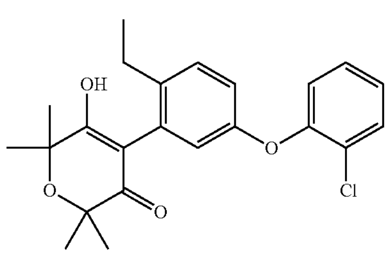 [SMILES: CCc1ccc(Oc2ccccc2Cl)cc1C1=C(O)C(C)(C)OC(C)(C)C1=O] | δ 7.45 (m, 1H), 7.30 (dd, 1H), 7.23 (m, 1H), 7.08 (m, 1H), 7.02 (m, 1H), 6.92 (m, 1H), 6.78 (dd, 1H), 5.61 (br. s, 1H), 2.41 (m, 2H), 1.59 (d, 6H), 1.47 (d, 6H), 1.11 (t, 3H) |

TABLE T1-continued

| Compound Number | Structure | ¹H NMR (CDCl₃ unless stated) or other physical data |
|---|---|---|
| A-7 | 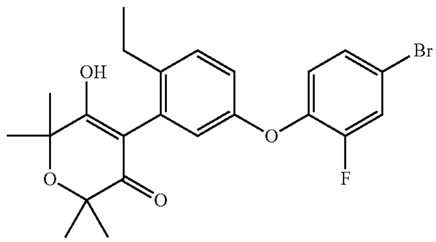 [SMILES: CCc1ccc(Oc2ccc(Br)cc2F)cc1C1=C(O)C(C)(C)OC(C)(C)C1=O] | δ 7.21-7.38 (m, 3H), 6.91-7.00 (m, 2H), 6.76 (dd, 1H), 5.64 (br. s, 1H), 2.41 (m, 2H), 1.59 (m, 6H), 1.47 (m, 6H), 1.11 (t, 3H) |
| A-8 | 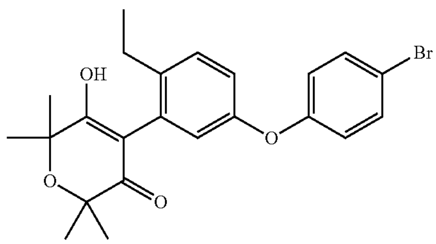 [SMILES: CCc1ccc(Oc2ccc(Br)cc2)cc1C1=C(O)C(C)(C)OC(C)(C)C1=O] | δ 7.43 (m, 2H), 7.31 (d, 1H), 6.98 (dd, 1H), 6.91 (m, 2H), 6.77 (d, 1H), 5.53 (br. s, 1H), 2.41 (m, 2H), 1.59 (d, 6H), 1.47 (d, 6H), 1.11 (t, 3H) |
| A-9 | 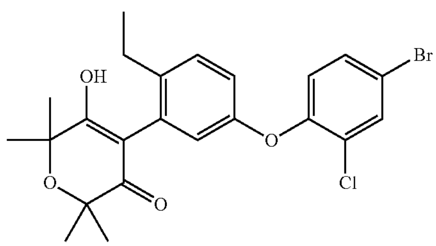 [SMILES: CCc1ccc(Oc2ccc(Br)cc2Cl)cc1C1=C(O)C(C)(C)OC(C)(C)C1=O] | δ 7.60 (dd, 1H), 7.32 (m, 2H), 6.93 (dd, 1H), 6.89 (d, 1H), 6.77 (d, 1H), 5.61 (br. s, 1H), 2.42 (m, 2H), 1.59 (d, 6H), 1.47 (d, 6H), 1.11 (t, 3H) |
| A-10 | 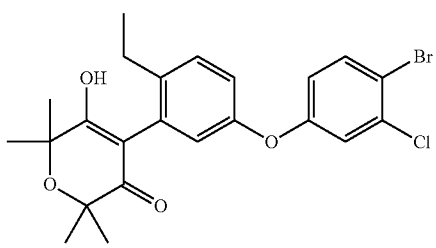 [SMILES: CCc1ccc(Oc2ccc(Br)c(Cl)c2)cc1C1=C(O)C(C)(C)OC(C)(C)C1=O] | δ 7.53 (dd, 1H), 7.33 (dd, 1H), 7.14 (dd, 1H), 7.00 (dd, 1H), 6.79 (m, 2H), 5.53 (br. s, 1H), 2.43 (m, 2H), 1.59 (d, 6H), 1.47 (d, 6H), 1.12 (t, 3H) |
| A-11 | 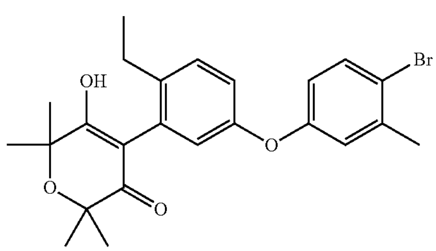 | δ 7.45 (dd, 1H), 7.30 (dd, 1H), 6.96 (dd, 1H), 6.93 (dd, 1H), 6.76 (dd, 1H), 6.73 (dd, 1H), 5.54 (br.s, 1H), 2.41 (m, 2H), 2.36 (s, 3H), 1.59 (d, 6H), 1.47 (d, 6H), 1.11 (t, 3H) |
| A-12 | 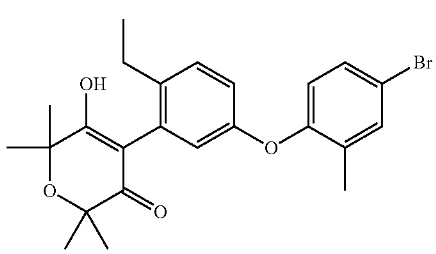 [SMILES: CCc1ccc(Oc2ccc(Br)cc2C)cc1C1=C(O)C(C)(C)OC(C)(C)C1=O] | δ 7.38 (dd, 1H), 7.23-7.30 (m, 2H), 6.85 (dd, 1H), 6.78 (dd, 1H), 6.71 (dd, 1H), 5.54 (br. s, 1H), 2.40 (m, 2H), 2.23 (s, 3H), 1.59 (d, 6H), 1.47 (d, 6H), 1.10 (t, 3H) |

TABLE T1-continued

| Compound Number | Structure | $^1$H NMR (CDCl$_3$ unless stated) or other physical data |
|---|---|---|
| A-13 | 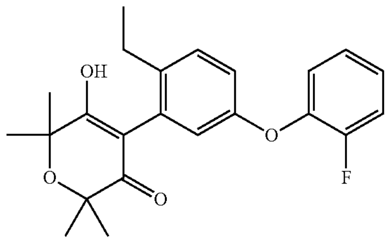 [SMILES: CCc1ccc(Oc2ccccc2F)cc1C1=C(O)C(C)(C)OC(C)(C)C1=O] | δ 7.28 (d, 1H), 7.04-7.20 (m, 4H), 6.92 (dd, 1H), 6.78 (d, 1H), 5.68 (br. s, 1H), 2.40 (m, 2H), 1.59 (d, 6H), 1.47 (d, 6H), 1.10 (t, 3H) |
| A-14 | 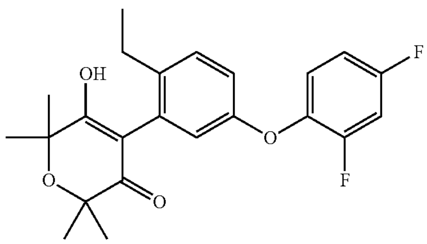 [SMILES: CCc1ccc(Oc2ccc(F)cc2F)cc1C1=C(O)C(C)(C)OC(C)(C)C1=O] | δ 7.27 (d, 1H), 7.09 (m, 1H), 6.95 (m, 1H), 6.82-6.90 (m, 2H), 6.73 (d, 1H), 5.65 (br. s, 1H), 2.40 (m, 2H), 1.59 (d, 6H), 1.47 (d, 6H), 1.10 (t, 3H) |
| A-15 | 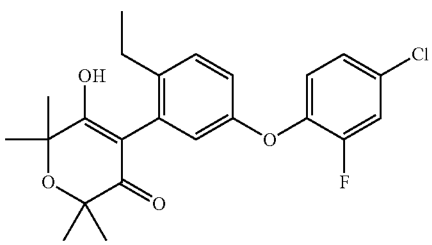 [SMILES: CCc1ccc(Oc2ccc(Cl)cc2F)cc1C1=C(O)C(C)(C)OC(C)(C)C1=O] | δ 7.29 (d, 1H), 7.21 (dd, 1H), 7.09 (m, 1H), 7.02 (t, 1H), 6.93 (dd, 1H), 6.76 (d, 1H), 5.65 (br. s, 1H), 2.41 (m, 2H), 1.59 (d, 6H), 1.47 (d, 6H), 1.10 (t, 3H) |
| A-16 | 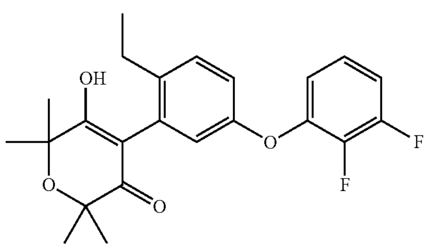 [SMILES: CCc1ccc(Oc2cccc(F)c2F)cc1C1=C(O)C(C)(C)OC(C)(C)C1=O] | δ 7.31 (d, 1H), 6.90-7.06 (m, 3H), 6.78-6.87 (m, 2H), 5.68 (br. s, 1H), 2.42 (m, 2H), 1.59 (d, 6H), 1.47 (d, 6H), 1.11 (t, 3H) |
| A-17 | 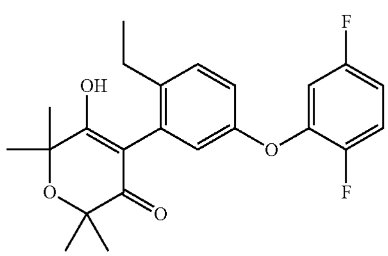 [SMILES: CCc1ccc(Oc2cc(F)ccc2F)cc1C1=C(O)C(C)(C)OC(C)(C)C1=O] | δ 7.31 (d, 1H), 7.08-7.16 (m, 1H), 6.97 (m, 1H), 6.75-6.83 (m, 3H), 5.68 (br. s, 1H), 2.42 (m, 2H), 1.59 (d, 6H), 1.47 (d, 6H), 1.11 (t, 3H) |
| A-18 | 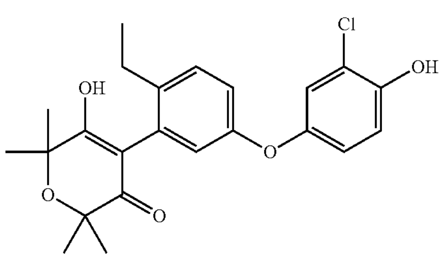 [SMILES: CCc1ccc(Oc2ccc(O)c(Cl)c2)cc1C1=C(O)C(C)(C)OC(C)(C)C1=O] | δ 7.35 (d, 1H), 6.92-7.09 (m, 4H), 6.86 (m, 1H), 5.81 (br. s, 1H), 3.32 (br. s, 1H), 2.46 (m, 2H), 1.42-1.76 (m, 12H), 1.15 (t, 3H) |

TABLE T1-continued

| Compound Number | Structure | ¹H NMR (CDCl₃ unless stated) or other physical data |
|---|---|---|
| A-19 | 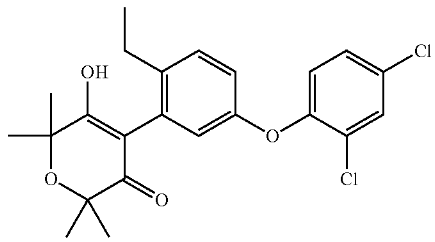 [SMILES: CCc1ccc(Oc2ccc(Cl)cc2Cl)cc1C1=C(O)C(C)(C)OC(C)(C)C1=O] | δ 7.46 (d, 1H), 7.31 (d, 1H), 7.19 (dd, 1H), 6.90-6.97 (m, 2H), 6.76 (d, 1H), 5.66 (br. s, 1H), 2.42 (m, 2H), 1.59 (d, 6H), 1.47 (d, 6H), 1.11 (t, 3H) |
| A-20 | 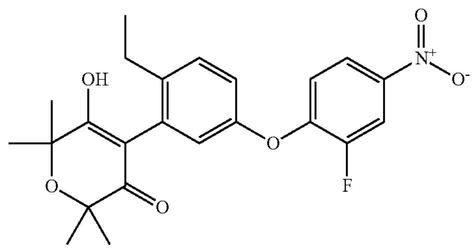 [SMILES: CCc1ccc(Oc2ccc([N+](=O)[O-])cc2F)cc1C1=C(O)C(C)(C)OC(C)(C)C1=O] | δ 8.08 (dd, 1H), 7.99 (m, 1H), 7.40 (d, 1H), 7.03-7.10 (m, 2H), 6.86 (d, 1H), 2.46 (q, 2H), 1.53 (br. m, 12H), 1.14 (t, 3H) |
| A-21 | 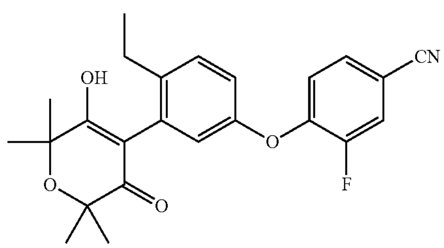 [SMILES: CCc1ccc(Oc2ccc(C#N)cc2F)cc1C1=C(O)C(C)(C)OC(C)(C)C1=O] | δ 7.47 (dd, 1H), 7.35-7.41 (m, 2H), 7.01-7.07 (m, 2H), 6.84 (d, 1H), 2.45 (q, 2H), 1.53 (br. m, 12H), 1.13 (t, 3H) |
| A-22 | 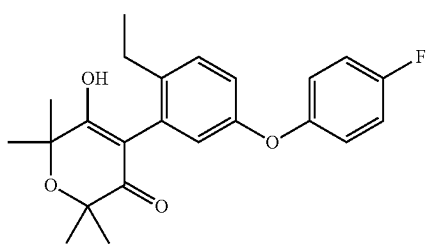 [SMILES: CCc1ccc(Oc2ccc(F)cc2)cc1C1=C(O)C(C)(C)OC(C)(C)C1=O] | δ 7.27-7.25 (m, 1H), 7.04-6.96 (m, 4H), 6.91 (dd, 1H), 6.72 (d, 1H), 5.78 (br. s, 1H), 2.44-2.33 (m, 2H), 1.57 (d, 6H), 1.45 (d, 6H), 1.09 (t, 3H). |
| A-23 | 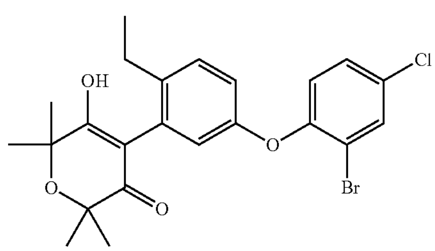 [SMILES: CCc1ccc(Oc2ccc(Cl)cc2Br)cc1C1=C(O)C(C)(C)OC(C)(C)C1=O] | δ 7.61 (d, 1H), 7.30 (d, 1H), 7.22 (dd, 1H), 6.93-6.90 (m, 2H), 6.75 (d, 1H), 5.66 (br. s, 1H), 2.44-2.37 (m, 2H), 1.58 (d, 6H), 1.46 (d, 6H), 1.10 (t, 3H) |
| A-24 | 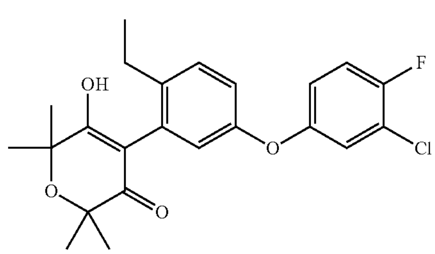 [SMILES: CCc1ccc(Oc2ccc(F)c(Cl)c2)cc1C1=C(O)C(C)(C)OC(C)(C)C1=O] | δ 7.29-7.25 (m, 1H), 7.10-7.05 (m, 2H), 6.93 (dd, 1H), 6.89-6.85 (m, 1H), 6.74 (d, 1H), 5.82 (br. s, 1H), 2.43-2.36 (m, 2H), 1.57 (d, 6H), 1.45 (d, 6H), 1.09 (t, 3H). |

TABLE T1-continued

| Compound Number | Structure | ¹H NMR (CDCl₃ unless stated) or other physical data |
|---|---|---|
| A-25 | 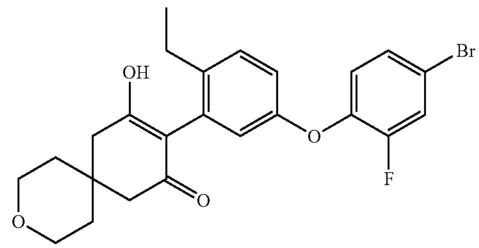 [SMILES: CCc1ccc(Oc2ccc(Br)cc2F)cc1C1=C(O)CC2(CCOCC2)CC1=O] | δ 7.34 (dd, 1H), 7.29 (d, 1H), 7.23 (m, 1H), 6.98 (d, 1H), 6.94 (dd, 1H), 6.66 (d, 1H), 5.76 (br. s, 1H), 3.74 (q, 4H), 2.45-2.68 (m, 4H), 2.38 (m, 2H), 1.69 (m, 4H), 1.09 (t, 3H) |
| A-26 | 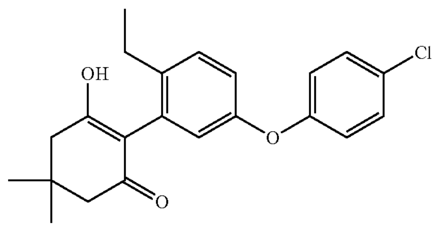 [SMILES: CCc1ccc(Oc2ccc(Cl)cc2)cc1C1=C(O)CC(C)(C)CC1=O] | δ 7.29 (m, 3H), 6.95 (app. d, 3H), 6.69 (d, 1H), 5.61 (br. s, 1H), 2.40-2.50 (m, 4H), 2.38 (s, 2H), 1.17 (s, 3H), 1.19 (s, 3H), 1.11 (t, 3H) |
| A-27 | 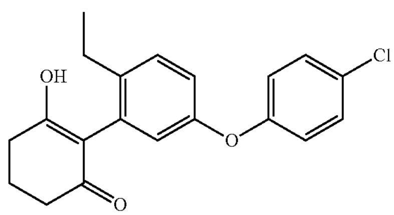 [SMILES: CCc1ccc(Oc2ccc(Cl)cc2)cc1C1=C(O)CCCC1=O] | δ 7.30 (m, 3H), 6.97 (m, 3H), 6.69 (d, 1H), 5.57 (br. s, 1H), 2.61 (br. s, 2H), 2.50 (br. s, 2H), 2.40 (m, 2H), 2.10 (m, 2H), 1.11 (t, 3H) |
| A-28 | 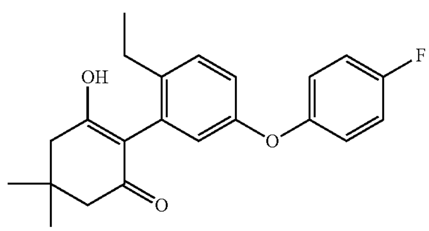 [SMILES: CCc1ccc(Oc2ccc(F)cc2)cc1C1=C(O)CC(C)(C)CC1=O] | d₄-MeOH: δ 7.21 (d, 1H), 7.00 (m, 4H), 6.84 (dd, 1H), 6.53 (d, 1H), 2.40 (m, 6H), 1.17 (s, 3H), 1.14 (s, 3H), 1.07 (t, 3H) |
| A-29 | 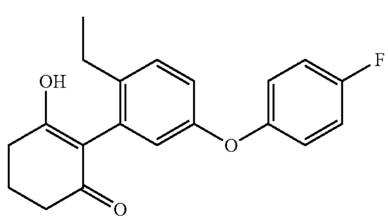 [SMILES: CCc1ccc(Oc2ccc(F)cc2)cc1C1=C(O)CCCC1=O] | d₄-MeOH: δ 7.25 (d, 1H), 7.05 (m, 4H), 6.88 (dd, 1H), 6.57 (d, 1H), 2.56 (m, 4H), 2.40 (q 2H), 2.10 (m, 2H), 1.10 (t, 3H) |
| A-30 | 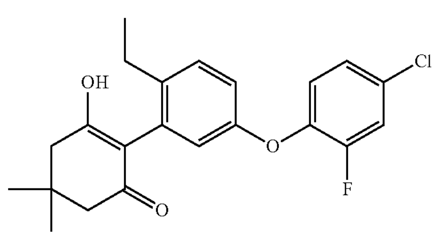 [SMILES: CCc1ccc(Oc2ccc(Cl)cc2F)cc1C1=C(O)CC(C)(C)CC1=O] | d4-MeOH δ 7.33 (dd, 1H), 7.25 (d, 1H), 7.10 (m, 2H), 6.89 (dd, 1H), 6.60 (d, 1H), 2.45 (m, 6H), 1.19 (app. d, 6H), 1.11 (t, 3H) |

TABLE T1-continued

| Compound Number | Structure | ¹H NMR (CDCl₃ unless stated) or other physical data |
|---|---|---|
| A-31 | 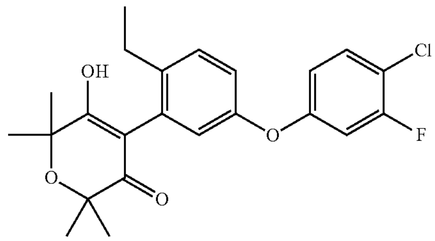 [SMILES: CCc1ccc(Oc2ccc(Cl)c(F)c2)cc1C1=C(O)C(C)(C)OC(C)(C)C1=O] | δ 7.34-7.29 (m, 2H), 7.01-6.99 (m, 1H), 6.83-6.73 (m, 3H), 5.55 (s, 1H), 2.46-2.38 (m, 2H), 1.58 (d, 6H), 1.46 (d, 6H), 1.11 (t, 3H). |
| A-32 | 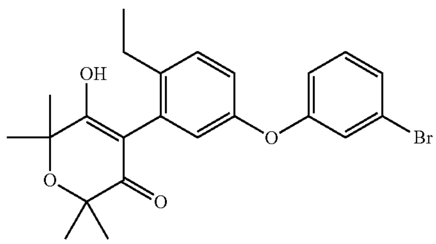 [SMILES: CCc1ccc(Oc2cccc(Br)c2)cc1C1=C(O)C(C)(C)OC(C)(C)C1=O] | δ 7.31 (d, 1H), 7.23-7.16 (m, 3H), 6.98 (dd, 1H), 6.94-6.92 (m, 1H), 6.78 (d, 1H), 5.57 (s, 1H), 2.45-2.38 (m, 2H), 1.58 (d, 6H), 1.46 (d, 6H), 1.11 (t, 3H). |
| A-33 | 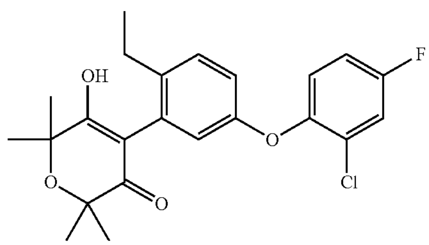 [SMILES: CCc1ccc(Oc2ccc(F)cc2Cl)cc1C1=C(O)C(C)(C)OC(C)(C)C1=O] | δ 7.27 (d, 1H), 7.20 (dd, 1H), 7.04-7.00 (m, 1H), 6.98-6.93 (m, 1H), 6.86 (dd, 1H), 6.72 (d, 1H), 2.40 (br. app. S, 2H), 1.57-1.45 (br. m, 12H), 1.10 (t, 3H). |
| A-34 | 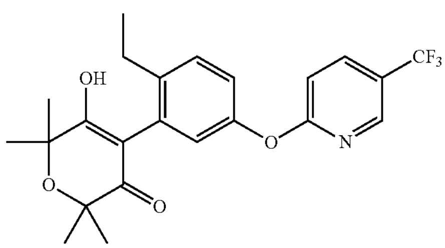 [SMILES: CCc1ccc(Oc2ccc(C(F)(F)F)cn2)cc1C1=C(O)C(C)(C)OC(C)(C)C1=O] | δ 8.28 (s, 1H), 7.92 (dd, 1H), 7.36 (d, 1H), 7.09 (d, 1H), 7.07-7.04 (m, 1H), 6.86 (d, 1H), 2.50-2.43 (m, 2H), 1.57 (d, 6H), 1.45 (d, 6H), 1.13 (t, 3H). |
| A-35 | 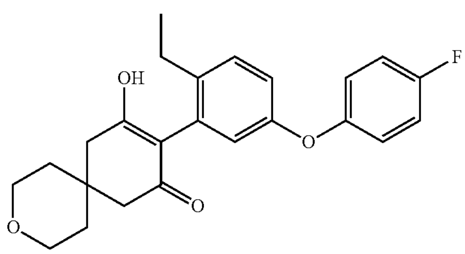 [SMILES: CCc1ccc(Oc2ccc(F)cc2)cc1C1=C(O)CC2(CCOCC2)CC1=O] | δ 7.28 (d, 1H), 6.95-7.07 (m, 4H), 6.93 (dd, 1H), 6.65 (d, 1H), 5.75 (br. s, 1H), 3.74 (q, 4H), 2.46-2.71 (m, 4H), 2.38 (m, 2H), 1.69 (m, 4H), 1.09 (t, 3H) |
| A-36 | 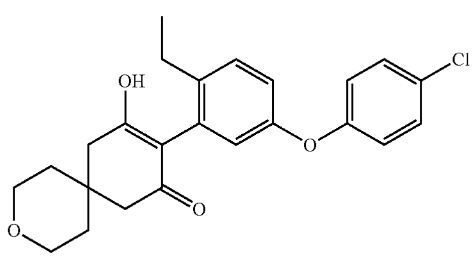 [SMILES: CCc1ccc(Oc2ccc(Br)cc2)cc1C1=C(O)CC2(CCOCC2)CC1=O] | δ 7.25-7.33 (m, 3H), 6.92-6.99 (m, 3H), 6.68 (d, 1H), 5.71 (br. s, 1H), 3.74 (q, 4H), 2.47-2.70 (m, 4H), 2.39 (m, 2H), 1.68 (m, 4H), 1.10 (t, 3H) |

TABLE T1-continued

| Compound Number | Structure | $^1$H NMR (CDCl$_3$ unless stated) or other physical data |
|---|---|---|
| A-37 | 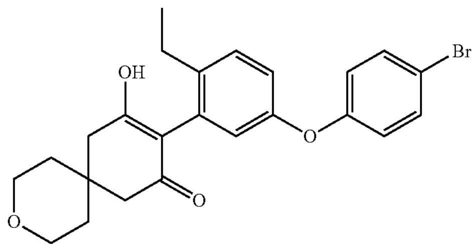 | δ 7.42 (m, 2H), 7.30 (d, 1H) 6.97 (dd, 1H), 6.90 (m, 2H), 6.68 (d, 1H), 5.69 (br. s, 1H), 3.74 (q, 4H), 2.47-2.68 (m, 4H), 2.39 (m, 2H), 1.68 (m, 4H), 1.10 (t, 3H) |
| A-38 | 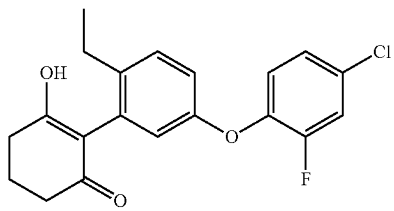 [SMILES: CCc1ccc(Oc2ccc(Cl)cc2F)cc1C1=C(O)CCCC1=O] | d$_4$-MeOH, δ 7.30 (dd, 1H), 7.22 (d, 1H), 7.05 (m, 2H), 6.84 (m, 1H), 6.56 (d, 1H), 2.53 (m, 4H), 2.38 (q 2H), 2.06 (m, 2H), 1.08 (t, 3H) |
| A-39 | 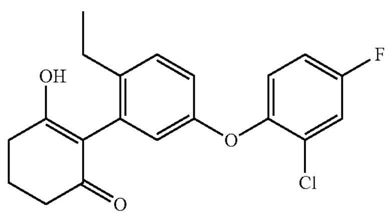 [SMILES: CCc1ccc(Oc2ccc(F)cc2Cl)cc1C1=C(O)CCCC1=O] | d$_4$-MeOH: δ 7.29 (m, 1H), 7.21 (d, 1H), 7.05 (m, 2H), 6.80 (m, 1H), 6.51 (d, 1H), 2.53 (m, 4H), 2.37 (q 2H), 2.05 (m, 2H), 1.08 (t, 3H) |
| A-40 | 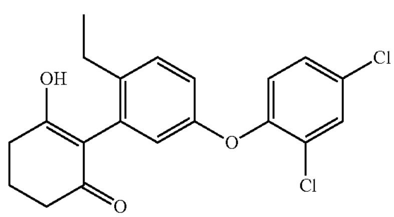 [SMILES: CCc1ccc(Oc2ccc(Cl)cc2Cl)cc1C1=C(O)CCCC1=O] | d$_4$-MeOH: δ 7.50 (d, 1H), 7.23 (m, 2H), 7.00 (d, 1H), 6.85 (m, 1H), 6.56 (d, 1H), 2.53 (m, 4H), 2.40 (q 2H), 2.06 (m, 2H), 1.09 (t, 3H) |
| A-41 | 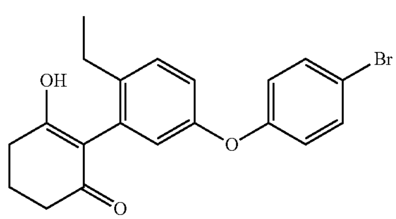 [SMILES: CCc1ccc(Oc2ccc(Br)cc2)cc1C1=C(O)CCCC1=O] | d$_4$-MeOH: δ 7.41 (m, 2H), 7.22 (d, 1H), 6.90 (m, 3H), 6.60 (d, 1H), 2.53 (m, 4H), 2.40 (q 2H), 2.06 (m, 2H), 1.10 (t, 3H) |
| A-42 | 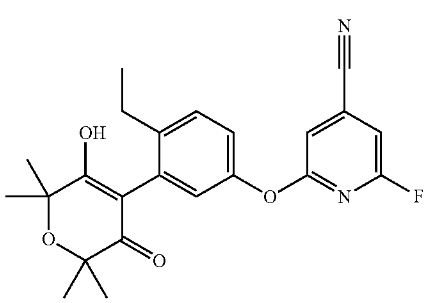 [SMILES: CCc1ccc(Oc2cc(C#N)cc(F)n2)cc1C1=C(O)C(C)(C)OC(C)(C)C1=O] | δ 7.38 (d, 1H), 7.10-7.07 (m, 2H), 6.85 (d, 1H), 6.82 (dd, 1H), 2.52-2.40 (m, 2H), 1.57 (d, 6H), 1.46 (d, 6H), 1.14 (t, 3H). |

TABLE T1-continued
| Compound Number | Structure | ¹H NMR (CDCl₃ unless stated) or other physical data |
|---|---|---|
| A-43 | 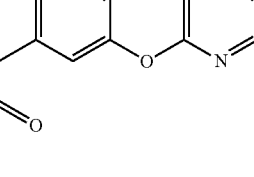 | δ 7.77 (q, 1H), 7.35 (d, 1H), 7.07 (dd, 1H), 6.85 (d, 1H), 6.82 (dd, 1H), 6.57 (dd, 1H), 2.51-2.40 (m, 2H), 1.57 (d, 6H), 1.46 (d, 6H), 1.13 (t, 3H). |
| A-44 | 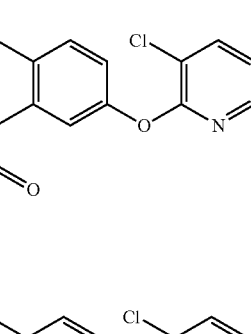 | δ 7.86 (d, 1H), 7.77 (d, 1H), 7.36 (d, 1H), 7.09 (dd, 1H), 6.86 (d, 1H), 2.52-2.37 (m, 2H), 1.56 (d, 6H), 1.45 (d, 6H), 1.12 (t, 3H) |
| A-45 | 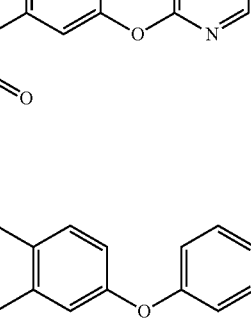 | δ 8.18-8.17 (m, 1H), 7.97 (d, 1H), 7.38 (d, 1H), 7.11 (dd, 1H), 6.89 (d, 1H), 2.50-2.42 (m, 2H), 1.56 (br. d, 6H), 1.45 (br. d, 6H), 1.13 (t, 3H). |
| A-46 | 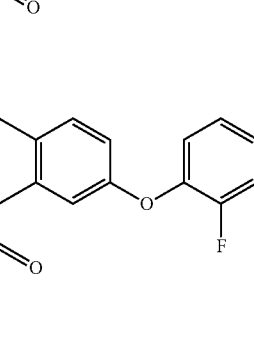 | d₄-MeOH δ 7.36 (t, 1H), 7.27 (d, 1H), 6.90 (m, 2H), 6.81 (m, 1H), 6.62 (d, 1H), 2.44 (m, 6H), 1.18 (s, 3H), 1.15 (s, 3H), 1.09 (t, 3H) |
| A-47 | 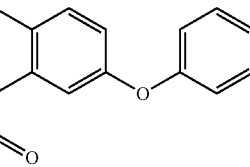 | d₄-MeOH: δ 7.21 (d, 1H), 7.10 (m, 2H), 6.90 (m, 1H), 6.80 (dd, 1H), 6.52 (d, 1H), 2.40 (m, 6H), 1.17 (s, 3H), 1.14 (s, 3H), 1.07 (t, 3H) |
| A-48 | 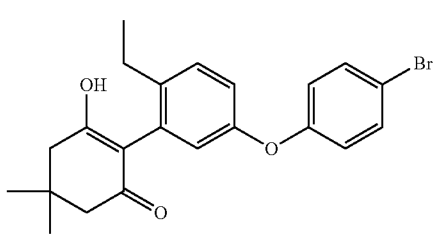 [SMILES: CCc1ccc(Oc2ccc(Br)cc2)cc1C1=C(O)CC(C)(C)CC1=O] | d₄-MeOH: δ 7.45 (d, 2H), 7.26 (d, 1H), 6.95 (m, 3H), 6.60 (d, 1H), 2.44 (m, 6H), 1.20 (s, 3H), 1.18 (s, 3H), 1.12 (t, 3H) |

TABLE T1-continued

| Compound Number | Structure | ¹H NMR (CDCl₃ unless stated) or other physical data |
|---|---|---|
| A-49 | 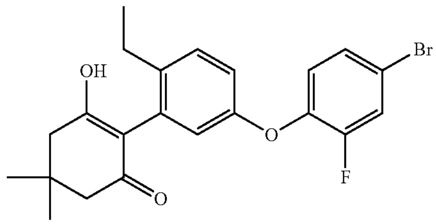 [SMILES: CCc1ccc(Oc2ccc(Br)cc2F)cc1C1=C(O)CC(C)(C)CC1=O] | d₄-MeOH: δ 7.43 (dd, 1H), 7.22 (m, 2H), 7.00 (t, 1H), 6.85 (dd, 1H), 6.56 (d, 1H), 2.40 (m, 6H), 1.17 (s, 3H), 1.14 (s, 3H), 1.08 (t, 3H) |
| A-50 | 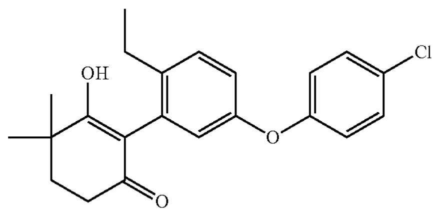 [SMILES: CCc1ccc(Oc2ccc(Cl)cc2)cc1C1=C(O)C(C)(C)CCC1=O] | d₄-MeOH δ 7.26 (d, 2H), 7.22 (d, 1H), 6.98 (d, 2H), 6.88 (dd, 1H), 6.55 (d, 1H), 2.62 (m, 2H), 2.37 (m, 2H), 1.90 (m, 2H), 1.19 (s, 3H), 1.15 (s, 3H), 1.07 (t. 3H) |
| A-51 | 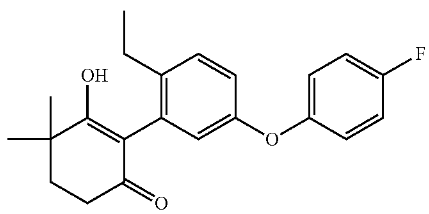 [SMILES: CCc1ccc(Oc2ccc(F)cc2)cc1C1=C(O)C(C)(C)CCC1=O] | d₄-MeOH: δ 7.20 (d, 1H), 7.00 (m, 4H), 6.84 (dd, 1H), 6.51 (d, 1H), 2.60 (m, 2H), 2.35 (m, 2H), 1.92 (m, 2H), 1.19 (s, 3H), 1.14 (s, 3H), 1.06 (t, 3H) |
| A-52 | 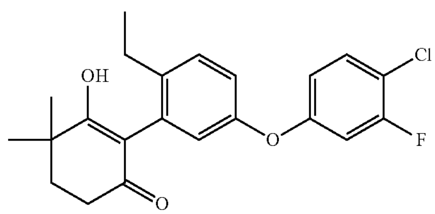 [SMILES: CCc1ccc(Oc2ccc(Cl)c(F)c2)cc1C1=C(O)C(C)(C)CCC1=O] | d₄-MeOH: δ 7.36 (t, 1H), 7.25 (d, 1H), 6.90 (m, 2H), 6.81 (m, 1H), 6.60 (d, 1H), 2.63 (m, 2H), 2.37 (m, 2H), 1.92 (m, 2H), 1.20 (s, 3H), 1.15 (s, 3H), 1.08 (t, 3H) |
| A-53 | 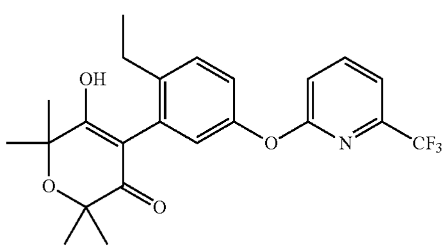 [SMILES: CCc1ccc(Oc2cccc(C(F)(F)F)n2)cc1C1=C(O)C(C)(C)OC(C)(C)C1=O] | δ 7.84 (t, 1H), 7.37 (d, 1H), 7.35 (d, 1H), 7.13 (d, 1H), 7.10 (dd, 1H), 6.92 (d, 1H), 2.49-2.42 (m, 2H), 1.56 (d, 6H), 1.46 (d, 6H), 1.13 (t, 3H). |
| A-54 | 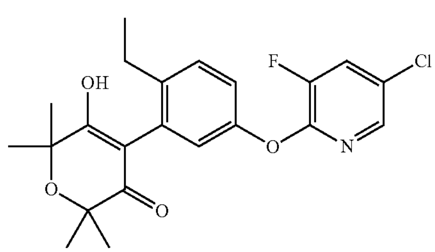 [SMILES: CCc1ccc(Oc2ncc(Cl)cc2F)cc1C1=C(O)C(C)(C)OC(C)(C)C1=O] | δ 7.79 (d, 1H), 7.50 (dd, 1H), 7.34 (d, 1H), 7.11 (dd, 1H), 6.86 (d, 1H), 2.46-2.39 (m, 2H), 1.56 (br. d, 6H), 1.45 (br. d, 6H), 1.11 (t, 3H). |

TABLE T1-continued

| Compound Number | Structure | ¹H NMR (CDCl₃ unless stated) or other physical data |
|---|---|---|
| A-55 | 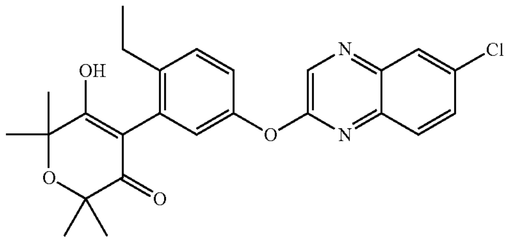 [SMILES: CCc1ccc(Oc2cnc3cc(Cl)ccc3n2)cc1C1=C(O)C(C)(C)OC(C)(C)C1=O] | δ 8.71 (s, 2H), 8.04 (d, 1H), 7.64-7.62 (m, 1H), 7.59-7.56 (m, 1H), 7.40 (d, 1H), 7.16 (dd, 1H), 6.98 (d, 1H), 2.53-2.45 (m, 2H), 1.57 (d, 6H), 1.46 (d, 6H), 1.16 (t, 3H). |
| A-56 | 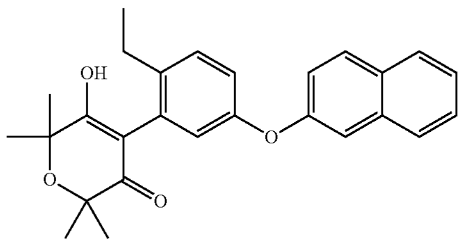 [SMILES: CCc1ccc(Oc2ccc3ccccc3c2)cc1C1=C(O)C(C)(C)OC(C)(C)C1=O] | δ 7.84-7.80 (m, 2H), 7.72 (d, 1H), 7.47-7.43 (m, 1H), 7.42-7.38 (m, 1H), 7.35 (d, 1H), 7.31 (d, 1H), 7.27-7.24 (m, 1H), 7.04 (dd, 1H), 6.83 (d, 1H), 5.73 (br. s, 1H), 2.47-2.39 (m, 2H), 1.58 (d, 6H), 1.47 (d, 6H), 1.12 (t, 3H). |
| A-57 | 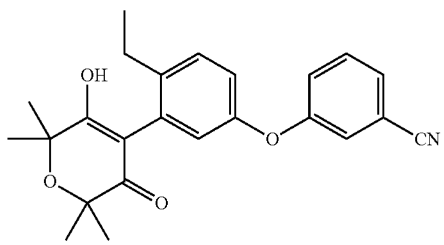 [SMILES: CCc1ccc(Oc2cccc(C#N)c2)cc1C1=C(O)C(C)(C)OC(C)(C)C1=O] | δ 7.43-7.39 (m, 1H), 7.35-7.33 (m, 2H), 7.27-7.26 (m, 1H), 7.24-7.21 (m, 1H), 6.99 (dd, 1H), 6.79 (d, 1H), 2.47-2.39 (m, 2H), 1.58 (d, 6H), 1.46 (d, 6H), 1.12 (t, 3H). |
| A-58 | 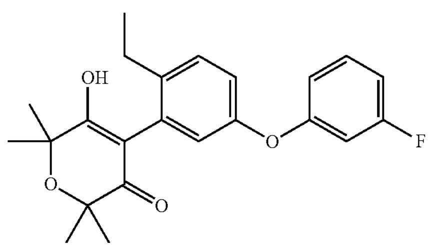 [SMILES: CCc1ccc(Oc2cccc(F)c2)cc1C1=C(O)C(C)(C)OC(C)(C)C1=O] | δ 7.33 (d, 1H), 7.31-7.25 (m, 1H), 7.02 (dd, 1H), 6.82-6.78 (m, 3H), 6.76-6.72 (m, 1H), 5.76 (br. s, 1H), 2.49-2.37 (m, 2H), 1.60 (d, 6H), 1.48 (d, 6H), 1.13 (t, 3H). |
| A-59 | 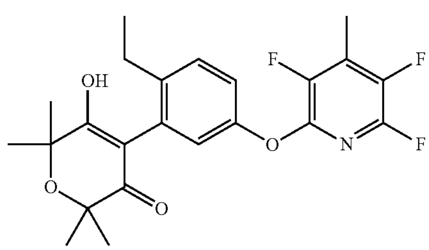 [SMILES: CCc1ccc(Oc2nc(F)c(F)c(C)c2F)cc1C1=C(O)C(C)(C)OC(C)(C)C1=O] | δ 7.34 (d, 1H), 7.06 (dd, 1H), 6.84 (d, 1H), 2.48-2.40 (m, 2H), 2.36 (t, 3H), 1.56 (d, 6H), 1.45 (d, 6H), 1.12 (t, 3H). |
| A-60 | 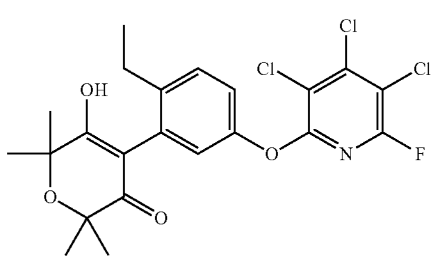 [SMILES: CCc1ccc(Oc2nc(F)c(Cl)c(Cl)c2Cl)cc1C1=C(O)C(C)(C)OC(C)(C)C1=O] | δ 7.39 (d, 1H), 7.10 (dd, 1H), 6.86 (d, 1H), 2.52-2.41 (m, 2H), 1.57 (d, 6H), 1.46 (d, 6H), 1.14 (t, 3H). |

TABLE T1-continued

| Compound Number | Structure | ¹H NMR (CDCl₃ unless stated) or other physical data |
|---|---|---|
| A-61 | 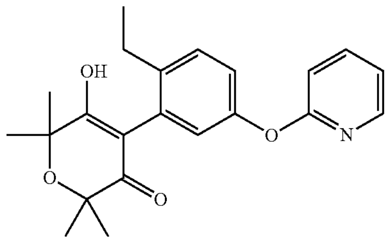 [SMILES: CCc1ccc(Oc2ccccn2)cc1C1=C(O)C(C)(C)OC(C)(C)C1=O] | δ 7.95 (dd, 1H), 7.74-7.70 (m, 1H), 7.34 (d, 1H), 7.04-7.00 (m, 2H), 6.97 (dd, 1H), 6.85 (d, 1H), 2.45 (q, 2H), 1.52-1.44 (br. m, 12H), 1.12 (t, 3H). |
| A-62 | 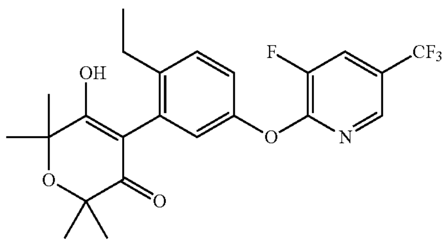 [SMILES: CCc1ccc(Oc2ncc(C(F)(F)F)cc2F)cc1C1=C(O)C(C)(C)OC(C)(C)C1=O] | δ 8.08 (d, 1H), 7.69 (dd, 1H), 7.38 (d, 1H), 7.12 (dd, 1H), 6.90 (d, 1H), 2.50-2.43 (m, 2H), 2.18 (br. s, 1H), 1.57 (d, 6H), 1.45 (d, 6H), 1.14 (t, 3H). |
| A-63 | 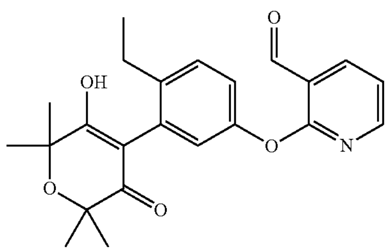 [SMILES: CCc1ccc(Oc2ncccc2C=O)cc1C1=C(O)C(C)(C)OC(C)(C)C1=O] | ™ 10.50 (s, 1H), 8.25 (dd, 1H), 8.18 (dd, 1H), 7.37 (d, 1H), 7.13-7.09 (m, 2H), 6.92 (d, 1H), 2.51-2.43 (br. m, 2H), 1.56 (6d, H), 1.45 (d, 6H), 1.14 (t, 3H). |
| A-64 | 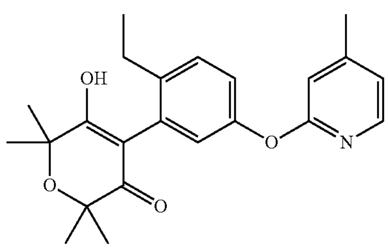 [SMILES: CCc1ccc(Oc2cc(C)ccn2)cc1C1=C(O)C(C)(C)OC(C)(C)C1=O] | δ 7.81-7.80 (m, 1H), 7.52 (dd, 1H), 7.32 (d, 1H), 7.04 (dd, 1H), 6.90 (d, 1H), 6.83 (d, 1H), 2.50-2.39 (m, 2H), 2.25 (s, 3H), 1.56 (d, 6H), 1.46 (d, 6H), 1.12 (t, 3H). |
| A-65 | 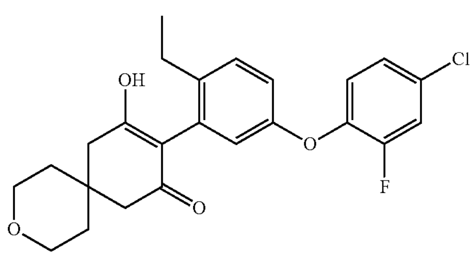 | LCMS (Method A): t$_r$ = 1.59 mins, MH⁺ = 431 |
| A-66 | 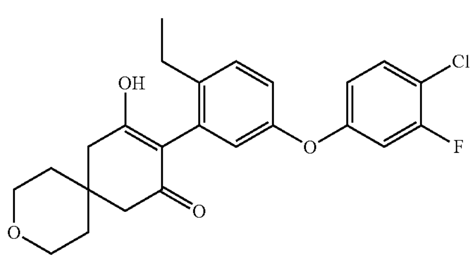 [SMILES: CCc1ccc(Oc2ccc(Cl)c(F)c2)cc1C1=C(O)CC2(CCOCC2)CC1=O] | LCMS (Method A): t$_r$ = 1.60 mins, MH⁺ = 431 |

TABLE T1-continued

| Compound Number | Structure | ¹H NMR (CDCl₃ unless stated) or other physical data |
|---|---|---|
| A-67 | 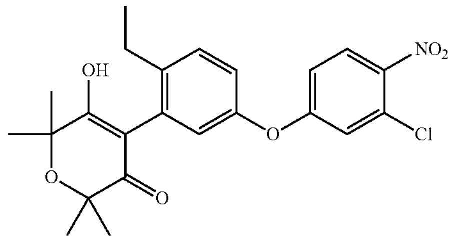 [SMILES: CCc1ccc(Oc2ccc([N+](=O)[O-])c(Cl)c2)cc1C1=C(O)C(C)(C)OC(C)(C)C1=O] | δ 7.95 (d, 1H), 7.40 (d, 1H), 7.11 (d, 1H), 7.07 (dd, 1H), 6.93 (dd, 1H), 6.83 (d, 1H), 5.52 (br. s, 1H), 2.47-2.44 (m, 2H), 1.59 (d, 6H), 1.47 (d, 6H), 1.14 (t, 3H). |
| A-68 | 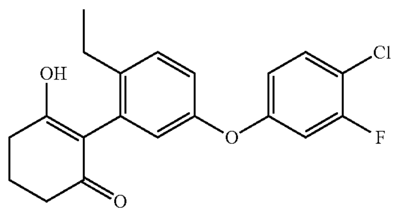 [SMILES: CCc1ccc(Oc2ccc(Cl)c(F)c2)cc1C1=C(O)CCCC1=O] | d₄-MeOH: δ 7.35 (t, 1H), 7.25 (d, 1H), 6.90 (m, 2H), 6.80 (m, 1H), 6.63 (d, 1H), 2.53 (m, 4H), 2.40 (q, 2H), 2.05 (m, 2H), 1.09 (t, 3H) |
| A-69 | 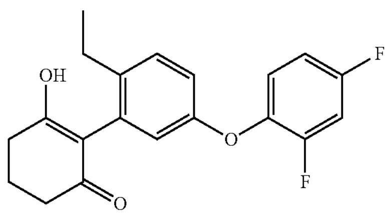 [SMILES: CCc1ccc(Oc2ccc(F)cc2F)cc1C1=C(O)CCCC1=O] | d₄-MeOH: δ 7.20 (d, 1H), 7.15-7.05 (m, 2H), 6.90 (m, 1H), 6.80 (m, 1H), 6.53 (d, 1H), 2.52 (m, 4H), 2.37 (q 2H), 2.05 (m, 2H), 1.07 (t, 3H) |
| A-70 | 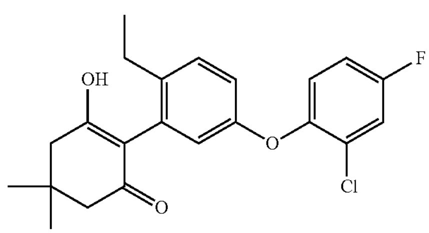 [SMILES: CCc1ccc(Oc2ccc(F)cc2Cl)cc1C1=C(O)CC(C)(C)CC1=O] | d₄-MeOH: δ 7.30 (dd, 1H), 7.21 (d, 1H), 7.10-7.00 (m, 2H), 6.80 (m, 1H), 6.51 (d, 1H), 2.41 (m, 6H), 1.17 (s, 3H), 1.14 (s, 3H), 1.07 (t, 3H) |
| A-71 | 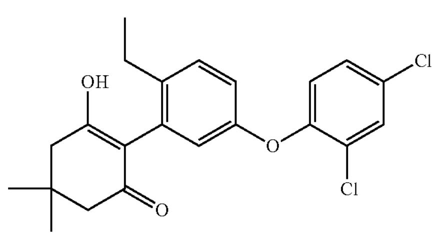 | d₄-MeOH: δ 7.49 (d, 1H), 7.23 (m, 2H), 6.98 (d, 1H), 6.85 (dd, 1H), 6.56 (d, 1H), 2.40 (m, 6H), 1.17 (s, 3H), 1.14 (s, 3H), 1.08 (t, 3H) |
| A-72 | 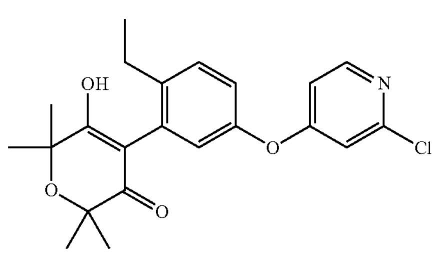 [SMILES: CCc1ccc(Oc2ccnc(Cl)c2)cc1C1=C(O)C(C)(C)OC(C)(C)C1=O] | δ 8.18 (d, 1H), 7.38 (d, 1H), 7.04 (dd, 1H), 6.89 (d, 1H), 6.83 (d, 1H), 6.81 (dd, 1H), 5.36 (br. s, 1H), 2.46 (q, 2H), 1.53 (s, 6H), 1.51 (s, 6H), 1.14 (t, 3H). |

TABLE T1-continued

| Compound Number | Structure | ¹H NMR (CDCl₃ unless stated) or other physical data |
|---|---|---|
| A-73 | 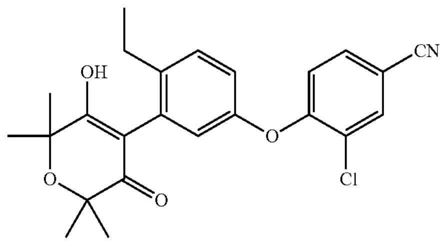 | δ 7.73 (d, 1H), 7.46 (dd, 1H), 7.39 (d, 1H), 7.05 (dd, 1H), 6.96 (d, 1H), 6.83 (d, 1H), 2.45-2.41 (br. m, 2H), 1.56-1.44 (br. m, 1H), 1.13 (t, 3H). |
| A-74 | 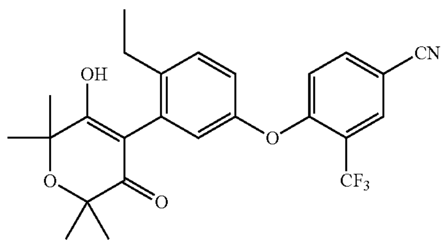 [SMILES: CCc1ccc(Oc2ccc(C#N)cc2Cl)cc1C1=C(O)C(C)(C)OC(C)(C)C1=O] | δ 7.93 (s, 1H), 7.70 (dd, 1H), 7.40 (d, 1H), 7.07 (dd, 1H), 7.01 (d, 1H), 6.86 (d, 1H), 2.51-2.36 (br. m, 2H), 1.56-1.45 (br. m, 12H), 1.13 (t, 3H). |
| A-75 | 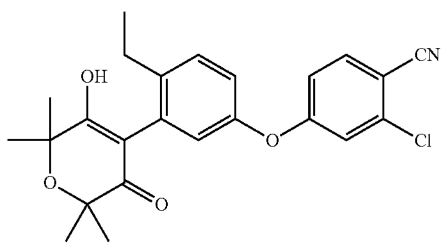 [SMILES: CCc1ccc(Oc2ccc(C#N)c(Cl)c2)cc1C1=C(O)C(C)(C)OC(C)(C)C1=O] | δ 7.58 (dd, 1H), 7.39 (d, 1H), 7.11-7.10 (m, 1H), 7.08-7.05 (m, 1H), 6.94-6.91 (m, 1H), 6.83-6.82 (m, 1H), 3.60 (br. s, 1H), 2.45-2.44 (m, 2H), 1.57-1.45 (m, 12H), 1.15-1.11 (m, 3H). |
| A-76 | 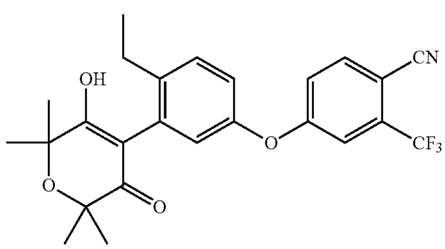 [SMILES: CCc1ccc(Oc2ccc(C#N)c(C(F)(F)F)c2)cc1C1=C(O)C(C)(C)OC(C)(C)C1=O] | δ 7.73 (d, 1H), 7.41-7.39 (m, 2H), 7.14 (dd, 1H), 7.06 (dd, 1H), 6.83 (d, 1H), 5.78 (br. s, 1H), 2.47-2.44 (br. m, 2H), 1.56-1.44 (br. m, 12H), 1.13 (t, 3H). |
| A-77 | 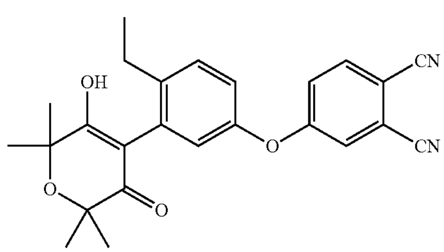 [SMILES: CCc1ccc(Oc2ccc(C#N)c(C#N)c2)cc1C1=C(O)C(C)(C)OC(C)(C)C1=O] | δ 7.70 (d, 1H), 7.40 (d, 1H), 7.34 (d, 1H), 7.27-7.24 (m, 1H), 7.03 (dd, 1H), 6.82 (d, 1H), 6.08 (br. s, 1H), 2.49-2.42 (m, 2H), 1.57 (d, 6H), 1.44 (d, 6H), 1.13 (t, 3H). |
| A-78 | 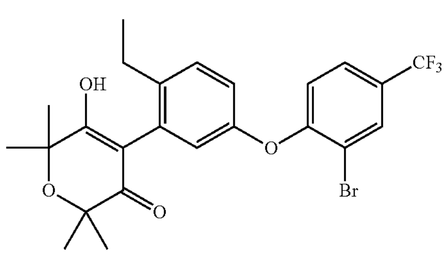 [SMILES: CCc1ccc(Oc2ccc(C(F)(F)F)cc2Br)cc1C1=C(O)C(C)(C)OC(C)(C)C1=O] | δ 7.87 (s, 1H), 7.47 (d, 1H), 7.35 (d, 1H), 7.01 (dd, 1H), 6.97 (d, 1H), 6.83 (d, 1H), 5.63 (br. s, 1H), 2.47-2.39 (m, 2H), 1.58 (d, 6H), 1.46 (d, 6H), 1.12 (t, 3H). |

TABLE T1-continued

| Compound Number | Structure | $^1$H NMR (CDCl$_3$ unless stated) or other physical data |
|---|---|---|
| A-79 | 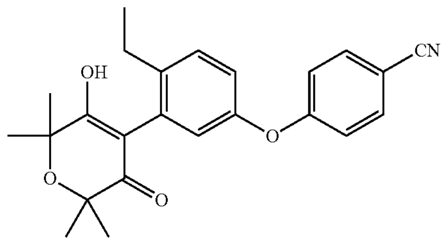 [SMILES: CCc1ccc(Oc2ccc(C#N)cc2)cc1C1=C(O)C(C)(C)OC(C)(C)C1=O] | δ 7.59-7.56 (m, 2H), 7.36 (d, 1H), 7.05-7.01 (m, 3H), 6.81 (d, 1H), 5.72 (br. s, 1H), 2.47-2.40 (m, 2H), 1.57 (d, 6H), 1.45 (d, 6H), 1.12 (t, 3H). |
| A-80 | 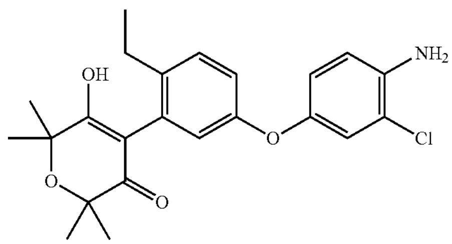 [SMILES: CCc1ccc(Oc2ccc(N)c(Cl)c2)cc1C1=C(O)C(C)(C)OC(C)(C)C1=O] | δ 7.23 (s, 1H), 7.01 (d, 1H), 6.88 (dd, 1H), 6.82-6.79 (m, 1H), 6.74 (d, 1H), 6.69 (d, 1H), 5.59 (br. s, 1H), 3.92 (br. s, 2H), 2.44-2.32 (m, 2H), 1.58 (d, 6H), 1.46 (d, 6H), 1.08 (t, 3H). |
| A-81 | 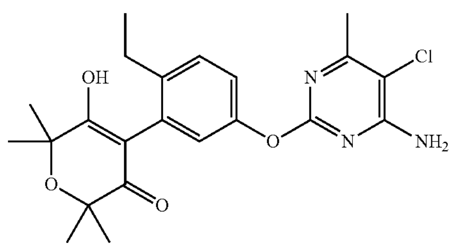 [SMILES: CCc1ccc(Oc2nc(C)c(Cl)c(N)n2)cc1C1=C(O)C(C)(C)OC(C)(C)C1=O] | δ 7.32 (d, 1H), 7.05 (dd, 1H), 6.84 (d, 1H), 6.26 (br. s, 2H), 2.47-2.41 (m, 5H), 1.53 (s, 6H), 1.50 (s, 6H), 1.12 (t, 3H). |
| A-82 | 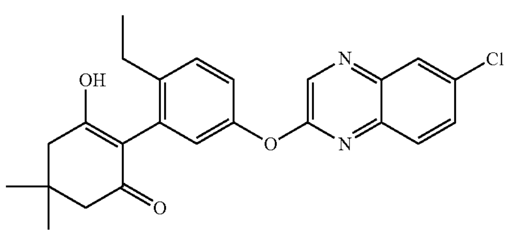 [SMILES: CCc1ccc(Oc2cnc3cc(Cl)ccc3n2)cc1C1=C(O)CC(C)(C)CC1=O] | d$_4$-MeOH: δ 8.73 (s, 1H), 8.03 (m, 1H), 7.70 (m, 2H), 7.37 (d, 1H), 7.19 (dd, 1H), 6.87 (d, 1H), 2.40-2.50 (m, 6H), 1.10-1.20 (m, 9H) |
| A-83 | 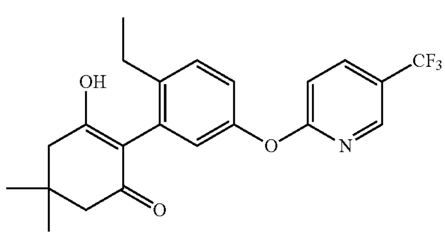 [SMILES: CCc1ccc(Oc2ccc(C(F)(F)F)cn2)cc1C1=C(O)CC(C)(C)CC1=O] | d$_4$-MeOH: δ 8.40 (s, 1H), 8.05 (m, 1H), 7.33 (d, 1H), 7.12 (d, 1H), 7.04 (dd, 1H), 6.74 (d, 1H), 2.40-2.50 (m, 6H), 1.10-1.20 (m, 9H) |
| A-84 | 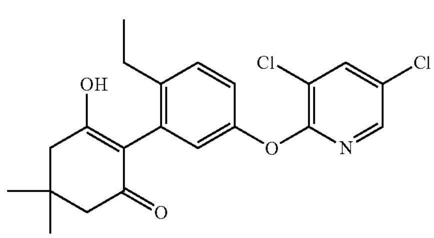 [SMILES: CCc1ccc(Oc2ncc(Cl)cc2Cl)cc1C1=C(O)CC(C)(C)CC1=O] | d$_4$-MeOH: δ 8.02 (d, 1H), 7.96 (d, 1H), 7.30 (d, 1H), 7.00 (dd, 1H), 6.70 (d, 1H), 2.45 (m, 6H), 1.18 (s, 3H), 1.15 (s, 3H), 1.11 (t, 3H) |

TABLE T1-continued

| Compound Number | Structure | ¹H NMR (CDCl₃ unless stated) or other physical data |
|---|---|---|
| A-85 | 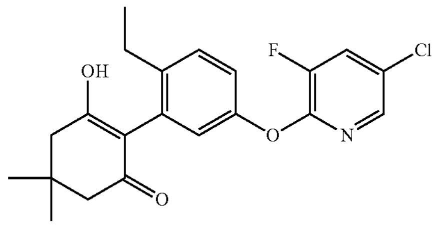 [SMILES: CCc1ccc(Oc2ncc(Cl)cc2F)cc1C1=C(O)CC(C)(C)CC1=O] | d₄-MeOH: δ 7.88 (d, 1H), 7.85 (dd, 1H), 7.33 (d, 1H), 7.07 (dd, 1H), 6.77 (d, 1H), 2.45 (m, 6H), 1.21 (s, 3H), 1.18 (s, 3H), 1.14 (t, 3H) |
| A-86 | 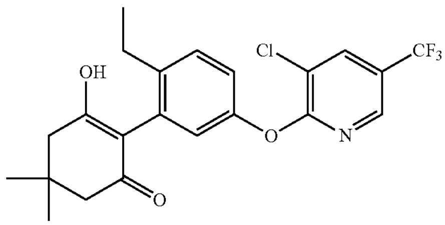 [SMILES: CCc1ccc(Oc2ncc(C(F)(F)F)cc2Cl)cc1C1=C(O)CC(C)(C)CC1=O] | d₄-MeOH: 8.29 (d, 1H), 8.26 (d, 1H), 7.35 (d, 1H), 7.08 (dd, 1H), 6.80 (d, 1H), 2.40-2.50 (m, 6H), 1.10-1.20 (m, 9H) |
| A-87 | 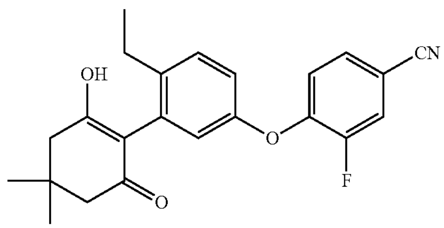 [SMILES: CCc1ccc(Oc2ccc(C#N)cc2F)cc1C1=C(O)CC(C)(C)CC1=O] | d₄-MeOH: 7.65 (d, 1H), 7.45 (d, 1H), 7.30 (d, 1H), 7.10 (t, 1H), 6.96 (dd, 1H), 6.67 (d, 1H), 2.44 (m, 6H), 1.18 (s, 3H), 1.15 (s, 3H), 1.10 (t, 3H) |
| A-88 | 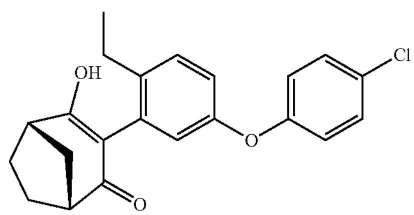 [SMILES: CCc1ccc(Oc2ccc(Cl)cc2)cc1C1=C(O)[C@H]2CC[C@H](C2)C1=O] | d₄-MeOH δ 7.30 (m, 2H, isomers A and B), 7.23 (m, 1H, isomers A and B), 7.00 (m, 2H, isomers A and B), 6.89 (m, 1H, isomers A and B), 6.62 (d, 0.6H, isomer A), 6.56 (d, 0.4H, isomer B), 3.00 (m, 2H, isomers A and B), 2.46 (q, 0.8H, isomer B), 2.33 (q, 1.2H, isomer A), 2.20 (m, 3H, isomers A and B), 1.85 (m, 2H, isomers A and B), 1.70 (m, 1H. isomers A and B), 1.10 (m, 3H, isomers A and B) |
| A-89 | 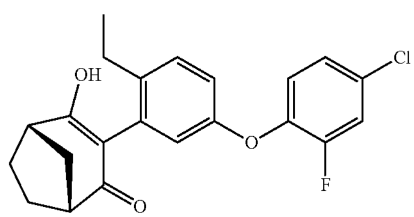 [SMILES: CCc1ccc(Oc2ccc(Cl)cc2F)cc1C1=C(O)[C@H]2CC[C@H](C2)C1=O] | d₄-MeOH: δ 7.28 (m, 1H, isomers A and B), 7.20 (m, 1H, isomers A and B), 7.00-7.12 (m, 2H, isomers A and B), 6.83 (m, 1H, isomers A and B), 6.56 (d, 0.6H, isomer A), 6.52 (d, 0.4H, isomer B), 2.96 (br. s, 2H, isomers A and B), 2.44 (q, 0.8H, isomer B), 2.30 (q, 1.2H, isomer A), 2.20 (m, 3H, isomers A and B), 1.80 (m, 2H, isomers A and B), 1.68 (m, 1H, isomers A and B), 1.05 (m, 3H, isomers A and B). |
| A-90 | 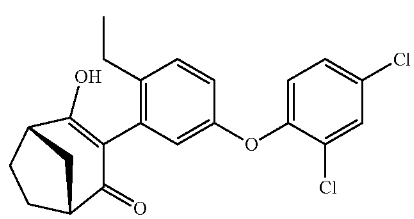 [SMILES: CCc1ccc(Oc2ccc(Cl)cc2Cl)cc1C1=C(O)[C@H]2CC[C@H](C2)C1=O] | d₄-MeOH: δ 7.50 (m, 1H, isomers A and B), 7.22 (m, 2H, isomers A and B), 6.98 (m, 1H, isomers A and B), 6.82 (m, 1H, isomers A and B), 6.56 (d, 0.6H, isomer A), 6.52 (d, 0.4H, isomer B), 2.97 (br. s, 2H, isomers A and B), 2.44 (q, 0.8H, isomer B), 2.30 (q, 1.2H, isomer A), 2.20 (m, 3H, isomers A and B), 1.80 (m, 2H, isomers A and B), 1.67 (m, 1H, isomers A and B), 1.05 (m, 3H, isomers A and B). |

TABLE T1-continued

| Compound Number | Structure | $^1$H NMR (CDCl$_3$ unless stated) or other physical data |
|---|---|---|
| A-91 | 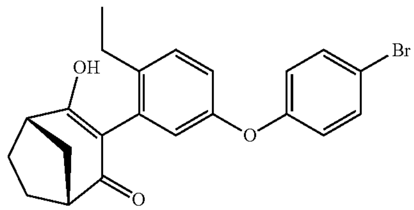 [SMILES: CCc1ccc(Oc2ccc(Br)cc2)cc1C1=C(O)[C@H]2CC[C@H](C2)C1=O] | d$_4$-MeOH: δ 7.40 (m, 2H, isomers A and B), 7.20 (m, 1H, isomers A and B), 6.90 (m, 3H, isomers A and B), 6.59 (d, 0.6H, isomer A), 6.53 (d, 0.4H, isomer B), 2.96 (br. s, 2H, isomers A and B), 2.44 (q, 0.8H, isomer B), 2.30 (q, 1.2H, isomer A), 2.15 (m, 3H, isomers A and B), 1.80 (m, 2H, isomers A and B), 1.65 (m, 1H, isomers A and B), 1.05 (m, 3H, isomers A and B). |
| A-92 | 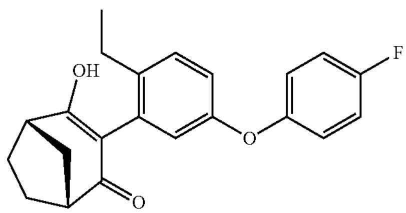 [SMILES: CCc1ccc(Oc2ccc(F)cc2)cc1C1=C(O)[C@H]2CC[C@H](C2)C1=O] | d$_4$-MeOH: δ 7.20 (m, 1H, isomers A and B), 7.00 (m, 4H, isomers A and B), 6.82 (m, 1H, isomers A and B), 6.55 (d, 0.6H, isomer A), 6.50 (d, 0.4H, isomer B), 2.96 (br. s, 2H, isomers A and B), 2.43 (q, 0.8H, isomer B), 2.30 (q, 1.2H, isomer A), 2.18 (m, 3H, isomers A and B), 1.80 (m, 2H, isomers A and B), 1.68 (m, 1H, isomers A and B), 1.05 (m, 3H, isomers A and B). |
| A-93 | 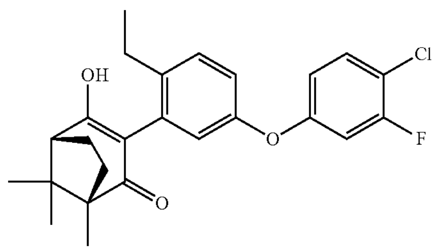 [SMILES: CCc1ccc(Oc2ccc(Cl)c(F)c2)cc1C1=C(O)[C@@H]2CC[C@](C)(C1=O)C2(C)C] | d$_4$-MeOH δ 7.35-7.20 (m, 2H, isomers A and B), 6.92-6.75 (m, 3H, isomers A and B), 6.63 (d, 0.65H, isomer A), 6.55 (d, 0.35H, isomer B), 2.55-2.30 (m, 4H, isomers A and B), 2.05-1.90 (m, 1H, isomers A and B), 1.80-1.70 (m, 2H, isomers A and B), 1.15-0.95 (m, 12H, isomers A and B). |
| A-94 | 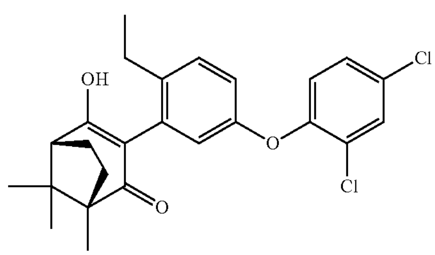 [SMILES: CCc1ccc(Oc2ccc(Cl)cc2Cl)cc1C1=C(O)[C@@H]2CC[C@](C)(C1=O)C2(C)C] | d$_4$-MeOH: δ 7.50 (m, 1H, isomers A and B), 7.22 (m, 2H, isomers A and B), 7.00 (m, 1H, isomers A and B), 6.83 (m, 1H, isomers A and B), 6.58 (d, 0.65H, isomer A), 6.51 (d, 0.35H, isomer B), 2.55-2.30 (m, 4H, isomers A and B), 2.05-1.90 (m, 1H, isomers A and B), 1.80-1.70 (m, 2H, isomers A and B), 1.15-0.95 (m, 12H, isomers A and B). |
| A-95 | 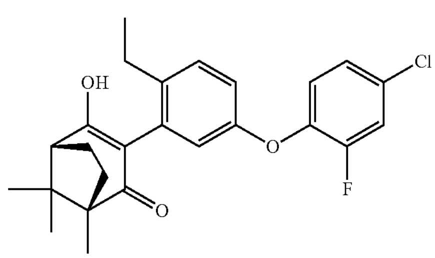 [SMILES: CCc1ccc(Oc2ccc(Cl)cc2F)cc1C1=C(O)[C@@H]2CC[C@](C)(C1=O)C2(C)C] | d$_4$-MeOH: δ 7.28 (m, 1H, isomers A and B), 7.22 (m, 1H, isomers A and B), 7.12-7.00 (m, 2H, isomers A and B), 6.82 (m, 1H, isomers A and B), 6.60 (d, 0.65H, isomer A), 6.52 (d, 0.35H, isomer B), 2.53 (m, 1H, isomers A and B), 2.50-2.28 (m, 3H, isomers A and B), 2.05-1.90 (m, 1H, isomers A and B), 1.80-1.70 (m, 2H, isomers A and B), 1.15-1.00 (m, 12H, isomers A and B). |
| A-96 | 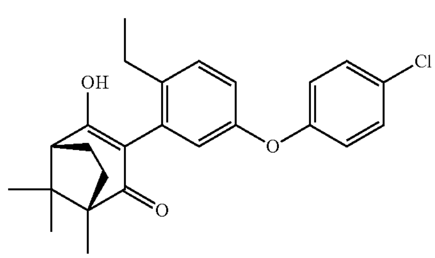 [SMILES: CCc1ccc(Oc2ccc(Cl)cc2)cc1C1=C(O)[C@@H]2CC[C@](C)(C1=O)C2(C)C] | d$_4$-MeOH: δ 7.30-7.00 (m, 3H, isomers A and B), 6.96 (m, 2H, isomers A and B), 6.86 (m, 1H, isomers A and B), 6.60 (d, 0.65H, isomer A), 6.51 (d, 0.35H, isomer B), 2.54 (m, 1H, isomers A and B), 2.50-2.28 (m, 3H, isomers A and B), 2.05-1.90 (m, 1H, isomers A and B), 1.80-1.68 (m, 2H, isomers A and B), 1.15-1.00 (m, 12H, isomers A and B). |

TABLE T1-continued

| Compound Number | Structure | ¹H NMR (CDCl₃ unless stated) or other physical data |
|---|---|---|
| A-97 | 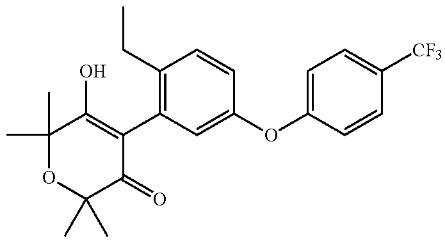 | δ 7.56 (d, 2H), 7.34 (d, 1H), 7.05 (d, 2H), 7.02 (dd, 1H), 6.81 (d, 1H), 5.70 (br. s, 1H), 2.47-2.39 (m, 2H), 1.57 (d, 6H), 1.46 (d, 6H), 1.12 (t, 3H). |
| A-98 | 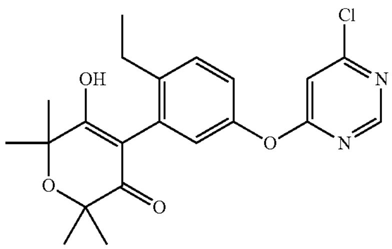 [SMILES: CCc1ccc(Oc2cc(Cl)ncn2)cc1C1=C(O)C(C)(C)OC(C)(C)C1=O] | δ 8.49 (s, 1H), 7.39 (d, 1H), 7.08 (dd, 1H), 7.02 (s, 1H), 6.86 (d, 1H), 2.51-2.43 (m, 2H), 1.58 (d, 6H), 1.46 (d, 6H), 1.14 (t, 3H). |
| A-99 | 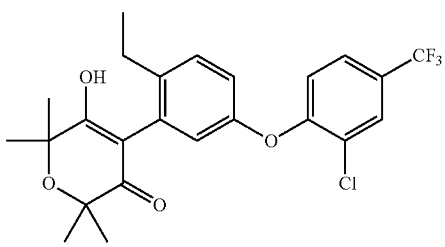 | δ 7.71 (s, 1H), 7.44-7.42 (m, 1H), 7.35 (d, 1H), 7.00 (dd, 2H), 6.82 (d, 1H), 5.63 (s, 1H), 2.47-2.39 (m, 2H), 1.58 (d, 6H), 1.46 (d, 6H), 1.12 (t, 3H). |
| A-100 | 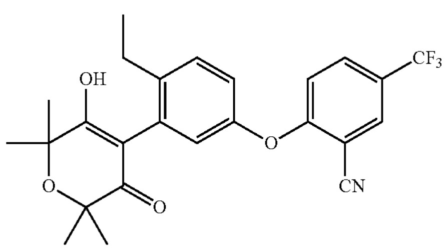 | δ 7.86 (d, 1H), 7.70 (dd, 1H), 7.39 (d, 1H), 7.09-7.05 (m, 2H), 6.89 (d, 1H), 6.12 (br. s, 1H), 2.51-2.42 (m, 2H), 1.57 (d, 6H), 1.45 (d, 6H), 1.13 (t, 3H) |
| A-101 | 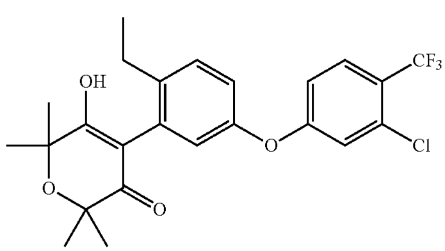 | δ 7.60 (d, 1H), 7.37 (d, 1H), 7.12 (d, 1H), 7.05 (dd, 1H), 6.82 (d, 1H), 6.91 (dd, 1H), 5.65 (br. s, 1H), 2.46-2.42 (br. m, 2H), 1.59 (br. d, 6H), 1.47 (br. d, 6H), 1.13 (t, 3H). |
| A-102 | 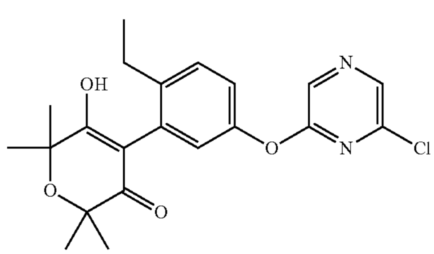 [SMILES: CCc1ccc(Oc2cncc(Cl)n2)cc1C1=C(O)C(C)(C)OC(C)(C)C1=O] | δ 8.33 (s, 1H), 8.26 (s, 1H), 7.39 (d, 1H), 7.12 (dd, 1H), 6.89 (d, 1H), 2.50-2.43 (m, 2H), 1.58 (d, 6H), 1.46 (d, 6H), 1.14 (t, 3H). |

TABLE T1-continued

| Compound Number | Structure | ¹H NMR (CDCl₃ unless stated) or other physical data |
|---|---|---|
| A-103 | 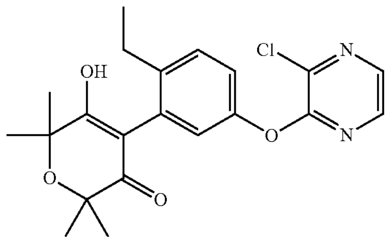 [SMILES: CCc1ccc(Oc2nccnc2Cl)cc1C1=C(O)C(C)(C)OC(C)(C)C1=O] | δ 8.05 (d, 1H), 7.90 (d, 1H), 7.39 (d, 1H), 7.14 (dd, 1H), 6.91 (d, 1H), 2.53-2.40 (m, 2H), 1.57 (d, 6H), 1.46 (d, 6H), 1.14 (t, 3H). |
| A-104 | 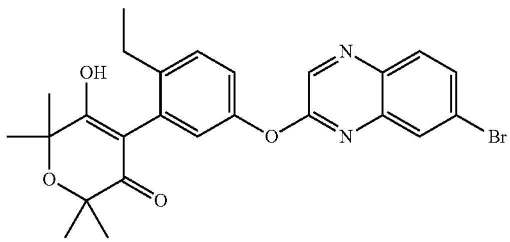 [SMILES: CCc1ccc(Oc2cnc3ccc(Br)cc3n2)cc1C1=C(O)C(C)(C)OC(C)(C)C1=O] | δ 8.72 (s, 1H), 7.93 (d, 1H), 7.90 (d, 1H), 7.71 (dd, 1H), 7.43 (d, 1H), 7.22 (dd, 1H), 6.99 (d, 1H), 2.51-2.47 (br. m, 2H), 1.55-1.46 (br. m, 12H), 1.17 (t, 3H). |
| A-105 | 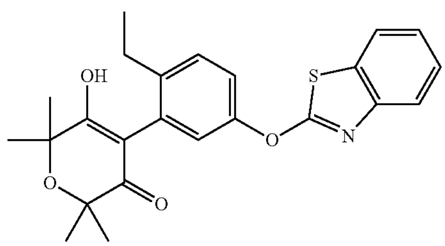 [SMILES: CCc1ccc(Oc2nc3ccccc3s2)cc1C1=C(O)C(C)(C)OC(C)(C)C1=O] | δ 7.71-7.67 (m, 1H), 7.59-7.56 (m, 1H), 7.42-7.36 (m, 2H), 7.31-7.23 (m, 2H), 7.07-7.06 (m, 1H), 2.54-2.46 (m, 2H), 1.61-1.57 (m, 6H), 1.50-1.46 (m, 6H), 1.19-1.14 (m, 3H). |
| A-106 | 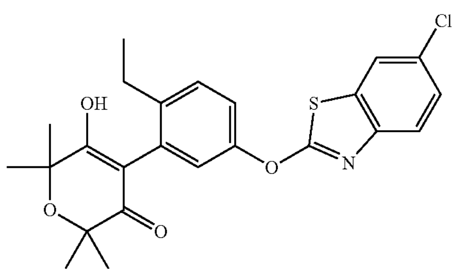 [SMILES: CCc1ccc(Oc2nc3ccc(Cl)cc3s2)cc1C1=C(O)C(C)(C)OC(C)(C)C1=O] | δ 7.65 (d, 1H), 7.49 (d, 1H), 7.40 (d, 1H), 7.32 (dd, 1H), 7.27-7.24 (m, 1H), 7.05 (d, 1H), 2.53-2.42 (m, 2H), 1.58 (d, 6H), 1.46 (d, 6H), 1.14 (t, 3H). |
| A-107 | 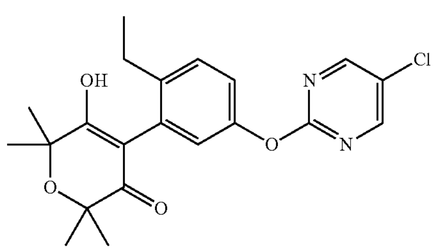 [SMILES: CCc1ccc(Oc2ncc(Cl)cn2)cc1C1=C(O)C(C)(C)OC(C)(C)C1=O] | δ 8.46 (s, 2H), 7.39 (d, 1H), 7.15 (dd, 1H), 6.90 (d, 1H), 2.47-2.44 (br. m, 2H), 1.57-1.45 (br. m, 12H), 1.14 (t, 3H). |
| A-108 | 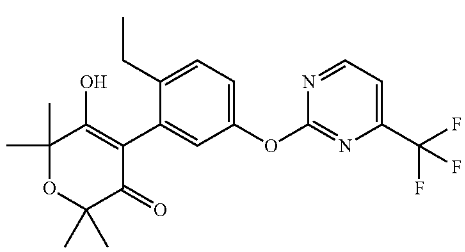 [SMILES: CCc1ccc(Oc2nccc(C(F)(F)F)n2)cc1C1=C(O)C(C)(C)OC(C)(C)C1=O] | δ 8.76 (d, 1H), 7.40 (d, 1H), 7.36 (d, 1H), 7.19 (dd, 1H), 6.96 (d, 1H), 2.52-2.42 (m, 2H), 1.58 (d, 6H), 1.46 (d, 6H), 1.15 (t, 3H). |

TABLE T1-continued

| Compound Number | Structure | ¹H NMR (CDCl₃ unless stated) or other physical data |
| --- | --- | --- |
| A-109 | 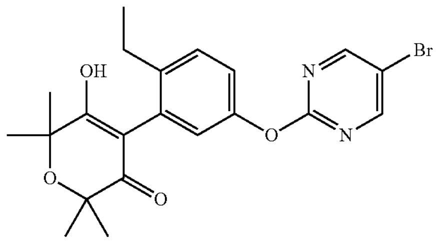 [SMILES: CCc1ccc(Oc2ncc(Br)cn2)cc1C1=C(O)C(C)(C)OC(C)(C)C1=O] | δ 8.53 (s, 2H), 7.38 (d, 1H), 7.13 (dd, 1H), 6.89 (d, 1H), 2.49-2.42 (m, 2H), 1.57 (d, 6H), 1.46 (d, 6H), 1.13 (t, 3H). |
| A-110 | 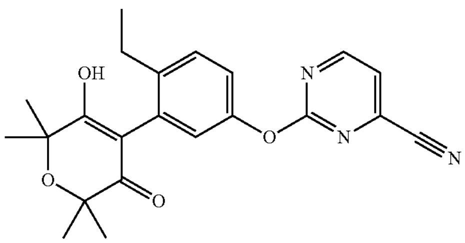 [SMILES: CCc1ccc(Oc2nccc(C#N)n2)cc1C1=C(O)C(C)(C)OC(C)(C)C1=O] | δ 8.77 (d, 1H), 7.41 (d, 1H), 7.37 (d, 1H), 7.17 (d, 1H), 6.92 (s, 1H), 4.12 (br. s, 1H), 2.47 (q, 2H), 1.53 (br. d, 12H), 1.15 (t, 3H). |
| A-111 | 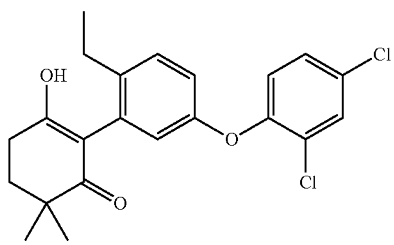 [SMILES: CCc1ccc(Oc2ccc(Cl)cc2Cl)cc1C1=C(O)CCC(C)(C)C1=O] | d₄-MeOH: δ 7.48 (m, 1H), 7.20 (m, 2H), 6.97 (m, 1H), 6.82 (m, 1H), 6.55 (d, 1H), 2.61 (m, 2H), 2.36 (m, 2H), 1.90 (m, 2H), 1.19 (s, 3H), 1.14 (s, 3H), 1.07 (t, 3H) |
| A-112 | 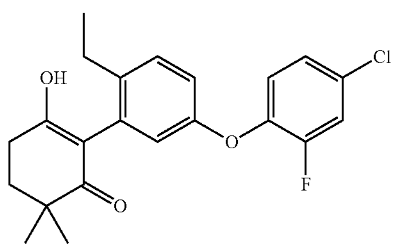 [SMILES: CCc1ccc(Oc2ccc(Cl)cc2F)cc1C1=C(O)CCC(C)(C)C1=O] | d₄-MeOH: δ 7.29 (dd, 1H), 7.21 (d, 1H), 7.10-7.00 (m, 2H), 6.84 (m, 1H), 6.55 (d, 1H), 2.61 (m, 2H), 2.35 (m, 2H), 1.90 (m, 2H), 1.19 (s, 3H), 1.14 (s, 3H), 1.06 (t, 3H) |
| A-113 | 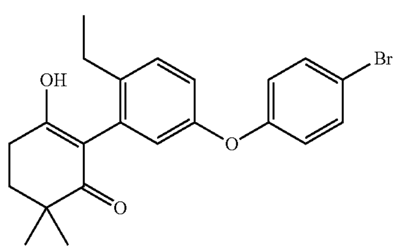 [SMILES: CCc1ccc(Oc2ccc(Br)cc2)cc1C1=C(O)CCC(C)(C)C1=O] | d₄-MeOH: δ 7.45 (m, 2H), 7.25 (d, 1H), 7.00-6.85 (m, 3H), 6.57 (d, 1H), 2.62 (m, 2H), 2.38 (m, 2H), 1.92 (m, 2H), 1.30-1.00 (m, 12H) |
| A-114 | 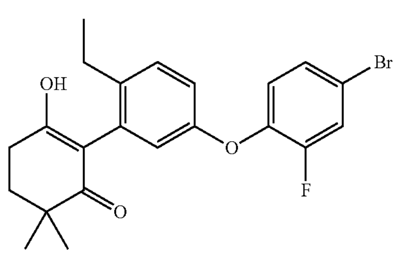 [SMILES: CCc1ccc(Oc2ccc(Br)cc2F)cc1C1=C(O)CCC(C)(C)C1=O] | d₄-MeOH: δ 7.40 (dd, 1H), 7.22 (m, 2H), 7.00 (t, 1H), 6.85 (m, 1H), 6.55 (d, 1H), 2.62 (m, 2H), 2.35 (m, 2H), 1.91 (m, 2H), 1.19 (s, 3H), 1.15 (s, 3H), 1.06 (t, 3H) |

TABLE T1-continued

| Compound Number | Structure | $^1$H NMR (CDCl$_3$ unless stated) or other physical data |
|---|---|---|
| A-115 | 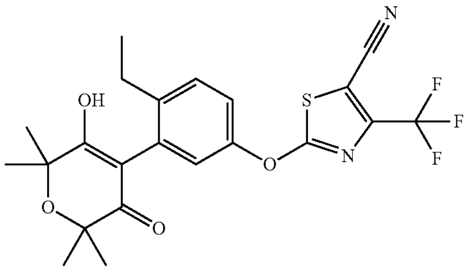 [SMILES: CCc1ccc(Oc2nc(C(F)(F)F)c(C#N)s2)cc1C1=C(O)C(C)(C)OC(C)(C)C1=O] | d$_6$-DMSO: δ 7.43-7.37 (m, 2H), 7.09-7.08 (m, 1H), 2.39 (q, 2H), 1.42 (br. app. s, 12H), 1.06 (t, 3H). |
| A-116 | 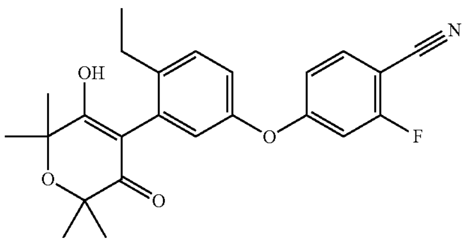 [SMILES: CCc1ccc(Oc2ccc(C#N)c(F)c2)cc1C1=C(O)C(C)(C)OC(C)(C)C1=O] | LCMS (Method A): t$_r$ = 1.73 mins, MH$^+$ = 410 |
| A-117 | 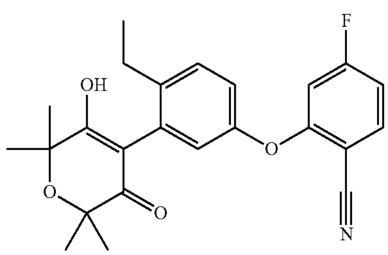 [SMILES: CCc1ccc(Oc2cc(F)ccc2C#N)cc1C1=C(O)C(C)(C)OC(C)(C)C1=O] | LCMS (Method A): t$_r$ = 1.73 mins, MH$^+$ = 410 |
| A-118 | 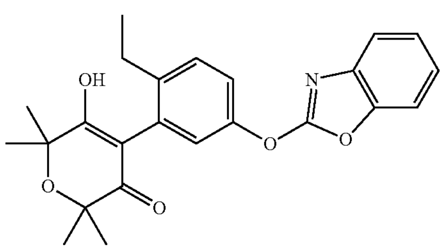 [SMILES: CCc1ccc(Oc2nc3ccccc3o2)cc1C1=C(O)C(C)(C)OC(C)(C)C1=O] | d$_4$-MeOH: δ 7.52-7.50 (m, 1H), 7.45 (d, 1H), 7.40-7.39 (m, 1H), 7.33 (dd, 1H), 7.30-7.28 (m, 2H), 7.06 (d, 1H), 2.49 (2q, H), 1.50 (s, 6H), 1.49 (s, 6H), 1.15 (t, 3H). |
| A-119 | 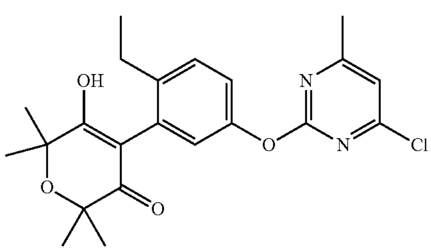 [SMILES: CCc1ccc(Oc2nc(C)cc(Cl)n2)cc1C1=C(O)C(C)(C)OC(C)(C)C1=O] | LCMS (Method B): t$_r$ = 1.59 mins, MH$^+$ = 417.2 |
| A-120 | 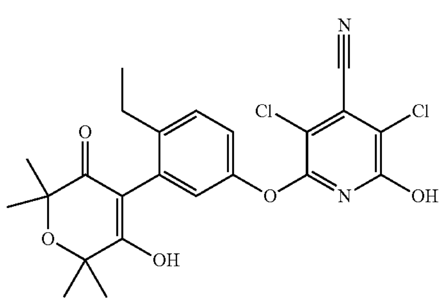 [SMILES: CCc1ccc(Oc2nc(O)c(Cl)c(C#N)c2Cl)cc1C1=C(O)C(C)(C)OC(C)(C)C1=O] | LCMS (Method B): t$_r$ = 1.79 mins, MH$^+$ = 477.0 |

TABLE T1-continued

| Compound Number | Structure | ¹H NMR (CDCl₃ unless stated) or other physical data |
|---|---|---|
| A-121 | 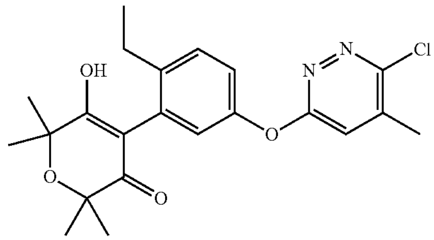 [SMILES: CCc1ccc(Oc2cc(C)c(Cl)nn2)cc1C1=C(O)C(C)(C)OC(C)(C)C1=O] | LCMS (Method B): $t_r$ = 1.61 mins, MH⁺ = 417.2 |
| A-122 | 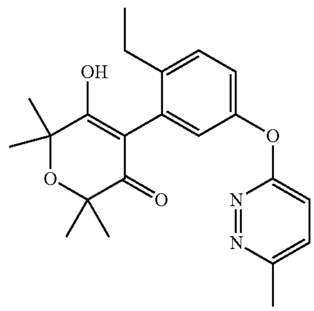 [SMILES: CCc1ccc(Oc2ccc(C)nn2)cc1C1=C(O)C(C)(C)OC(C)(C)C1=O] | LCMS (Method B): $t_r$ = 1.35 mins, MH⁺ = 383.2 |
| A-123 | 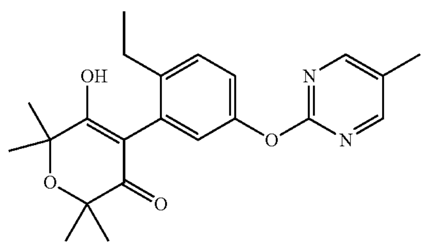 | LCMS (Method B): $t_r$ = 1.47 mins, MH⁺ = 383.2 |
| A-124 | 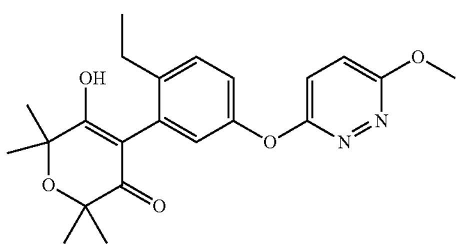 | LCMS (Method B): $t_r$ = 1.53 mins, MH⁺ = 399.2 |
| A-125 | 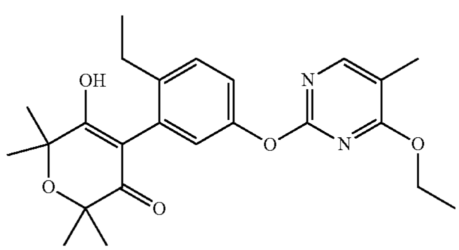 [SMILES: CCOc1nc(Oc2ccc(CC)c(C3=C(O)C(C)(C)OC(C)(C)C3=O)c2)ncc1C] | LCMS (Method B): $t_r$ = 1.72 mins, MH⁺ = 427.2 |
| A-126 | 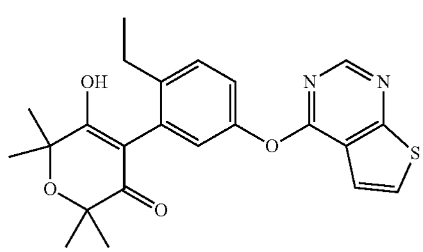 [SMILES: CCc1ccc(Oc2ncnc3sccc23)cc1C1=C(O)C(C)(C)OC(C)(C)C1=O] | LCMS (Method B): $t_r$ = 1.63 mins, MH⁺ = 425.1 |

TABLE T1-continued
| Compound Number | Structure | ¹H NMR (CDCl₃ unless stated) or other physical data |
|---|---|---|
| A-127 | 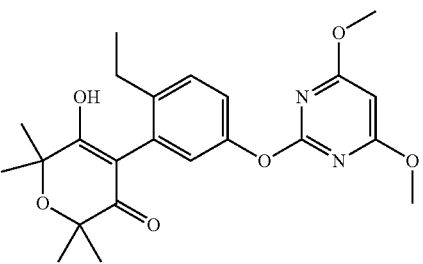 | LCMS (Method B): $t_r$ = 1.62 mins, MH⁺ = 429.2 |
| A-128 | 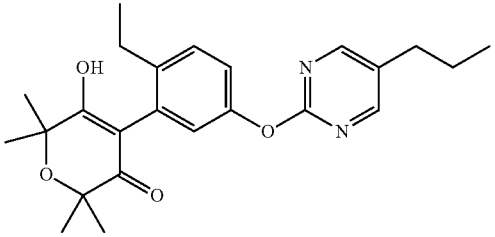 [SMILES: CCCc1cnc(Oc2ccc(CC)c(C3=C(O)C(C)(C)OC(C)(C)C3=O)c2)nc1] | LCMS (Method B): $t_r$ = 1.64 mins, MH⁺ = 411.2 |
| A-129 | 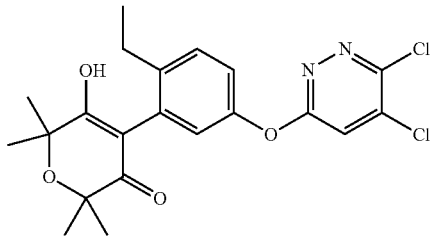 [SMILES: CCc1ccc(Oc2cc(Cl)c(Cl)nn2)cc1C1=C(O)C(C)(C)OC(C)(C)C1=O] | LCMS (Method B): $t_r$ = 1.62 mins, MH⁺ = 437.1 |
| A-130 | 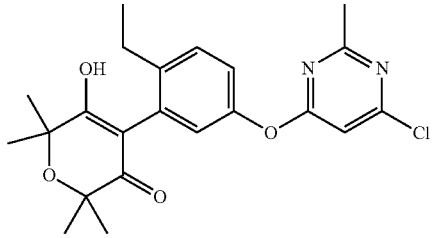 [SMILES: CCc1ccc(Oc2cc(Cl)nc(C)n2)cc1C1=C(O)C(C)(C)OC(C)(C)C1=O] | LCMS (Method B): $t_r$ = 1.62 mins, MH⁺ = 417.2 |
| A-131 | 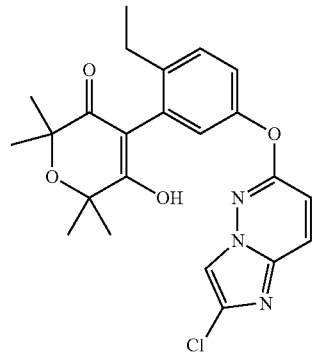 [SMILES: CCc1ccc(Oc2ccc3nc(Cl)cn3n2)cc1C1=C(O)C(C)(C)OC(C)(C)C1=O] | LCMS (Method B): $t_r$ = 1.61 mins, MH⁺ = 442.1 |

TABLE T1-continued

| Compound Number | Structure | ¹H NMR (CDCl₃ unless stated) or other physical data |
|---|---|---|
| A-132 | 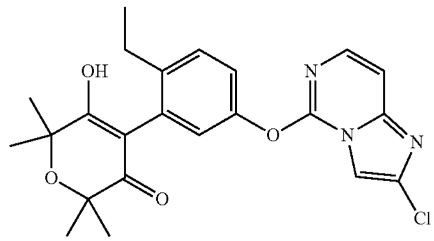 [SMILES: CCc1ccc(Oc2nccc3nc(Cl)cn23)cc1C1=C(O)C(C)(C)OC(C)(C)C1=O] | LCMS (Method B): $t_r$ = 1.58 mins, MH⁺ = 442.1 |
| A-133 | 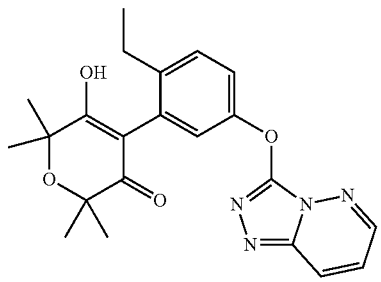 [SMILES: CCc1ccc(Oc2nnc3cccnn23)cc1C1=C(O)C(C)(C)OC(C)(C)C1=O] | LCMS (Method B): $t_r$ = 1.36 mins, MH⁺ = 409.2 |
| A-134 | 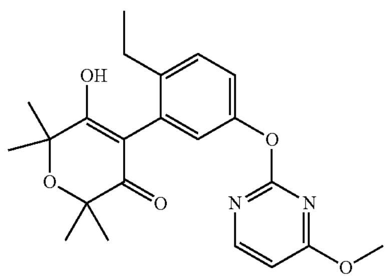 | LCMS (Method B): $t_r$ = 1.53 mins, MH⁺ = 399.2 |
| A-135 | 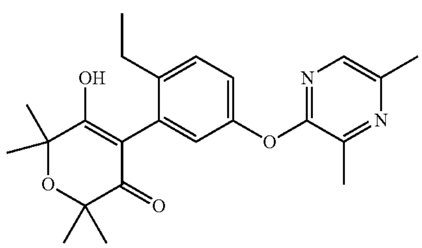 | LCMS (Method B): $t_r$ = 1.55 mins, MH⁺ = 397.2 |
| A-136 | 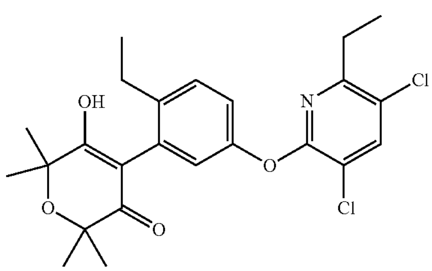 [SMILES: CCc1ccc(Oc2nc(CC)c(Cl)cc2Cl)cc1C1=C(O)C(C)(C)OC(C)(C)C1=O] | LCMS (Method B): $t_r$ = 2.05 mins, MH⁺ = 464.0 |
| A-137 | 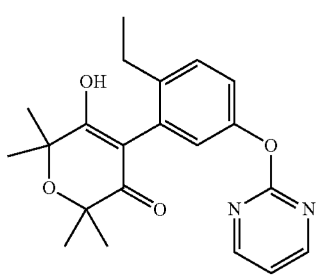 [SMILES: CCc1ccc(Oc2ncccn2)cc1C1=C(O)C(C)(C)OC(C)(C)C1=O] | LCMS (Method B): $t_r$ = 1.40 mins, MH⁺ = 369.2 |

TABLE T1-continued

| Compound Number | Structure | ¹H NMR (CDCl₃ unless stated) or other physical data |
|---|---|---|
| A-138 | 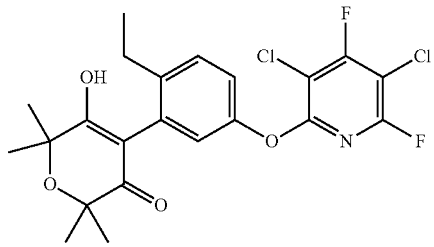 [SMILES: CCc1ccc(Oc2nc(F)c(Cl)c(F)c2Cl)cc1C1=C(O)C(C)(C)OC(C)(C)C1=O] | LCMS (Method B): $t_r$ = 1.68 mins, MH⁺ = 472.1 |
| A-139 | 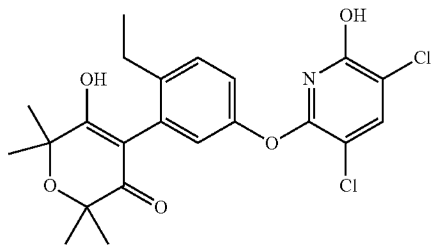 [SMILES: CCc1ccc(Oc2nc(O)c(Cl)cc2Cl)cc1C1=C(O)C(C)(C)OC(C)(C)C1=O] | δ 7.68 (s, 1H), 7.36 (d, 1H), 7.10 (dd, 1H), 6.84 (d, 1H), 2.49-2.39 (m, 2H), 1.59 (d, 6H), 1.46 (d, 6H), 1.13 (t, 3H). |
| A-140 | 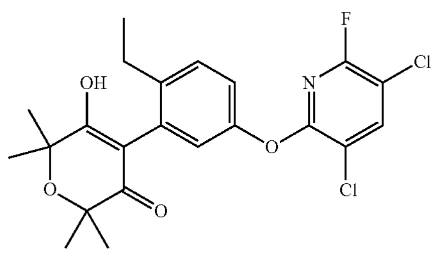 [SMILES: CCc1ccc(Oc2nc(F)c(Cl)cc2Cl)cc1C1=C(O)C(C)(C)OC(C)(C)C1=O] | δ 7.88 (d, 1H), 7.40 (d, 1H), 7.15 (dd, 1H), 6.89 (d, 1H), 2.49-2.39 (m, 2H), 1.59 (d, 6H), 1.46 (d, 6H), 1.15 (t, 3H). |
| A-141 | 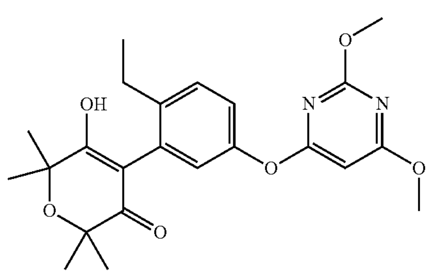 | LCMS (Method B): $t_r$ = 1.67 mins, MH⁺ = 429.0 |
| A-142 | 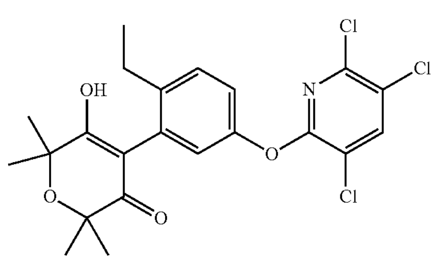 | LCMS (Method B): $t_r$ = 1.92 mins, MH⁺ = 470.1 |
| A-143 | 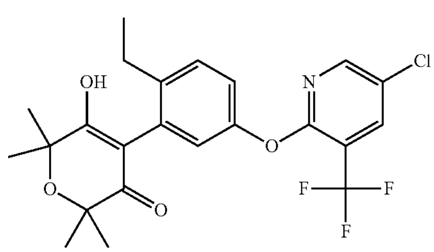 [SMILES: CCc1ccc(Oc2ncc(Cl)cc2C(F)(F)F)cc1C1=C(O)C(C)(C)OC(C)(C)C1=O] | LCMS (Method B): $t_r$ = 1.87 mins, MH⁺ = 470.1 |

TABLE T1-continued

| Compound Number | Structure | $^1$H NMR (CDCl$_3$ unless stated) or other physical data |
|---|---|---|
| A-144 | 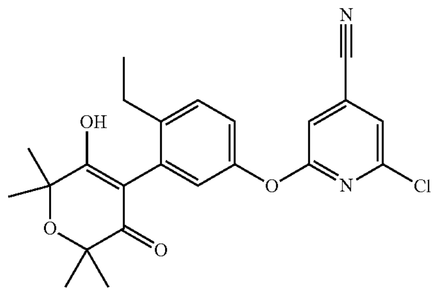 [SMILES: CCc1ccc(Oc2cc(C#N)cc(Cl)n2)cc1C1=C(O)C(C)(C)OC(C)(C)C1=O] | LCMS (Method B): t$_r$ = 1.72 mins, MH$^+$ = 427.1 |
| A-145 | 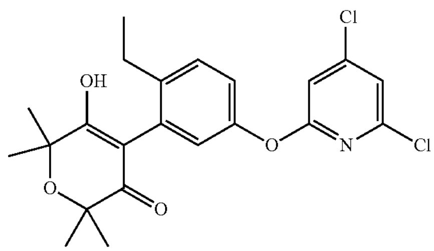 [SMILES: CCc1ccc(Oc2cc(Cl)cc(Cl)n2)cc1C1=C(O)C(C)(C)OC(C)(C)C1=O] | LCMS (Method B): t$_r$ = 1.85 mins, MH$^+$ = 436.1 |
| A-146 | 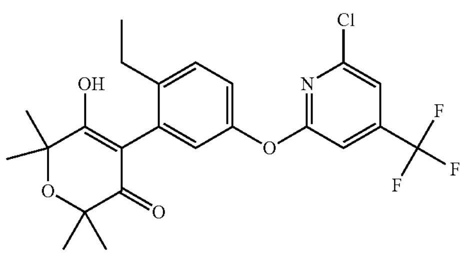 [SMILES: CCc1ccc(Oc2cc(C(F)(F)F)cc(Cl)n2)cc1C1=C(O)C(C)(C)OC(C)(C)C1=O] | LCMS (Method B): t$_r$ = 1.89 mins, MH$^+$ = 470.1 |
| A-147 | 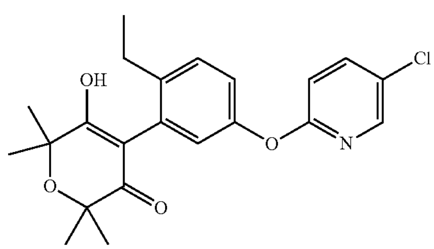 [SMILES: CCc1ccc(Oc2ccc(Cl)cn2)cc1C1=C(O)C(C)(C)OC(C)(C)C1=O] | LCMS (Method B): t$_r$ = 1.72 mins, MH$^+$ = 402.1 |
| A-148 | 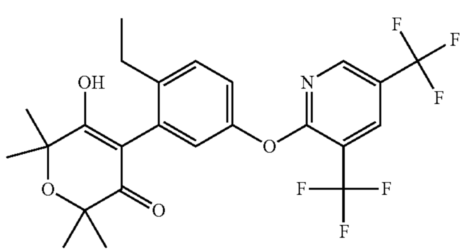 [SMILES: CCc1ccc(Oc2ncc(C(F)(F)F)cc2C(F)(F)F)cc1C1=C(O)C(C)(C)OC(C)(C)C1=O] | LCMS (Method B): t$_r$ = 1.90 mins, MH$^+$ = 504.2 |
| A-149 | 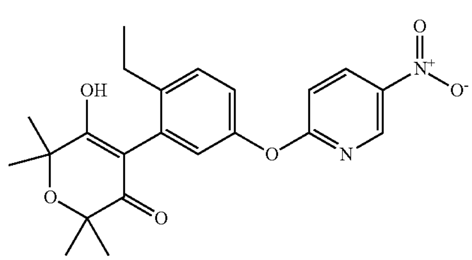 [SMILES: CCc1ccc(Oc2ccc([N+](=O)[O-])cn2)cc1C1=C(O)C(C)(C)OC(C)(C)C1=O] | LCMS (Method B): t$_r$ = 1.65 mins, MH$^+$ = 413.2 |

TABLE T1-continued

| Compound Number | Structure | $^1$H NMR (CDCl$_3$ unless stated) or other physical data |
| --- | --- | --- |
| A-150 | 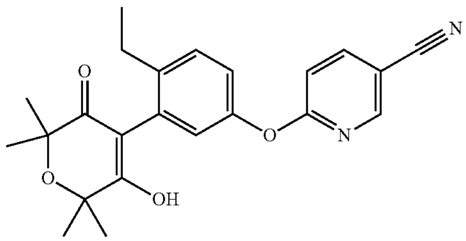 [SMILES: CCc1ccc(Oc2ccc(C#N)cn2)cc1C1=C(O)C(C)(C)OC(C)(C)C1=O] | LCMS (Method B): $t_r$ = 1.59 mins, MH$^+$ = 393.2 |
| A-151 | 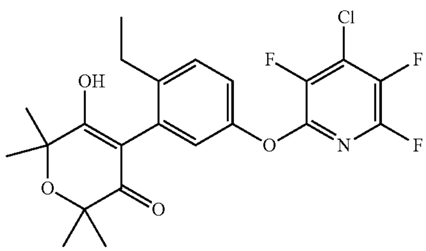 [SMILES: CCc1ccc(Oc2nc(F)c(F)c(Cl)c2F)cc1C1=C(O)C(C)(C)OC(C)(C)C1=O] | LCMS (Method B): $t_r$ = 1.84 mins, MH$^+$ = 456.1 |
| A-152 | 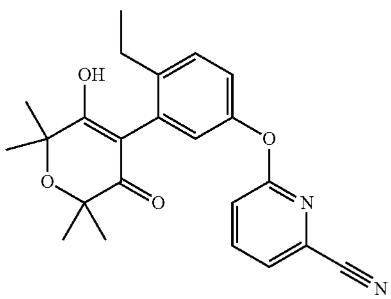 [SMILES: CCc1ccc(Oc2cccc(C#N)n2)cc1C1=C(O)C(C)(C)OC(C)(C)C1=O] | LCMS (Method B): $t_r$ = 1.61 mins, MH$^+$ = 393.2 |
| A-153 | 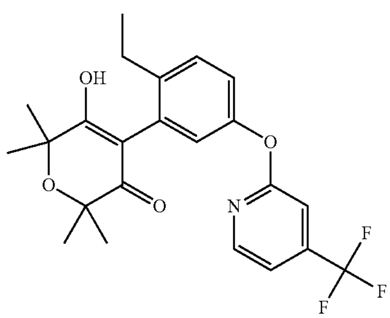 [SMILES: CCc1ccc(Oc2cc(C(F)(F)F)ccn2)cc1C1=C(O)C(C)(C)OC(C)(C)C1=O] | LCMS (Method B): $t_r$ = 1.78 mins, MH$^+$ = 436.2 |
| A-154 | 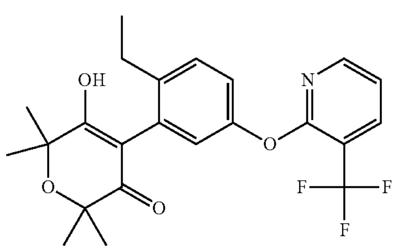 [SMILES: CCc1ccc(Oc2ncccc2C(F)(F)F)cc1C1=C(O)C(C)(C)OC(C)(C)C1=O] | LCMS (Method B): $t_r$ = 1.74 mins, MH$^+$ = 436.2 |

TABLE T1-continued

| Compound Number | Structure | ¹H NMR (CDCl₃ unless stated) or other physical data |
|---|---|---|
| A-155 | 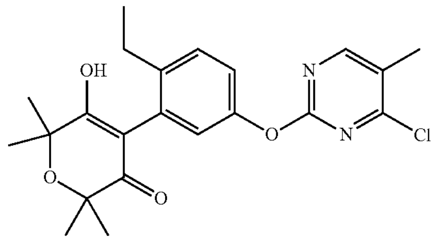 | LCMS (Method B): $t_r$ = 1.63 mins, MH⁺ = 417.2 |
| A-156 | 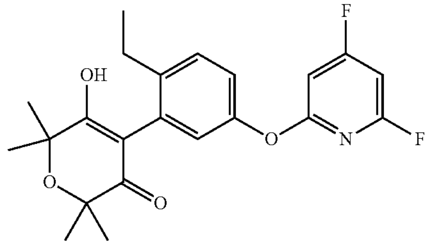 [SMILES: CCc1ccc(Oc2cc(F)cc(F)n2)cc1C1=C(O)C(C)(C)OC(C)(C)C1=O] | LCMS (Method B): $t_r$ = 1.71 mins, MH⁺ = 404.2 |
| A-157 | 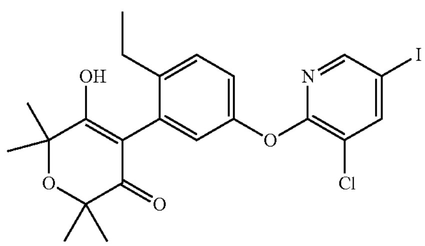 [SMILES: CCc1ccc(Oc2ncc(I)cc2Cl)cc1C1=C(O)C(C)(C)OC(C)(C)C1=O] | LCMS (Method B): $t_r$ = 1.90 mins, MH⁺ = 528.0 |
| A-158 | 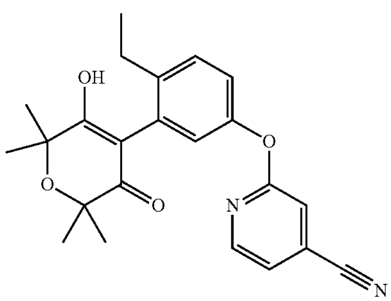 [SMILES: CCc1ccc(Oc2cc(C#N)ccn2)cc1C1=C(O)C(C)(C)OC(C)(C)C1=O] | LCMS (Method B): $t_r$ = 1.60 mins, MH⁺ = 393.2 |
| A-159 | 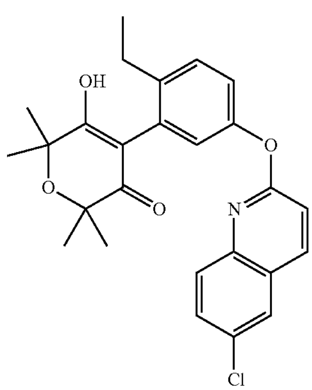 [SMILES: CCc1ccc(Oc2ccc3cc(Cl)ccc3n2)cc1C1=C(O)C(C)(C)OC(C)(C)C1=O] | δ 8.09 (d, 1H), 7.76 (d, 1H), 7.69 (d, 1H), 7.54 (dd, 1H), 7.41 (d, 1H), 7.21 (d, 1H), 7.16 (dd, 1H), 6.99 (d, 1H), 2.52 (q, 2H), 1.56-1.51 (br. m, 12H), 1.19 (t, 3H). |

TABLE T1-continued

| Compound Number | Structure | $^1$H NMR (CDCl$_3$ unless stated) or other physical data |
|---|---|---|
| A-160 | 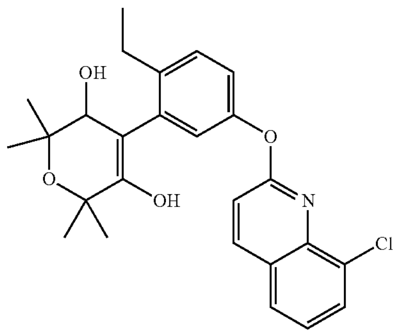 [SMILES: CCc1ccc(Oc2ccc3cccc(Cl)c3n2)cc1C1=C(O)C(C)(C)OC(C)(C)C1O] | LCMS (Method B): t$_r$ = 1.87 mins, MH$^+$ = 452.2 |
| A-161 | 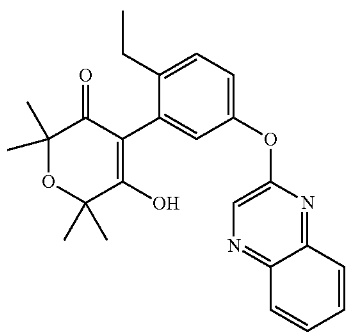 [SMILES: CCc1ccc(Oc2cnc3ccccc3n2)cc1C1=C(O)C(C)(C)OC(C)(C)C1=O] | LCMS (Method B): t$_r$ = 1.67 mins, MH$^+$ = 419.2 |
| A-162 | 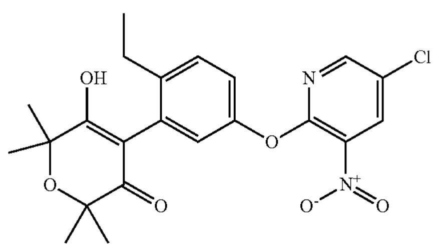 [SMILES: CCc1ccc(Oc2ncc(Cl)cc2[N+](=O)[O-])cc1C1=C(O)C(C)(C)OC(C)(C)C1=O] | LCMS (Method B): t$_r$ = 1.72 mins, MH$^+$ = 447.1 |
| A-163 | 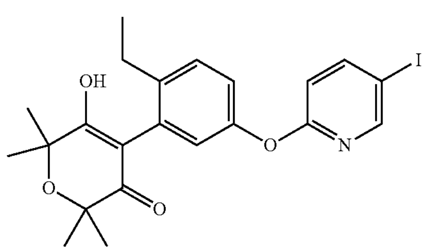 [SMILES: CCc1ccc(Oc2ccc(I)cn2)cc1C1=C(O)C(C)(C)OC(C)(C)C1=O] | LCMS (Method B): t$_r$ = 1.79 mins, MH$^+$ = 494.1 |
| A-164 | 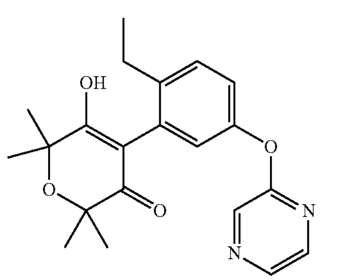 | LCMS (Method B): t$_r$ = 1.45 mins, MH$^+$ = 369.2 |

TABLE T1-continued

| Compound Number | Structure | ¹H NMR (CDCl₃ unless stated) or other physical data |
| --- | --- | --- |
| A-165 | 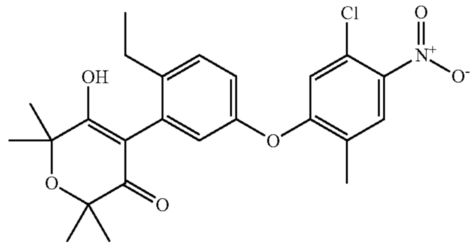 [SMILES: CCc1ccc(Oc2cc(Cl)c([N+](=O)[O-])cc2C)cc1C1=C(O)C(C)(C)OC(C)(C)C1=O] | δ 7.95-7.91 (m, 1H), 7.41 (d, 1H), 7.03 (dd, 1H), 6.91 (d, 1H), 6.84 (d, 1H), 5.62 (br. s, 1H), 2.52-2.43 (m, 2H), 2.35 (d, 3H), 1.61 (d, 6H), 1.49 (d, 6H), 1.16 (t, 3H). |
| A-166 | 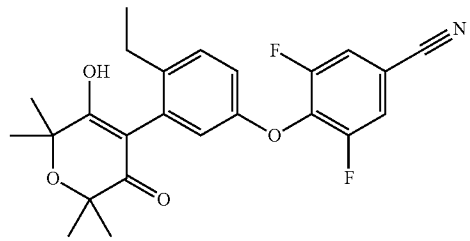 [SMILES: CCc1ccc(Oc2c(F)cc(C#N)cc2F)cc1C1=C(O)C(C)(C)OC(C)(C)C1=O] | δ 7.37-7.35 (m, 2H), 7.29 (d, 1H), 6.88 (dd, 1H), 6.75 (d, 1H), 5.67 (br. s, 1H), 2.48-2.37 (m, 2H), 1.61-1.59 (m, 6H), 1.48 (d, 6H), 1.11 (t, 3H). |
| A-167 | 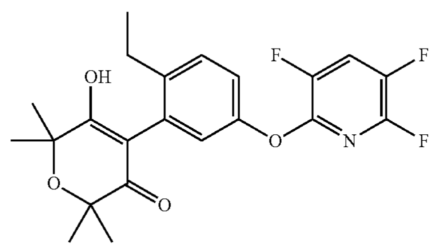 [SMILES: CCc1ccc(Oc2nc(F)c(F)cc2F)cc1C1=C(O)C(C)(C)OC(C)(C)C1=O] | δ 7.54 (q, 1H), 7.38 (d, 1H), 7.12 (dd, 1H), 6.89 (d, 1H), 2.51-2.43 (m, 2H), 1.59 (d, 6H), 1.48 (d, 6H), 1.15 (t, 3H). |
| A-168 | 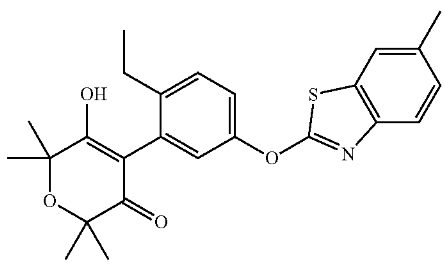 | δ 7.48 (d, 1H), 7.46 (s, 1H), 7.37 (d, 1H), 7.28-7.25 (m, 1H), 7.17 (dd, 1H), 7.06 (d, 1H), 2.50-2.43 (m, 5H), 1.60-1.47 (m, 12H), 1.15 (t, 3H). |
| A-169 | 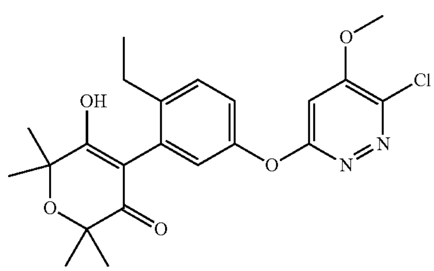 [SMILES: CCc1ccc(Oc2cc(OC)c(Cl)nn2)cc1C1=C(O)C(C)(C)OC(C)(C)C1=O] | LCMS (Method B): t$_r$ = 1.54 mins, MH⁺ = 433.1 |
| A-170 | 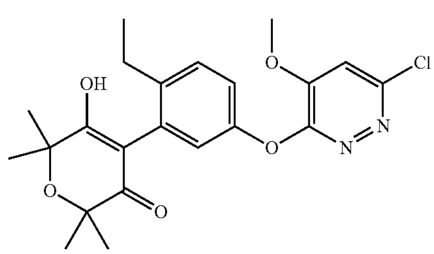 [SMILES: CCc1ccc(Oc2nnc(Cl)cc2OC)cc1C1=C(O)C(C)(C)OC(C)(C)C1=O] | LCMS (Method B): t$_r$ = 1.59 mins, MH⁺ = 433.1 |

TABLE T1-continued

| Compound Number | Structure | $^1$H NMR (CDCl$_3$ unless stated) or other physical data |
|---|---|---|
| A-171 | 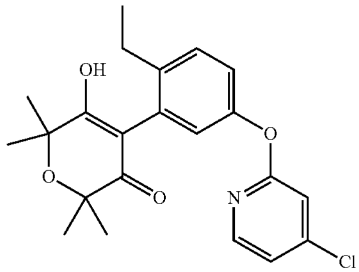 [SMILES: CCc1ccc(Oc2cc(Cl)ccn2)cc1C1=C(O)C(C)(C)OC(C)(C)C1=O] | LCMS (Method B): $t_r$ = 1.72 mins, MH$^+$ = 402.1 |
| A-172 | 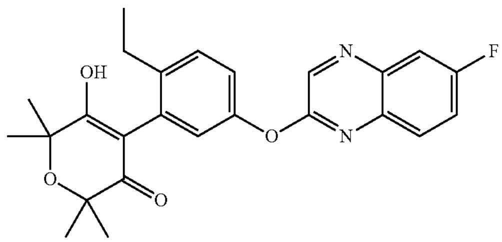 [SMILES: CCc1ccc(Oc2cnc3cc(F)ccc3n2)cc1C1=C(O)C(C)(C)OC(C)(C)C1=O] | δ 8.75 (s, 1H), 7.75-7.71 (m, 2H), 7.44 (d, 2H), 7.22 (dd, 1H), 7.02 (d, 1H), 2.58-2.46 (m, 2H), 1.60 (d, 6H), 1.51 (d, 6H), 1.19 (t, 3H). |
| A-173 | 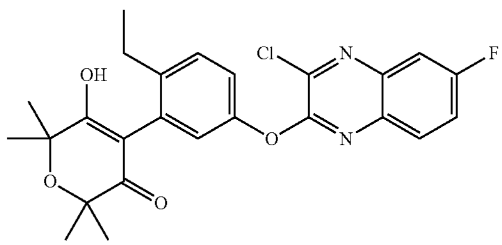 [SMILES: CCc1ccc(Oc2nc3ccc(F)cc3nc2Cl)cc1C1=C(O)C(C)(C)OC(C)(C)C1=O] | δ 7.97 (dd, 1H), 7.45 (d, 1H), 7.42-7.36 (m, 2H), 7.24 (dd, 1H), 7.03 (d, 1H), 2.56-2.48 (m, 2H), 1.60 (d, 6H), 1.49 (d, 6H), 1.19 (t, 3H). |
| A-174 | 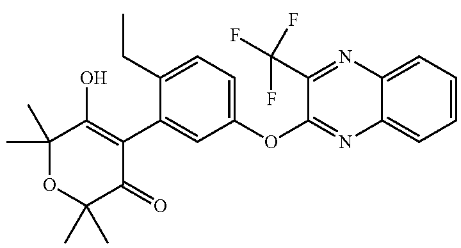 [SMILES: CCc1ccc(Oc2nc3ccccc3nc2C(F)(F)F)cc1C1=C(O)C(C)(C)OC(C)(C)C1=O] | δ 8.18 (d, 1H), 7.79 (d, 2H), 7.74-7.70 (m, 1H), 7.45 (d, 1H), 7.24 (dd, 1H), 7.05 (d, 1H), 2.56-2.48 (m, 2H), 1.59 (d, 6H), 1.48 (d, 6H), 1.19 (t, 3H). |
| A-175 | 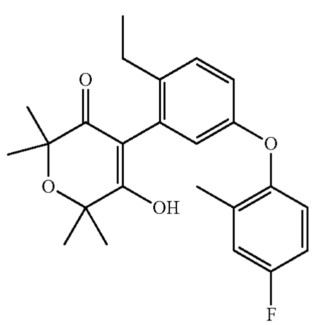 [SMILES: CCc1ccc(Oc2ccc(F)cc2C)cc1C1=C(O)C(C)(C)OC(C)(C)C1=O] | LCMS (Method B): $t_r$ = 1.84 mins, MH$^+$ = 399.2 |
| A-176 | 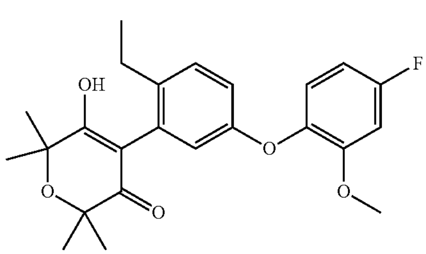 [SMILES: CCc1ccc(Oc2ccc(F)cc2OC)cc1C1=C(O)C(C)(C)OC(C)(C)C1=O] | LCMS (Method B): $t_r$ = 1.72 mins, MH$^+$ = 415.2 |

TABLE T1-continued

| Compound Number | Structure | ¹H NMR (CDCl₃ unless stated) or other physical data |
|---|---|---|
| A-177 | 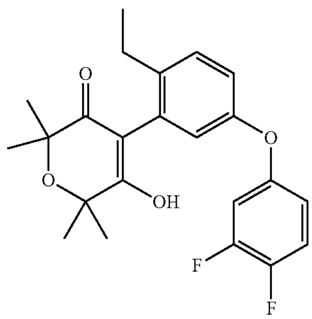 [SMILES: CCc1ccc(Oc2ccc(F)c(F)c2)cc1C1=C(O)C(C)(C)OC(C)(C)C1=O] | LCMS (Method B): $t_r$ = 1.79 mins, MH⁺ = 403.2 |
| A-178 | 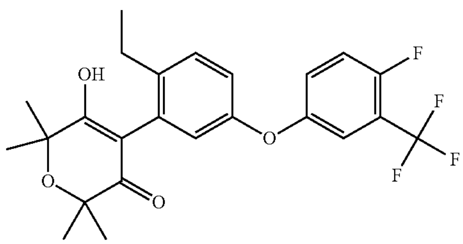 | LCMS (Method B): $t_r$ = 1.89 mins, MH⁺ = 453.2 |
| A-179 | 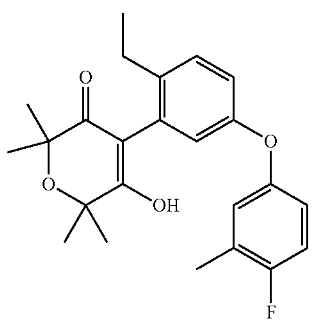 [SMILES: CCc1ccc(Oc2ccc(F)c(C)c2)cc1C1=C(O)C(C)(C)OC(C)(C)C1=O] | LCMS (Method B): $t_r$ = 1.83 mins, MH⁺ = 399.2 |
| A-180 | 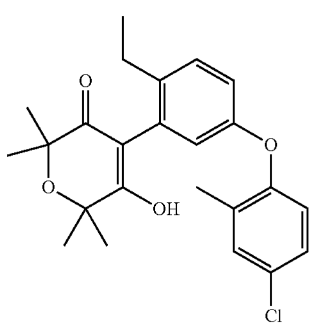 [SMILES: CCc1ccc(Oc2ccc(Cl)cc2C)cc1C1=C(O)C(C)(C)OC(C)(C)C1=O] | LCMS (Method B): $t_r$ = 1.92 mins, MH⁺ = 415.2 |
| A-181 | 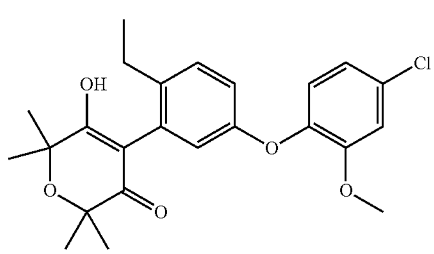 [SMILES: CCc1ccc(Oc2ccc(Cl)cc2OC)cc1C1=C(O)C(C)(C)OC(C)(C)C1=O] | LCMS (Method B): $t_r$ = 1.80 mins, MH⁺ = 431.2 |

TABLE T1-continued

| Compound Number | Structure | $^1$H NMR (CDCl$_3$ unless stated) or other physical data |
|---|---|---|
| A-182 | 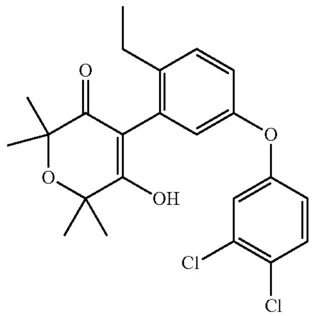 [SMILES: CCc1ccc(Oc2ccc(Cl)c(Cl)c2)cc1C1=C(O)C(C)(C)OC(C)(C)C1=O] | LCMS (Method B): t$_r$ = 1.95 mins, MH$^+$ = 435.1 |
| A-183 | 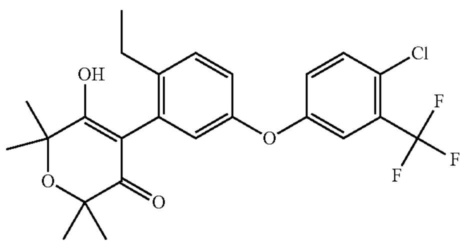 [SMILES: CCc1ccc(Oc2ccc(Cl)c(C(F)(F)F)c2)cc1C1=C(O)C(C)(C)OC(C)(C)C1=O] | LCMS (Method B): t$_r$ = 1.97 mins, MH$^+$ = 469.1 |
| A-184 | 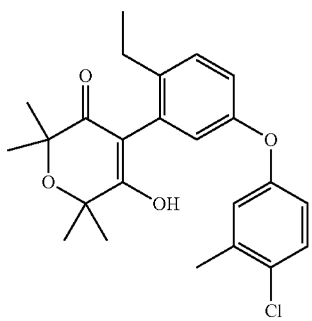 [SMILES: CCc1ccc(Oc2ccc(Cl)c(C)c2)cc1C1=C(O)C(C)(C)OC(C)(C)C1=O] | LCMS (Method B): t$_r$ = 1.93 mins, MH$^+$ = 415.2 |
| A-185 | 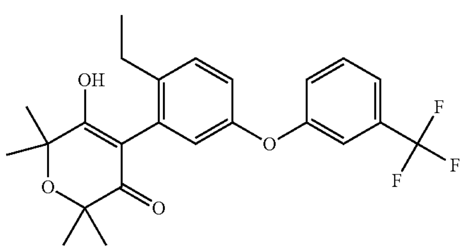 [SMILES: CCc1ccc(Oc2cccc(C(F)(F)F)c2)cc1C1=C(O)C(C)(C)OC(C)(C)C1=O] | LCMS (Method B): t$_r$ = 1.88 mins, MH$^+$ = 435.2 |
| A-186 | 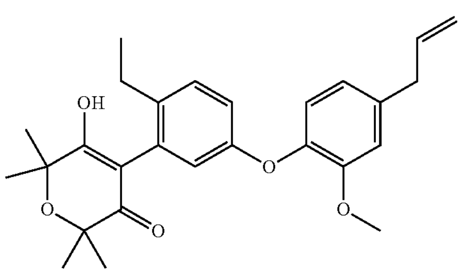 [SMILES: C=CCc1ccc(Oc2ccc(CC)c(C3=C(O)C(C)(C)OC(C)(C)C3=O)c2)c(OC)c1] | LCMS (Method B): t$_r$ = 1.86 mins, MH$^+$ = 437.2 |

TABLE T1-continued

| Compound Number | Structure | ¹H NMR (CDCl₃ unless stated) or other physical data |
|---|---|---|
| A-187 | 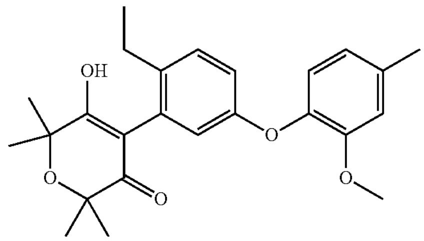 | LCMS (Method B): $t_r$ = 1.76 mins, MH⁺ = 411.2 |
| A-188 | 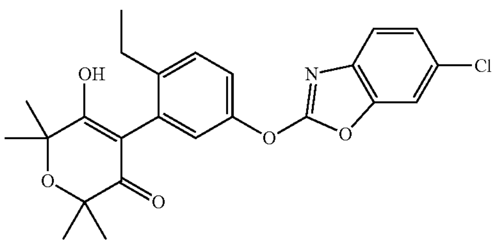 [SMILES: CCc1ccc(Oc2nc3ccc(Cl)cc3o2)cc1C1=C(O)C(C)(C)OC(C)(C)C1=O] | δ 7.47 (d, 1H), 7.45-7.43 (m, 1H), 7.38-7.34 (m, 2H), 7.26-7.22 (m, 1H), 7.11 (d, 1H), 2.53-2.44 (m, 2H), 1.60 (d, 6H), 1.49 (d, 6H), 1.15 (t, 3H). |
| A-189 | 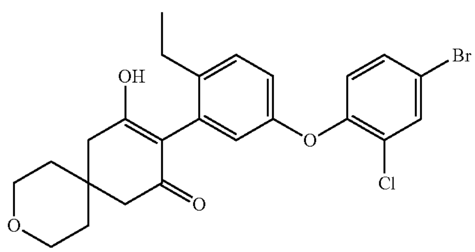 | δ 7.60 (d, 1H), 7.34-7.30 (m, 2H), 6.94 (dd, 1H), 6.90 (d, 1H), 6.65 (d, 1H), 3.74 (q, 4H), 2.65-2.55 (br. m, 4H), 2.41-2.37 (br. m, 2H), 1.72-1.66 (m, 4H), 1.10 (t, 3H). |
| A-190 | 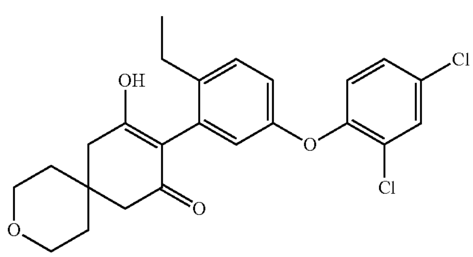 [SMILES: CCc1ccc(Oc2ccc(Br)cc2Cl)cc1C1=C(O)CC2(CCOCC2)CC1=O] | δ 7.42 (d, 1H), 7.25 (d, 1H), 7.14 (dd, 1H), 6.92-6.88 (m, 2H), 6.61 (d, 1H), 3.72 (q, 4H), 2.58-2.48 (br. m, 4H), 2.39-2.31 (m, 2H), 1.67-1.62 (m, 4H), 1.07 (t, 3H). |
| A-191 | 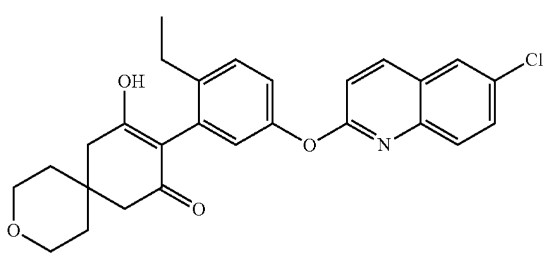 [SMILES: CCc1ccc(Oc2ccc3cc(Cl)ccc3n2)cc1C1=C(O)CC2(CCOCC2)CC1=O] | δ 8.08 (d, 1H), 7.75 (d, 1H), 7.68 (d, 1H), 7.54 (dd, 1H), 7.40 (d, 1H), 7.19 (d, 1H), 7.15 (dd, 1H), 6.93 (d, 1H), 3.73 (dt, 4H), 2.58 (q, 4H), 2.48 (q, 2H), 1.73-1.71 (m, 2H), 1.68-1.65 (m, 2H), 1.17 (t, 3H). |
| A-192 | 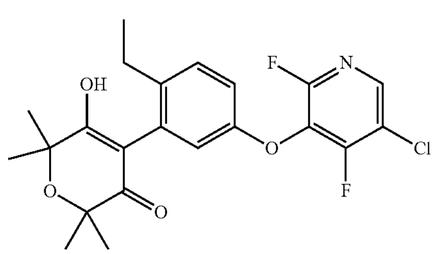 [SMILES: CCc1ccc(Oc2c(F)ncc(Cl)c2F)cc1C1=C(O)C(C)(C)OC(C)(C)C1=O] | LCMS (Method B): $t_r$ = 1.74 mins, MH⁺ = 438.1 |

TABLE T1-continued

| Compound Number | Structure | ¹H NMR (CDCl₃ unless stated) or other physical data |
|---|---|---|
| A-193 | 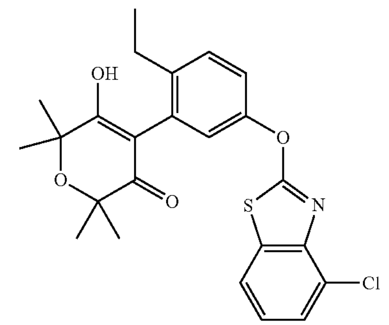 [SMILES: CCc1ccc(Oc2nc3c(Cl)cccc3s2)cc1C1=C(O)C(C)(C)OC(C)(C)C1=O] | LCMS (Method B): $t_r$ = 1.88 mins, MH⁺ = 458.1 |
| A-194 | 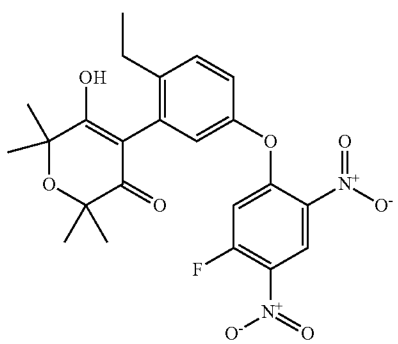 [SMILES: CCc1ccc(Oc2cc(F)c([N+](=O)[O-])cc2[N+](=O)[O-])cc1C1=C(O)C(C)(C)OC(C)(C)C1=O] | LCMS (Method B): $t_r$ = 1.92 mins, MH⁺ = 475.1 |
| A-195 | 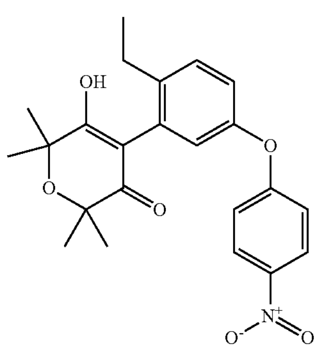 [SMILES: CCc1ccc(Oc2ccc([N+](=O)[O-])cc2)cc1C1=C(O)C(C)(C)OC(C)(C)C1=O] | LCMS (Method B): $t_r$ = 1.75 mins, MH⁺ = 412.2 |
| A-196 | 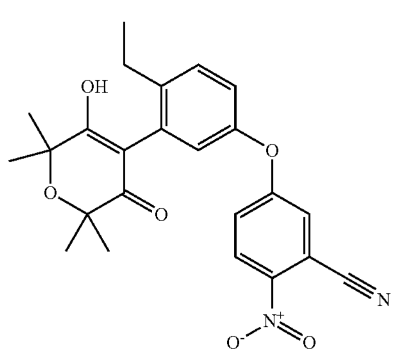 [SMILES: CCc1ccc(Oc2ccc([N+](=O)[O-])c(C#N)c2)cc1C1=C(O)C(C)(C)OC(C)(C)C1=O] | LCMS (Method B): $t_r$ = 1.71 mins, MH⁺ = 437.2 |

TABLE T1-continued

| Compound Number | Structure | $^1$H NMR (CDCl$_3$ unless stated) or other physical data |
|---|---|---|
| A-197 | 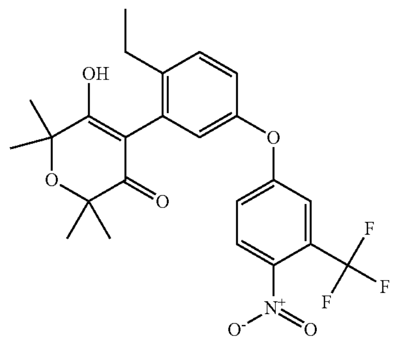 [SMILES: CCc1ccc(Oc2ccc([N+](=O)[O-])c(C(F)(F)F)c2)cc1C1=C(O)C(C)(C)OC(C)(C)C1=O] | LCMS (Method B): t$_r$ = 1.86 mins, MH$^+$ = 480.2 |
| A-198 | 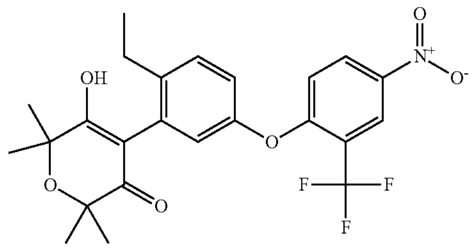 [SMILES: CCc1ccc(Oc2ccc([N+](=O)[O-])cc2C(F)(F)F)cc1C1=C(O)C(C)(C)OC(C)(C)C1=O] | LCMS (Method B): t$_r$ = 1.88 mins, MH$^+$ = 480.2 |
| A-199 | 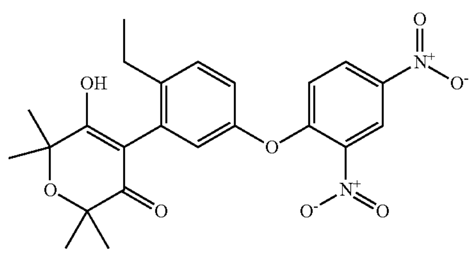 [SMILES: CCc1ccc(Oc2ccc([N+](=O)[O-])cc2[N+](=O)[O-])cc1C1=C(O)C(C)(C)OC(C)(C)C1=O] | LCMS (Method B): t$_r$ = 1.75 mins, MH$^+$ = 457.2 |
| A-200 | 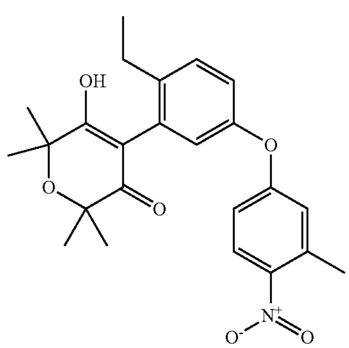 | LCMS (Method B): t$_r$ = 1.81 mins, MH$^+$ = 426.2 |
| A-201 | 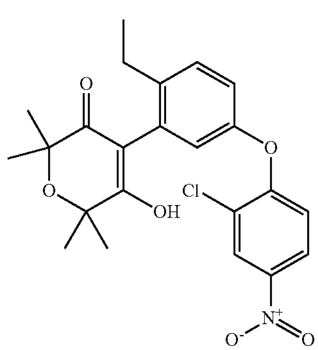 [SMILES: CCc1ccc(Oc2ccc([N+](=O)[O-])cc2Cl)cc1C1=C(O)C(C)(C)OC(C)(C)C1=O] | LCMS (Method B): t$_r$ = 1.83 mins, MH$^+$ = 446.1 |

TABLE T1-continued

| Compound Number | Structure | ¹H NMR (CDCl₃ unless stated) or other physical data |
|---|---|---|
| A-202 | 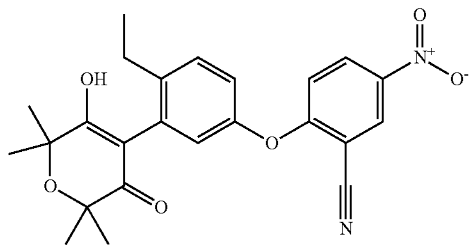 [SMILES: CCc1ccc(Oc2ccc([N+](=O)[O-])cc2C#N)cc1C1=C(O)C(C)(C)OC(C)(C)C1=O] | LCMS (Method B): $t_r$ = 1.72 mins, MH⁺ = 437.2 |
| A-203 | 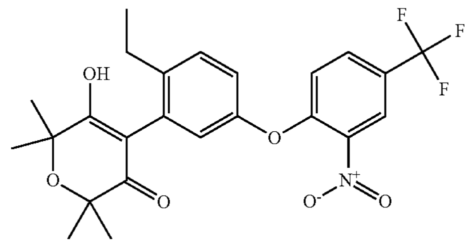 [SMILES: CCc1ccc(Oc2ccc(C(F)(F)F)cc2[N+](=O)[O-])cc1C1=C(O)C(C)(C)OC(C)(C)C1=O] | LCMS (Method B): $t_r$ = 1.85 mins, MH⁺ = 480.2 |
| A-204 | 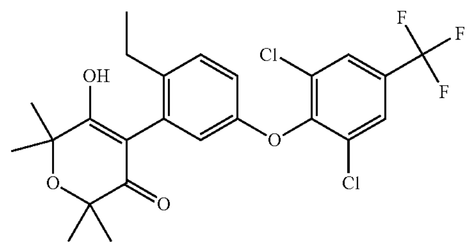 [SMILES: CCc1ccc(Oc2c(Cl)cc(C(F)(F)F)cc2Cl)cc1C1=C(O)C(C)(C)OC(C)(C)C1=O] | LCMS (Method B): $t_r$ = 1.97 mins, MH⁺ = 503.1 |
| A-205 | 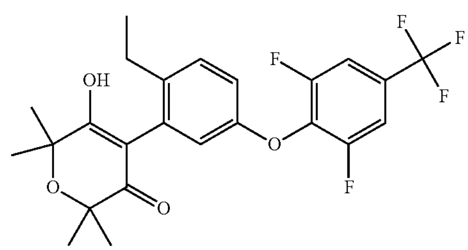 [SMILES: CCc1ccc(Oc2c(F)cc(C(F)(F)F)cc2F)cc1C1=C(O)C(C)(C)OC(C)(C)C1=O] | δ 7.31 (d, 1H), 7.26 (d, 1H), 6.85 (dd, 1H), 6.77 (d, 1H), 6.18 (br. s, 1H), 2.44-2.36 (m, 2H), 1.59 (d, 6H), 1.47 (d, 6H), 1.10 (t, 3H). |
| A-206 | 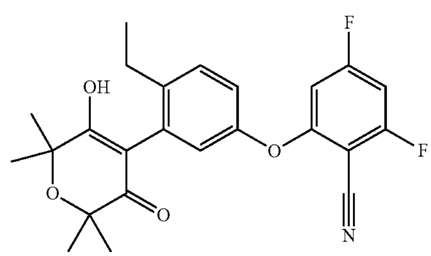 [SMILES: CCc1ccc(Oc2cc(F)cc(F)c2C#N)cc1C1=C(O)C(C)(C)OC(C)(C)C1=O] | δ 7.38 (d, 1H), 7.06 (dd, 1H), 6.89 (d, 1H), 6.61 (td, 1H), 6.53 (dt, 1H), 2.50-2.43 (m, 2H), 1.58 (d, 6H), 1.46 (d, 6H), 1.14 (t, 3H). |
| A-207 | 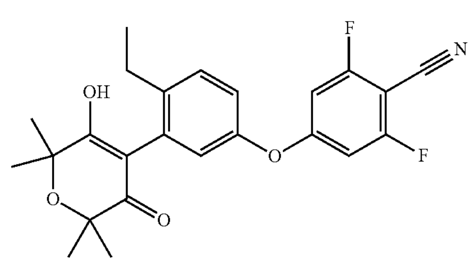 [SMILES: CCc1ccc(Oc2cc(F)c(C#N)c(F)c2)cc1C1=C(O)C(C)(C)OC(C)(C)C1=O] | δ 7.39 (d, 1H), 7.09-7.03 (m, 1H), 6.91-6.83 (m, 1H), 6.67-6.51 (m, 2H), 2.51-2.44 (m, 2H), 1.59 (d, 6H), 1.47 (d, 6H), 1.15 (t, 3H). |

TABLE T1-continued
| Compound Number | Structure | $^1$H NMR (CDCl$_3$ unless stated) or other physical data |
|---|---|---|
| A-208 | 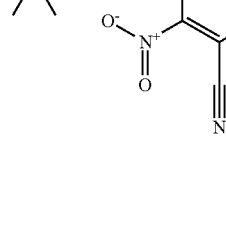 | LCMS (Method B): t$_r$ = 1.69 mins, MH$^+$ = 437.2 |
| A-209 | 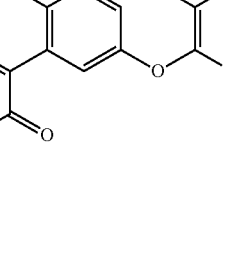 | δ 7.41 (d, 1H), 7.14 (dd, 1H), 6.91 (d, 1H), 2.52-2.45 (m, 2H), 1.60 (d, 6H), 1.48 (d, 6H), 1.19-1.14 (m, 3H). |
| A-210 | 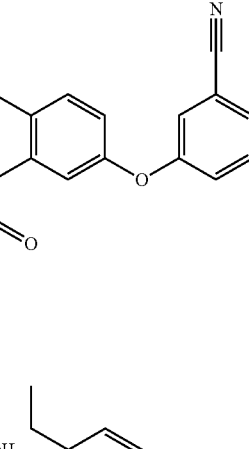 | LCMS (Method B): t$_r$ = 1.84 mins, MH$^+$ = 460.2 |
| A-211 | 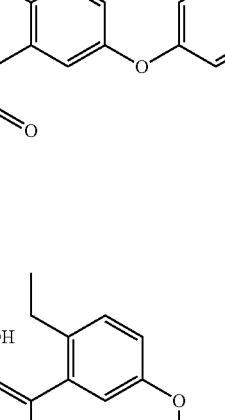 | LCMS (Method B): t$_r$ = 1.74 mins, MH$^+$ = 469.1 |

TABLE T1-continued
| Compound Number | Structure | ¹H NMR (CDCl₃ unless stated) or other physical data |
|---|---|---|
| A-212 | 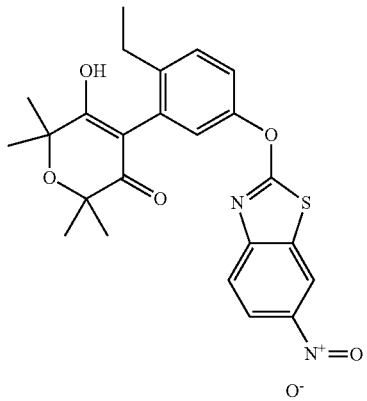 | LCMS (Method B): $t_r$ = 1.79 mins, MH⁺ = 469.1 |
| A-213 | 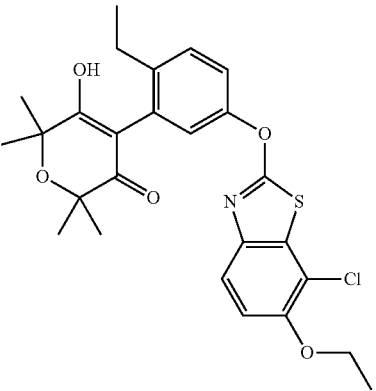 [SMILES: CCOc1ccc2nc(Oc3ccc(CC)c(C4=C(O)C(C)(C)OC(C)(C)C4=O)c3)sc2c1Cl] | LCMS (Method B): $t_r$ = 2.04 mins, MH⁺ = 502.1 |
| A-214 | 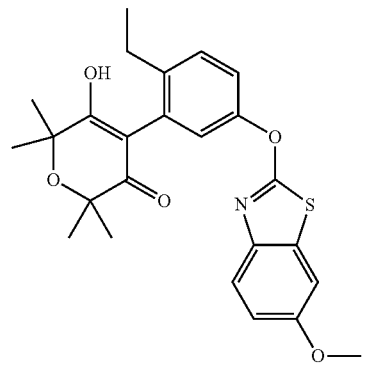 | LCMS (Method B): $t_r$ = 1.80 mins, MH⁺ = 454.2 |
| A-215 | 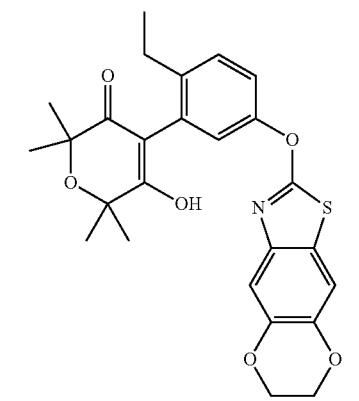 [SMILES: CCc1ccc(Oc2nc3cc4c(cc3s2)OCCO4)cc1C1=C(O)C(C)(C)OC(C)(C)C1=O] | LCMS (Method B): $t_r$ = 1.80 mins, MH⁺ = 482.2 |

TABLE T1-continued

| Compound Number | Structure | $^1$H NMR (CDCl$_3$ unless stated) or other physical data |
| --- | --- | --- |
| A-216 | 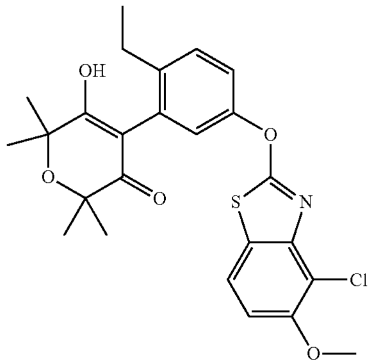 [SMILES: CCc1ccc(Oc2nc3c(Cl)c(OC)ccc3s2)cc1C1=C(O)C(C)(C)OC(C)(C)C1=O] | LCMS (Method B): t$_r$ = 1.83 mins, MH$^+$ = 488.1 |
| A-217 | 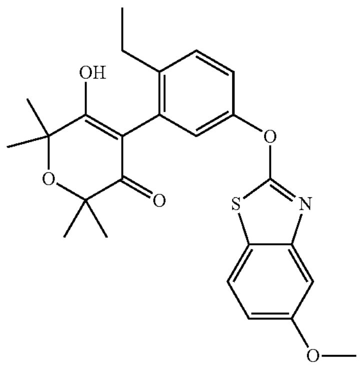 | δ 7.49 (d, 1H), 7.33 (d, 1H), 7.16 (dd, 1H), 7.06 (d, 1H), 7.00 (d, 1H), 6.86 (dd, 1H), 3.76 (s, 3H), 2.48-2.43 (m, 2H), 1.53-1.44 (br. m, 12H), 1.12 (t, 3H). |
| A-218 | 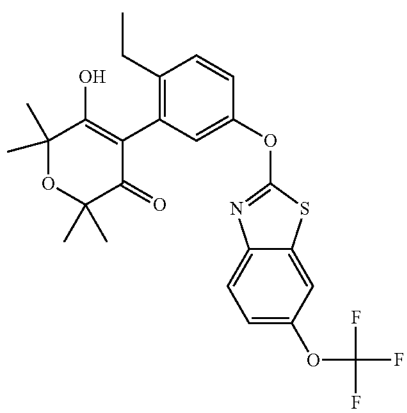 [SMILES: CCc1ccc(Oc2nc3ccc(OC(F)(F)F)cc3s2)cc1C1=C(O)C(C)(C)OC(C)(C)C1=O] | LCMS (Method B): t$_r$ = 1.97 mins, MH$^+$ = 508.1 |
| A-219 | 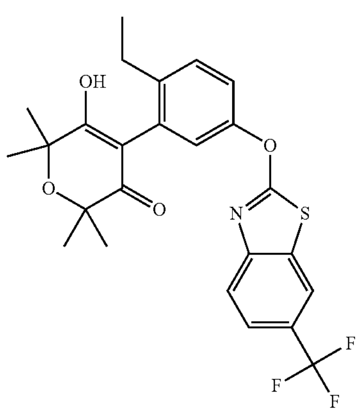 [SMILES: CCc1ccc(Oc2nc3ccc(C(F)(F)F)cc3s2)cc1C1=C(O)C(C)(C)OC(C)(C)C1=O] | LCMS (Method B): t$_r$ = 1.94 mins, MH$^+$ = 492.1 |

TABLE T1-continued
| Compound Number | Structure | $^1$H NMR (CDCl$_3$ unless stated) or other physical data |
|---|---|---|
| A-220 | 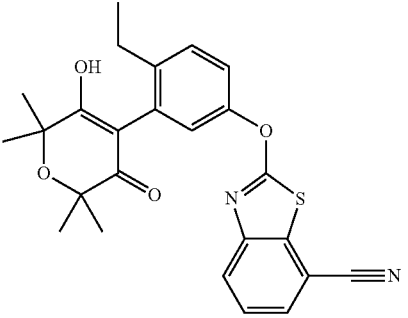 [SMILES: CCc1ccc(Oc2nc3cccc(C#N)c3s2)cc1C1=C(O)C(C)(C)OC(C)(C)C1=O] | LCMS (Method B): t$_r$ = 1.78 mins, MH$^+$ = 449.1 |
| A-221 | 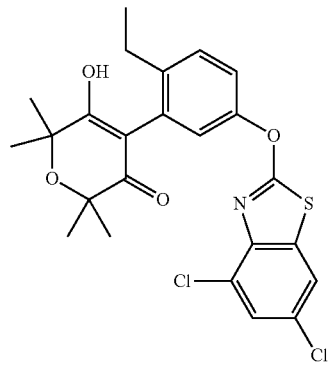 [SMILES: CCc1ccc(Oc2nc3c(Cl)cc(Cl)cc3s2)cc1C1=C(O)C(C)(C)OC(C)(C)C1=O] | LCMS (Method B): t$_r$ = 2.02 mins, MH$^+$ = 492.1 |
| A-222 | 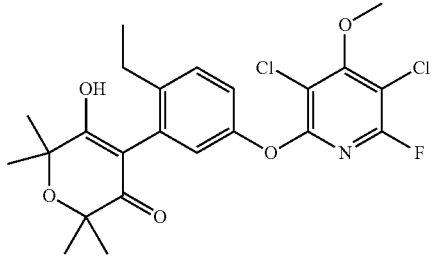 [SMILES: CCc1ccc(Oc2nc(F)c(Cl)c(OC)c2Cl)cc1C1=C(O)C(C)(C)OC(C)(C)C1=O] | LCMS (Method B): t$_r$ = 1.93 mins, MH$^+$ = 484.1 |
| A-223 | 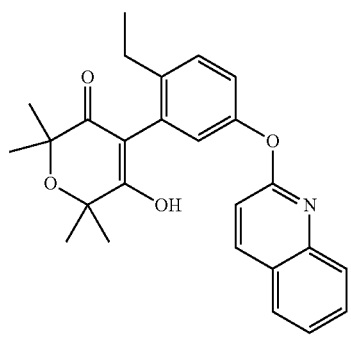 [SMILES: CCc1ccc(Oc2ccc3ccccc3n2)cc1C1=C(O)C(C)(C)OC(C)(C)C1=O] | LCMS (Method B): t$_r$ = 1.78 mins, MH$^+$ = 418.2 |

TABLE T1-continued

| Compound Number | Structure | $^1$H NMR (CDCl$_3$ unless stated) or other physical data |
|---|---|---|
| A-224 | 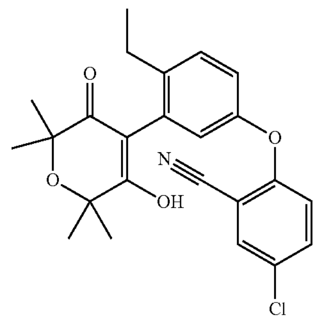 [SMILES: CCc1ccc(Oc2ccc(Cl)cc2C#N)cc1C1=C(O)C(C)(C)OC(C)(C)C1=O] | LCMS (Method B): t$_r$ = 1.80 mins, MH$^+$ = 426.1 |
| A-225 | 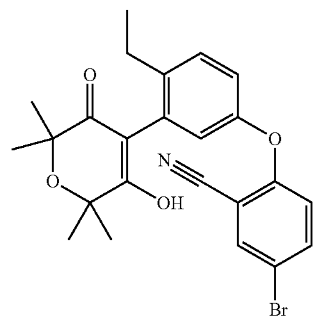 | LCMS (Method B): t$_r$ = 1.82 mins, MH$^+$ = 470.1 |
| A-226 | 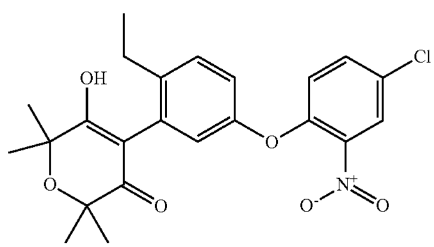 [SMILES: CCc1ccc(Oc2ccc(Cl)cc2[N+](=O)[O-])cc1C1=C(O)C(C)(C)OC(C)(C)C1=O] | LCMS (Method B): t$_r$ = 1.82 mins, MH$^+$ = 446.1 |
| A-227 | 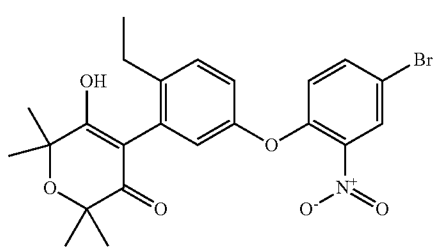 [SMILES: CCc1ccc(Oc2ccc(Br)cc2[N+](=O)[O-])cc1C1=C(O)C(C)(C)OC(C)(C)C1=O] | LCMS (Method B): t$_r$ = 1.85 mins, MH$^+$ = 490.1 |
| A-228 | 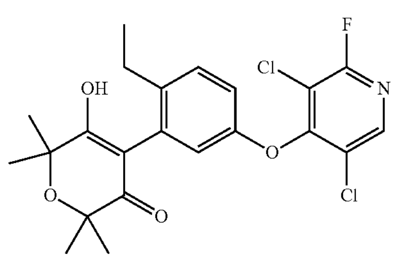 [SMILES: CCc1ccc(Oc2c(Cl)cnc(F)c2Cl)cc1C1=C(O)C(C)(C)OC(C)(C)C1=O] | δ 8.18 (d, 1H), 7.29 (d, 1H), 6.77 (dd, 1H), 6.71 (d, 1H), 2.48-2.37 (m, 2H), 1.61 (d, 6H), 1.48 (d, 6H), 1.12 (t, 3H). |

TABLE T1-continued

| Compound Number | Structure | $^1$H NMR (CDCl$_3$ unless stated) or other physical data |
|---|---|---|
| A-229 | 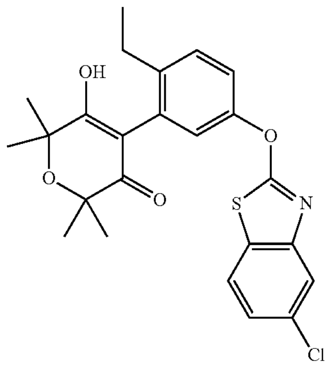 [SMILES: CCc1ccc(Oc2nc3cc(Cl)ccc3s2)cc1C1=C(O)C(C)(C)OC(C)(C)C1=O] | LCMS (Method B): t$_r$ = 1.92 mins, MH$^+$ = 458.1 |
| A-230 | 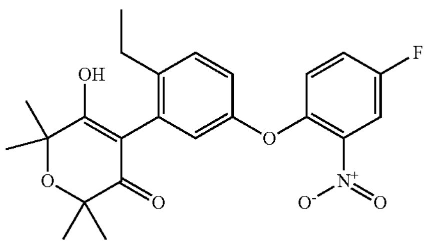 [SMILES: CCc1ccc(Oc2ccc(F)cc2[N+](=O)[O-])cc1C1=C(O)C(C)(C)OC(C)(C)C1=O] | LCMS (Method B): t$_r$ = 1.74 mins, MH$^+$ = 430.2 |
| A-231 | 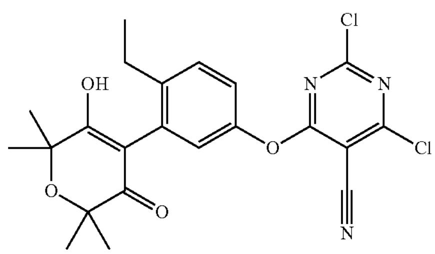 [SMILES: CCc1ccc(Oc2nc(Cl)nc(Cl)c2C#N)cc1C1=C(O)C(C)(C)OC(C)(C)C1=O] | LCMS (Method B): t$_r$ = 1.47 mins, MH$^+$ = 444.0 |
| A-232 | 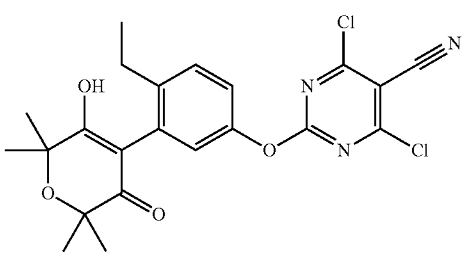 [SMILES: CCc1ccc(Oc2nc(Cl)c(C#N)c(Cl)n2)cc1C1=C(O)C(C)(C)OC(C)(C)C1=O] | LCMS (Method B): t$_r$ = 1.47 mins, MH$^+$ = 444.0 |
| A-233 | 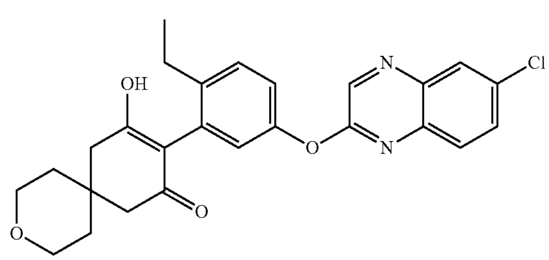 [SMILES: CCc1ccc(Oc2cnc3cc(Cl)ccc3n2)cc1C1=C(O)CC2(CCOCC2)CC1=O] | δ 8.64 (s, 1H), 8.02 (d, 1H), 7.64-7.62 (m, 1H), 7.59-7.56 (m, 1H), 7.37 (d, 1H), 7.19 (dd, 1H), 6.94 (d, 1H), 3.75-3.68 (m, 4H), 2.63-2.43 (m, 6H), 1.72-1.64 (m, 4H), 1.15 (t, 3H). |

TABLE T1-continued

| Compound Number | Structure | ¹H NMR (CDCl₃ unless stated) or other physical data |
|---|---|---|
| A-234 | 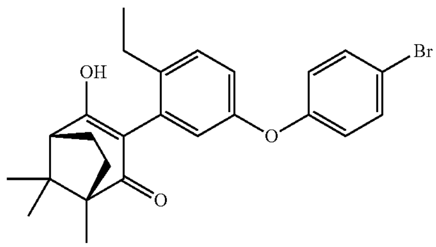 [SMILES: CCc1ccc(Oc2ccc(Br)cc2)cc1C1=C(O)[C@@H]2CC[C@](C)(C1=O)C2(C)C] | LCMS (Method A): $t_r$ = 1.97 mins, MH⁺ = 455 |
| A-235 | 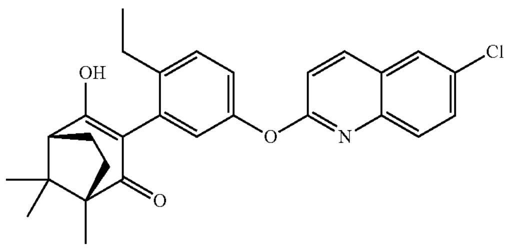 [SMILES: CCc1ccc(Oc2ccc3cc(Cl)ccc3n2)cc1C1=C(O)[C@@H]2CC[C@](C)(C1=O)C2(C)C] | LCMS (Method A): $t_r$ = 2.00 mins, MH⁺ = 462 |
| A-236 | 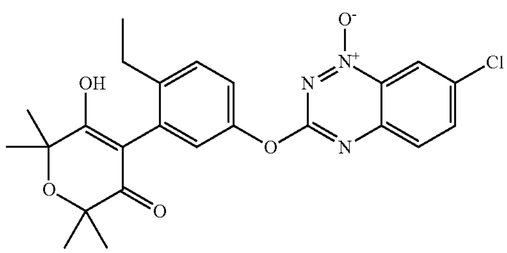 [SMILES: CCc1ccc(Oc2nc3ccc(Cl)cc3[n+]([O-])n2)cc1C1=C(O)C(C)(C)OC(C)(C)C1=O] | d₄-MeOH: δ 8.40 (d, 1H), 7.94 (dd, 1H), 7.76 (d, 1H), 7.44 (d, 1H), 7.26 (dd, 1H), 6.97 (d, 1H), 2.51 (q, 2H), 1.52 (s, 6H), 1.48 (s, 6H), 1.17 (t, 3H). |
| A-237 | 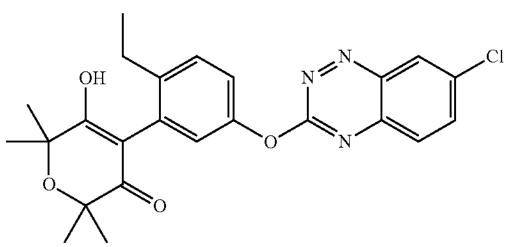 [SMILES: CCc1ccc(Oc2nnc3cc(Cl)ccc3n2)cc1C1=C(O)C(C)(C)OC(C)(C)C1=O] | d₄-MeOH: δ 8.41 (d, 1H), 7.95 (dd, 1H), 7.77 (d, 1H), 7.44 (d, 1H), 7.26 (dd, 1H), 6.97 (d, 1H), 2.51 (q, 2H), 1.52 (s, 6H), 1.48 (s, 6H), 1.17 (t, 3H). |
| A-238 | 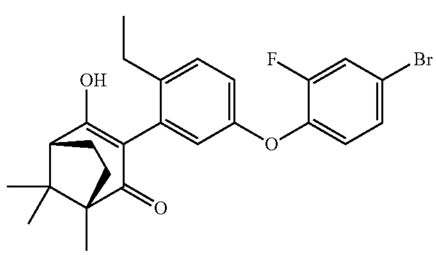 [SMILES: CCc1ccc(Oc2ccc(Br)cc2F)cc1C1=C(O)[C@@H]2CC[C@](C)(C1=O)C2(C)C] | LCMS (Method A): $t_r$ = 1.96 mins, MH⁺ = 473 |
| A-239 | 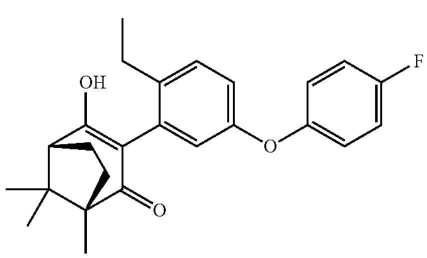 [SMILES: CCc1ccc(Oc2ccc(F)cc2)cc1C1=C(O)[C@@H]2CC[C@](C)(C1=O)C2(C)C] | LCMS (Method A): $t_r$ = 1.86 mins, MH⁺ = 395 |

TABLE T1-continued

| Compound Number | Structure | ¹H NMR (CDCl₃ unless stated) or other physical data |
|---|---|---|
| A-240 | 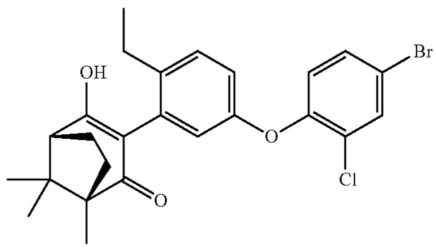 [SMILES: CCc1ccc(Oc2ccc(Br)cc2Cl)cc1C1=C(O)[C@@H]2CC[C@](C)(C1=O)C2(C)C] | LCMS (Method A): $t_r$ = 2.03 mins, MH⁺ = 489 |
| A-241 | 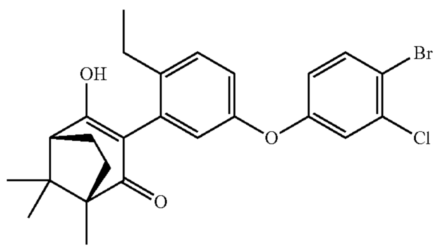 [SMILES: CCc1ccc(Oc2ccc(Br)c(Cl)c2)cc1C1=C(O)[C@@H]2CC[C@](C)(C1=O)C2(C)C] | LCMS (Method A): $t_r$ = 2.04 mins, MH⁺ = 489 |
| A-242 | 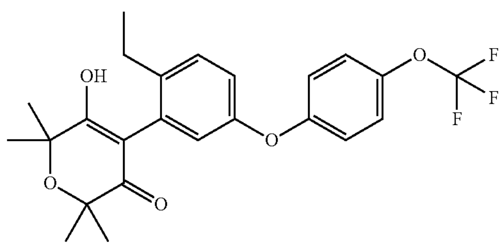 [SMILES: CCc1ccc(Oc2ccc(OC(F)(F)F)cc2)cc1C1=C(O)C(C)(C)OC(C)(C)C1=O] | δ 7.32 (d, 1H), 7.20-7.17 (m, 2H), 7.04-6.97 (m, 3H), 6.79 (d, 1H), 5.71 (br. s, 1H), 2.48-2.37 (m, 2H), 1.59 (d, 6H), 1.49 (d, 6H), 1.14-1.09 (m, 3H). |
| A-243 | 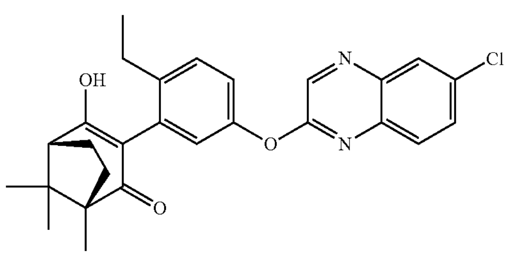 [SMILES: CCc1ccc(Oc2cnc3cc(Cl)ccc3n2)cc1C1=C(O)[C@@H]2CC[C@](C)(C1=O)C2(C)C] | δ 8.70-8.69 (m, 1H), 8.04 (d, 1H), 7.67-7.62 (m, 1H), 7.61-7.58 (m, 1H), 7.41-7.37 (m, 1H), 7.17 (br. d, 1H), 6.97 and 6.85 (d, 1H), 2.56-2.32 (br. m, 4H), 1.96-1.74 (br. m, 3H), 1.21-1.00 (m, 12H). |
| A-244 | 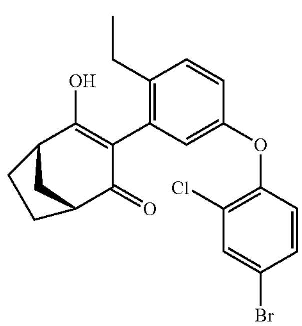 [SMILES: CCc1ccc(Oc2ccc(Br)cc2Cl)cc1C1=C(O)[C@H]2CC[C@H](C2)C1=O] | LCMS (Method B): $t_r$ = 1.71 mins, MH⁺ = 447.0 |

TABLE T1-continued

| Compound Number | Structure | ¹H NMR (CDCl₃ unless stated) or other physical data |
|---|---|---|
| A-245 | 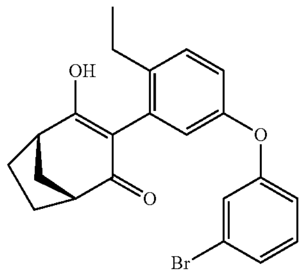 [SMILES: CCc1ccc(Oc2cccc(Br)c2)cc1C1=C(O)[C@H]2CC[C@H](C2)C1=O] | LCMS (Method B): $t_r$ = 1.62 mins, MH⁺ = 413.1 |
| A-246 | 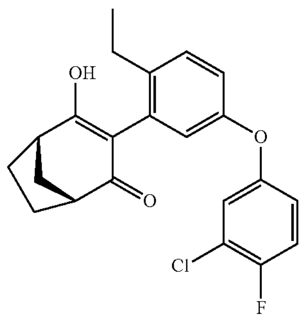 [SMILES: CCc1ccc(Oc2ccc(F)c(Cl)c2)cc1C1=C(O)[C@H]2CC[C@H](C2)C1=O] | LCMS (Method B): $t_r$ = 1.62 mins, MH⁺ = 387.1 |
| A-247 | 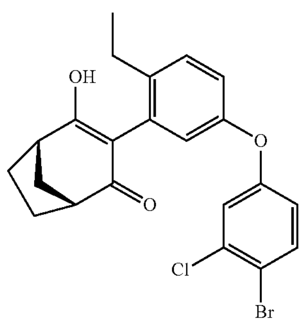 [SMILES: CCc1ccc(Oc2ccc(Br)c(Cl)c2)cc1C1=C(O)[C@H]2CC[C@H](C2)C1=O] | LCMS (Method B): $t_r$ = 1.72 mins, MH⁺ = 447.0 |
| A-248 | 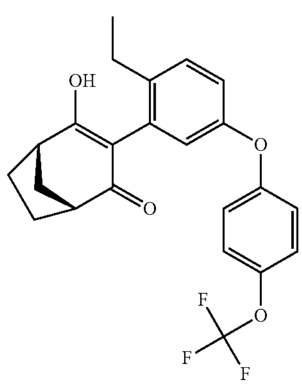 [SMILES: CCc1ccc(Oc2ccc(OC(F)(F)F)cc2)cc1C1=C(O)[C@H]2CC[C@H](C2)C1=O] | LCMS (Method B): $t_r$ = 1.71 mins, MH⁺ = 419.1 |

TABLE T1-continued

| Compound Number | Structure | ¹H NMR (CDCl₃ unless stated) or other physical data |
|---|---|---|
| A-249 | 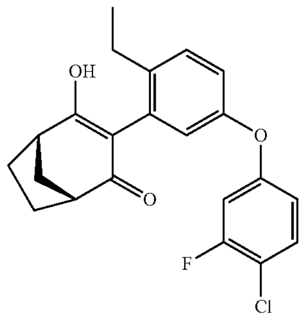 [SMILES: CCc1ccc(Oc2ccc(Cl)c(F)c2)cc1C1=C(O)[C@H]2CC[C@H](C2)C1=O] | LCMS (Method B): $t_r$ = 1.63 mins, MH⁺ = 387.1 |
| A-250 | 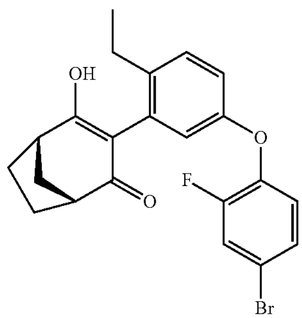 [SMILES: CCc1ccc(Oc2ccc(Br)cc2F)cc1C1=C(O)[C@H]2CC[C@H](C2)C1=O] | LCMS (Method B): $t_r$ = 1.67 mins, MH⁺ = 431.1 |
| A-251 | 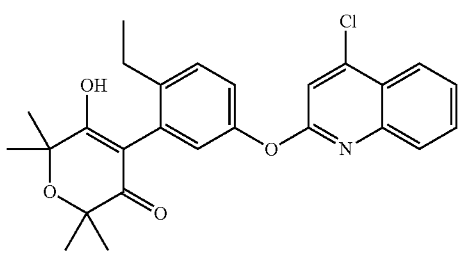 [SMILES: CCc1ccc(Oc2cc(Cl)c3ccccc3n2)cc1C1=C(O)C(C)(C)OC(C)(C)C1=O] | δ 8.17 (d, 1H), 7.75 (d, 1H), 7.66 (t, 1H), 7.52 (t, 1H), 7.41 (d, 1H), 7.32 (s, 1H), 7.15 (dd, 1H), 6.99 (d, 1H), 2.53-2.50 (br. m, 2H), 1.60-1.47 (br. m, 12H), 1.19 (t, 3H). |
| A-252 | 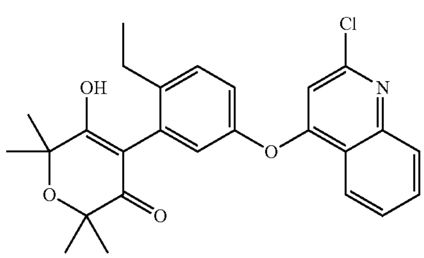 [SMILES: CCc1ccc(Oc2cc(Cl)nc3ccccc23)cc1C1=C(O)C(C)(C)OC(C)(C)C1=O] | δ 8.27 (d, 1H), 7.98 (d, 1H), 7.77 (t, 1H), 7.58 (t, 1H), 7.45 (d, 1H), 7.18 (dd, 1H), 6.99 (d, 1H), 6.62 (s, 1H), 2.55-2.50 (br. m, 2H), 1.62-1.46 (br. m, 12H), 1.19 (t, 3H). |
| A-253 | 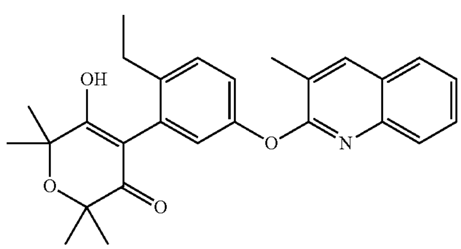 [SMILES: CCc1ccc(Oc2nc3ccccc3cc2C)cc1C1=C(O)C(C)(C)OC(C)(C)C1=O] | δ 8.09 (d, 1H), 7.82 (d, 1H), 7.77 (d, 1H), 7.61 (t, 1H), 7.47 (t, 1H), 7.43 (d, 1H), 7.18 (dd, 1H), 7.00 (d, 1H), 2.56-2.50 (m, 5H), 1.56 (s, 6H), 1.50 (s, 6H), 1.20 (t, 3H). |

TABLE T1-continued

| Compound Number | Structure | $^1$H NMR (CDCl$_3$ unless stated) or other physical data |
| --- | --- | --- |
| A-254 | 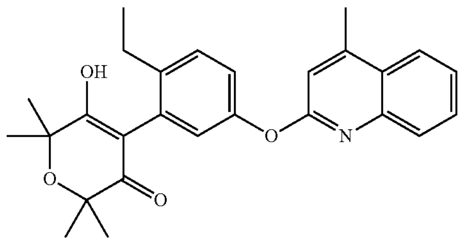 [SMILES: CCc1ccc(Oc2cc(C)c3ccccc3n2)cc1C1=C(O)C(C)(C)OC(C)(C)C1=O] | δ 7.95 (d, 1H), 7.82 (d, 1H), 7.64 (t, 1H) 7.50 (t, 1H), 7.40 (d, 1H), 7.15 (dd, 1H), 7.09 (s, 1H), 6.98 (d, 1H), 4.80 (br. s, 1H), 2.75 (s, 3H), 2.52 (q, 2H), 1.56 (s, 6H), 1.50 (s, 6H), 1.19 (t, 3H). |
| A-255 | 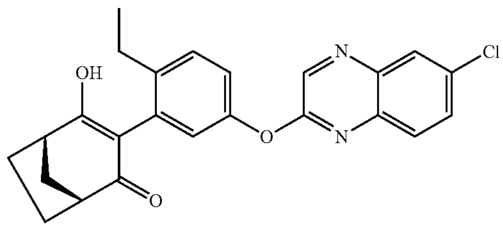 [SMILES: CCc1ccc(Oc2cnc3cc(Cl)ccc3n2)cc1C1=C(O)[C@H]2CC[C@H](C2)C1=O] | LCMS (Method A): t$_r$ = 1.65 mins, MH$^+$ = 421 |
| A-256 | 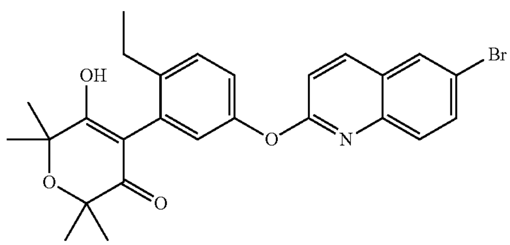 [SMILES: CCc1ccc(Oc2ccc3cc(Br)ccc3n2)cc1C1=C(O)C(C)(C)OC(C)(C)C1=O] | δ 8.10 (d, 1H), 7.94 (s, 1H), 7.69-7.62 (m, 2H), 7.41 (d, 1H), 7.21 (d, 1H), 7.16 (dd, 1H), 6.99 (d, 1H), 2.52 (q, 2H), 1.56 (s, 6H), 1.51 (s, 6H), 1.19 (t, 3H). |
| A-257 | 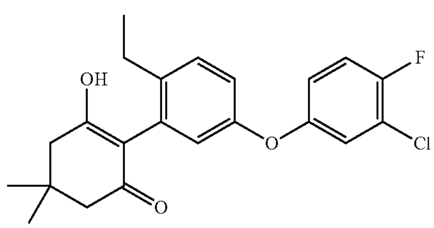 [SMILES: CCc1ccc(Oc2ccc(F)c(Cl)c2)cc1C1=C(O)CC(C)(C)CC1=O] | LCMS (Method A): t$_r$ = 1.75 mins, MH$^+$ = 389 |
| A-258 | 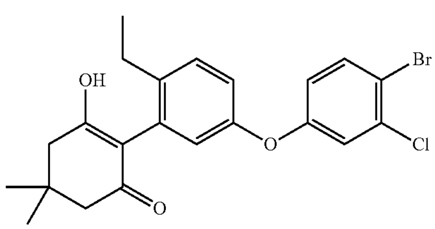 [SMILES: CCc1ccc(Oc2ccc(Br)c(Cl)c2)cc1C1=C(O)CC(C)(C)CC1=O] | LCMS (Method A): t$_r$ = 1.86 mins, MH$^+$ = 449 |
| A-259 | 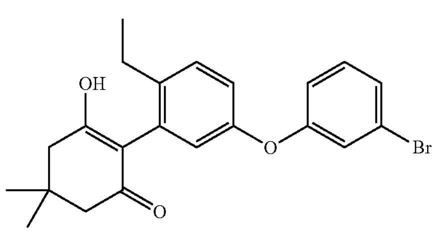 [SMILES: CCc1ccc(Oc2cccc(Br)c2)cc1C1=C(O)CC(C)(C)CC1=O] | LCMS (Method A): t$_r$ = 1.78 mins, MH$^+$ = 415 |

TABLE T1-continued

| Compound Number | Structure | $^1$H NMR (CDCl$_3$ unless stated) or other physical data |
|---|---|---|
| A-260 | 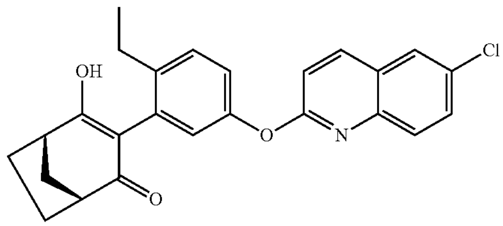 [SMILES: CCc1ccc(Oc2ccc3cc(Cl)ccc3n2)cc1C1=C(O)[C@H]2CC[C@H](C2)C1=O] | LCMS (Method A): t$_r$ = 1.73 mins, MH$^+$ = 420 |
| A-261 | 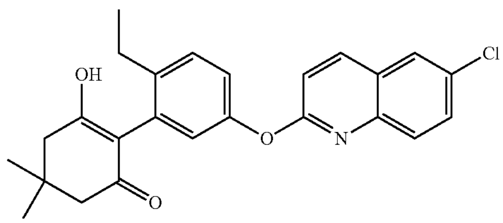 [SMILES: CCc1ccc(Oc2ccc3cc(Cl)ccc3n2)cc1C1=C(O)CC(C)(C)CC1=O] | δ 8.04 (d, 1H), 7.73 (d, 1H), 7.67-7.65 (m, 1H), 7.51 (dd, 1H), 7.38 (d, 1H), 7.16 (d, 1H), 7.14 (dd, 1H), 6.94 (d, 1H), 2.65-2.37 (m, 6H), 1.19-1.15 (m, 9H). |
| A-262 | 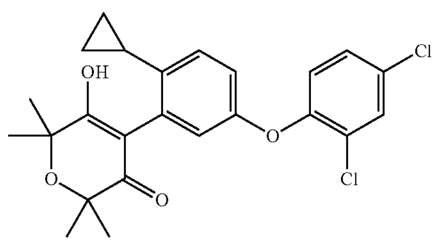 [SMILES: CC1(C)OC(C)(C)C(O)=C(c2cc(Oc3ccc(Cl)cc3Cl)ccc2C2CC2)C1=O] | δ 7.46 (1H, d), 7.20 (1H, dd), 7.06 (1H, d), 6.96 (1H, d), 6.88 (1H, dd), 6.78 (1H, d), 5.76 (1H, br. s), 1.71-1.64 (1H, m), 1.60 (6H, d), 1.49 (6H, d), 0.85-0.82 (2H, m), 0.70-0.67 (1H, m), 1.51-1.49 (1H, m). |
| A-263 | 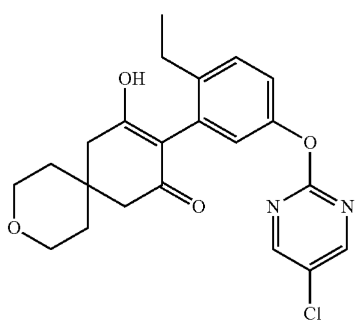 [SMILES: CCc1ccc(Oc2ncc(Cl)cn2)cc1C1=C(O)CC2(CCOCC2)CC1=O] | LCMS (Method B): t$_r$ = 1.36 mins, MH$^+$ = 415.1 |
| A-264 | 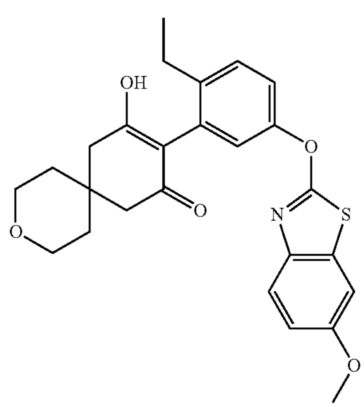 [SMILES: CCc1ccc(Oc2nc3ccc(OC)cc3s2)cc1C1=C(O)CC2(CCOCC2)CC1=O] | LCMS (Method B): t$_r$ = 1.45 mins, MH$^+$ = 466.2 |

TABLE T1-continued

| Compound Number | Structure | ¹H NMR (CDCl₃ unless stated) or other physical data |
|---|---|---|
| A-265 | 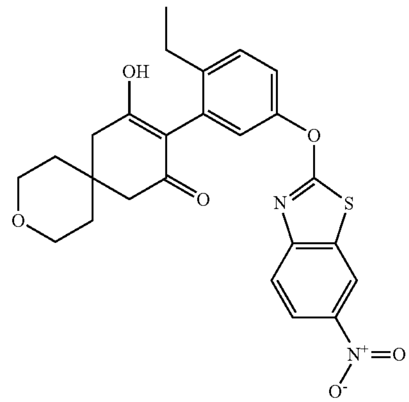 [SMILES: CCc1ccc(Oc2nc3ccc([N+](=O)[O-])cc3s2)cc1C1=C(O)CC2(CCOCC2)CC1=O] | LCMS (Method B): $t_r$ = 1.53 mins, MH⁺ = 481.1 |
| A-266 | 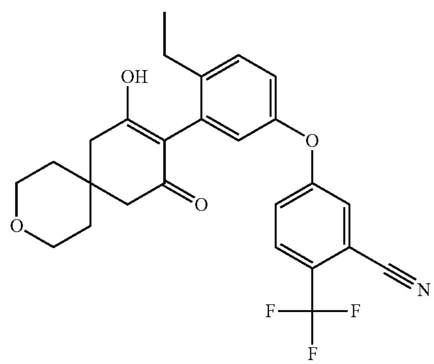 [SMILES: CCc1ccc(Oc2ccc(C(F)(F)F)c(C#N)c2)cc1C1=C(O)CC2(CCOCC2)CC1=O] | LCMS (Method B): $t_r$ = 1.54 mins, MH⁺ = 472.2 |
| A-267 | 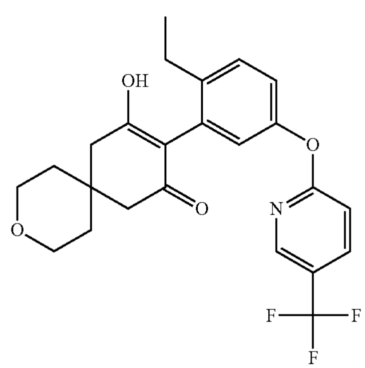 [SMILES: CCc1ccc(Oc2ccc(C(F)(F)F)cn2)cc1C1=C(O)CC2(CCOCC2)CC1=O] | LCMS (Method B): $t_r$ = 1.50 mins, MH⁺ = 448.2 |
| A-268 | 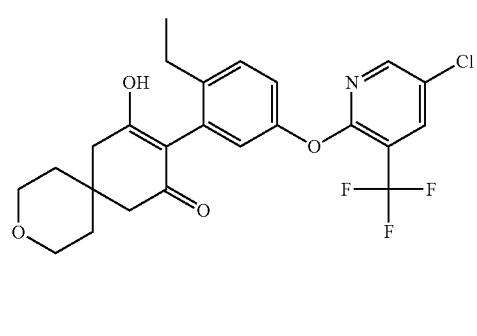 [SMILES: CCc1ccc(Oc2ncc(Cl)cc2C(F)(F)F)cc1C1=C(O)CC2(CCOCC2)CC1=O] | LCMS (Method B): $t_r$ = 1.60 mins, MH⁺ = 482.1 |

TABLE T1-continued

| Compound Number | Structure | $^1$H NMR (CDCl$_3$ unless stated) or other physical data |
|---|---|---|
| A-269 | 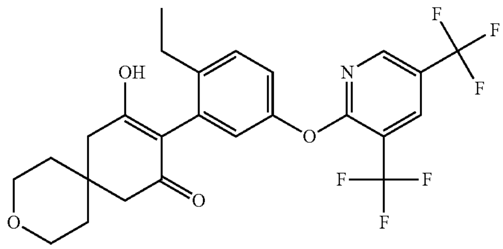 [SMILES: CCc1ccc(Oc2ncc(C(F)(F)F)cc2C(F)(F)F)cc1C1=C(O)CC2(CCOCC2)CC1=O] | δ 8.49 (s, 1H), 8.18 (d, 1H), 7.37 (d, 1H), 7.11-7.10 (m, 1H), 6.84 (d, 1H), 3.74-3.69 (m, 4H), 2.55-2.43 (m, 6H), 1.70-1.64 (m, 4H), 1.13 (t, 3H). |
| A-270 | 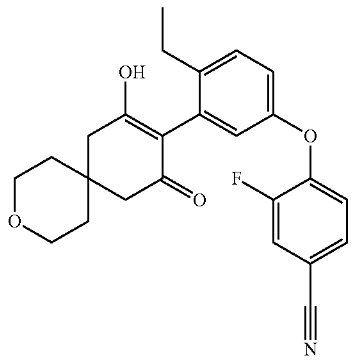 [SMILES: CCc1ccc(Oc2ccc(C#N)cc2F)cc1C1=C(O)CC2(CCOCC2)CC1=O] | LCMS (Method B): t$_r$ = 1.45 mins, MH$^+$ = 422.2 |
| A-271 | 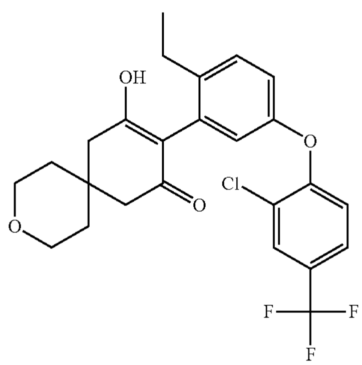 [SMILES: CCc1ccc(Oc2ccc(C(F)(F)F)cc2Cl)cc1C1=C(O)CC2(CCOCC2)CC1=O] | LCMS (Method B): t$_r$ = 1.70 mins, MH$^+$ = 481.1 |
| A-272 | 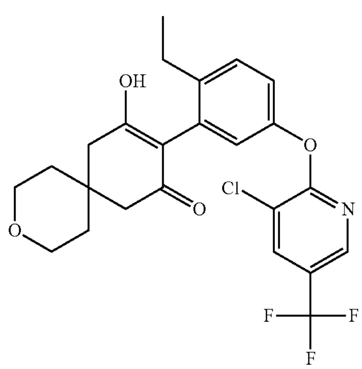 [SMILES: CCc1ccc(Oc2ncc(C(F)(F)F)cc2Cl)cc1C1=C(O)CC2(CCOCC2)CC1=O] | LCMS (Method B): t$_r$ = 1.60 mins, MH$^+$ = 482.1 |

TABLE T1-continued

| Compound Number | Structure | ¹H NMR (CDCl₃ unless stated) or other physical data |
|---|---|---|
| A-273 | 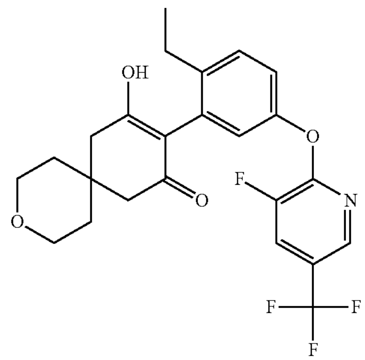 [SMILES: CCc1ccc(Oc2ncc(C(F)(F)F)cc2F)cc1C1=C(O)CC2(CCOCC2)CC1=O] | LCMS (Method B): $t_r$ = 1.53 mins, MH⁺ = 466.2 |
| A-274 | 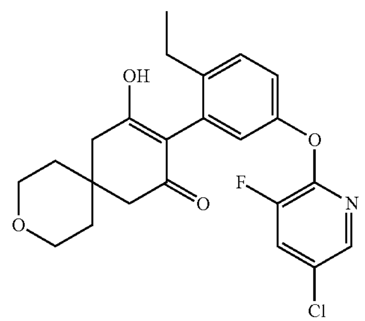 [SMILES: CCc1ccc(Oc2ncc(Cl)cc2F)cc1C1=C(O)CC2(CCOCC2)CC1=O] | LCMS (Method B): $t_r$ = 1.46 mins, MH⁺ = 432.1 |
| A-275 | 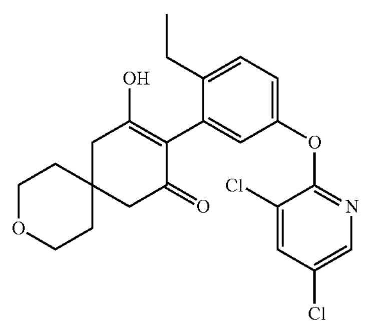 [SMILES: CCc1ccc(Oc2ncc(Cl)cc2Cl)cc1C1=C(O)CC2(CCOCC2)CC1=O] | LCMS (Method B): $t_r$ = 1.55 mins, MH⁺ = 448.1 |
| A-276 | 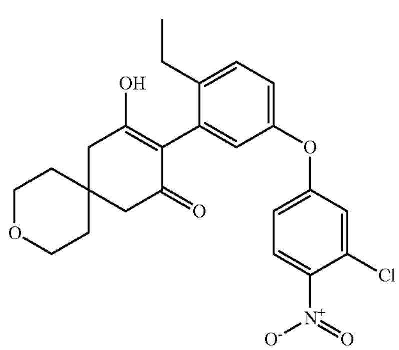 [SMILES: CCc1ccc(Oc2ccc([N+](=O)[O-])c(Cl)c2)cc1C1=C(O)CC2(CCOCC2)CC1=O] | LCMS (Method B): $t_r$ = 1.56 mins, MH⁺ = 458.1 |

TABLE T1-continued

| Compound Number | Structure | $^1$H NMR (CDCl$_3$ unless stated) or other physical data |
|---|---|---|
| A-277 | 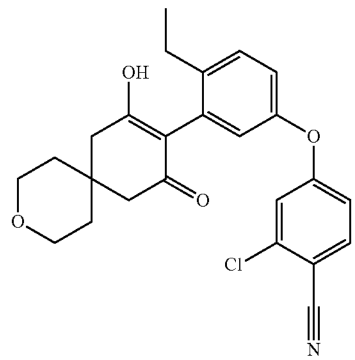 [SMILES: CCc1ccc(Oc2ccc(C#N)c(Cl)c2)cc1C1=C(O)CC2(CCOCC2)CC1=O] | LCMS (Method B): t$_r$ = 1.51 mins, MH$^+$ = 438.1 |
| A-278 | 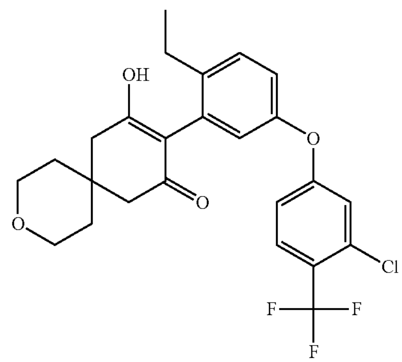 [SMILES: CCc1ccc(Oc2ccc(C(F)(F)F)c(Cl)c2)cc1C1=C(O)CC2(CCOCC2)CC1=O] | LCMS (Method B): t$_r$ = 1.71 mins, MH$^+$ = 481.1 |
| A-279 | 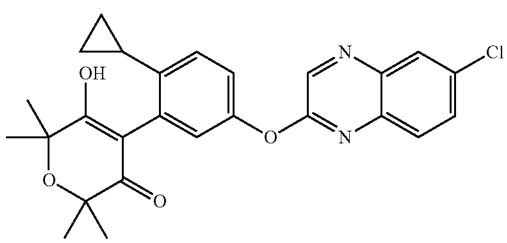 [SMILES: CC1(C)OC(C)(C)C(O)=C(c2cc(Oc3cnc4cc(Cl)ccc4n3)ccc2C2CC2)C1=O] | δ 8.74 (s, 1H), 8.07 (d, 1H), 7.67-7.59 (m, 2H), 7.20-7.14 (m, 2H), 7.03 (d, 1H), 1.87-1.76 (m, 1H), 1.60 (d, 6H), 1.49 (d, 6H), 0.90-0.87 (m, 2H), 0.78-0.75 (m, 1H), 0.58-0.55 (m, 1H). |
| A-280 | 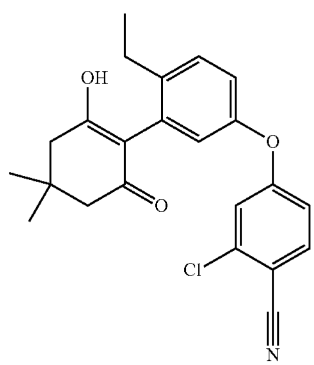 [SMILES: CCc1ccc(Oc2ccc(C#N)c(Cl)c2)cc1C1=C(O)CC(C)(C)CC1=O] | LCMS (Method B): t$_r$ = 1.65 mins, MH$^+$ = 396.1 |
| A-281 | 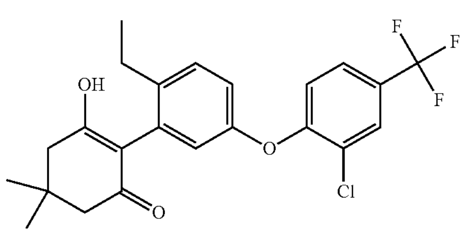 [SMILES: CCc1ccc(Oc2ccc(C(F)(F)F)cc2Cl)cc1C1=C(O)CC(C)(C)CC1=O] | LCMS (Method B): t$_r$ = 1.81 mins, MH$^+$ = 439.1 |

TABLE T1-continued

| Compound Number | Structure | $^1$H NMR (CDCl$_3$ unless stated) or other physical data |
|---|---|---|
| A-282 | 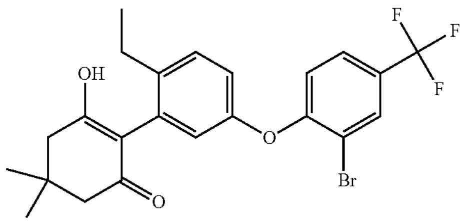 [SMILES: CCc1ccc(Oc2ccc(C(F)(F)F)cc2Br)cc1C1=C(O)CC(C)(C)CC1=O] | LCMS (Method B): t$_r$ = 1.85 mins, MH$^+$ = 485.1 |
| A-283 | 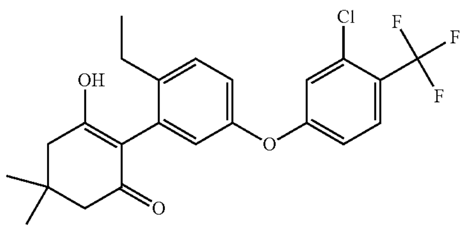 [SMILES: CCc1ccc(Oc2ccc(C(F)(F)F)c(Cl)c2)cc1C1=C(O)CC(C)(C)CC1=O] | LCMS (Method B): t$_r$ = 1.83 mins, MH$^+$ = 439.1 |
| A-284 | 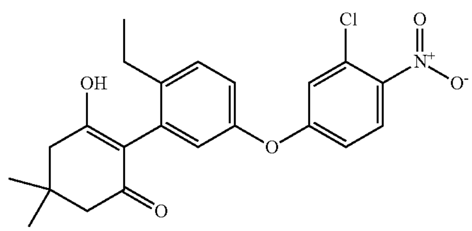 [SMILES: CCc1ccc(Oc2ccc([N+](=O)[O-])c(Cl)c2)cc1C1=C(O)CC(C)(C)CC1=O] | LCMS (Method B): t$_r$ = 1.68 mins, MH$^+$ = 416.1 |
| A-285 | 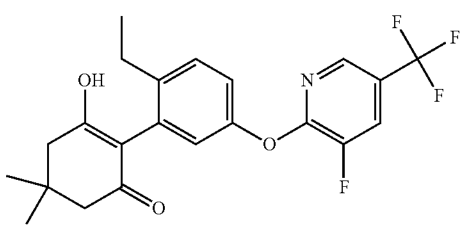 [SMILES: CCc1ccc(Oc2ncc(C(F)(F)F)cc2F)cc1C1=C(O)CC(C)(C)CC1=O] | LCMS (Method B): t$_r$ = 1.66 mins, MH$^+$ = 424.1 |
| A-286 | 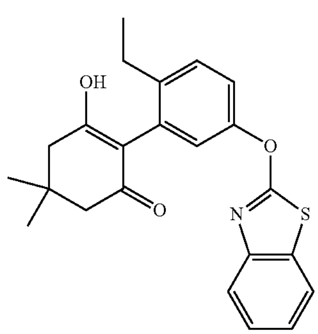 [SMILES: CCc1ccc(Oc2nc3ccccc3s2)cc1C1=C(O)CC(C)(C)CC1=O] | LCMS (Method B): t$_r$ = 1.63 mins, MH$^+$ = 394.1 |

TABLE T1-continued
| Compound Number | Structure | ¹H NMR (CDCl₃ unless stated) or other physical data |
|---|---|---|
| A-287 | 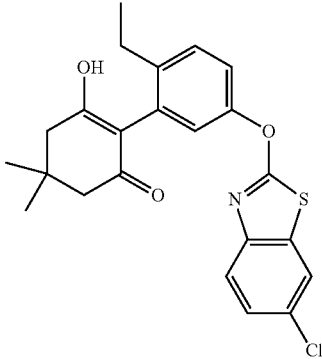 | LCMS (Method B): $t_r$ = 1.75 mins, MH⁺ = 428.1 |
| A-288 | 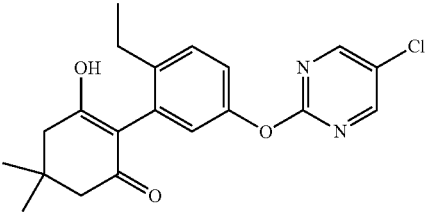 [SMILES: CCc1ccc(Oc2ncc(Cl)cn2)cc1C1=C(O)CC(C)(C)CC1=O] | δ 8.44 (s, 2H), 7.34 (d, 1H), 7.09 (dd, 1H), 6.84 (d, 1H), 2.48-2.40 (m, 6H), 1.17-1.11 (m, 9H). |
| A-289 | 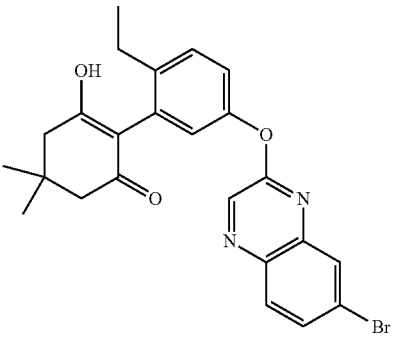 [SMILES: CCc1ccc(Oc2cnc3ccc(Br)cc3n2)cc1C1=C(O)CC(C)(C)CC1=O] | LCMS (Method B): $t_r$ = 1.70 mins, MH⁺ = 469.1 |
| A-290 | 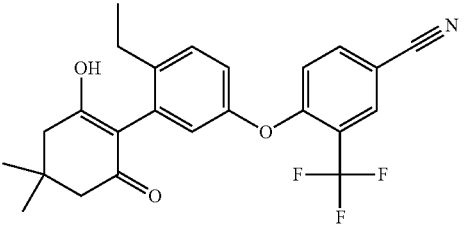 [SMILES: CCc1ccc(Oc2ccc(C#N)cc2C(F)(F)F)cc1C1=C(O)CC(C)(C)CC1=O] | LCMS (Method B): $t_r$ = 1.68 mins, MH⁺ = 430.2 |
| A-291 | 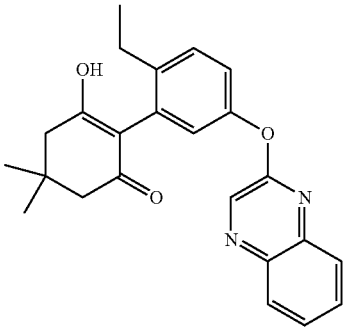 [SMILES: CCc1ccc(Oc2cnc3ccccc3n2)cc1C1=C(O)CC(C)(C)CC1=O] | LCMS (Method B): $t_r$ = 1.53 mins, MH⁺ = 389.2 |

TABLE T1-continued

| Compound Number | Structure | $^1$H NMR (CDCl$_3$ unless stated) or other physical data |
|---|---|---|
| A-292 | 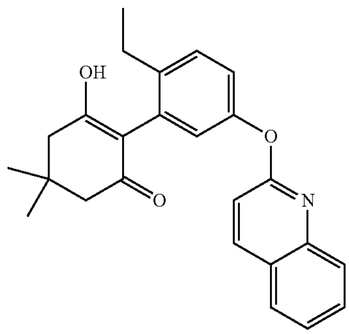 [SMILES: CCc1ccc(Oc2ccc3ccccc3n2)cc1C1=C(O)CC(C)(C)CC1=O] | LCMS (Method B): t$_r$ = 1.60 mins, MH$^+$ = 388.2 |
| A-293 | 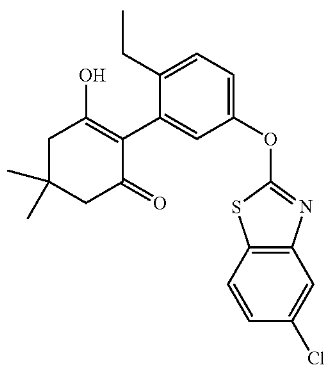 [SMILES: CCc1ccc(Oc2nc3cc(Cl)ccc3s2)cc1C1=C(O)CC(C)(C)CC1=O] | LCMS (Method B): t$_r$ = 1.75 mins, MH$^+$ = 428.1 |
| A-294 | 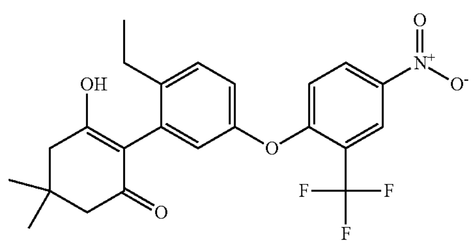 [SMILES: CCc1ccc(Oc2ccc([N+](=O)[O-])cc2C(F)(F)F)cc1C1=C(O)CC(C)(C)CC1=O] | LCMS (Method B): t$_r$ = 1.73 mins, MH$^+$ = 450.1 |
| A-295 | 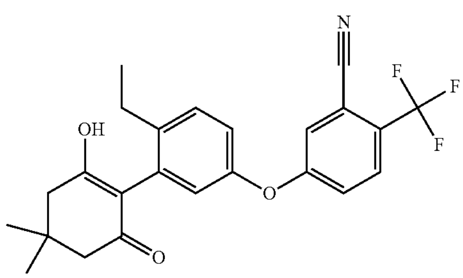 [SMILES: CCc1ccc(Oc2ccc(C(F)(F)F)c(C#N)c2)cc1C1=C(O)CC(C)(C)CC1=O] | LCMS (Method B): t$_r$ = 1.71 mins, MH$^+$ = 430.2 |
| A-296 | 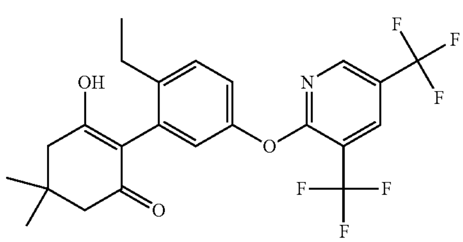 [SMILES: CCc1ccc(Oc2ncc(C(F)(F)F)cc2C(F)(F)F)cc1C1=C(O)CC(C)(C)CC1=O] | LCMS (Method B): t$_r$ = 1.76 mins, MH$^+$ = 474.1 |

TABLE T1-continued

| Compound Number | Structure | ¹H NMR (CDCl₃ unless stated) or other physical data |
|---|---|---|
| A-297 | 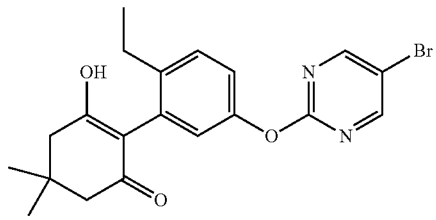 [SMILES: CCc1ccc(Oc2ncc(Br)cn2)cc1C1=C(O)CC(C)(C)CC1=O] | LCMS (Method B): $t_r$ = 1.45 mins, MH⁺ = 419.1 |
| A-298 | 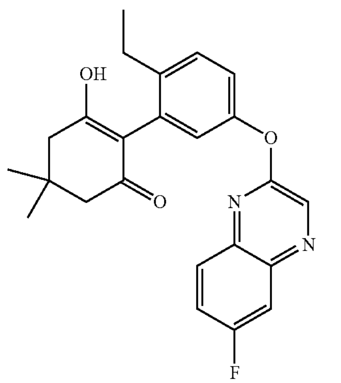 [SMILES: CCc1ccc(Oc2cnc3cc(F)ccc3n2)cc1C1=C(O)CC(C)(C)CC1=O] | LCMS (Method B): $t_r$ = 1.58 mins, MH⁺ = 407.2 |
| A-299 | 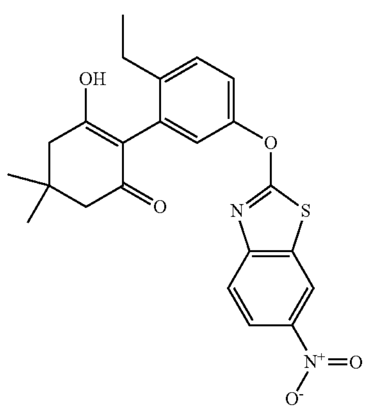 [SMILES: CCc1ccc(Oc2nc3ccc([N+](=O)[O-])cc3s2)cc1C1=C(O)CC(C)(C)CC1=O] | LCMS (Method B): $t_r$ = 1.65 mins, MH⁺ = 439.1 |
| A-300 | 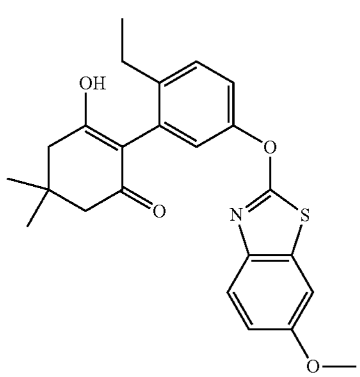 | LCMS (Method B): $t_r$ = 1.61 mins, MH⁺ = 424.2 |

TABLE T1-continued

| Compound Number | Structure | ¹H NMR (CDCl₃ unless stated) or other physical data |
|---|---|---|
| A-301 | 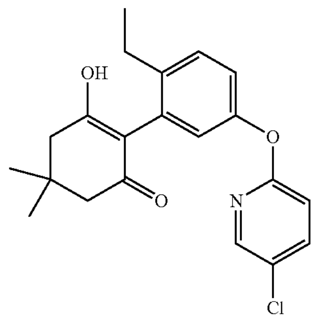 [SMILES: CCc1ccc(Oc2ccc(Cl)cn2)cc1C1=C(O)CC(C)(C)CC1=O] | LCMS (Method B): $t_r$ = 1.55 mins, MH⁺ = 372.1 |
| A-302 | 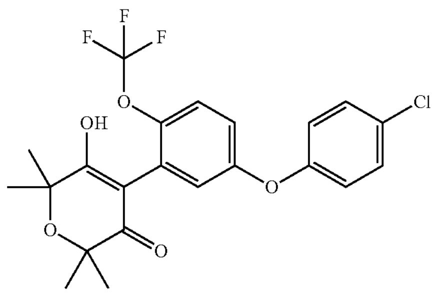 [SMILES: CC1(C)OC(C)(C)C(O)=C(c2cc(Oc3ccc(Cl)cc3)ccc2OC(F)(F)F)C1=O] | LCMS (Method A): $t_r$ = 1.95 mins, MH⁺ = 457, 459 |
| A-303 | 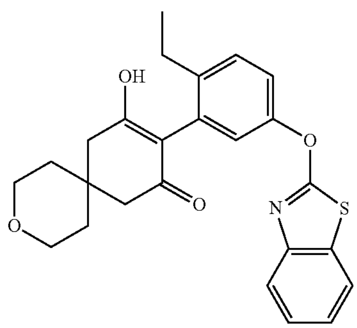 [SMILES: CCc1ccc(Oc2nc3ccccc3s2)cc1C1=C(O)CC2(CCOCC2)CC1=O] | LCMS (Method B): $t_r$ = 1.56 mins, MH⁺ = 436.2 |
| A-304 | 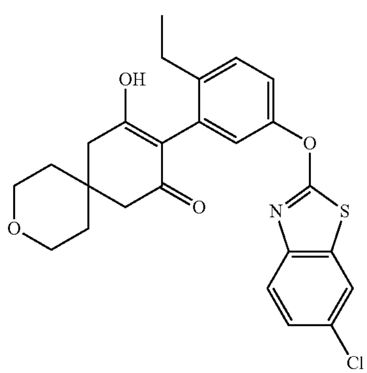 [SMILES: CCc1ccc(Oc2nc3ccc(Cl)cc3s2)cc1C1=C(O)CC2(CCOCC2)CC1=O] | LCMS (Method B): $t_r$ = 1.63 mins, MH⁺ = 470.1 |
| A-305 | 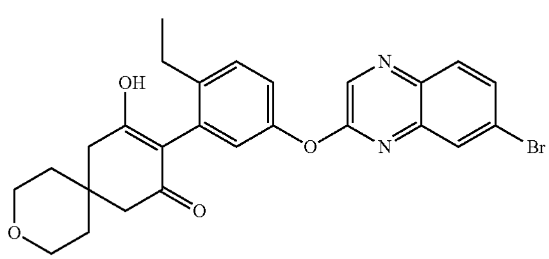 [SMILES: CCc1ccc(Oc2cnc3ccc(Br)cc3n2)cc1C1=C(O)CC2(CCOCC2)CC1=O] | LCMS (Method B): $t_r$ = 1.56 mins, MH⁺ = 509.1 |

TABLE T1-continued
| Compound Number | Structure | ¹H NMR (CDCl₃ unless stated) or other physical data |
|---|---|---|
| A-306 | 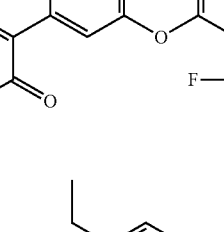 | LCMS (Method B): t_r = 1.50 mins, MH⁺ = 472.2 |
| A-307 | 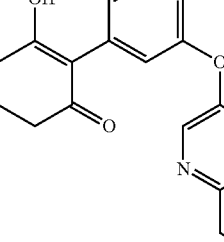 | LCMS (Method B): t_r = 1.38 mins, MH⁺ = 431.2 |
| A-308 | 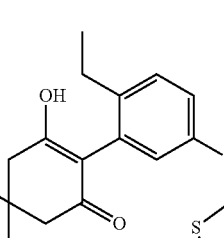 | LCMS (Method B): t_r = 1.61 mins, MH⁺ = 470.1 |
| A-309 | 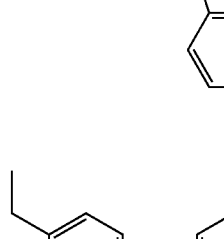 | LCMS (Method B): t_r = 1.61 mins, MH⁺ = 492.2 |
| A-310 | 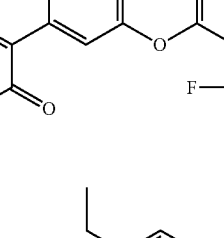 | LCMS (Method B): t_r = 1.30 mins, MH⁺ = 459.1 |

TABLE T1-continued

| Compound Number | Structure | ¹H NMR (CDCl₃ unless stated) or other physical data |
|---|---|---|
| A-311 | 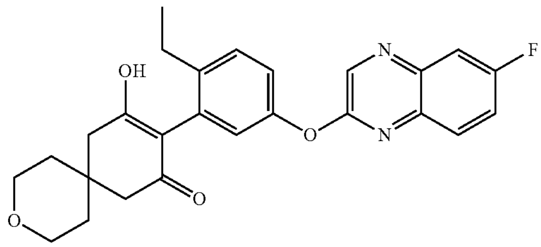 [SMILES: CCc1ccc(Oc2cnc3cc(F)ccc3n2)cc1C1=C(O)CC2(CCOCC2)CC1=O] | LCMS (Method B): $t_r$ = 1.45 mins, MH⁺ = 449.2 |
| A-312 | 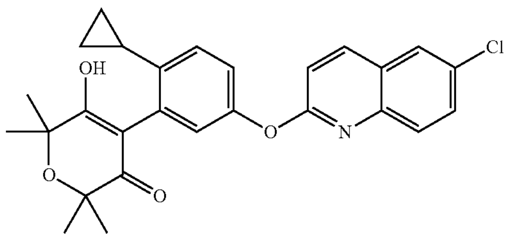 [SMILES: CC1(C)OC(C)(C)C(O)=C(c2cc(Oc3ccc4cc(Cl)ccc4n3)ccc2C2CC2)C1=O] | δ 8.10 (d, 1H), 7.76 (d, 1H), 7.69 (d, 1H), 7.55 (dd, 1H), 7.22-7.11 (m, 3H), 7.01 (m, 1H), 1.82-1.75 (m, 1H), 1.56 (s, 6H), 1.52 (s, 6H), 0.88-0.85 (m, 2H), 0.65 (br. app. s, 2H). |
| A-313 | 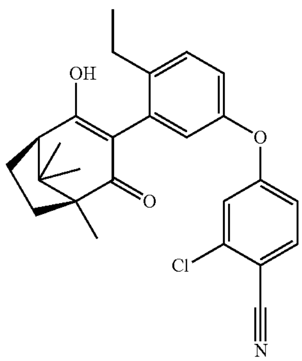 [SMILES: CCc1ccc(Oc2ccc(C#N)c(Cl)c2)cc1C1=C(O)[C@@H]2CC[C@](C)(C1=O)C2(C)C] | LCMS (Method B): $t_r$ = 1.81 mins, MH⁺ = 436.2 |
| A-314 | 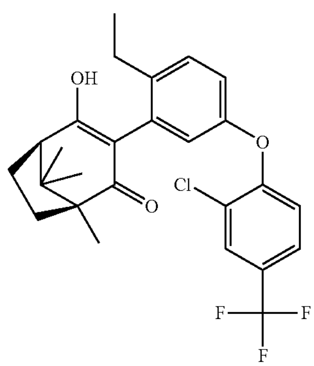 [SMILES: CCc1ccc(Oc2ccc(C(F)(F)F)cc2Cl)cc1C1=C(O)[C@@H]2CC[C@](C)(C1=O)C2(C)C] | LCMS (Method B): $t_r$ = 1.94 mins, MH⁺ = 479.2 |
| A-315 | 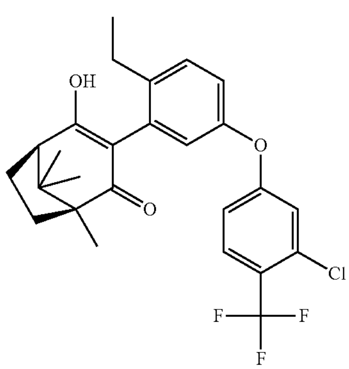 [SMILES: CCc1ccc(Oc2ccc(C(F)(F)F)c(Cl)c2)cc1C1=C(O)[C@@H]2CC[C@](C)(C1=O)C2(C)C] | LCMS (Method B): $t_r$ = 1.96 mins, MH⁺ = 479.2 |

TABLE T1-continued

| Compound Number | Structure | $^1$H NMR (CDCl$_3$ unless stated) or other physical data |
|---|---|---|
| A-316 | 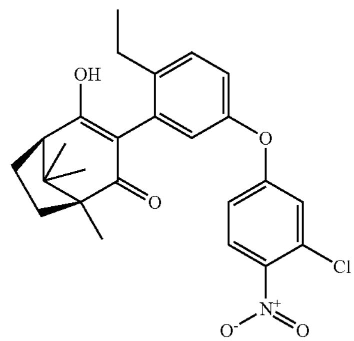 [SMILES: CCc1ccc(Oc2ccc([N+](=O)[O-])c(Cl)c2)cc1C1=C(O)[C@@H]2CC[C@](C)(C1=O)C2(C)C] | LCMS (Method B): t$_r$ = 1.81 mins, MH$^+$ = 456.1 |
| A-317 | 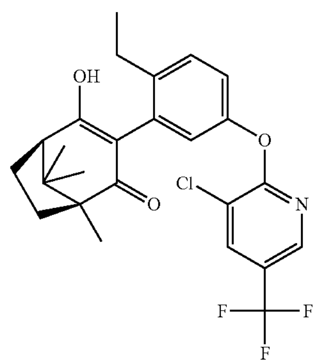 [SMILES: CCc1ccc(Oc2ncc(C(F)(F)F)cc2Cl)cc1C1=C(O)[C@@H]2CC[C@](C)(C1=O)C2(C)C] | LCMS (Method B): t$_r$ = 1.84 mins, MH$^+$ = 480.1 |
| A-318 | 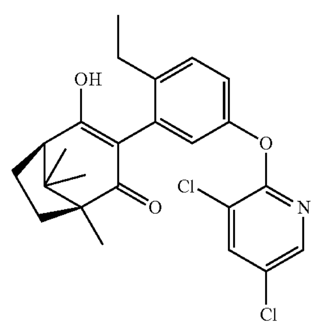 [SMILES: CCc1ccc(Oc2ncc(Cl)cc2Cl)cc1C1=C(O)[C@@H]2CC[C@](C)(C1=O)C2(C)C] | LCMS (Method B): t$_r$ = 1.81 mins, MH$^+$ = 446.1 |
| A-319 | 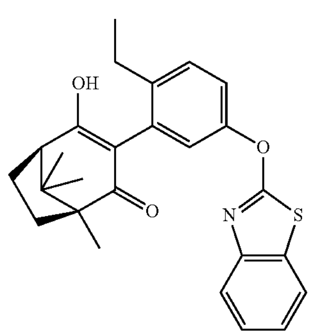 [SMILES: CCc1ccc(Oc2nc3ccccc3s2)cc1C1=C(O)[C@@H]2CC[C@](C)(C1=O)C2(C)C] | LCMS (Method B): t$_r$ = 1.76 mins, MH$^+$ = 434.2 |

TABLE T1-continued

| Compound Number | Structure | ¹H NMR (CDCl₃ unless stated) or other physical data |
|---|---|---|
| A-320 | 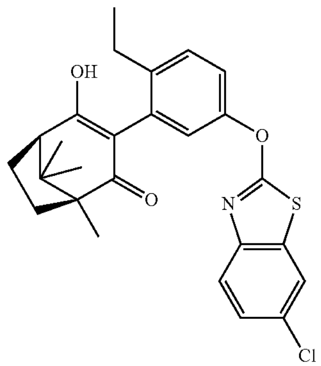 [SMILES: CCc1ccc(Oc2nc3ccc(Cl)cc3s2)cc1C1=C(O)[C@@H]2CC[C@](C)(C1=O)C2(C)C] | LCMS (Method B): $t_r$ = 1.87 mins, MH⁺ = 468.1 |
| A-321 | 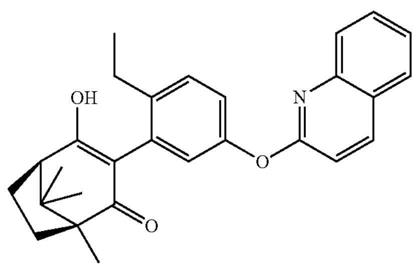 [SMILES: CCc1ccc(Oc2ccc3ccccc3n2)cc1C1=C(O)[C@@H]2CC[C@](C)(C1=O)C2(C)C] | LCMS (Method B): $t_r$ = 1.72 mins, MH⁺ = 428.2 |
| A-322 | 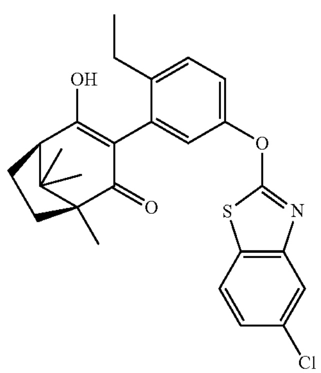 [SMILES: CCc1ccc(Oc2nc3cc(Cl)ccc3s2)cc1C1=C(O)[C@@H]2CC[C@](C)(C1=O)C2(C)C] | LCMS (Method B): $t_r$ = 1.87 mins, MH⁺ = 468.1 |
| A-323 | 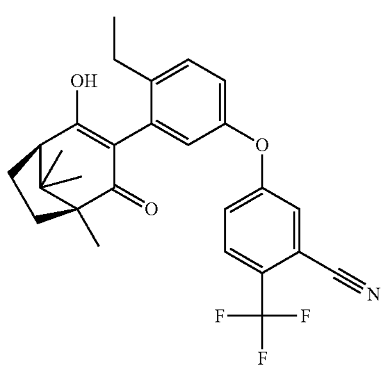 [SMILES: CCc1ccc(Oc2ccc(C(F)(F)F)c(C#N)c2)cc1C1=C(O)[C@@H]2CC[C@](C)(C1=O)C2(C)C] | LCMS (Method B): $t_r$ = 1.81 mins, MH⁺ = 470.2 |

TABLE T1-continued

| Compound Number | Structure | $^1$H NMR (CDCl$_3$ unless stated) or other physical data |
|---|---|---|
| A-324 | 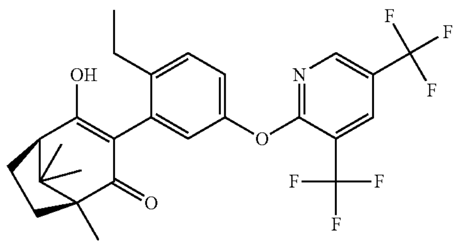 [SMILES: CCc1ccc(Oc2ncc(C(F)(F)F)cc2C(F)(F)F)cc1C1=C(O)[C@@H]2CC[C@](C)(C1=O)C2(C)C] | LCMS (Method B): t$_r$ = 1.87 mins, MH$^+$ = 514.2 |
| A-325 | 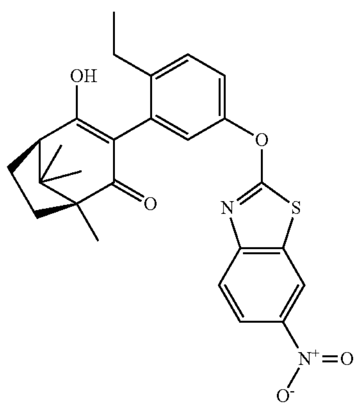 [SMILES: CCc1ccc(Oc2nc3ccc([N+](=O)[O-])cc3s2)cc1C1=C(O)[C@@H]2CC[C@](C)(C1=O)C2(C)C] | LCMS (Method B): t$_r$ = 1.77 mins, MH$^+$ = 479.2 |
| A-326 | 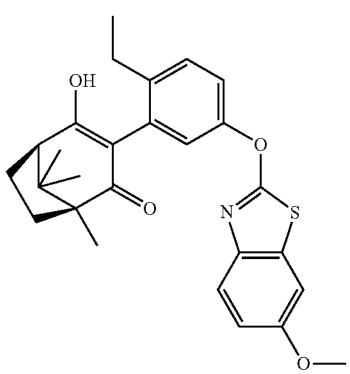 [SMILES: CCc1ccc(Oc2nc3ccc(OC)cc3s2)cc1C1=C(O)[C@@H]2CC[C@](C)(C1=O)C2(C)C] | LCMS (Method B): t$_r$ = 1.76 mins, MH$^+$ = 464.2 |
| A-327 | 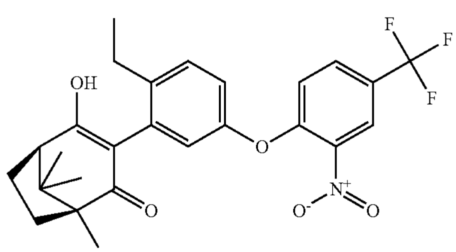 [SMILES: CCc1ccc(Oc2ccc(C(F)(F)F)cc2[N+](=O)[O-])cc1C1=C(O)[C@@H]2CC[C@](C)(C1=O)C2(C)C] | LCMS (Method B): t$_r$ = 1.84 mins, MH$^+$ = 490.2 |

TABLE T1-continued

| Compound Number | Structure | ¹H NMR (CDCl₃ unless stated) or other physical data |
|---|---|---|
| A-328 | 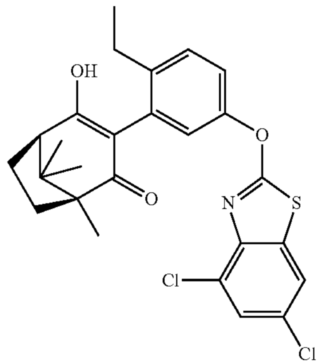 [SMILES: CCc1ccc(Oc2nc3c(Cl)cc(Cl)cc3s2)cc1C1=C(O)[C@@H]2CC[C@](C)(C1=O)C2(C)C] | LCMS (Method B): $t_r$ = 1.97 mins, MH⁺ = 502.1 |
| A-329 | 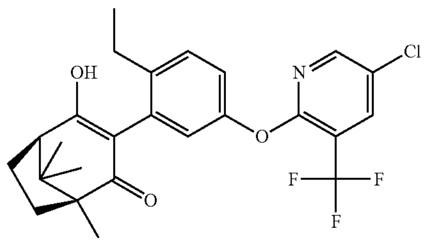 [SMILES: CCc1ccc(Oc2ncc(Cl)cc2C(F)(F)F)cc1C1=C(O)[C@@H]2CC[C@](C)(C1=O)C2(C)C] | LCMS (Method B): $t_r$ = 1.84 mins, MH⁺ = 480.1 |
| A-330 | 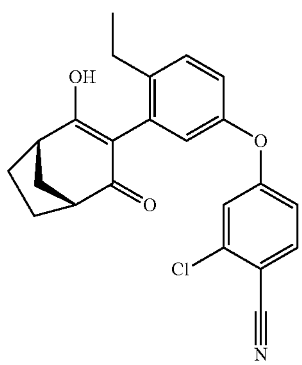 [SMILES: CCc1ccc(Oc2ccc(C#N)c(Cl)c2)cc1C1=C(O)[C@H]2CC[C@H](C2)C1=O] | LCMS (Method B): $t_r$ = 1.61 mins, MH⁺ = 394.1 |
| A-331 | 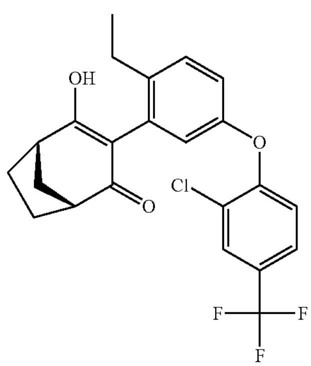 [SMILES: CCc1ccc(Oc2ccc(C(F)(F)F)cc2Cl)cc1C1=C(O)[C@H]2CC[C@H](C2)C1=O] | LCMS (Method B): $t_r$ = 1.77 mins, MH⁺ = 437.1 |

TABLE T1-continued

| Compound Number | Structure | ¹H NMR (CDCl₃ unless stated) or other physical data |
|---|---|---|
| A-332 | 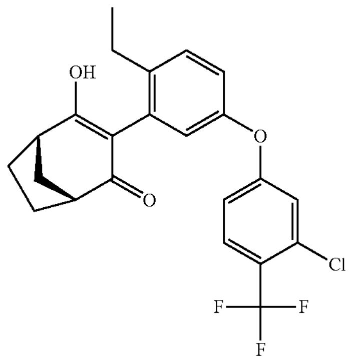 [SMILES: CCc1ccc(Oc2ccc(C(F)(F)F)c(Cl)c2)cc1C1=C(O)[C@H]2CC[C@H](C2)C1=O] | LCMS (Method B): $t_r$ = 1.74 mins, MH⁺ = 437.1 |
| A-333 | 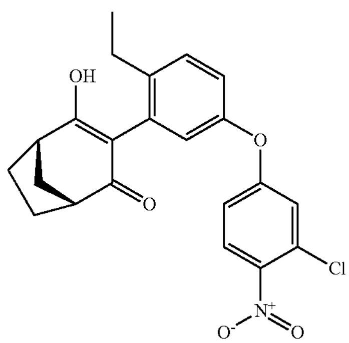 [SMILES: CCc1ccc(Oc2ccc([N+](=O)[O-])c(Cl)c2)cc1C1=C(O)[C@H]2CC[C@H](C2)C1=O] | LCMS (Method B): $t_r$ = 1.62 mins, MH⁺ = 414.1 |
| A-334 | 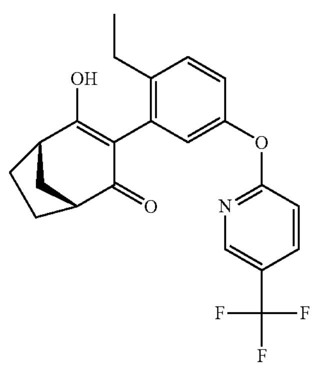 [SMILES: CCc1ccc(Oc2ccc(C(F)(F)F)cn2)cc1C1=C(O)[C@H]2CC[C@H](C2)C1=O] | LCMS (Method B): $t_r$ = 1.52 mins, MH⁺ = 404.1 |
| A-335 | 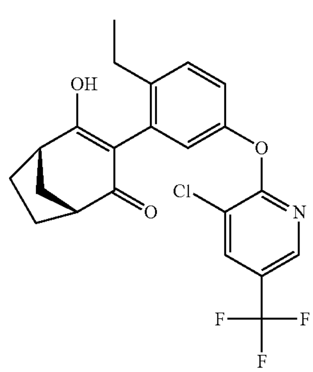 [SMILES: CCc1ccc(Oc2ncc(C(F)(F)F)cc2Cl)cc1C1=C(O)[C@H]2CC[C@H](C2)C1=O] | LCMS (Method B): $t_r$ = 1.62 mins, MH⁺ = 438.1 |

TABLE T1-continued

| Compound Number | Structure | ¹H NMR (CDCl₃ unless stated) or other physical data |
|---|---|---|
| A-336 | 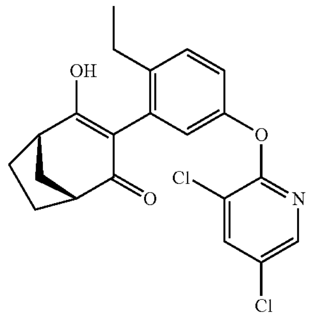 [SMILES: CCc1ccc(Oc2ncc(Cl)cc2Cl)cc1C1=C(O)[C@H]2CC[C@H](C2)C1=O] | LCMS (Method B): $t_r$ = 1.57 mins, MH⁺ = 404.1 |
| A-337 | 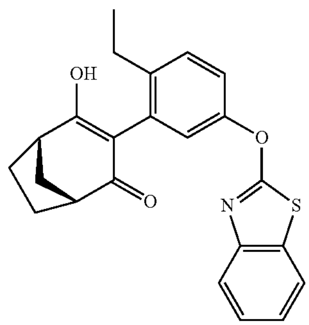 [SMILES: CCc1ccc(Oc2nc3ccccc3s2)cc1C1=C(O)[C@H]2CC[C@H](C2)C1=O] | LCMS (Method B): $t_r$ = 1.52 mins, MH⁺ = 392.1 |
| A-338 | 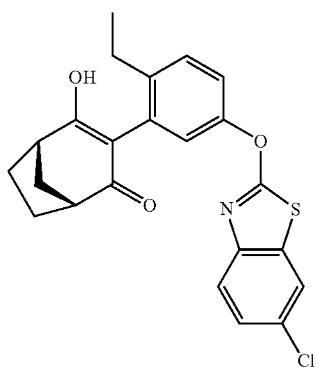 [SMILES: CCc1ccc(Oc2nc3ccc(Cl)cc3s2)cc1C1=C(O)[C@H]2CC[C@H](C2)C1=O] | LCMS (Method B): $t_r$ = 1.66 mins, MH⁺ = 426.1 |
| A-339 | 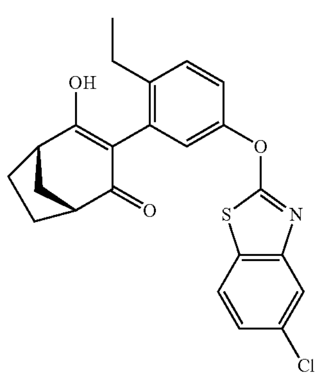 [SMILES: CCc1ccc(Oc2nc3cc(Cl)ccc3s2)cc1C1=C(O)[C@H]2CC[C@H](C2)C1=O] | LCMS (Method B): $t_r$ = 1.66 mins, MH⁺ = 426.1 |

TABLE T1-continued

| Compound Number | Structure | $^1$H NMR (CDCl$_3$ unless stated) or other physical data |
|---|---|---|
| A-340 | 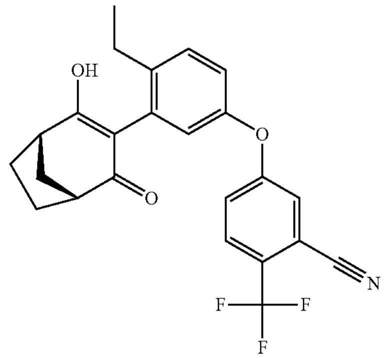 [SMILES: CCc1ccc(Oc2ccc(C(F)(F)F)c(C#N)c2)cc1C1=C(O)[C@H]2CC[C@H](C2)C1=O] | LCMS (Method B): t$_r$ = 1.61 mins, MH$^+$ = 428.1 |
| A-341 | 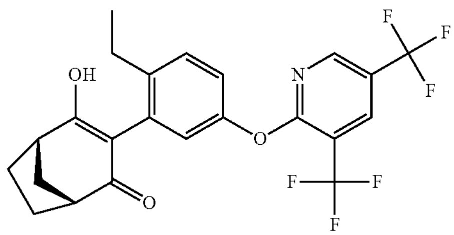 [SMILES: CCc1ccc(Oc2ncc(C(F)(F)F)cc2C(F)(F)F)cc1C1=C(O)[C@H]2CC[C@H](C2)C1=O] | LCMS (Method B): t$_r$ = 1.67 mins, MH$^+$ = 472.1 |
| A-342 | 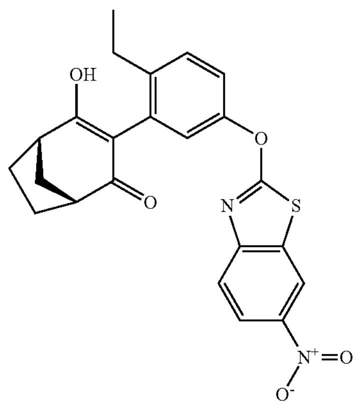 [SMILES: CCc1ccc(Oc2nc3ccc([N+](=O)[O-])cc3s2)cc1C1=C(O)[C@H]2CC[C@H](C2)C1=O] | LCMS (Method B): t$_r$ = 1.56 mins, MH$^+$ = 437.1 |
| A-343 | 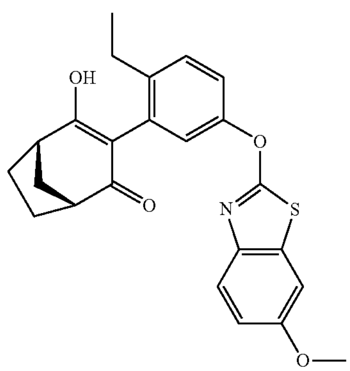 [SMILES: CCc1ccc(Oc2nc3ccc(OC)cc3s2)cc1C1=C(O)[C@H]2CC[C@H](C2)C1=O] | LCMS (Method B): t$_r$ = 1.54 mins, MH$^+$ = 422.1 |
| A-344 | 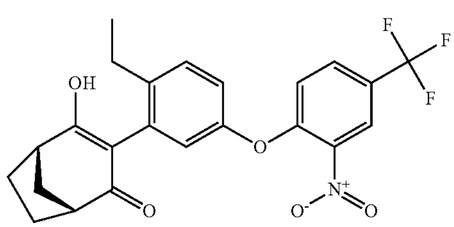 [SMILES: CCc1ccc(Oc2ccc(C(F)(F)F)cc2[N+](=O)[O-])cc1C1=C(O)[C@H]2CC[C@H](C2)C1=O] | LCMS (Method B): t$_r$ = 1.62 mins, MH$^+$ = 448.1 |

TABLE T1-continued

| Compound Number | Structure | $^1$H NMR (CDCl$_3$ unless stated) or other physical data |
|---|---|---|
| A-345 | 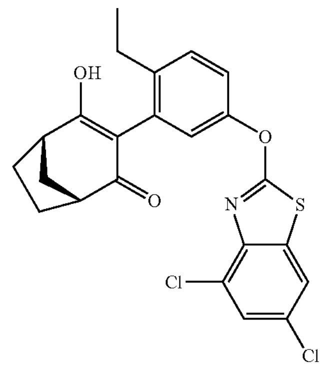 [SMILES: CCc1ccc(Oc2nc3c(Cl)cc(Cl)cc3s2)cc1C1=C(O)[C@H]2CC[C@H](C2)C1=O] | LCMS (Method B): t$_r$ = 1.76 mins, MH$^+$ = 460.0 |
| A-346 | 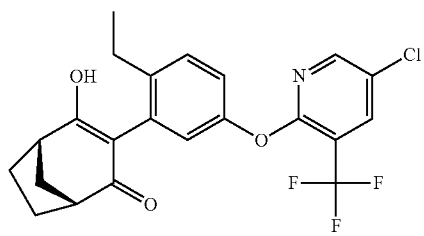 [SMILES: CCc1ccc(Oc2ncc(Cl)cc2C(F)(F)F)cc1C1=C(O)[C@H]2CC[C@H](C2)C1=O] | LCMS (Method B): t$_r$ = 1.62 mins, MH$^+$ = 438.1 |
| A-347 | 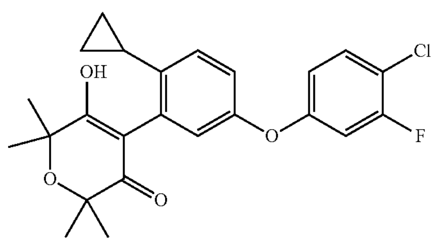 [SMILES: CC1(C)OC(C)(C)C(O)=C(c2cc(Oc3ccc(Cl)c(F)c3)ccc2C2CC2)C1=O] | LCMS (Method B): t$_r$ = 1.87 mins, MH$^+$ = 431.1 |
| A-348 | 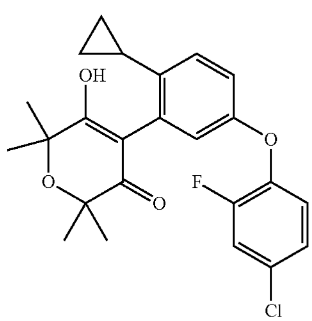 [SMILES: CC1(C)OC(C)(C)C(O)=C(c2cc(Oc3ccc(Cl)cc3F)ccc2C2CC2)C1=O] | LCMS (Method B): t$_r$ = 1.84 mins, MH$^+$ = 431.1 |
| A-349 | 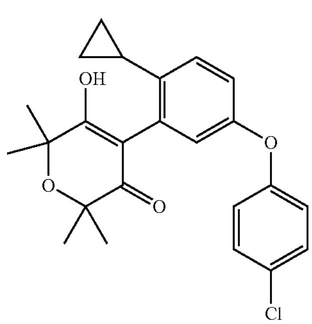 [SMILES: CC1(C)OC(C)(C)C(O)=C(c2cc(Oc3ccc(Cl)cc3)ccc2C2CC2)C1=O] | LCMS (Method B): t$_r$ = 1.84 mins, MH$^+$ = 413.1 |

TABLE T1-continued

| Compound Number | Structure | $^1$H NMR (CDCl$_3$ unless stated) or other physical data |
| --- | --- | --- |
| A-350 | 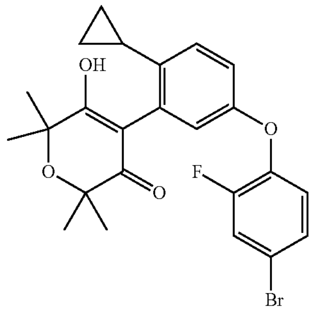 [SMILES: CC1(C)OC(C)(C)C(O)=C(c2cc(Oc3ccc(Br)cc3F)ccc2C2CC2)C1=O] | LCMS (Method B): t$_r$ = 1.86 mins, MH$^+$ = 477.1 |
| A-351 | 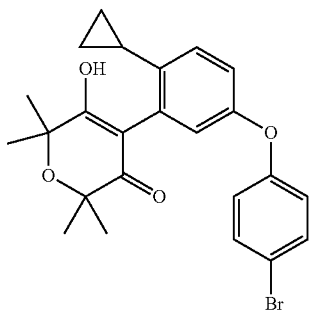 | LCMS (Method B): t$_r$ = 1.86 mins, MH$^+$ = 459.1 |
| A-352 | 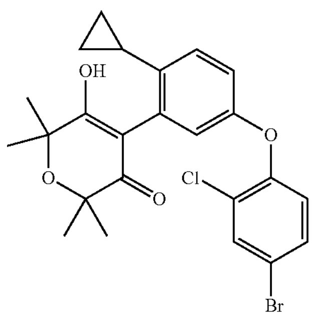 [SMILES: CC1(C)OC(C)(C)C(O)=C(c2cc(Oc3ccc(Br)cc3Cl)ccc2C2CC2)C1=O] | LCMS (Method B): t$_r$ = 1.94 mins, MH$^+$ = 493.1 |
| A-353 | 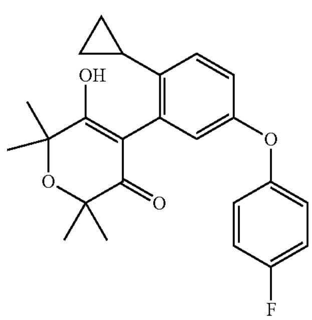 [SMILES: CC1(C)OC(C)(C)C(O)=C(c2cc(Oc3ccc(F)cc3)ccc2C2CC2)C1=O] | LCMS (Method B): t$_r$ = 1.74 mins, MH$^+$ = 397.2 |
| A-354 | 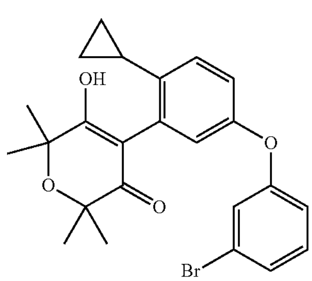 [SMILES: CC1(C)OC(C)(C)C(O)=C(c2cc(Oc3cccc(Br)c3)ccc2C2CC2)C1=O] | LCMS (Method B): t$_r$ = 1.86 mins, MH$^+$ = 459.1 |

TABLE T1-continued

| Compound Number | Structure | ¹H NMR (CDCl₃ unless stated) or other physical data |
|---|---|---|
| A-355 | 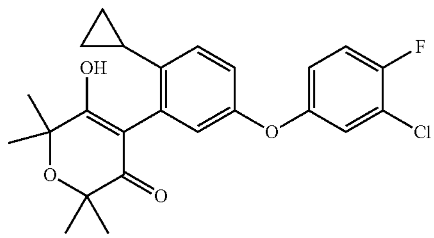 [SMILES: CC1(C)OC(C)(C)C(O)=C(c2cc(Oc3ccc(F)c(Cl)c3)ccc2C2CC2)C1=O] | LCMS (Method B): t$_r$ = 1.84 mins, MH⁺ = 431.1 |
| A-356 | 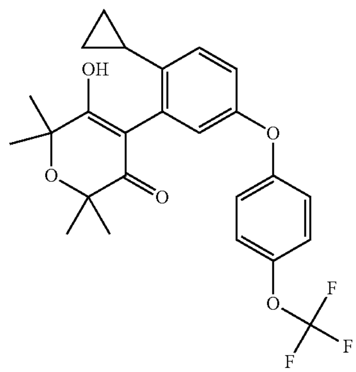 [SMILES: CC1(C)OC(C)(C)C(O)=C(c2cc(Oc3ccc(OC(F)(F)F)cc3)ccc2C2CC2)C1=O] | LCMS (Method B): t$_r$ = 1.89 mins, MH⁺ = 463.2 |
| A-357 | 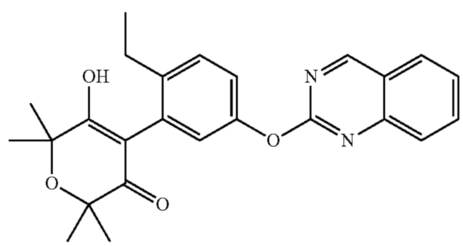 [SMILES: CCc1ccc(Oc2ncc3ccccc3n2)cc1C1=C(O)C(C)(C)OC(C)(C)C1=O] | δ 9.33 (s, 1H), 7.93 (d, 1H), 7.89-7.85 (m, 1H), 7.81-7.79 (m, 1H), 7.42 (d, 1H), 7.21 (dd, 1H), 7.03 (d, 1H), 2.52 (q, 2H), 1.56 (s, 6H), 1.51 (s, 6H), 1.18 (t, 3H). |
| A-358 | 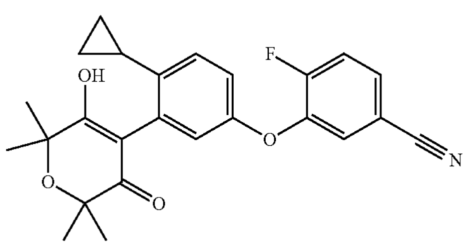 [SMILES: CC1(C)OC(C)(C)C(O)=C(c2cc(Oc3cc(C#N)ccc3F)ccc2C2CC2)C1=O] | LCMS (Method B): t$_r$ = 1.71 mins, MH⁺ = 422.2 |
| A-359 | 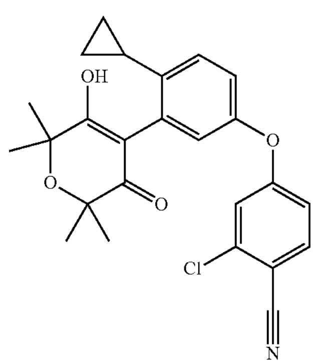 [SMILES: CC1(C)OC(C)(C)C(O)=C(c2cc(Oc3ccc(C#N)c(Cl)c3)ccc2C2CC2)C1=O] | LCMS (Method B): t$_r$ = 1.77 mins, MH⁺ = 438.1 |

TABLE T1-continued

| Compound Number | Structure | $^1$H NMR (CDCl$_3$ unless stated) or other physical data |
|---|---|---|
| A-360 | 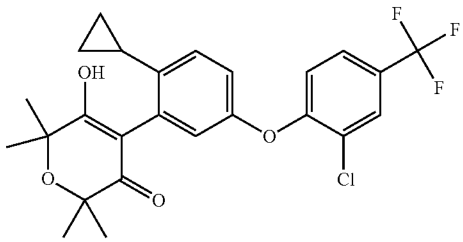 [SMILES: CC1(C)OC(C)(C)C(O)=C(c2cc(Oc3ccc(C(F)(F)F)cc3Cl)ccc2C2CC2)C1=O] | LCMS (Method B): t$_r$ = 1.96 mins, MH$^+$ = 481.1 |
| A-361 | 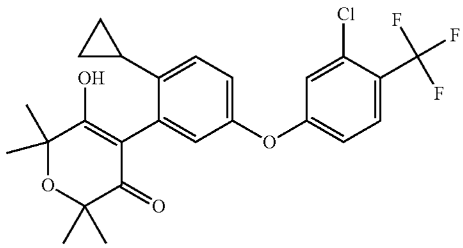 [SMILES: CC1(C)OC(C)(C)C(O)=C(c2cc(Oc3ccc(C(F)(F)F)c(Cl)c3)ccc2C2CC2)C1=O] | LCMS (Method B): t$_r$ = 1.97 mins, MH$^+$ = 481.1 |
| A-362 | 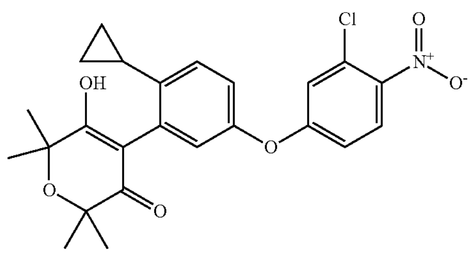 [SMILES: CC1(C)OC(C)(C)C(O)=C(c2cc(Oc3ccc([N+](=O)[O-])c(Cl)c3)ccc2C2CC2)C1=O] | LCMS (Method B): t$_r$ = 1.81 mins, MH$^+$ = 458.1 |
| A-363 | 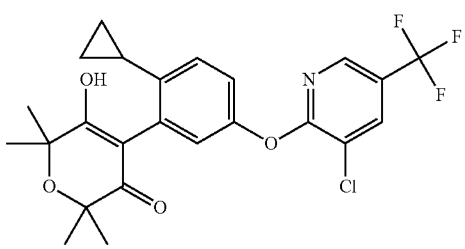 [SMILES: CC1(C)OC(C)(C)C(O)=C(c2cc(Oc3ncc(C(F)(F)F)cc3Cl)ccc2C2CC2)C1=O] | LCMS (Method B): t$_r$ = 1.86 mins, MH$^+$ = 482.1 |
| A-364 | 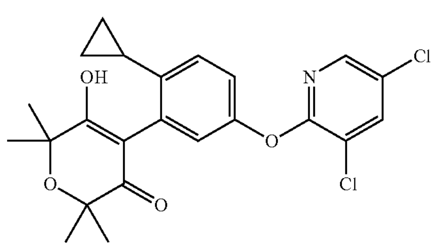 [SMILES: CC1(C)OC(C)(C)C(O)=C(c2cc(Oc3ncc(Cl)cc3Cl)ccc2C2CC2)C1=O] | LCMS (Method B): t$_r$ = 1.81 mins, MH$^+$ = 448.1 |
| A-365 | 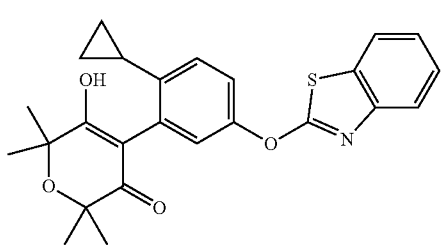 [SMILES: CC1(C)OC(C)(C)C(O)=C(c2cc(Oc3nc4ccccc4s3)ccc2C2CC2)C1=O] | LCMS (Method B): t$_r$ = 1.77 mins, MH$^+$ = 436.2 |

TABLE T1-continued

| Compound Number | Structure | ¹H NMR (CDCl₃ unless stated) or other physical data |
|---|---|---|
| A-366 | 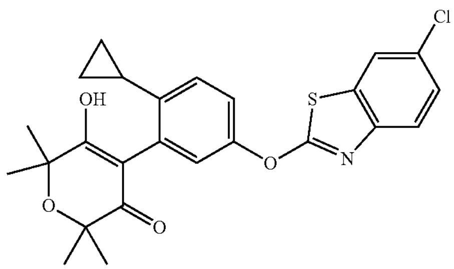 [SMILES: CC1(C)OC(C)(C)C(O)=C(c2cc(Oc3nc4ccc(Cl)cc4s3)ccc2C2CC2)C1=O] | LCMS (Method B): $t_r$ = 1.91 mins, MH⁺ = 470.1 |
| A-367 | 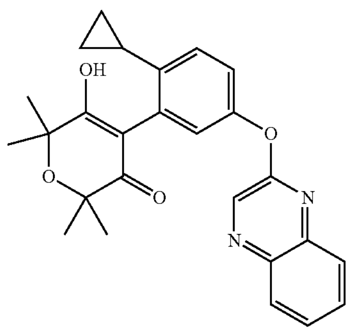 [SMILES: CC1(C)OC(C)(C)C(O)=C(c2cc(Oc3cnc4ccccc4n3)ccc2C2CC2)C1=O] | LCMS (Method B): $t_r$ = 1.67 mins, MH⁺ = 431.2 |
| A-368 | 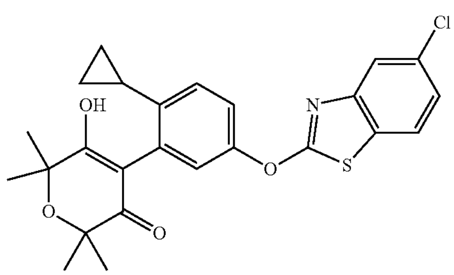 [SMILES: CC1(C)OC(C)(C)C(O)=C(c2cc(Oc3nc4cc(Cl)ccc4s3)ccc2C2CC2)C1=O] | LCMS (Method B): $t_r$ = 1.91 mins, MH⁺ = 470.1 |
| A-369 | 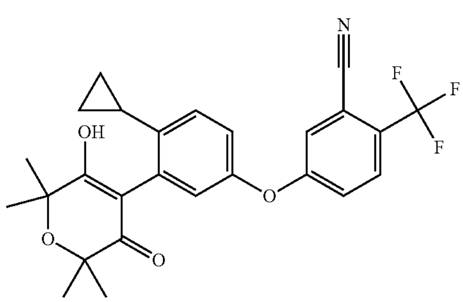 [SMILES: CC1(C)OC(C)(C)C(O)=C(c2cc(Oc3ccc(C(F)(F)F)c(C#N)c3)ccc2C2CC2)C1=O] | LCMS (Method B): $t_r$ = 1.82 mins, MH⁺ = 472.2 |
| A-370 | 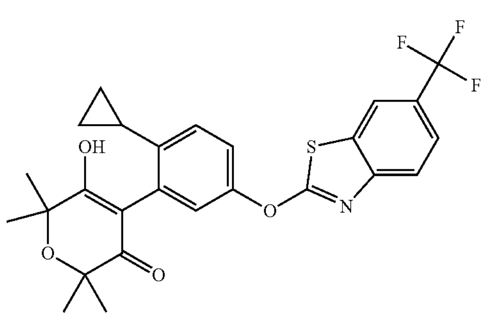 [SMILES: CC1(C)OC(C)(C)C(O)=C(c2cc(Oc3nc4ccc(C(F)(F)F)cc4s3)ccc2C2CC2)C1=O] | LCMS (Method B): $t_r$ = 1.92 mins, MH⁺ = 504.1 |

TABLE T1-continued

| Compound Number | Structure | ¹H NMR (CDCl₃ unless stated) or other physical data |
|---|---|---|
| A-371 | 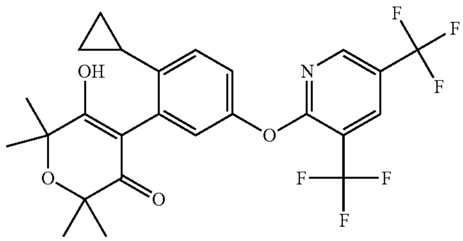 [SMILES: CC1(C)OC(C)(C)C(O)=C(c2cc(Oc3ncc(C(F)(F)F)cc3C(F)(F)F)ccc2C2CC2)C1=O] | LCMS (Method B): $t_r$ = 1.89 mins, MH⁺ = 516.2 |
| A-372 | 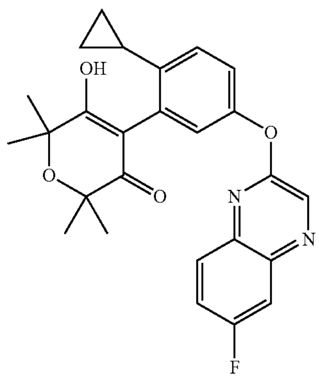 [SMILES: CC1(C)OC(C)(C)C(O)=C(c2cc(Oc3cnc4cc(F)ccc4n3)ccc2C2CC2)C1=O] | LCMS (Method B): $t_r$ = 1.72 mins, MH⁺ = 449.2 |
| A-373 | 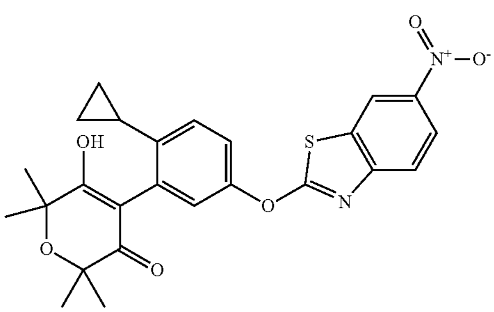 [SMILES: CC1(C)OC(C)(C)C(O)=C(c2cc(Oc3nc4ccc([N+](=O)[O-])cc4s3)ccc2C2CC2)C1=O] | LCMS (Method B): $t_r$ = 1.79 mins, MH⁺ = 481.1 |
| A-374 | 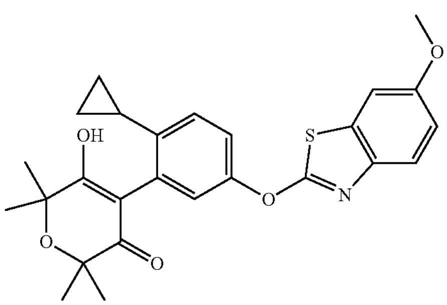 [SMILES: COc1ccc2nc(Oc3ccc(C4CC4)c(C4=C(O)C(C)(C)OC(C)(C)C4=O)c3)sc2c1] | LCMS (Method B): $t_r$ = 1.79 mins, MH⁺ = 466.2 |
| A-375 | 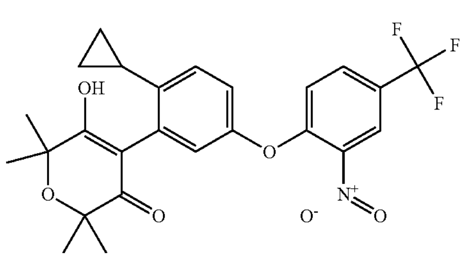 | LCMS (Method B): $t_r$ = 1.84 mins, MH⁺ = 492.2 |

TABLE T1-continued

| Compound Number | Structure | $^1$H NMR (CDCl$_3$ unless stated) or other physical data |
|---|---|---|
| A-376 | 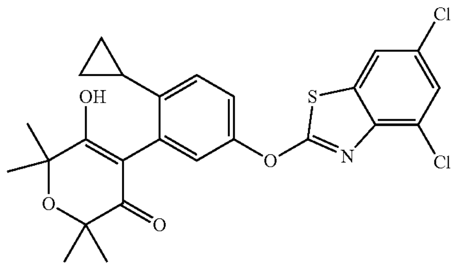 [SMILES: CC1(C)OC(C)(C)C(O)=C(c2cc(Oc3nc4c(Cl)cc(Cl)cc4s3)ccc2C2CC2)C1=O] | LCMS (Method B): t$_r$ = 2.01 mins, MH$^+$ = 504.1 |
| A-377 | 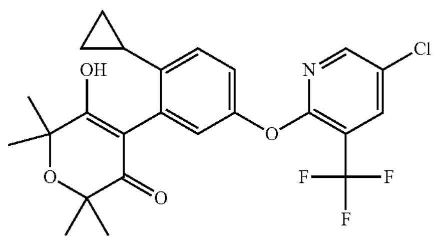 [SMILES: CC1(C)OC(C)(C)C(O)=C(c2cc(Oc3ncc(Cl)cc3C(F)(F)F)ccc2C2CC2)C1=O] | LCMS (Method B): t$_r$ = 1.86 mins, MH$^+$ = 482.1 |

TABLE P1

| Compound Number | Structure | $^1$H NMR (CDCl$_3$ unless stated) or other physical data |
|---|---|---|
| P-1 | 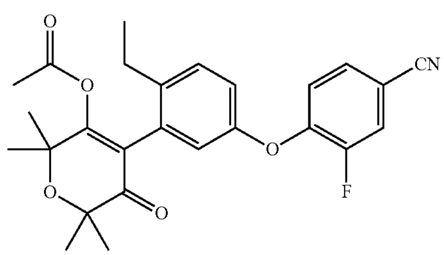 [SMILES: CCc1ccc(Oc2ccc(C#N)cc2F)cc1C1=C(OC(C)=O)C(C)(C)OC(C)(C)C1=O] | δ 7.45 (1H, dd), 7.38-7.36 (1H, m), 7.30 (1H, d), 7.01 (1H, dd), 6.96 (1H, t), 6.71 (1H, d), 2.46 (2H, q), 1.86 (3H, s), 1.55 (12H, s), 1.51-1.49 (6H, m), 1.17 (3H, t). |
| P-2 | 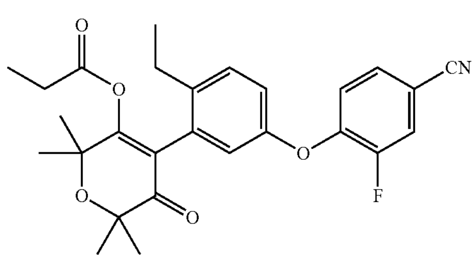 [SMILES: CCC(=O)OC1=C(c2cc(Oc3ccc(C#N)cc3F)ccc2CC)C(=O)C(C)(C)OC1(C)C] | δ 7.45 (1H, dd), 7.38-7.35 (1H, m), 7.29 (1H, d), 6.99 (1H, dd), 6.98-6.93 (1H, m), 6.72 (1H, d), 2.46 (2H, q), 2.19-2.08 (2H, m), 1.55 (3H, s), 1.51-1.50 (9H, m), 1.17 (3H, t), 0.88 (3H, t). |

TABLE P1-continued

| Compound Number | Structure | $^1$H NMR (CDCl$_3$ unless stated) or other physical data |
|---|---|---|
| P-3 | 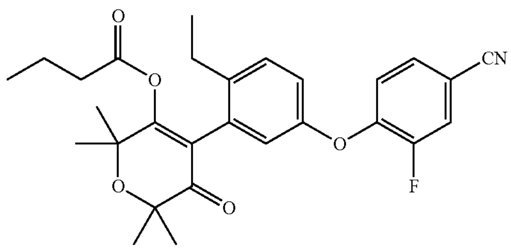 [SMILES: CCCC(=O)OC1=C(c2cc(Oc3ccc(C#N)cc3F)ccc2CC)C(=O)C(C)(C)OC1(C)C] | δ 7.45 (1H, dd), 7.36 (1H, dt), 7.29-7.27 (1H, m), 7.00-6.94 (2H, m), 6.72 (1H, d), 2.46 (2H, q), 2.10 (2H, td), 1.55 (3H, s), 1.51-1.49 (9H, m), 1.40-1.35 (2H, m), 1.16 (3H, t), 0.74 (3H, t) |
| P-4 | 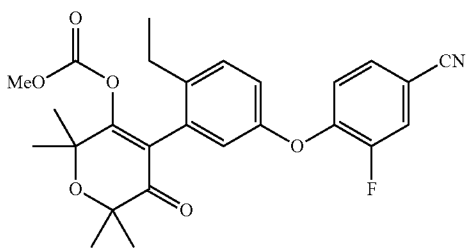 [SMILES: CCc1ccc(Oc2ccc(C#N)cc2F)cc1C1=C(OC(=O)OC)C(C)(C)OC(C)(C)C1=O] | δ 7.46 (1H, dd), 7.37-7.34 (1H, m), 7.32 (1H, d), 7.02 (1H, dd), 6.96 (1H, t), 6.76 (1H, d), 3.59 (3H, s), 2.46 (2H, qd), 1.59-1.50 (12H, m), 1.18 (3H, t). |
| P-5 | 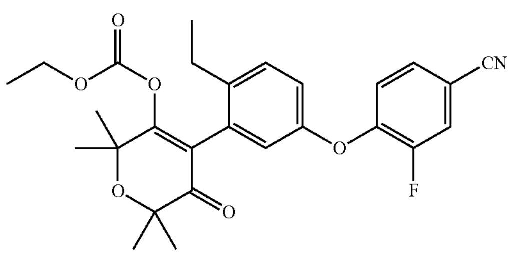 [SMILES: CCOC(=O)OC1=C(c2cc(Oc3ccc(C#N)cc3F)ccc2CC)C(=O)C(C)(C)OC1(C)C] | δ 7.45 (1H, dd), 7.37-7.34 (1H, m), 7.31 (1H, d), 7.02-6.95 (2H, m), 6.66 (1H, d), 3.98 (2H, q), 2.50-2.43 (2H, m), 1.58-1.49 (12H, m), 1.18 (3H, t), 1.09 (3H, t). |
| P-6 | 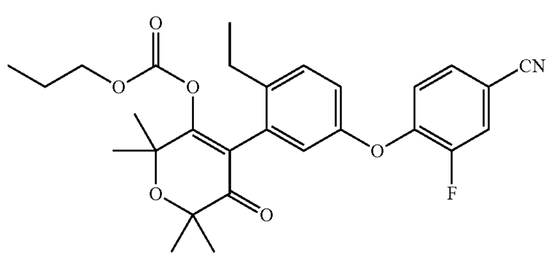 [SMILES: CCCOC(=O)OC1=C(c2cc(Oc3ccc(C#N)cc3F)ccc2CC)C(=O)C(C)(C)OC1(C)C] | δ 7.45 (1H, dd), 7.37-7.34 (1H, m), 7.31 (1H, d), 7.02-6.96 (2H, m), 6.77 (1H, d), 3.89 (2H, t), 2.50-2.44 (2H, m), 1.59-1.44 (14H, m), 1.18 (3H, t), 0.79 (3H, t). |

It should be noted that certain compounds of the invention exist as a mixture of isomers, including atropisomers, noted above, under the conditions used to obtain the $^1$H NMR data. Where this has occurred, the characterising data are reported for all isomers present at ambient temperature in the specified solvent. Unless otherwise stated, proton NMR spectra were recorded at ambient temperature. Compounds characterised by HPLC-MS were analysed using one of two methods described below.

Method A

Compounds characterised by HPLC-MS were analysed using a Waters 2795 HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using a three minute run time, according to the following gradient table:

| Time (mins) | Solvent A (%) | Solvent B (%) | Flow (ml/mn) |
|---|---|---|---|
| 0.00 | 90.0 | 10.0 | 2.00 |
| 0.25 | 90.0 | 100 | 2.00 |
| 2.00 | 10.0 | 90.0 | 2.00 |
| 2.50 | 10.0 | 90.0 | 2.00 |
| 2.60 | 90.0 | 10.0 | 2.00 |
| 3.0 | 90.0 | 10.0 | 2.00 |

Solvent A: H$_2$O containing 0.1% HCOOH
Solvent B: CH$_3$CN containing 0.1% HCOOH Method B Compounds characterised by HPLC-MS were analysed using an Waters 2777 injector with a 1525 micro pump HPLC equipped with a Waters Atlantis dC18 IS column (column length 20 mm, internal diameter of column 3 mm, particle size 3 micron), Waters 2996 photodiode array, Waters 2420 ELSD and Micromass ZQ2000. The analysis was conducted using a three minute run time, according to the following gradient table:

| Time (mins) | Solvent A (%) | Solvent B (%) | Flow (ml/mn) |
|---|---|---|---|
| 0.00 | 95.0 | 5 | 1.300 |
| 2.50 | 0.0 | 100 | 1.300 |
| 2.80 | 0.00 | 100 | 1.300 |
| 2.90 | 95.0 | 5 | 1.300 |

Solvent A: $H_2O$ with 0.05% TFA
Solvent B: $CH_3CN$ with 0.05% TFA

The characteristic values obtained for each compound were the retention time (rt, recorded in minutes) and the molecular ion (typically the cation $MH^+$), as listed in Table T1.

The compounds of the following Tables 1 to 57 can be obtained in an analogous manner. Table 1 covers compounds of the following type

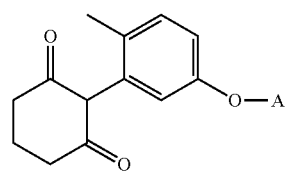

wherein A is as defined in Table 1.

TABLE 1

| Compound Number | A | Compound Number | A |
|---|---|---|---|
| 1.001 | phenyl | 1.002 | 2-bromophenyl |
| 1.003 | 2-chlorophenyl | 1.004 | 2-cyanophenyl |
| 1.005 | 2-difluoromethoxyphenyl | 1.006 | 2-fluorophenyl |
| 1.007 | 2-methoxyphenyl | 1.008 | 2-methylphenyl |
| 1.009 | 2-nitrophenyl | 1.010 | 2-trifluoromethoxyphenyl |
| 1.011 | 2-trifluoromethylphenyl | 1.012 | 3-bromophenyl |
| 1.013 | 3-chlorophenyl | 1.014 | 3-cyanophenyl |
| 1.015 | 3-difluoromethoxyphenyl | 1.016 | 3-fluorophenyl |
| 1.017 | 3-methoxyphenyl | 1.018 | 3-methylphenyl |
| 1.019 | 3-nitrophenyl | 1.020 | 3-trifluoromethoxyphenyl |
| 1.021 | 3-trifluoromethylphenyl | 1.022 | 4-bromophenyl |
| 1.023 | 4-chlorophenyl | 1.024 | 4-cyanophenyl |
| 1.025 | 4-difluoromethoxyphenyl | 1.026 | 4-fluorophenyl |
| 1.027 | 4-methanesulfonyl | 1.028 | 4-methoxyphenyl |
| 1.029 | 4-methylphenyl | 1.030 | 4-nitrophenyl |
| 1.031 | 4-trifluoromethoxyphenyl | 1.032 | 4-trifluoromethylphenyl |
| 1.033 | 4-bromo-2-chlorophenyl | 1.034 | 2,4-dichlorophenyl |
| 1.035 | 2-chloro-4-cyanophenyl | 1.036 | 2-chloro-4-difluoromethoxyphenyl |
| 1.037 | 2-chloro-4-fluorophenyl | 1.038 | 2-chloro-4-methoxyphenyl |
| 1.039 | 2-chloro-4-methylphenyl | 1.040 | 2-chloro-4-nitrophenyl |
| 1.041 | 2-chloro-4-trifluoromethoxyphenyl | 1.042 | 2-chloro-4-trifluoromethylphenyl |
| 1.043 | 4-bromo-3-chlorophenyl | 1.044 | 3,4-dichlorophenyl |
| 1.045 | 3-chloro-4-cyanophenyl | 1.046 | 3-chloro-4-difluoromethoxyphenyl |
| 1.047 | 3-chloro-4-fluorophenyl | 1.048 | 3-chloro-4-methoxyphenyl |
| 1.049 | 3-chloro-4-methylphenyl | 1.050 | 3-chloro-4-nitrophenyl |
| 1.051 | 3-chloro-4-trifluoromethoxyphenyl | 1.052 | 3-chloro-4-trifluoromethylphenyl |
| 1.053 | 2-bromo-4-chlorophenyl | 1.054 | 4-chloro-2-difluoromethoxyphenyl |
| 1.055 | 4-chloro-2-cyanophenyl | 1.056 | 4-chloro-2-methoxyphenyl |
| 1.057 | 4-chloro-2-fluorophenyl | 1.058 | 4-chloro-2-nitrophenyl |
| 1.059 | 4-chloro-2-methylphenyl | 1.060 | 4-chloro-2-trifluoromethylphenyl |
| 1.061 | 4-chloro-2-trifluoromethoxyphenyl | 1.062 | 4-chloro-3-trifluoromethoxyphenyl |
| 1.063 | 3-bromo-4-chlorophenyl | 1.064 | 4-chloro-3-difluoromethoxyphenyl |
| 1.065 | 4-chloro-3-cyanophenyl | 1.066 | 4-chloro-3-methoxyphenyl |
| 1.067 | 4-chloro-3-fluorophenyl | 1.068 | 4-chloro-3-nitrophenyl |
| 1.069 | 4-chloro-3-methylphenyl | 1.070 | 4-chloro-3-trifluoromethylphenyl |
| 1.071 | 4-bromo-2-fluorophenyl | 1.072 | 2-difluoro-4-difluoromethoxyphenyl |
| 1.073 | 4-cyano-2-fluorophenyl | 1.074 | 2-fluoro-4-methoxyphenyl |
| 1.075 | 2,4-fluorophenyl | 1.076 | 2-fluoro-4-nitrophenyl |
| 1.077 | 2-fluoro-4-methylphenyl | 1.078 | 2-fluoro-4-trifluoromethylphenyl |
| 1.079 | 2-fluoro-4-trifluoromethoxyphenyl | 1.080 | 4-bromo-3-fluorophenyl |
| 1.081 | 4-cyano-3-fluorophenyl | 1.082 | 3-difluoro-4-difluoromethoxyphenyl |
| 1.083 | 3,4-fluorophenyl | 1.084 | 3-fluoro-4-methoxyphenyl |
| 1.085 | 3-fluoro-4-methylphenyl | 1.086 | 3-fluoro-4-nitrophenyl |
| 1.087 | 3-fluoro-4-trifluoromethoxyphenyl | 1.088 | 3-fluoro-4-trifluoromethylphenyl |
| 1.089 | 4-chloro-2,3-difluorophenyl | 1.090 | 4-chloro-2,5-difluorophenyl |
| 1.091 | 4-chloro-2,6-difluorophenyl | 1.092 | 4-chloro-3,5-difluorophenyl |
| 1.093 | 2,4-dichloro-3-fluorophenyl | 1.094 | 2,4-dichloro-5-fluorophenyl |
| 1.095 | 2,4-dichloro-6-fluorophenyl | 1.096 | 2,3,4-trifluorophenyl |
| 1.097 | 2,4,6-trifluorophenyl | 1.098 | 2,4,5-trifluorophenyl |
| 1.099 | 3,4,5-trifluorophenyl | 1.100 | pentafluorophenyl |
| 1.101 | 2-bromo-4-cyanophenyl | 1.102 | 3-bromo-4-cyanophenyl |
| 1.103 | 4-bromo-2-cyanophenyl | 1.104 | 4-bromo-3-cyanophenyl |
| 1.105 | 2-cyano-4-nitrophenyl | 1.106 | 3-cyano-4-nitrophenyl |
| 1.107 | 2-cyano-4-trifluoromethylphenyl | 1.108 | 3-cyano-4-trifluoromethylphenyl |

TABLE 1-continued

| Compound Number | A | Compound Number | A |
|---|---|---|---|
| 1.109 | 2,4-dicyanophenyl | 1.110 | 3,4-dicyanophenyl |
| 1.111 | 3-chloropyridin-2-yl | 1.112 | 4-chloropyridin-2-yl |
| 1.113 | 5-chloropyridin-2-yl | 1.114 | 6-chloropyridin-2-yl |
| 1.115 | 2-chloropyridin-3-yl | 1.116 | 4-chloropyridin-3-yl |
| 1.117 | 5-chloropyridin-3-yl | 1.118 | 6-chloropyridin-3-yl |
| 1.119 | 2-chloropyridin-4-yl | 1.120 | 3-chloropyridin-4-yl |
| 1.121 | 3,4-dichloropyridin-2-yl | 1.122 | 3,5-dichloropyridin-2-yl |
| 1.123 | 3,6-dichloropyridin-2-yl | 1.124 | 2,5-dichloropyridin-3-yl |
| 1.125 | 2,6-dichloropyridin-3-yl | 1.126 | 2,3-dichloropyridin-4-yl |
| 1.127 | 2,5-dichloropyridin-4-yl | 1.128 | 3,5,6-trichloropyridin-2-yl |
| 1.129 | 3-fluoropyridin-2-yl | 1.130 | 4-fluoropyridin-2-yl |
| 1.131 | 5-fluoropyridin-2-yl | 1.132 | 6-fluoropyridin-2-yl |
| 1.133 | 2-fluoropyridin-3-yl | 1.134 | 4-fluoropyridin-3-yl |
| 1.135 | 5-fluoropyridin-3-yl | 1.136 | 6-fluoropyridin-3-yl |
| 1.137 | 2-fluoropyridin-4-yl | 1.138 | 3-fluoropyridin-4-yl |
| 1.139 | 3,4-difluoropyridin-2-yl | 1.140 | 3,5-difluoropyridin-2-yl |
| 1.141 | 3,6-difluoropyridin-2-yl | 1.142 | 2,5-difluoropyridin-3-yl |
| 1.143 | 2,6-difluoropyridin-3-yl | 1.144 | 2,3-difluoropyridin-4-yl |
| 1.145 | 2,5-difluoropyridin-4-yl | 1.146 | 3,5,6-trifluoropyridin-2-yl |
| 1.147 | 3-trifluoromethylpyridin-2-yl | 1.148 | 4-trifluoromethylpyridin-2-yl |
| 1.149 | 5-trifluoromethylpyridin-2-yl | 1.150 | 6-trifluoromethylpyridin-2-yl |
| 1.151 | 2-trifluoromethylpyridin-3-yl | 1.152 | 4-trifluoromethylpyridin-3-yl |
| 1.153 | 5-trifluoromethylpyridin-3-yl | 1.154 | 6-trifluoromethylpyridin-3-yl |
| 1.155 | 2-trifluoromethylpyridin-4-yl | 1.156 | 3-trifluoromethylpyridin-4-yl |
| 1.157 | 4-chloro-3-fluoropyridin-2-yl | 1.158 | 5-chloro-3-fluoropyridin-2-yl |
| 1.159 | 6-chloro-3-fluoropyridin-2-yl | 1.160 | 3-chloro-4-fluoropyridin-2-yl |
| 1.161 | 3-chloro-5-fluoropyridin-2-yl | 1.162 | 3-chloro-6-fluoropyridin-2-yl |
| 1.163 | 3-chloro-5-trifluoromethylpyridin-2-yl | 1.164 | 3-fluoro-5-trifluoromethylpyridin-2-yl |
| 1.165 | 6-fluoro-3,4,5-trichloropyridin-2-yl | 1.166 | 4-methyl-3,5,6-trifluoropyridin-2-yl |
| 1.167 | pyrimidin-2-yl | 1.168 | 5-fluoropyrimidin-2-yl |
| 1.169 | 5-chloropyrimidin-2-yl | 1.170 | 5-bromopyrimidin-2-yl |
| 1.171 | 6-chloropyridazin-3-yl | 1.172 | 6-bromopyridazin-3-yl |
| 1.173 | quinoline-2-yl | 1.174 | 6-fluoroquinolin-2-yl |
| 1.175 | 7-fluoroquinolin-2-yl | 1.176 | 6-chloroquinolin-2-yl |
| 1.177 | 7-chloroquinolin-2-yl | 1.178 | 6-bromoquinolin-2-yl |
| 1.179 | 7-bromoquinolin-2-yl | 1.180 | 6-trifluoromethylquinolin-2-yl |
| 1.181 | 7-trifluoromethylquinolin-2-yl | 1.182 | quinoxalin-2-yl |
| 1.183 | 6-fluoroquinoxazin-2-yl | 1.184 | 7-fluoroquinoxalin-2-yl |
| 1.185 | 6-chloroquinoxalin-2-yl | 1.186 | 7-chloroquinoxalin-2-yl |
| 1.187 | 6-bromoquinoxalin-2-yl | 1.188 | 7-bromoquinoxalin-2-yl |
| 1.189 | 6-trifluoromethylquinoxalin-2-yl | 1.190 | 7-trifluoromethylquinoxalin-2-yl |
| 1.191 | quinazolin-2-yl | 1.192 | 6-fluoroquinazolin-2-yl |
| 1.193 | 7-fluoroquinazolin-2-yl | 1.194 | 6-chloroquinazolin-2-yl |
| 1.195 | 7-chloroquinazolin-2-yl | 1.196 | 6-bromoquinazolin-2-y |
| 1.197 | 7-bromoquinazolin-2-yl | 1.198 | benzoxazol-2-yl |
| 1.199 | 5-fluorobenzoxazol-2-yl | 1.200 | 6-fluorobenzoxazol-2-yl |
| 1.201 | 5-chlorobenzoxazol-2-yl | 1.202 | 6-chlorobenzoxazol-2-yl |
| 1.203 | 5-bromobenzoxazol-2-yl | 1.204 | 6-bromobenzoxazol-2-yl |
| 1.205 | 5-trifluoromethylbenzoxazol-2-yl | 1.206 | 6-trifluoromethylbenzoxazol-2-yl |
| 1.207 | benzothiazol-2-yl | 1.208 | 5-fluorobenzothiazol-2-yl |
| 1.209 | 6-fluorobenzothiazol-2-yl | 1.210 | 5-chlorobenzothiazol-2-yl |
| 1.211 | 6-chlorobenzothiazol-2-yl | 1.212 | 5-bromobenzothiazol-2-yl |
| 1.213 | 6-bromobenzothiazol-2-yl | 1.214 | 5-trifluoromethylbenzothiazol-2-yl |
| 1.215 | 6-trifluoromethylbenzothiazol-2-yl | 1.216 | benzo[1,2,4]triazin-3-yl |
| 1.217 | 6-fluorobenzo[1,2,4]triazin-3-yl | 1.218 | 7-fluorobenzo[1,2,4]triazin-3-yl |
| 1.219 | 6-chlorobenzo[1,2,4]triazin-3-yl | 1.220 | 7-chlorobenzo[1,2,4]triazin-3-yl |
| 1.221 | 6-bromobenzo[1,2,4]triazin-3-yl | 1.222 | 7-bromo benzo[1,2,4]triazin-3-yl |

Table 2 covers compounds of the following type

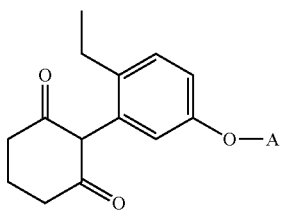

wherein A is as defined in Table 1.

Table 3 covers compounds of the following type

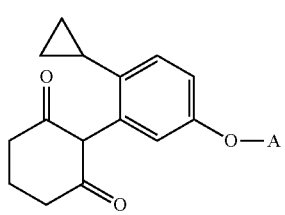

wherein A is as defined in Table 1.

Table 4 covers compounds of the following type

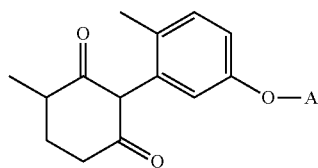

wherein A is as defined in Table 1.

Table 5 covers compounds of the following type

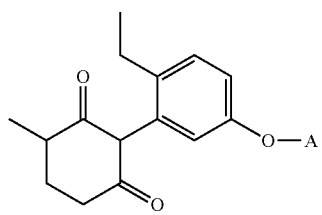

wherein A is as defined in Table 1.

Table 6 covers compounds of the following type

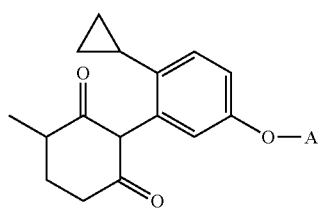

wherein A is as defined in Table 1.

Table 7 covers compounds of the following type

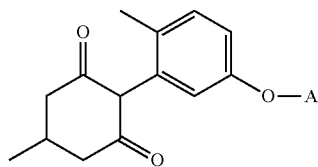

wherein A is as defined in Table 1.

Table 8 covers compounds of the following type

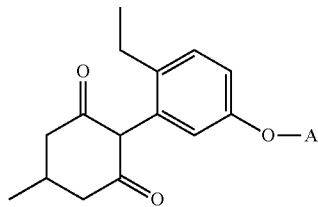

wherein A is as defined in Table 1.

Table 9 covers compounds of the following type

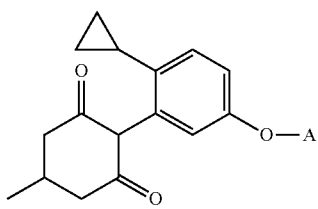

wherein A is as defined in Table 1.

Table 10 covers compounds of the following type

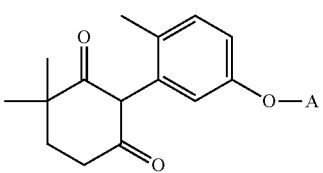

wherein A is as defined in Table 1.

Table 11 covers compounds of the following type

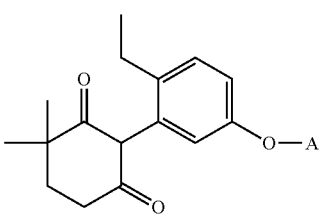

wherein A is as defined in Table 1.

Table 12 covers compounds of the following type

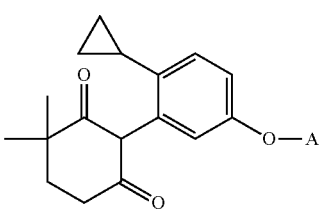

wherein A is as defined in Table 1.

Table 13 covers compounds of the following type

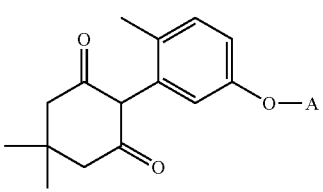

wherein A is as defined in Table 1.

Table 14 covers compounds of the following type

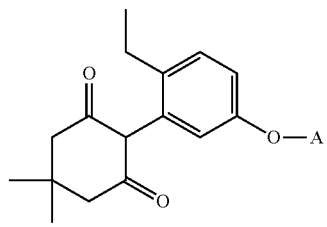

wherein A is as defined in Table 1.
Table 15 covers compounds of the following type

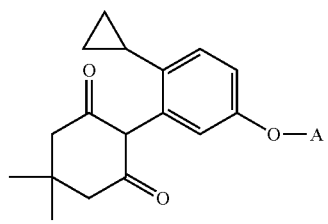

wherein A is as defined in Table 1.
Table 16 covers compounds of the following type

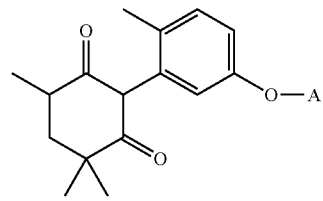

wherein A is as defined in Table 1.
Table 17 covers compounds of the following type

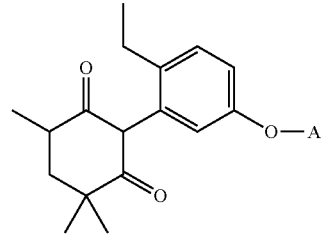

wherein A is as defined in Table 1.
Table 18 covers compounds of the following type

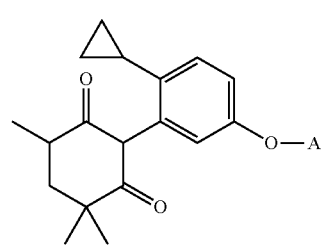

wherein A is as defined in Table 1.

Table 19 covers compounds of the following type

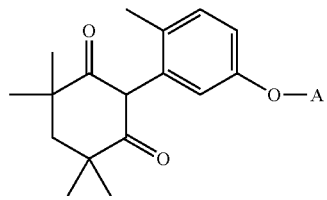

wherein A is as defined in Table 1.
Table 20 covers compounds of the following type

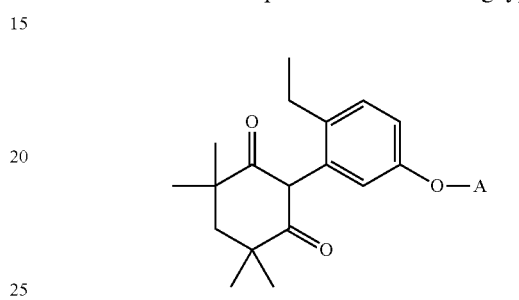

wherein A is as defined in Table 1.
Table 21 covers compounds of the following type

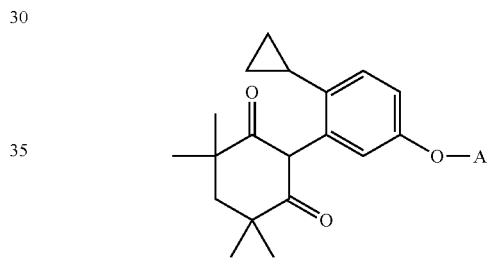

wherein A is as defined in Table 1.
Table 22 covers compounds of the following type

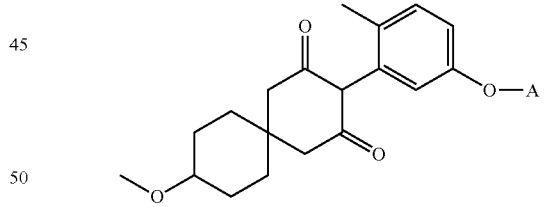

wherein A is as defined in Table 1.
Table 23 covers compounds of the following type

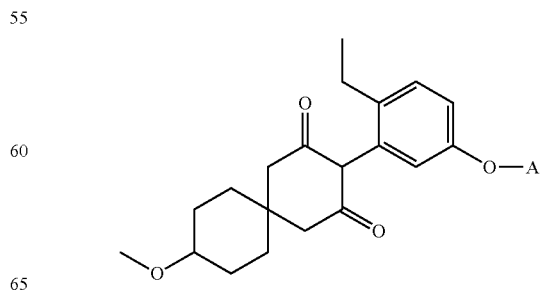

wherein A is as defined in Table 1.

Table 24 covers compounds of the following type

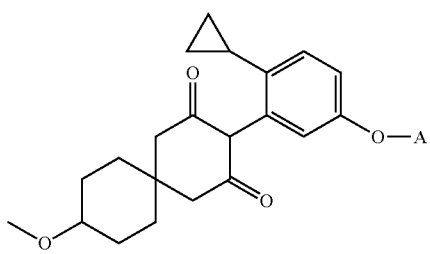

wherein A is as defined in Table 1.

Table 25 covers compounds of the following type

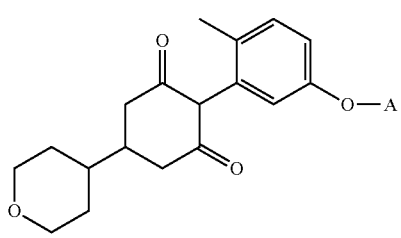

wherein A is as defined in Table 1.

Table 26 covers compounds of the following type

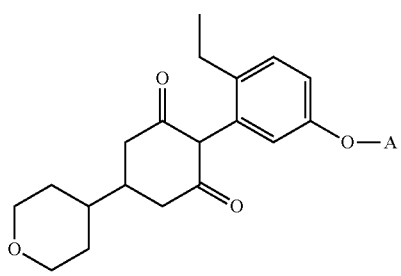

wherein A is as defined in Table 1.

Table 27 covers compounds of the following type

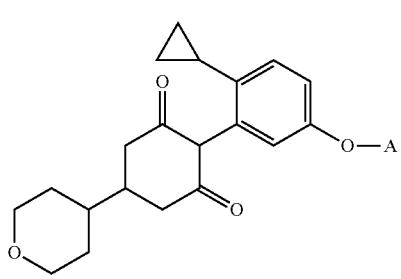

wherein A is as defined in Table 1.

Table 28 covers compounds of the following type

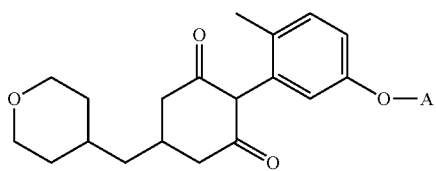

wherein A is as defined in Table 1.

Table 29 covers compounds of the following type

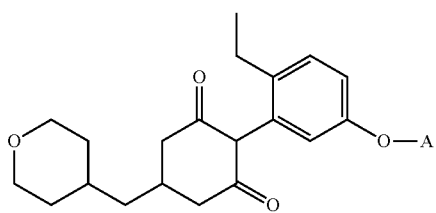

wherein A is as defined in Table 1.

Table 30 covers compounds of the following type

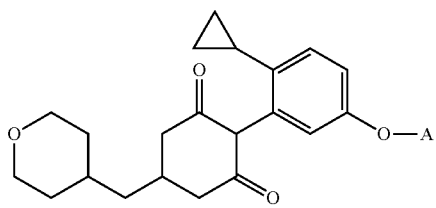

wherein A is as defined in Table 1.

Table 31 covers compounds of the following type

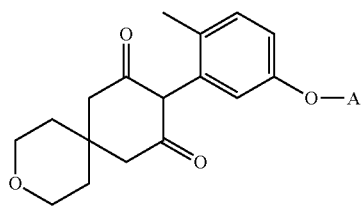

wherein A is as defined in Table 1.

Table 32 covers compounds of the following type

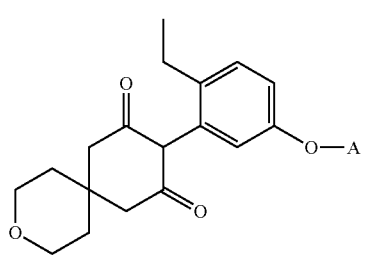

wherein A is as defined in Table 1.

Table 33 covers compounds of the following type

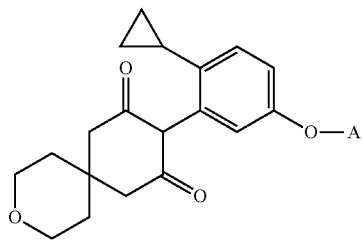

wherein A is as defined in Table 1.

Table 34 covers compounds of the following type

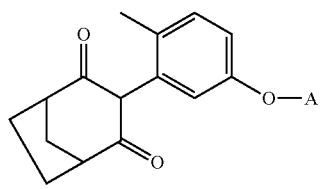

wherein A is as defined in Table 1.

Table 35 covers compounds of the following type

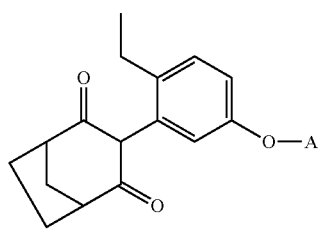

wherein A is as defined in Table 1.

Table 36 covers compounds of the following type

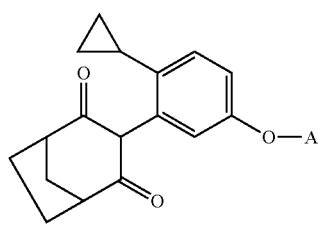

wherein A is as defined in Table 1.

Table 37 covers compounds of the following type

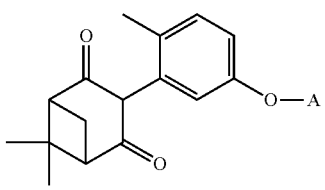

wherein A is as defined in Table 1.

Table 38 covers compounds of the following type

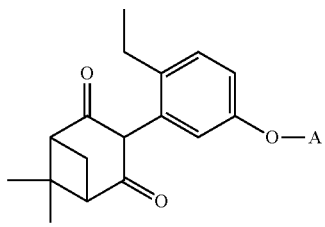

wherein A is as defined in Table 1.

Table 39 covers compounds of the following type

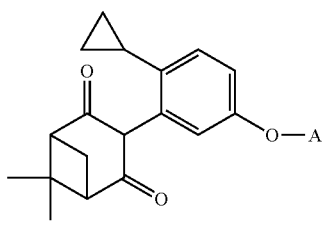

wherein A is as defined in Table 1.

Table 40 covers compounds of the following type

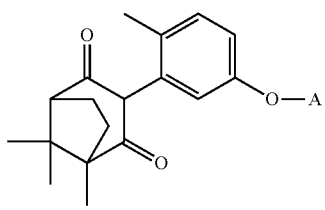

wherein A is as defined in Table 1.

Table 41 covers compounds of the following type

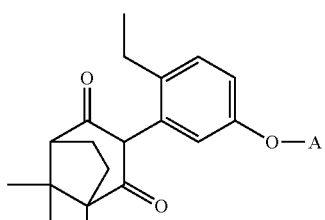

wherein A is as defined in Table 1.

Table 42 covers compounds of the following type

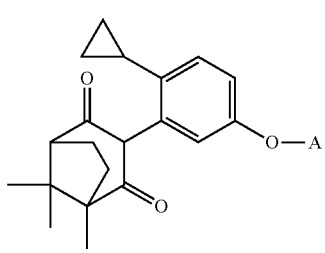

wherein A is as defined in Table 1.

Table 43 covers compounds of the following type

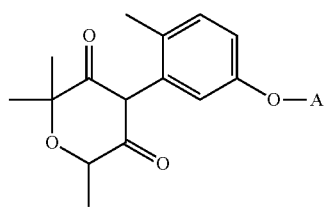

wherein A is as defined in Table 1.

Table 44 covers compounds of the following type

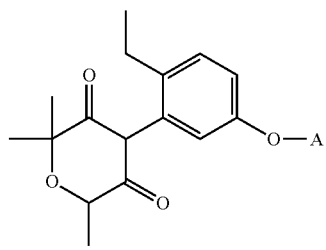

wherein A is as defined in Table 1.

Table 45 covers compounds of the following type

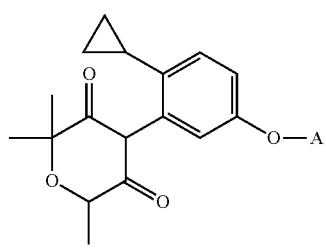

wherein A is as defined in Table 1.

Table 46 covers compounds of the following type

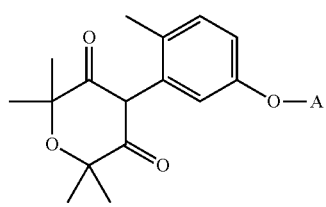

wherein A is as defined in Table 1.

Table 47 covers compounds of the following type

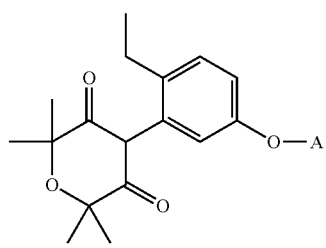

wherein A is as defined in Table 1.

Table 48 covers compounds of the following type

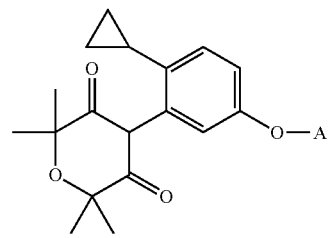

wherein A is as defined in Table 1.

Table 49 covers compounds of the following type

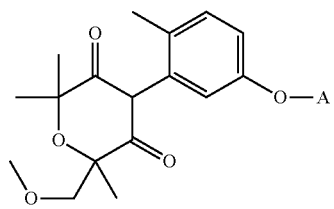

wherein A is as defined in Table 1.

Table 50 covers compounds of the following type

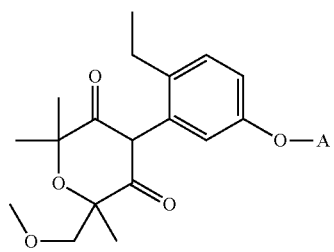

Table 51 covers compounds of the following type

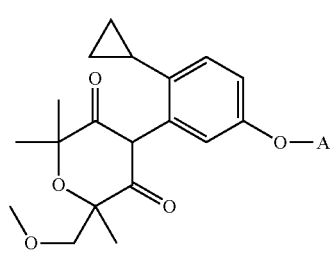

wherein A is as defined in Table 1.

Table 52 covers compounds of the following type

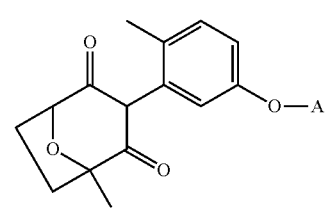

wherein A is as defined in Table 1.

Table 53 covers compounds of the following type

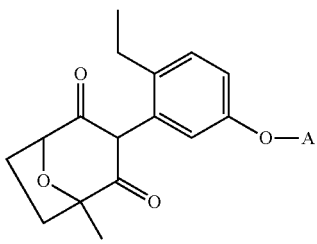

wherein A is as defined in Table 1.

Table 54 covers compounds of the following type

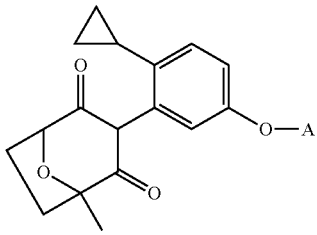

wherein A is as defined in Table 1.

Table 55 covers compounds of the following type

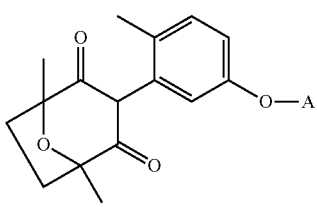

wherein A is as defined in Table 1.

Table 56 covers compounds of the following type

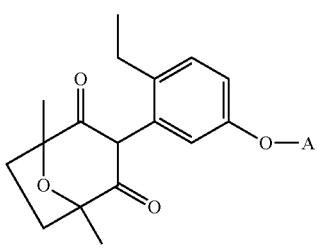

wherein A is as defined in Table 1.

Table 57 covers compounds of the following type

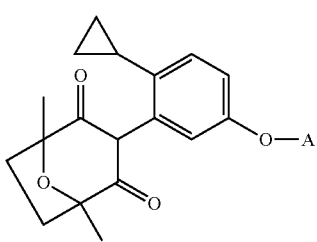

wherein A is as defined in Table 1.

Biological Examples

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

Test Plants:

*Lolium perenne* (LOLPE), *Alopecurus myosuroides* (ALOMY), *Echinochloa crus-galli* (ECHCG), and *Avena fatua* (AVEFA).

Pre-Emergence Activity

| Compound Number | Rate g/ha | LOLPE | ALOMY | ECHCG | AVEFA |
| --- | --- | --- | --- | --- | --- |
| A-1 | 250 | — | 0 | 0 | 0 |
| A-2 | 250 | — | 0 | 0 | 0 |
| A-4 | 250 | — | 40 | 100 | 0 |
| A-5 | 250 | — | 0 | 90 | 0 |
| A-6 | 250 | — | 0 | 30 | 0 |
| A-7 | 250 | — | 60 | 100 | 60 |
| A-8 | 250 | 100 | 60 | 100 | 10 |
| A-9 | 250 | 80 | 60 | 100 | 30 |
| A-10 | 250 | 30 | 0 | 90 | 20 |
| A-11 | 250 | 0 | 0 | 0 | 0 |
| A-12 | 250 | 0 | 0 | 0 | 0 |
| A-13 | 250 | 0 | 0 | 0 | 0 |
| A-14 | 250 | 0 | 0 | 0 | 0 |
| A-15 | 250 | 100 | 100 | 100 | 60 |
| A-16 | 250 | 0 | 0 | 100 | 0 |
| A-19 | 250 | 80 | 50 | 100 | 70 |
| A-20 | 250 | 0 | 40 | 100 | 20 |
| A-21 | 250 | 20 | 0 | 30 | 0 |
| A-22 | 250 | 60 | 20 | 80 | 10 |
| A-23 | 250 | 90 | 70 | 90 | 70 |
| A-24 | 250 | 90 | 30 | 90 | 40 |
| A-25 | 250 | 80 | 70 | 90 | 80 |
| A-26 | 250 | 80 | 70 | 100 | 40 |
| A-27 | 250 | 60 | 40 | 100 | 60 |
| A-28 | 250 | 40 | 20 | 70 | 0 |
| A-29 | 250 | 30 | 0 | 40 | 10 |
| A-30 | 250 | 70 | 70 | 80 | 50 |
| A-31 | 250 | 100 | 90 | 100 | 80 |
| A-32 | 250 | 80 | 30 | 90 | 20 |
| A-33 | 250 | 80 | 20 | 90 | 10 |
| A-34 | 250 | 100 | 100 | 100 | 100 |
| A-35 | 250 | 70 | 90 | 100 | 70 |
| A-36 | 250 | 90 | 90 | 100 | 90 |
| A-37 | 250 | 80 | 70 | 100 | 70 |

| Compound Number | Rate g/ha | LOLPE | ALOMY | ECHCG | AVEFA |
|---|---|---|---|---|---|
| A-38 | 250 | 70 | 50 | 70 | 10 |
| A-39 | 250 | 30 | 30 | 40 | 0 |
| A-40 | 250 | 50 | 50 | 80 | 20 |
| A-41 | 250 | 60 | 40 | 100 | 20 |
| A-43 | 250 | 10 | 10 | 90 | 0 |
| A-44 | 250 | 100 | 100 | 100 | 100 |
| A-45 | 250 | 100 | 100 | 100 | 100 |
| A-46 | 250 | 70 | 100 | 90 | 30 |
| A-47 | 250 | 40 | 50 | 90 | 0 |
| A-48 | 250 | 70 | 100 | 100 | 30 |
| A-49 | 250 | 100 | 90 | 100 | 40 |
| A-50 | 250 | 70 | 0 | 100 | 0 |
| A-52 | 250 | 70 | 40 | 60 | 20 |
| A-53 | 250 | 40 | 0 | 20 | 0 |
| A-54 | 250 | 100 | 100 | 100 | 90 |
| A-55 | 250 | 100 | 80 | 100 | 90 |
| A-56 | 250 | 100 | 80 | 80 | 30 |
| A-58 | 250 | 0 | 0 | 70 | 0 |
| A-59 | 250 | 100 | 80 | 100 | 70 |
| A-60 | 250 | 40 | 0 | 50 | 0 |
| A-62 | 250 | 100 | 100 | 100 | 100 |
| A-64 | 250 | 80 | 60 | 20 | 0 |
| A-65 | 250 | 80 | 70 | 100 | 90 |
| A-66 | 250 | 80 | 100 | 100 | 90 |
| A-67 | 250 | 100 | 90 | 100 | 90 |
| A-68 | 250 | 70 | 30 | 100 | 30 |
| A-69 | 250 | 30 | 20 | 80 | 0 |
| A-70 | 250 | 50 | 60 | 100 | 10 |
| A-71 | 250 | 40 | 30 | 90 | 0 |
| A-72 | 250 | 70 | 60 | 90 | 30 |
| A-73 | 250 | 80 | 90 | 100 | 80 |
| A-74 | 250 | 100 | 60 | 100 | 90 |
| A-75 | 250 | 100 | 100 | 100 | 80 |
| A-76 | 250 | 60 | 70 | 100 | 80 |
| A-77 | 250 | 30 | 40 | 70 | 20 |
| A-78 | 250 | 100 | 100 | 100 | 80 |
| A-79 | 250 | 90 | 80 | 100 | 80 |
| A-81 | 250 | 40 | 30 | 90 | 10 |
| A-82 | 250 | 100 | 70 | 100 | 90 |
| A-83 | 250 | 90 | 70 | 100 | 90 |
| A-84 | 250 | 100 | 70 | 100 | 60 |
| A-85 | 250 | 100 | 100 | 100 | 100 |
| A-86 | 250 | 100 | 90 | 100 | 100 |
| A-87 | 250 | 40 | 30 | 60 | 20 |
| A-88 | 250 | 100 | 80 | 100 | 60 |
| A-89 | 250 | 100 | 80 | 100 | 80 |
| A-90 | 250 | 90 | 70 | 100 | 70 |
| A-91 | 250 | 100 | 80 | 100 | 70 |
| A-92 | 250 | 90 | 40 | 100 | 30 |
| A-93 | 250 | 90 | 60 | 100 | 60 |
| A-94 | 250 | 100 | 40 | 90 | 20 |
| A-95 | 250 | 90 | 70 | 90 | 80 |
| A-96 | 250 | 100 | 70 | 90 | 40 |
| A-97 | 250 | 100 | 80 | 100 | 90 |
| A-98 | 250 | 60 | 40 | 80 | 20 |
| A-99 | 250 | 100 | 60 | 100 | 30 |
| A-100 | 250 | 80 | 40 | 100 | 40 |
| A-101 | 250 | 90 | 60 | 90 | 80 |
| A-102 | 250 | 20 | 0 | 10 | 0 |
| A-103 | 250 | 40 | 10 | 30 | 0 |
| A-104 | 250 | 100 | 90 | 100 | 30 |
| A-105 | 250 | 100 | 70 | 100 | 10 |
| A-106 | 250 | 100 | 60 | 90 | 20 |
| A-107 | 250 | 100 | 90 | 100 | 80 |
| A-108 | 250 | 70 | 40 | 80 | 40 |
| A-109 | 250 | 80 | 80 | 100 | 70 |
| A-111 | 250 | 40 | 10 | 40 | 30 |
| A-112 | 250 | 90 | 40 | 60 | 30 |
| A-113 | 250 | 100 | 30 | 60 | 30 |
| A-114 | 250 | 90 | 20 | 60 | 50 |
| A-115 | 250 | 0 | 0 | 0 | 0 |
| A-116 | 250 | 20 | 0 | 20 | 0 |
| A-117 | 250 | 20 | 0 | 20 | 0 |
| A-118 | 250 | 100 | 100 | 100 | 80 |
| A-121 | 250 | 0 | 10 | 10 | 0 |
| A-123 | 250 | 20 | 30 | 30 | 0 |
| A-124 | 250 | 0 | 0 | 10 | 0 |
| A-126 | 250 | 0 | 0 | 10 | 0 |
| A-127 | 250 | 0 | 0 | 0 | 0 |
| A-128 | 250 | 60 | 20 | 50 | 10 |
| A-129 | 250 | 10 | 10 | 30 | 0 |
| A-130 | 250 | 0 | 0 | 30 | 0 |
| A-131 | 250 | 60 | 30 | 90 | 40 |
| A-135 | 250 | 10 | 10 | 30 | 0 |
| A-140 | 250 | 50 | 20 | 50 | 0 |
| A-142 | 250 | 10 | 20 | 40 | 0 |
| A-143 | 250 | 70 | 60 | 100 | 40 |
| A-145 | 250 | 10 | 10 | 20 | 0 |
| A-146 | 250 | 0 | 10 | 10 | 0 |
| A-147 | 250 | 80 | 50 | 100 | 20 |
| A-148 | 250 | 100 | 50 | 90 | 90 |
| A-149 | 250 | 20 | 10 | 60 | 10 |
| A-150 | 250 | 70 | 10 | 80 | 10 |
| A-151 | 250 | 50 | 30 | 70 | 20 |
| A-153 | 250 | 60 | 50 | 100 | 20 |
| A-154 | 250 | 10 | 0 | 20 | 0 |
| A-156 | 250 | 20 | 20 | 60 | 0 |
| A-157 | 250 | 50 | 40 | 80 | 30 |
| A-159 | 250 | 100 | 30 | 90 | 40 |
| A-160 | 250 | 0 | 0 | 50 | 0 |
| A-161 | 250 | 90 | 70 | 100 | 50 |
| A-162 | 250 | 50 | 30 | 60 | 10 |
| A-163 | 250 | 100 | 70 | 100 | 70 |
| A-166 | 250 | 10 | 20 | 40 | 20 |
| A-167 | 250 | 30 | 30 | 100 | 10 |
| A-168 | 250 | 80 | 60 | 70 | 10 |
| A-169 | 250 | 10 | 20 | 30 | 0 |
| A-172 | 250 | 100 | 90 | 100 | 60 |
| A-173 | 250 | 10 | 0 | 50 | 0 |
| A-174 | 250 | 70 | 50 | 100 | 40 |
| A-177 | 250 | 30 | 0 | 60 | 0 |
| A-178 | 250 | 0 | 10 | 10 | 0 |
| A-179 | 250 | 0 | 0 | — | 0 |
| A-180 | 250 | 0 | 0 | — | 0 |
| A-181 | 250 | 0 | 0 | 0 | 0 |
| A-182 | 250 | 80 | 30 | 90 | 30 |
| A-183 | 250 | 80 | 30 | 60 | 20 |
| A-184 | 250 | 50 | 10 | 50 | 0 |
| A-185 | 250 | 0 | 0 | 30 | 0 |
| A-188 | 250 | 100 | 90 | 90 | 90 |
| A-189 | 250 | 60 | 50 | 90 | 40 |
| A-190 | 250 | 50 | 30 | 80 | 30 |
| A-191 | 250 | 60 | 40 | 90 | 40 |
| A-192 | 250 | 0 | 0 | 20 | 0 |
| A-193 | 250 | 70 | 30 | 90 | 20 |
| A-195 | 250 | 40 | 30 | 100 | 0 |
| A-196 | 250 | 0 | 0 | 0 | 0 |
| A-197 | 250 | 20 | 0 | 30 | 10 |
| A-198 | 250 | 10 | 0 | 60 | 0 |
| A-200 | 250 | 60 | 20 | 50 | 0 |
| A-201 | 250 | 30 | 10 | 60 | 0 |
| A-202 | 250 | 10 | 0 | 60 | 0 |
| A-203 | 250 | 90 | 20 | 50 | 30 |
| A-204 | 250 | 10 | 0 | 20 | 0 |
| A-205 | 250 | 60 | 20 | 60 | 10 |
| A-206 | 250 | 10 | 0 | 30 | 0 |
| A-207 | 250 | 60 | 30 | 70 | 10 |
| A-210 | 250 | 20 | 30 | 60 | 10 |
| A-212 | 250 | 50 | 30 | 70 | 10 |
| A-214 | 250 | 40 | 50 | 90 | 30 |
| A-215 | 250 | 0 | 0 | 20 | 0 |
| A-216 | 250 | 10 | 30 | 70 | 0 |
| A-217 | 250 | 60 | 30 | 40 | 0 |
| A-218 | 250 | 20 | 20 | 50 | 10 |
| A-219 | 250 | 80 | 50 | 90 | 30 |
| A-220 | 250 | 10 | 10 | 30 | 0 |
| A-221 | 250 | 60 | 60 | 70 | 40 |
| A-222 | 250 | 0 | 0 | 0 | 0 |
| A-223 | 250 | 90 | 80 | 100 | 50 |
| A-224 | 250 | 30 | 20 | 20 | 10 |
| A-225 | 250 | 10 | 0 | 60 | 0 |
| A-226 | 250 | 30 | 0 | 60 | 10 |

| Compound Number | Rate g/ha | LOLPE | ALOMY | ECHCG | AVEFA |
|---|---|---|---|---|---|
| A-227 | 250 | 60 | 30 | 80 | 20 |
| A-229 | 250 | 60 | 30 | 70 | 0 |
| A-230 | 250 | 0 | 0 | 20 | 0 |
| A-233 | 250 | 90 | 70 | 100 | 70 |
| A-234 | 250 | 90 | 70 | 100 | 40 |
| A-235 | 250 | 70 | 50 | 100 | 30 |
| A-236 | 250 | 20 | 40 | 80 | 20 |
| A-237 | 250 | 20 | 10 | 40 | 10 |
| A-238 | 250 | 90 | 60 | 100 | 40 |
| A-239 | 250 | 60 | 20 | 90 | 0 |
| A-240 | 250 | 70 | 30 | 70 | 0 |
| A-241 | 250 | 70 | 30 | 80 | 0 |
| A-242 | 250 | 80 | 70 | — | 40 |
| A-243 | 250 | 100 | 90 | — | 80 |
| A-244 | 250 | 70 | 20 | 90 | 0 |
| A-245 | 250 | 50 | 0 | 80 | 0 |
| A-246 | 250 | 60 | 70 | 100 | 50 |
| A-247 | 250 | 90 | 90 | 100 | 50 |
| A-248 | 250 | 100 | 90 | 100 | 80 |
| A-249 | 250 | 90 | 60 | 90 | 60 |
| A-250 | 250 | 80 | 80 | 90 | 50 |
| A-251 | 250 | 80 | 40 | 100 | 20 |
| A-253 | 250 | 100 | 70 | 80 | 30 |
| A-255 | 250 | 100 | 100 | 100 | 100 |
| A-256 | 250 | 80 | 50 | 80 | 20 |
| A-257 | 250 | 20 | 0 | 40 | 0 |
| A-258 | 250 | 30 | 30 | 70 | 10 |
| A-260 | 250 | 90 | 80 | 90 | 0 |
| A-261 | 250 | 80 | 80 | 90 | 50 |
| A-262 | 250 | 70 | 30 | 70 | 0 |
| A-263 | 250 | 50 | 60 | 100 | 20 |
| A-264 | 250 | 90 | 90 | 100 | 80 |
| A-265 | 250 | 80 | 60 | 90 | 0 |
| A-266 | 250 | 90 | 50 | 90 | 50 |
| A-267 | 250 | 100 | 100 | 100 | 100 |
| A-268 | 250 | 100 | 90 | 100 | 80 |
| A-269 | 250 | 90 | 100 | 100 | 80 |
| A-270 | 250 | 90 | 90 | 100 | 60 |
| A-271 | 250 | 90 | 90 | 100 | 50 |
| A-272 | 250 | 100 | 100 | 100 | 100 |
| A-273 | 250 | 100 | 100 | 100 | 100 |
| A-274 | 250 | 100 | 100 | 100 | 100 |
| A-275 | 250 | 100 | 100 | 100 | 90 |
| A-276 | 250 | 70 | 40 | 100 | 10 |
| A-277 | 250 | 100 | 30 | 100 | 30 |
| A-278 | 250 | 70 | 60 | 0 | 70 |
| A-279 | 250 | 100 | 90 | 100 | 100 |
| A-280 | 250 | 70 | 70 | 100 | 40 |
| A-281 | 250 | 80 | 70 | 100 | 0 |
| A-282 | 250 | 60 | 10 | 100 | 10 |
| A-283 | 250 | 60 | 70 | 90 | 10 |
| A-284 | 250 | 70 | 60 | 100 | 0 |
| A-285 | 250 | 100 | 90 | 100 | 70 |
| A-286 | 250 | 100 | 90 | 100 | 40 |
| A-287 | 250 | 100 | 100 | 100 | 90 |
| A-288 | 250 | 100 | 90 | 100 | 60 |
| A-289 | 250 | 90 | 60 | 100 | 40 |
| A-290 | 250 | 0 | 0 | 20 | 0 |
| A-291 | 250 | 100 | 70 | 100 | 90 |
| A-292 | 250 | 100 | 90 | 100 | 50 |
| A-293 | 250 | 100 | 80 | 100 | 30 |
| A-294 | 250 | 70 | 60 | 90 | 0 |
| A-295 | 250 | 50 | 50 | 70 | 20 |
| A-297 | 250 | 100 | 70 | 100 | 50 |
| A-298 | 250 | 100 | 100 | 100 | 100 |
| A-299 | 250 | 100 | 50 | 100 | 20 |
| A-300 | 250 | 100 | 80 | 100 | 0 |
| A-301 | 250 | 100 | 70 | 100 | 60 |
| A-302 | 250 | 20 | 10 | 60 | 40 |
| A-303 | 250 | 90 | 80 | 100 | 80 |
| A-304 | 250 | 70 | 80 | 100 | 80 |
| A-305 | 250 | 90 | 80 | 100 | 60 |
| A-306 | 250 | 70 | 60 | 100 | 0 |
| A-307 | 250 | 90 | 100 | 100 | 70 |
| A-308 | 250 | 70 | 90 | 100 | 80 |
| A-309 | 250 | 20 | 40 | 70 | 0 |
| A-310 | 250 | 70 | 100 | 100 | 50 |
| A-311 | 250 | 100 | 90 | 100 | 100 |
| A-312 | 250 | 100 | 70 | 100 | 70 |
| A-313 | 250 | 100 | 80 | 100 | 70 |
| A-314 | 250 | 100 | 30 | 100 | 20 |
| A-315 | 250 | 100 | 80 | 100 | 60 |
| A-316 | 250 | 100 | 70 | 100 | 60 |
| A-317 | 250 | 100 | 100 | 100 | 100 |
| A-318 | 250 | 100 | 90 | 100 | 90 |
| A-319 | 250 | 100 | 90 | 100 | 70 |
| A-320 | 250 | 100 | 80 | 100 | 80 |
| A-321 | 250 | 90 | 70 | 100 | 50 |
| A-322 | 250 | 100 | 60 | 100 | 40 |
| A-323 | 250 | 100 | 70 | 100 | 80 |
| A-324 | 250 | 100 | 90 | 100 | 90 |
| A-325 | 250 | 90 | 60 | 100 | 20 |
| A-326 | 250 | 90 | 30 | 70 | 10 |
| A-327 | 250 | 90 | 70 | 100 | 20 |
| A-328 | 250 | 90 | 50 | 100 | 30 |
| A-329 | 250 | 100 | 90 | 100 | 90 |
| A-330 | 250 | 100 | 80 | 100 | 80 |
| A-331 | 250 | 100 | 90 | 100 | 80 |
| A-332 | 250 | 100 | 80 | 100 | 70 |
| A-333 | 250 | 90 | 50 | 100 | 40 |
| A-334 | 250 | 100 | 100 | 100 | 100 |
| A-335 | 250 | 100 | 100 | 100 | 90 |
| A-336 | 250 | 100 | 90 | 100 | 80 |
| A-337 | 250 | 100 | 90 | 100 | 70 |
| A-338 | 250 | 100 | 90 | 100 | 80 |
| A-339 | 250 | 90 | 100 | 100 | 80 |
| A-340 | 250 | 70 | 80 | 100 | 50 |
| A-341 | 250 | 100 | 100 | 100 | 90 |
| A-342 | 250 | 100 | 90 | 100 | 60 |
| A-343 | 250 | 100 | 50 | 100 | 50 |
| A-344 | 250 | 80 | 40 | 100 | 30 |
| A-345 | 250 | 100 | 90 | 100 | 60 |
| A-346 | 250 | 100 | 100 | 100 | 90 |
| A-347 | 250 | 100 | 70 | 100 | 10 |
| A-348 | 250 | 100 | 60 | 100 | 10 |
| A-349 | 250 | 90 | 40 | 100 | 10 |
| A-350 | 250 | 100 | 90 | 100 | 50 |
| A-351 | 250 | 90 | 60 | 100 | 10 |
| A-352 | 250 | 90 | 70 | 100 | 20 |
| A-353 | 250 | 30 | 0 | 100 | 0 |
| A-356 | 250 | 100 | 90 | 100 | 70 |
| A-358 | 250 | 90 | 60 | 90 | 0 |
| A-364 | 250 | 90 | 70 | 100 | 60 |
| A-365 | 250 | 90 | 80 | 100 | 0 |
| A-366 | 250 | 90 | 50 | 90 | 30 |
| A-370 | 250 | 90 | 50 | 70 | 30 |
| A-372 | 250 | 100 | 70 | 90 | 90 |
| A-374 | 250 | 100 | 50 | 90 | 30 |
| A-375 | 250 | 90 | 30 | 90 | 60 |
| A-377 | 250 | 80 | 70 | 100 | 60 |

| Compound Number | Rate g/ha | LOLPE | ALOMY | ECHCG | AVEFA |
|---|---|---|---|---|---|
| P-1 | 250 | 100 | 80 | 100 | 20 |
| P-2 | 250 | 100 | 80 | 100 | 70 |
| P-3 | 250 | 100 | 70 | 100 | 70 |
| P-4 | 250 | 100 | 80 | 100 | 60 |
| P-5 | 250 | 100 | 100 | 100 | 70 |
| P-6 | 250 | 90 | 80 | 100 | 20 |

Post-Emergence Activity

| Compound Number | Rate g/ha | LOLPE | ALOMY | ECHCG | AVEFA |
|---|---|---|---|---|---|
| A-1 | 250 | — | 20 | 60 | 0 |
| A-2 | 250 | — | 60 | 90 | 50 |
| A-4 | 250 | — | 80 | 100 | 0 |
| A-5 | 250 | — | 20 | 90 | 0 |
| A-6 | 250 | — | 0 | 70 | 0 |
| A-7 | 250 | — | 90 | 100 | 70 |
| A-8 | 250 | 100 | 100 | 100 | 0 |
| A-9 | 250 | 80 | 90 | 100 | 100 |
| A-10 | 250 | 100 | 100 | 100 | 90 |
| A-11 | 250 | 50 | 50 | 60 | 20 |
| A-12 | 250 | 50 | 20 | 70 | 0 |
| A-13 | 250 | 0 | 0 | 70 | 0 |
| A-14 | 250 | 40 | 0 | 100 | 10 |
| A-15 | 250 | 100 | 90 | 100 | 70 |
| A-16 | 250 | 20 | 0 | 80 | 0 |
| A-19 | 250 | 90 | 60 | 100 | 60 |
| A-20 | 250 | 50 | 0 | 80 | 70 |
| A-21 | 250 | 70 | 100 | 100 | 60 |
| A-22 | 250 | 30 | 20 | 100 | 30 |
| A-23 | 250 | 90 | 80 | 100 | 80 |
| A-24 | 250 | 70 | 70 | 100 | 70 |
| A-25 | 250 | 90 | 90 | 100 | 100 |
| A-26 | 250 | 70 | 80 | 100 | 40 |
| A-27 | 250 | 30 | 30 | 90 | 40 |
| A-28 | 250 | 40 | 30 | 80 | 20 |
| A-29 | 250 | 10 | 0 | 70 | 0 |
| A-30 | 250 | 60 | 70 | 100 | 60 |
| A-31 | 250 | 100 | 90 | 100 | 80 |
| A-32 | 250 | 40 | 30 | 100 | 20 |
| A-33 | 250 | 50 | 40 | 100 | 50 |
| A-34 | 250 | 100 | 100 | 100 | 100 |
| A-35 | 250 | 80 | 80 | 100 | 90 |
| A-36 | 250 | 90 | 100 | 100 | 100 |
| A-37 | 250 | 90 | 100 | 100 | 100 |
| A-38 | 250 | 30 | 20 | 80 | 30 |
| A-39 | 250 | 30 | 30 | 70 | 0 |
| A-40 | 250 | 30 | 30 | 90 | 40 |
| A-41 | 250 | 30 | 30 | 90 | 10 |
| A-43 | 250 | 20 | 0 | 70 | 0 |
| A-44 | 250 | 100 | 100 | 100 | 100 |
| A-45 | 250 | 100 | 100 | 100 | 100 |
| A-46 | 250 | 60 | 80 | 100 | 50 |
| A-47 | 250 | 30 | 30 | 80 | 10 |
| A-48 | 250 | 70 | 80 | 100 | 40 |
| A-49 | 250 | 90 | 90 | 100 | 70 |
| A-50 | 250 | 60 | 0 | 50 | 0 |
| A-52 | 250 | 50 | 30 | 90 | 40 |
| A-53 | 250 | 30 | 0 | 80 | 0 |
| A-54 | 250 | 100 | 100 | 100 | 100 |
| A-55 | 250 | 100 | 100 | 100 | 100 |
| A-56 | 250 | 100 | 100 | 100 | 0 |
| A-58 | 250 | 0 | 0 | 80 | 0 |
| A-59 | 250 | 70 | 80 | 100 | 70 |
| A-60 | 250 | 0 | 0 | 0 | 0 |
| A-62 | 250 | 100 | 100 | 100 | 100 |
| A-64 | 250 | 40 | 40 | 30 | 0 |
| A-65 | 250 | 80 | 90 | 100 | 90 |
| A-66 | 250 | 80 | 100 | 100 | 100 |
| A-67 | 250 | 90 | 100 | 100 | 80 |
| A-68 | 250 | 60 | 60 | 100 | 40 |
| A-69 | 250 | 20 | 10 | 60 | 0 |
| A-70 | 250 | 10 | 30 | 70 | 10 |
| A-71 | 250 | 60 | 60 | 90 | 30 |
| A-72 | 250 | 40 | 60 | 90 | 50 |
| A-73 | 250 | 70 | 90 | 100 | 40 |
| A-74 | 250 | 80 | 90 | 100 | 80 |
| A-75 | 250 | 100 | 100 | 100 | 90 |
| A-76 | 250 | 70 | 80 | 100 | 70 |
| A-77 | 250 | 30 | 60 | 70 | 30 |
| A-78 | 250 | 90 | 100 | 90 | 90 |
| A-79 | 250 | 80 | 100 | 100 | 60 |
| A-81 | 250 | 30 | 50 | 70 | 50 |
| A-82 | 250 | 90 | 100 | 100 | 100 |
| A-83 | 250 | 60 | 90 | 100 | 100 |
| A-84 | 250 | 90 | 100 | 100 | 50 |
| A-85 | 250 | 90 | 100 | 100 | 90 |
| A-86 | 250 | 70 | 90 | 100 | 100 |
| A-87 | 250 | 40 | 70 | 80 | 40 |
| A-88 | 250 | 50 | 70 | 90 | 70 |
| A-89 | 250 | 60 | 90 | 100 | 90 |
| A-90 | 250 | 80 | 60 | 90 | 30 |
| A-91 | 250 | 80 | 90 | 100 | 90 |
| A-92 | 250 | 30 | 20 | 80 | 10 |
| A-93 | 250 | 20 | 60 | 50 | 20 |
| A-94 | 250 | 20 | 10 | 40 | 0 |
| A-95 | 250 | 50 | 60 | 80 | 80 |
| A-96 | 250 | 30 | 60 | 60 | 20 |
| A-97 | 250 | 90 | 100 | 100 | 90 |
| A-98 | 250 | 30 | 70 | 100 | 60 |
| A-99 | 250 | 80 | 80 | 100 | 90 |
| A-100 | 250 | 40 | 80 | 90 | 80 |
| A-101 | 250 | 100 | 100 | 100 | 90 |
| A-102 | 250 | 20 | 10 | 40 | 0 |
| A-103 | 250 | 20 | 10 | 40 | 0 |
| A-104 | 250 | 90 | 90 | 100 | 80 |
| A-105 | 250 | 90 | 90 | 90 | 10 |
| A-106 | 250 | 80 | 90 | 90 | 50 |
| A-107 | 250 | 40 | 80 | 100 | 80 |
| A-108 | 250 | 50 | 60 | 100 | 70 |
| A-109 | 250 | 90 | 90 | 100 | 90 |
| A-111 | 250 | 50 | 10 | 40 | 0 |
| A-112 | 250 | 60 | 20 | 70 | 20 |
| A-113 | 250 | 40 | 10 | 90 | 0 |
| A-114 | 250 | 50 | 10 | 80 | 10 |
| A-115 | 250 | 0 | 0 | 60 | 10 |
| A-116 | 250 | 40 | 80 | 100 | 30 |
| A-117 | 250 | 40 | 80 | 100 | 30 |
| A-118 | 250 | 100 | 90 | 100 | 80 |
| A-121 | 250 | 20 | 10 | 50 | 0 |
| A-123 | 250 | 30 | 20 | 50 | 10 |
| A-124 | 250 | 10 | 10 | 40 | 0 |
| A-126 | 250 | 10 | 10 | 50 | 20 |
| A-127 | 250 | 10 | 0 | 30 | 0 |
| A-128 | 250 | 40 | 50 | 70 | 30 |
| A-129 | 250 | 10 | 10 | 30 | 10 |
| A-130 | 250 | 10 | 10 | 40 | 0 |
| A-131 | 250 | 70 | 70 | 90 | 80 |
| A-135 | 250 | 30 | 30 | 50 | 20 |
| A-140 | 250 | 70 | 70 | 100 | 70 |
| A-142 | 250 | 10 | 20 | 70 | 20 |
| A-143 | 250 | 100 | 100 | 100 | 100 |
| A-145 | 250 | 20 | 20 | 70 | 20 |
| A-146 | 250 | 20 | 30 | 70 | 30 |
| A-147 | 250 | 90 | 80 | 100 | 70 |
| A-148 | 250 | 90 | 90 | 100 | 100 |
| A-149 | 250 | 30 | 10 | 50 | 30 |
| A-150 | 250 | 40 | 60 | 100 | 70 |
| A-151 | 250 | 30 | 20 | 70 | 20 |
| A-153 | 250 | 30 | 70 | 90 | 80 |
| A-154 | 250 | 20 | 20 | 60 | 10 |
| A-156 | 250 | 20 | 30 | 50 | 20 |
| A-157 | 250 | 90 | 90 | 100 | 100 |
| A-159 | 250 | 100 | 80 | 100 | 80 |
| A-160 | 250 | 20 | 20 | 60 | 10 |
| A-161 | 250 | 90 | 100 | 100 | 70 |
| A-162 | 250 | 70 | 80 | 90 | 50 |
| A-163 | 250 | 100 | 90 | 100 | 90 |
| A-166 | 250 | 20 | 30 | 60 | 20 |
| A-167 | 250 | 50 | 60 | 100 | 40 |
| A-168 | 250 | 90 | 90 | 90 | 20 |
| A-169 | 250 | 20 | 20 | 30 | 30 |
| A-172 | 250 | 100 | 100 | 100 | 100 |
| A-173 | 250 | 10 | 0 | 20 | 10 |
| A-174 | 250 | 90 | 90 | 100 | 100 |
| A-177 | 250 | 40 | 0 | 70 | 20 |
| A-178 | 250 | 30 | 40 | 80 | 40 |
| A-179 | 250 | 20 | 0 | 20 | 0 |
| A-180 | 250 | 10 | 0 | 30 | 0 |
| A-181 | 250 | 20 | 0 | 30 | 0 |
| A-182 | 250 | 60 | 90 | 100 | 60 |
| A-183 | 250 | 40 | 70 | 90 | 50 |

-continued

| Compound Number | Rate g/ha | LOLPE | ALOMY | ECHCG | AVEFA |
|---|---|---|---|---|---|
| A-184 | 250 | 30 | 20 | 30 | 0 |
| A-185 | 250 | 30 | 20 | 70 | 20 |
| A-188 | 250 | 100 | 100 | 100 | 100 |
| A-189 | 250 | 90 | 90 | 100 | 100 |
| A-190 | 250 | 90 | 80 | 100 | 90 |
| A-191 | 250 | 100 | 100 | 100 | 100 |
| A-192 | 250 | 10 | 0 | 40 | 10 |
| A-193 | 250 | 100 | 80 | 100 | 10 |
| A-195 | 250 | 80 | 60 | 100 | 60 |
| A-196 | 250 | 10 | 0 | 20 | 0 |
| A-197 | 250 | 60 | 70 | 100 | 70 |
| A-198 | 250 | 70 | 70 | 100 | 60 |
| A-200 | 250 | 70 | 70 | 90 | 10 |
| A-201 | 250 | 70 | 60 | 100 | 60 |
| A-202 | 250 | 30 | 10 | 60 | 20 |
| A-203 | 250 | 90 | 90 | 90 | 100 |
| A-204 | 250 | 40 | 60 | 70 | 50 |
| A-205 | 250 | 90 | 70 | 100 | 60 |
| A-206 | 250 | 50 | 20 | 70 | 30 |
| A-207 | 250 | 90 | 80 | 100 | 80 |
| A-210 | 250 | 100 | 90 | 100 | 90 |
| A-212 | 250 | 70 | 60 | 90 | 90 |
| A-214 | 250 | 100 | 100 | 100 | 70 |
| A-215 | 250 | 20 | 10 | 40 | 0 |
| A-216 | 250 | 70 | 60 | 80 | 70 |
| A-217 | 250 | 60 | 60 | 70 | 50 |
| A-218 | 250 | 80 | 70 | 100 | 100 |
| A-219 | 250 | 90 | 90 | 100 | 100 |
| A-220 | 250 | 80 | 60 | 100 | 30 |
| A-221 | 250 | 90 | 80 | 100 | 50 |
| A-222 | 250 | 30 | 20 | 30 | 20 |
| A-223 | 250 | 90 | 100 | 100 | 60 |
| A-224 | 250 | 70 | 50 | 70 | 50 |
| A-225 | 250 | 70 | 60 | 90 | 50 |
| A-226 | 250 | 60 | 60 | 100 | 60 |
| A-227 | 250 | 70 | 70 | 90 | 60 |
| A-229 | 250 | 100 | 90 | 100 | 10 |
| A-230 | 250 | 40 | 20 | 80 | 60 |
| A-233 | 250 | 100 | 100 | 100 | 100 |
| A-234 | 250 | 80 | 80 | 100 | 90 |
| A-235 | 250 | 100 | 90 | 100 | 100 |
| A-236 | 250 | 30 | 100 | 100 | 100 |
| A-237 | 250 | 10 | 10 | 70 | 10 |
| A-238 | 250 | 90 | 70 | 100 | 90 |
| A-239 | 250 | 30 | 20 | 70 | 10 |
| A-240 | 250 | 60 | 30 | 70 | 40 |
| A-241 | 250 | 60 | 40 | 90 | 70 |
| A-242 | 250 | 100 | 100 | 100 | 100 |
| A-243 | 250 | 100 | 100 | 100 | 100 |
| A-244 | 250 | 80 | 60 | 90 | 70 |
| A-245 | 250 | 20 | 0 | 80 | 10 |
| A-246 | 250 | 20 | 50 | 100 | 60 |
| A-247 | 250 | 100 | 90 | 100 | 100 |
| A-248 | 250 | 100 | 100 | 100 | 100 |
| A-249 | 250 | 70 | 90 | 100 | 100 |
| A-250 | 250 | 80 | 90 | 100 | 80 |
| A-251 | 250 | 0 | 80 | 100 | 30 |
| A-253 | 250 | 70 | 50 | 70 | 40 |
| A-255 | 250 | 100 | 100 | 100 | 100 |
| A-256 | 250 | 90 | 90 | 90 | 80 |
| A-257 | 250 | 50 | 30 | 80 | 0 |
| A-258 | 250 | 80 | 70 | 100 | 70 |
| A-260 | 250 | 80 | 90 | 90 | 100 |
| A-261 | 250 | 100 | 90 | 100 | 100 |
| A-262 | 250 | 60 | 80 | 90 | 50 |
| A-263 | 250 | 60 | 100 | 100 | 90 |
| A-264 | 250 | 100 | 90 | 100 | 90 |
| A-265 | 250 | 70 | 70 | 100 | 70 |
| A-266 | 250 | 70 | 90 | 100 | 90 |
| A-267 | 250 | 100 | 100 | 100 | 100 |
| A-268 | 250 | 70 | 90 | 100 | 90 |
| A-269 | 250 | 70 | 90 | 100 | 90 |
| A-270 | 250 | 70 | 90 | 100 | 90 |
| A-271 | 250 | 70 | 90 | 100 | 90 |
| A-272 | 250 | 70 | 90 | 100 | 90 |
| A-273 | 250 | 100 | 100 | 100 | 100 |
| A-274 | 250 | 100 | 100 | 100 | 100 |
| A-275 | 250 | 100 | 90 | 100 | 100 |
| A-276 | 250 | 40 | 60 | 100 | 10 |
| A-277 | 250 | 100 | 30 | 100 | 80 |
| A-278 | 250 | 100 | 100 | 100 | 100 |
| A-279 | 250 | 100 | 100 | 100 | 100 |
| A-280 | 250 | 60 | 90 | 100 | 70 |
| A-281 | 250 | 60 | 90 | 100 | 80 |
| A-282 | 250 | 40 | 70 | 100 | 60 |
| A-283 | 250 | 90 | 80 | 90 | 90 |
| A-284 | 250 | 60 | 60 | 100 | 0 |
| A-285 | 250 | 100 | 100 | 100 | 100 |
| A-286 | 250 | 100 | 100 | 100 | 90 |
| A-287 | 250 | 100 | 100 | 100 | 100 |
| A-288 | 250 | 90 | 100 | 100 | 90 |
| A-289 | 250 | 100 | 100 | 100 | 100 |
| A-290 | 250 | 10 | 0 | 60 | 0 |
| A-291 | 250 | 100 | 100 | 100 | 100 |
| A-292 | 250 | 90 | 100 | 100 | 90 |
| A-293 | 250 | 100 | 100 | 100 | 100 |
| A-294 | 250 | 20 | 40 | 80 | 40 |
| A-295 | 250 | 40 | 80 | 100 | 60 |
| A-297 | 250 | 100 | 100 | 100 | 100 |
| A-298 | 250 | 100 | 100 | 100 | 100 |
| A-299 | 250 | 80 | 90 | 100 | 90 |
| A-300 | 250 | 60 | 80 | 100 | 70 |
| A-301 | 250 | 90 | 100 | 100 | 60 |
| A-302 | 250 | 70 | 60 | 100 | 50 |
| A-303 | 250 | 100 | 100 | 100 | 100 |
| A-304 | 250 | 100 | 100 | 100 | 100 |
| A-305 | 250 | 100 | 100 | 100 | 100 |
| A-306 | 250 | 60 | 70 | 100 | 80 |
| A-307 | 250 | 100 | 100 | 100 | 100 |
| A-308 | 250 | 100 | 90 | 100 | 100 |
| A-309 | 250 | 50 | 50 | 100 | 70 |
| A-310 | 250 | 90 | 100 | 100 | 80 |
| A-311 | 250 | 100 | 100 | 100 | 100 |
| A-312 | 250 | 100 | 100 | 100 | 100 |
| A-313 | 250 | 80 | 90 | 100 | 90 |
| A-314 | 250 | 70 | 40 | 100 | 70 |
| A-315 | 250 | 90 | 40 | 90 | 80 |
| A-316 | 250 | 40 | 50 | 100 | 80 |
| A-317 | 250 | 100 | 100 | 100 | 100 |
| A-318 | 250 | 100 | 90 | 100 | 90 |
| A-319 | 250 | 100 | 100 | 100 | 100 |
| A-320 | 250 | 90 | 100 | 100 | 100 |
| A-321 | 250 | 90 | 90 | 100 | 90 |
| A-322 | 250 | 90 | 90 | 100 | 80 |
| A-323 | 250 | 70 | 60 | 90 | 80 |
| A-324 | 250 | 100 | 100 | 100 | 100 |
| A-325 | 250 | 40 | 50 | 100 | 30 |
| A-326 | 250 | 90 | 30 | 100 | 90 |
| A-327 | 250 | 70 | 80 | 100 | 90 |
| A-328 | 250 | 70 | 60 | 100 | 80 |
| A-329 | 250 | 70 | 80 | 100 | 90 |
| A-330 | 250 | 70 | 70 | 100 | 80 |
| A-331 | 250 | 80 | 80 | 100 | 80 |
| A-332 | 250 | 100 | 100 | 100 | 100 |
| A-333 | 250 | 60 | 60 | 100 | 70 |
| A-334 | 250 | 100 | 90 | 100 | 100 |
| A-335 | 250 | 100 | 100 | 100 | 90 |
| A-336 | 250 | 100 | 90 | 100 | 80 |
| A-337 | 250 | 90 | 90 | 100 | 90 |
| A-338 | 250 | 100 | 100 | 100 | 100 |
| A-339 | 250 | 100 | 100 | 100 | 90 |
| A-340 | 250 | 70 | 60 | 100 | 80 |
| A-341 | 250 | 100 | 90 | 100 | 100 |
| A-342 | 250 | 60 | 60 | 100 | 70 |
| A-343 | 250 | 80 | 50 | 100 | 80 |
| A-344 | 250 | 70 | 60 | 90 | 90 |
| A-345 | 250 | 100 | 80 | 100 | 100 |
| A-346 | 250 | 90 | 70 | 100 | 90 |
| A-347 | 250 | 100 | 90 | 100 | 50 |
| A-348 | 250 | 90 | 100 | 100 | 60 |
| A-349 | 250 | 80 | 60 | 100 | 0 |
| A-350 | 250 | 90 | 90 | 100 | 90 |

-continued

| Compound Number | Rate g/ha | LOLPE | ALOMY | ECHCG | AVEFA |
|---|---|---|---|---|---|
| A-351 | 250 | 100 | 90 | 100 | 10 |
| A-352 | 250 | 90 | 90 | 100 | 70 |
| A-353 | 250 | 50 | 10 | 100 | 10 |
| A-356 | 250 | 100 | 100 | 100 | 100 |
| A-358 | 250 | 60 | 90 | 100 | 60 |
| A-364 | 250 | 90 | 100 | 100 | 90 |
| A-365 | 250 | 100 | 100 | 100 | 10 |
| A-366 | 250 | 100 | 100 | 100 | 80 |
| A-370 | 250 | 80 | 90 | 100 | 100 |
| A-372 | 250 | 100 | 100 | 100 | 100 |
| A-374 | 250 | 100 | 90 | 100 | 90 |
| A-375 | 250 | 70 | 90 | 100 | 90 |
| A-377 | 250 | 100 | 100 | 100 | 100 |

| Compound Number | Rate g/ha | LOLPE | ALOMY | ECHCG | AVEFA |
|---|---|---|---|---|---|
| P-1 | 250 | 90 | 80 | 100 | 60 |
| P-2 | 250 | 90 | 90 | 100 | 70 |
| P-3 | 250 | 90 | 90 | 100 | 60 |
| P-4 | 250 | 90 | 90 | 100 | 60 |
| P-5 | 250 | 80 | 80 | 100 | 70 |
| P-6 | 250 | 70 | 90 | 90 | 50 |

What is claimed is:

1. A compound of formula I

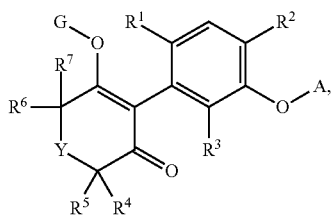

wherein

A is a 5- or 6-membered monocyclic heteroaryl or a bicyclic 8- to 10-membered heteroaryl,
wherein the heteroaryl contains a heteroatom selected from nitrogen, oxygen and sulfur, and wherein A is unsubstituted or substituted $R^1$ is methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy;

$R^2$ and $R^3$ are independently of each other hydrogen, methyl, ethyl, n-propyl, isopropyl, cyclopropyl, halomethyl, haloethyl, vinyl, propenyl, ethynyl, propynyl, halogen, methoxy, ethoxy, halomethoxy or haloethoxy; and $R^4$, $R^5$, $R^6$ and $R^7$ are independently of each other hydrogen, $C_1$-$C_6$alkyl, $C_1$-$C_6$alkyl substituted by $C_1$-$C_4$alkoxy or halogen, $C_2$-$C_6$ alkenyl, $C_2$-$C_6$ alkenyl substituted by $C_1$-$C_4$alkoxy or halogen, $C_2$-$C_6$alkynyl, $C_2$-$C_6$alkynyl substituted by $C_1$-$C_4$alkoxy or halogen, $C_3$-$C_7$cycloalkyl, $C_3$-$C_7$cycloalkyl substituted by $C_1$-$C_4$alkyl or $C_1$-$C_4$alkoxy, $C_5$-$C_7$cycloalkenyl, $C_5$-$C_7$cycloalkenyl substituted by $C_1$-$C_4$alkyl or $C_1$-$C_4$alkoxy, or heterocyclyl or heterocyclyl substituted by $C_1$-$C_4$alkyl or $C_1$-$C_4$alkoxy; or $R^4$ and $R^5$, or $R^6$ and $R^7$, together with the atoms to which they are bonded, form a 5- to 8-membered spiro-carbocyclyl or spiro-heterocyclyl, which contains one or two heteroatoms selected from nitrogen, oxygen and sulfur; or $R^5$ and $R^6$, together with the atoms to which they are bonded, form a 5- to 8-membered carbocyclyl or heterocyclyl, which contains one or two heteroatoms selected from nitrogen, oxygen and sulfur; and Y is O, S(O)$_n$, C=O, $CR^8R^9$ or $CR^{10}R^{11}CR^{12}R^{13}$;

n is 0, 1 or 2; and $R^8$ and $R^9$ are independently of each other hydrogen, $C_1$-$C_6$alkyl, $C_1$-$C_6$alkyl substituted by $C_1$-$C_4$alkoxy or halogen, $C_2$-$C_6$ alkenyl, $C_2$-$C_6$ alkenyl substituted by $C_1$-$C_4$alkoxy or halogen, $C_2$-$C_6$alkynyl, $C_2$-$C_6$alkynyl substituted by $C_1$-$C_4$alkoxy or halogen, $C_3$-$C_7$cycloalkyl, $C_3$-$C_7$cycloalkyl substituted by $C_1$-$C_4$alkyl or $C_1$-$C_4$alkoxy, $C_5$-$C_7$cycloalkenyl, $C_5$-$C_7$cycloalkenyl substituted by $C_1$-$C_4$alkyl or $C_1$-$C_4$alkoxy, or heterocyclyl or heterocyclyl substituted by $C_1$-$C_4$alkyl or $C_1$-$C_4$alkoxy; or $R^8$ and $R^9$, together with the atoms to which they are bonded, form a 5- to 8-membered spiro-carbocyclyl or spiro-heterocyclyl, which contains one or two heteroatoms selected from nitrogen, oxygen and sulfur; and $R^{10}$, $R^{11}$, $R^{12}$ and $R^{13}$ are independently of each other hydrogen, $C_1$-$C_6$alkyl or $C_1$-$C_6$alkoxy; and G is hydrogen or an agriculturally acceptable metal, sulfonium, ammonium or latentiating group;

and wherein, when G is a latentiating group, then G is a group which is phenyl$C_1$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), heteroaryl$C_1$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano or by nitro), $C_3$alkenyl, $C_3$haloalkenyl, $C_3$alkynyl, $C(X^a)$—$R^a$, $C(X^b)$—$X^c$—$R^b$, $C(X^d)$—N($R^c$)—$R^d$, —$SO_2$—$R^e$, —P($X^e$)($R^f$)—$R^g$ or $CH_2$—$X^f$—$R^h$;

wherein $X^a$, $X^b$, $X^b$, $X^d$, $X^e$ and $X^f$ are independently of each other oxygen or sulfur; and wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_5$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_5$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_5$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_5$cycloalkyl;

phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_5$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_5$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_6$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; or $C_3$-$C_7$cycloalkylamino, di-$C_3$-$C_7$cycloalkylamino or $C_3$-$C_7$cycloalkoxy;

or $R^c$ and $R^d$ are joined together to form a 3-7 membered ring, wherein the ring optionally contains one heteroatom selected from O and S in addition to the N from the $C(X^d)$—$N(R^c)$—$R^d$ group; and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$alkoxy, $C_1$-$C_{10}$haloalkoxy, $C_1$-$C_5$alkylamino or $C_2$-$C_8$dialkylamino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino, di$C_3$-$C_7$cycloalkylamino, $C_3$-$C_7$cycloalkoxy, $C_1$-$C_{10}$haloalkoxy, $C_1$-$C_5$alkylamino or $C_2$-$C_8$dialkylamino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy($C_1$-$C_5$)alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy($C_1$-$C_5$)alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein, when present, the optional substituents on aryl and heteroaryl are selected, independently, from: halogen, nitro, cyano, rhodano, isothiocyanato, $C_1$-$C_6$alkyl, $C_1$-$C_6$haloalkyl, $C_1$-$C_6$alkoxy($C_1$-$C_6$)alkyl, $C_2$-$C_6$alkenyl, $C_2$-$C_6$haloalkenyl, $C_2$-$C_6$alkynyl, $C_3$-$C_7$cycloalkyl (itself optionally substituted with $C_1$-$C_6$alkyl or halogen), $C_{5-7}$cycloalkenyl (itself optionally substituted with $C_1$-$C_6$alkyl or halogen), hydroxy, $C_1$-$C_{10}$alkoxy, $C_1$-$C_{10}$alkoxy($C_1$-$C_{10}$)alkoxy, tri($C_1$-$C_4$)alkylsilyl($C_1$-$C_6$)alkoxy, $C_1$-$C_6$alkoxycarbonyl($C_1$-$C_{10}$)alkoxy, $C_1$-$C_{10}$haloalkoxy, aryl($C_1$-$C_4$)alkoxy (where the aryl group is optionally substituted with halogen or $C_1$-$C_6$alkyl), $C_3$-$C_7$cycloalkyloxy (where the cycloalkyl group is optionally substituted with $C_1$-$C_6$alkyl or halogen), $C_3$-$C_{10}$alkenyloxy, $C_3$-$C_{10}$alkynyloxy, mercapto, $C_1$-$C_{10}$alkylthio, $C_1$-$C_{10}$haloalkylthio, aryl($C_1$-$C_4$)alkylthio, $C_3$-$C_7$cycloalkylthio (where the cycloalkyl group is optionally substituted with $C_1$-$C_6$alkyl or halogen), tri($C_1$-$C_4$)-alkylsilyl($C_1$-$C_6$)alkylthio, arylthio, $C_1$-$C_6$alkylsulfonyl, $C_1$-$C_6$haloalkylsulfonyl, $C_1$-$C_6$alkylsulfinyl, $C_1$-$C_6$haloalkylsulfinyl, arylsulfonyl, tri($C_1$-$C_4$)alkylsilyl, aryldi($C_1$-$C_4$)alkylsilyl, $C_1$-$C_4$alkyldiarylsilyl, triarylsilyl, $C_1$-$C_{10}$alkylcarbonyl, $HO_2C$, $C_1$-$C_{10}$alkoxycarbonyl, aminocarbonyl, $C_1$-$C_6$alkylaminocarbonyl, di($C_1$-$C_6$alkyl)-aminocarbonyl, N—($C_1$-$C_3$ alkyl)-N—($C_1$-$C_3$alkoxy)aminocarbonyl, $C_1$-$C_6$alkylcarbonyloxy, arylcarbonyloxy, di($C_1$-$C_6$)alkylaminocarbonyloxy, aryl (itself optionally substituted with $C_1$-$C_6$alkyl or halogen), heteroaryl (itself optionally substituted with $C_1$-$C_6$alkyl or halogen), heterocyclyl (itself optionally substituted with $C_1$-$C_6$alkyl or halogen), aryloxy (where the aryl group is optionally substituted with $C_1$-$C_6$alkyl or halogen), heteroaryloxy (where the heteroaryl group is optionally substituted with $C_1$-$C_6$alkyl or halogen), heterocyclyloxy (where the heterocyclyl group is optionally substituted with $C_1$-$C_6$alkyl or halogen), amino, $C_1$-$C_6$alkylamino, di($C_1$-$C_6$)alkylamino, $C_1$-$C_6$alkylcarbonylamino, N—($C_1$-$C_6$)alkylcarbonyl-N—($C_1$-$C_6$)alkylamino, and arylcarbonyl (where the aryl group is itself optionally substituted with halogen or $C_1$-$C_6$alkyl);

or two adjacent positions on a heteroaryl system are cyclised to form a 5, 6 or 7 membered carbocyclic or heterocyclic ring, itself optionally substituted with halogen or $C_1$-$C_6$alkyl;

and wherein:

"aryl" means phenyl; and

"heteroaryl", unless otherwise defined, means an aromatic ring system containing at least one heteroatom and consisting either of a single ring or of two fused rings.

2. The compound according to claim 1, wherein A is a bicyclic 8- to 10-membered heteroaryl.

3. The compound according to claim 1, wherein A is substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro, cyano, $C_3$-$C_6$cycloalkyl, $C_1$-$C_3$alkylcarbonyl, $C_1$-$C_4$alkoxycarbonyl, aminocarbonyl, $C_1$-$C_3$alkylaminocarbonyl, di-$C_1$-$C_3$alkylaminocarbonyl, $C_1$-$C_3$alkylaminocarbonyloxy, di-$C_1$-$C_3$alkylaminocarbonyloxy, aminothiocarbonyl, $C_1$-$C_3$alkylaminothiocarbonyl, di$C_1$-$C_3$alkylaminothiocarbonyl, $C_1$-$C_4$alkylcarbonylamino, $C_3$-$C_6$cycloalkylcarbonylamino, $C_1$-$C_4$alkoxycarbonylamino, $C_1$-$C_4$alkylthiocarbonylamino, $C_1$-$C_3$alkoxy$C_1$-$C_3$alkyl, $C_1$-$C_6$alkylthio$C_1$-$C_6$alkyl, $C_1$-$C_6$alkylsulfinyl$C_1$-$C_6$alkyl, $C_1$-$C_6$alkylsulfonyl$C_1$-$C_6$alkyl, $C_1$-$C_3$alkylsulfonyloxy, $C_1$-$C_3$haloalkylsulfonyloxy or di$C_1$-$C_6$alkylaminosulfonyl, or 2 substituents on adjacent carbon atoms of A together form a $C_3$-$C_4$alkylene, wherein 1 or 2 methylene groups are optionally substituted by halogen, or wherein 1 or 2 of these methylene groups are replaced by oxygen.

4. The compound according to claim 1, wherein A is pyridyl, pyrazinyl, pyrimidinyl, pyridazinyl, benzothiazolyl, benzoxazolyl, cinnolinyl, quinolinyl, quinazolinyl, quinoxalinyl or benzotriazinyl, in each case substituted by halogen, methyl, ethyl, trifluoromethyl, methoxy, difluoromethoxy, trifluoromethoxy, nitro or cyano.

5. The compound according to claim 1, wherein $R^1$ is methyl, ethyl, n-propyl, cyclopropyl, halogen or $C_1$-$C_2$haloalkoxy.

6. The compound according to claim 1, wherein $R^2$ and $R^3$ are independently of each other hydrogen, methyl or halogen.

7. The compound according to claim 6, wherein $R^2$ and $R^3$ are hydrogen.

8. The compound according to claim 1, wherein:
$R^4$, $R^5$, $R^6$ and $R^7$ are independently of each other hydrogen or $C_1$-$C_6$alkyl; or
$R^4$ and $R^5$, or $R^6$ and $R^7$, together with the atoms to which they are bonded, form a spiro-tetrahydropyranyl or a spiro-tetrahydrofuranyl; or
$R^5$ and $R^6$, together with the atoms to which they are bonded, form a 6- or 7-membered carbocyclyl.

9. The compound according to claim 1, wherein Y is O or $CR^8R^9$, wherein $R^8$ and $R^9$ are as defined in claim 1.

10. The compound according to claim 1, wherein $R^8$ and $R^9$ are independently of each other hydrogen or methyl; or $R^8$ and $R^9$, together with the atoms to which they are bonded, form a spiro-tetrahydropyranyl or a spiro-tetrahydrofuranyl.

11. The compound according to claim 1, wherein:
"heterocyclyl" means a non-aromatic monocyclic or bicyclic ring system containing up to 7 atoms including one or two heteroatoms selected from O, S and N.

12. The compound according to claim 1, wherein, when G is a latentiating group, then G is a group —C($X^a$)—$R^a$ or —C($X^b$)—$X^c$—$R^b$, and the meanings of $X^a$, $R^a$, $X^b$, $X^c$ and $R^b$ are as defined in claim 1.

13. The compound according to claim 1, wherein G is hydrogen, an alkali metal or an alkaline earth metal.

14. The compound according to claim 1, wherein G is hydrogen.

15. The compound according to claim 1, wherein A is pyridyl, pyrazinyl, pyrimidinyl, pyridazinyl, benzothiazolyl, benzoxazolyl, cinnolinyl, quinolinyl, quinazolinyl, quinoxalinyl or benzotriazinyl, in each case substituted by halogen, methyl, trifluoromethyl, nitro or cyano;
$R^1$ is ethyl;
$R^2$ and $R^3$ are hydrogen; and
$R^4$ to $R^7$ are hydrogen or methyl, or $R^5$ and $R^6$, together with the atoms to which they are bonded, form a 6- or 7-membered carbocyclyl; and
Y is O or $CR^8R^9$;
wherein $R^8$ and $R^9$ are independently of each other hydrogen or methyl, or $R^8$ and $R^9$, together with the atoms to which they are bonded, form a spiro-tetrahydropyranyl or a spiro-tetrahydrofuranyl; and
G is hydrogen.

16. The compound according to claim 1, wherein
$R^1$ is methyl, ethyl or cyclopropyl;
$R^2$ and $R^3$ are hydrogen; and
$R^4$, $R^5$, $R^6$ and $R^7$ are independently of each other hydrogen or methyl; or $R^4$ and $R^5$, or $R^6$ and $R^7$, together with the atoms to which they are bonded, form a spiro-tetrahydropyranyl or spiro-tetrahydrofuranyl; or $R^5$ and $R^6$, together with the atoms to which they are bonded, form a 6- or 7-membered carbocyclyl; and
Y is O or $CR^8R^9$;
wherein $R^8$ and $R^9$ are independently of each other hydrogen or methyl; or $R^8$ and $R^9$, together with the atoms to which they are bonded, form a spiro-tetrahydropyranyl or a spiro-tetrahydrofuranyl; and
G is hydrogen; and
A is phenyl, naphthyl, pyridyl, pyrazinyl, pyrimidinyl, pyridazinyl, benzothiazolyl, benzoxazolyl, quinolinyl or quinoxalinyl, in each case unsubstituted or substituted by hydroxyl, methoxy, ethoxy, fluoro, chloro, bromo, iodo, methyl, trifluoromethyl, amino, formyl, nitro or cyano.

17. A process for the preparation of a compound of formula I according to claim 1, wherein G is hydrogen, which comprises the reaction of a compound of formula (K)

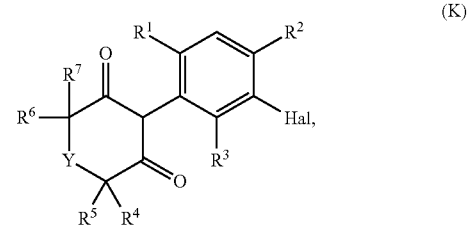

wherein Y and $R^1$ to $R^7$ are as defined in claim 1 and Hal is bromine or iodine, with a compound A-OH, wherein A is as defined in claim 1, in the presence of a catalyst, a ligand or additive, and a base, in a solvent.

18. A process for the preparation of a compound of formula I according to claim 1, wherein G is hydrogen, which comprises the reaction of a compound of formula (M)

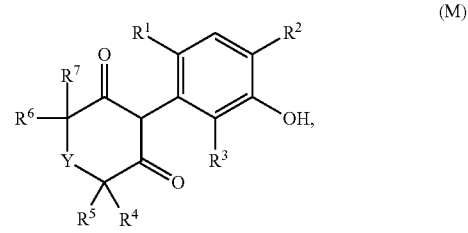

wherein Y and $R^1$ to $R^7$ are as defined in claim 1, with a compound A-Hal, wherein A is as defined in claim 1 and Hal is fluorine, chlorine, bromine or iodine, in the presence or absence of a catalyst and ligand, and in the presence of a base, and in a solvent.

19. A herbicidal composition, which, in addition to comprising formulation adjuvants, comprises a herbicidally effective amount of a compound of formula I as defined in claim 1.

20. A method of controlling grasses in crops of useful plants, which comprises applying a herbicidally effective amount of a compound of formula I as defined in claim 1, or of a composition comprising such a compound, to the plants or to the locus thereof.

21. The method according to claim 20, which comprises applying a herbicidally effective amount of the composition comprising the compound, to the plants or to the locus thereof, and wherein the crops of useful plants are wheat, barley, rice, corn, rape, sugarbeet, sugarcane, soybean, cotton, sunflower, or peanut.

22. A mixture of a compound of formula I, as defined in claim 1, in combination with a further herbicide, wherein the mixture of the compound of formula I is selected from:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fenoxasulfone, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+flurochloridone, compound of formula I+fluroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone, compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron, compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenyl-chlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester, compound of formula I+4-[(4,5-dihydro-3-methoxy-4-methyl-5-oxo)-1H-1,2,4-triazol-1-ylcarbonylsulfamoyl]-5-methylthiophene-3-carboxylic acid, compound of formula I+BAY747 as defined in CAS Registry Number 335104-84-2, compound of formula I+topramezone, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one, and compound of formula I+4-hydroxy-3-[[2-(3-methoxypropyl)-6-(difluoromethyl)-3-pyridinyl]carbonyl]-bicyclo[3.2.1]oct-3-en-2-one;
and wherein the further herbicide mixed with the compound of formula I is optionally in the form of an ester or a salt.

23. A compound of the following formula:

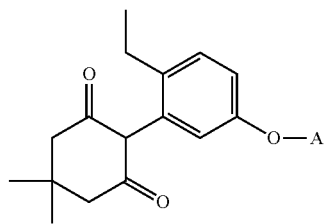

wherein A is 3-chloropyridin-2-yl, 4-chloropyridin-2-yl, 5-chloropyridin-2-yl, 6-chloropyridin-2-yl, 2-chloropyridin-3-yl, 4-chloropyridin-3-yl, 5-chloropyridin-3-yl, 6-chloropyridin-3-yl, 2-chloropyridin-4-yl, 3-chloropyridin-4-yl, 3,4-dichloropyridin-2-yl, 3,5-dichloropyridin-2-yl, 3,6-dichloropyridin-2-yl, 2,5-dichloropyridin-3-yl, 2,6-dichloropyridin-3-yl, 2,3-dichloropyridin-4-yl, 2,5-dichloropyridin-4-yl, 3,5,6-trichloropyridin-2-yl, 3-fluoropyridin-2-yl, 4-fluoropyridin-2-yl, 5-fluoropyridin-2-yl, 6-fluoropyridin-2-yl, 2-fluoropyridin-3-yl, 4-fluoropyridin-3-yl, 5-fluoropyridin-3-yl, 6-fluoropyridin-3-yl, 2-fluoropyridin-4-yl, 3-fluoropyridin-4-yl, 3,4-difluoropyridin-2-yl, 3,5-difluoropyridin-2-yl, 3,6-difluoropyridin-2-yl, 2,5-difluoropyridin-3-yl, 2,6-difluoropyridin-3-yl, 2,3-difluoropyridin-4-yl, 2,5-difluoropyridin-4-yl, 3,5,6-trifluoropyridin-2-yl, 3-trifluoromethylpyridin-2-yl, 4-trifluoromethylpyridin-2-yl, 5-trifluoromethylpyridin-2-yl, 6-trifluoromethylpyridin-2-yl, 2-trifluoromethylpyridin-3-yl, 4-trifluoromethylpyridin-3-yl, 5-trifluoromethylpyridin-3-yl, 6-trifluoromethylpyridin-3-yl, 2-trifluoromethylpyridin-4-yl, 3-trifluoromethylpyridin-4-yl, 4-chloro-3-fluoropyridin-2-yl, 5-chloro-3-fluoropyridin-2-yl, 6-chloro-3-fluoropyridin-2-yl, 3-chloro-4-fluoropyridin-2-yl, 3-chloro-5-fluoropyridin-2-yl, 3-chloro-6-fluoropyridin-2-yl, 3-chloro-5-trifluoromethylpyridin-2-yl, 3-fluoro-5-trifluoromethylpyridin-2-yl, 6-fluoro-3,4,5-trichloropyridin-2-yl, 4-methyl-3,5,6-trifluoropyridin-2-yl, pyrimidin-2-yl, 5-fluoropyrimidin-2-yl, 5-chloropyrimidin-2-yl, 5-bromopyrimidin-2-yl, 6-chloropyridazin-3-yl, 6-bromopyridazin-3-yl, quinoline-2-yl, 6-fluoroquinolin-2-yl, 7-fluoroquinolin-2-yl, 6-chloroquinolin-2-yl, 7-chloroquinolin-2-yl, 6-bromoquinolin-2-yl, 7-bromoquinolin-2-yl, 6-trifluoromethylquinolin-2-yl, 7-trifluoromethylquinolin-2-yl, quinoxalin-2-yl, 6-fluoroquinoxazin-2-yl, 7-fluoroquinoxalin-2-yl, 6-chloroquinoxalin-2-yl, 7-chloroquinoxalin-2-yl, 6-bromoquinoxalin-2-yl, 7-bromoquinoxalin-2-yl, 6-trifluoromethylquinoxalin-2-yl, 7-trifluoromethylquinoxalin-2-yl, quinazolin-2-yl, 6-fluoroquinazolin-2-yl, 7-fluoroquinazolin-2-yl, 6-chloroquinazolin-2-yl, 7-chloroquinazolin-2-yl, 6-bromoquinazolin-2-yl, 7-bromoquinazolin-2-yl, benzoxazol-2-yl, 5-fluorobenzoxazol-2-yl, 6-fluorobenzoxazol-2-yl, 5-chlorobenzoxazol-2-yl, 6-chlorobenzoxazol-2-yl, 5-bromobenzoxazol-2-yl, 6-bromobenzoxazol-2-yl, 5-trifluoromethylbenzoxazol-2-yl, 6-trifluoromethylbenzoxazol-2-yl, benzothiazol-2-yl, 5-fluorobenzothiazol-2-yl, 6-fluorobenzothiazol-2-yl, 5-chlorobenzothiazol-2-yl, 6-chlorobenzothiazol-2-yl, 5-bromobenzothiazol-2-yl, 6-bromobenzothiazol-2-yl, 5-trifluoromethylbenzothiazol-2-yl, 6-trifluoromethylbenzothiazol-2-yl, benzo[1,2,4]triazin-3-yl, 6-fluorobenzo[1,2,4]triazin-3-yl, 7-fluorobenzo[1,2,4]triazin-3-yl, 6-chlorobenzo[1,2,4]triazin-3-yl, 7-chlorobenzo[1,2,4]triazin-3-yl, 6-bromobenzo[1,2,4]triazin-3-yl, or 7-bromobenzo[1,2,4]triazin-3-yl.

24. A compound of the following formula:

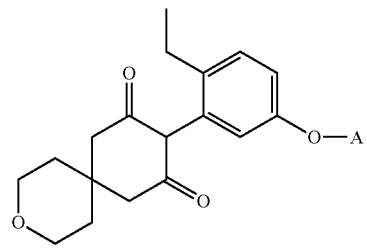

wherein A is 3-chloropyridin-2-yl, 4-chloropyridin-2-yl, 5-chloropyridin-2-yl, 6-chloropyridin-2-yl, 2-chloropyridin-3-yl, 4-chloropyridin-3-yl, 5-chloropyridin-3-yl, 6-chloropyridin-3-yl, 2-chloropyridin-4-yl, 3-chloropyridin-4-yl, 3,4-dichloropyridin-2-yl, 3,5-dichloropyridin-2-yl, 3,6-dichloropyridin-2-yl, 2,5-dichloropyridin-3-yl, 2,6-dichloropyridin-3-yl, 2,3-dichloropyridin-4-yl, 2,5-dichloropyridin-4-yl, 3,5,6-trichloropyridin-2-yl, 3-fluoropyridin-2-yl, 4-fluoropyridin-2-yl, 5-fluoropyridin-2-yl, 6-fluoropyridin-2-yl, 2-fluoropyridin-3-yl, 4-fluoropyridin-3-yl, 5-fluoropyridin-3-yl, 6-fluoropyridin-3-yl, 2-fluoropyridin-4-yl, 3-fluoropyridin-4-yl, 3,4-difluoropyridin-2-yl, 3,5-difluoropyridin-2-yl, 3,6-difluoropyridin-2-yl, 2,5-difluoropyridin-3-yl, 2,6-difluoropyridin-3-yl, 2,3-difluoropyridin-4-yl, 2,5-difluoropyridin-4-yl, 3,5,6-trifluoropyridin-2-yl, 3-trifluoromethylpyridin-2-yl, 4-trifluoromethylpyridin-2-yl, 5-trifluoromethylpyridin-2-yl, 6-trifluoromethylpyridin-2-yl, 2-trifluoromethylpyridin-3-yl, 4-trifluoromethylpyridin-3-yl, 5-trifluoromethylpyridin-3-yl, 6-trifluoromethylpyridin-3-yl, 2-trifluoromethylpyridin-4-yl, 3-trifluoromethylpyridin-4-yl, 4-chloro-3-fluoropyridin-2-yl, 5-chloro-3-fluoropyridin-2-yl, 6-chloro-3-fluoropyridin-2-yl, 3-chloro-4-fluoropyridin-2-yl, 3-chloro-5-fluoropyridin-2-yl, 3-chloro-6-fluoropyridin-2-yl, 3-chloro-5-trifluoromethylpyridin-2-yl, 3-fluoro-5-trifluoromethylpyridin-2-yl, 6-fluoro-3,4,5-trichloropyridin-2-yl, 4-methyl-3,5,6-trifluoropyridin-2-yl, pyrimidin-2-yl, 5-fluoropyrimidin-2-yl, 5-chloropyrimidin-2-yl, 5-bromopyrimidin-2-yl, 6-chloropyridazin-3-yl, 6-bromopyridazin-3-yl, quinoline-2-yl, 6-fluoroquinolin-2-yl, 7-fluoroquinolin-2-yl, 6-chloroquinolin-2-yl, 7-chloroquinolin-2-yl, 6-bromoquinolin-2-yl, 7-bromoquinolin-2-yl, 6-trifluoromethylquinolin-2-yl, 7-trifluoromethylquinolin-2-yl, quinoxalin-2-yl, 6-fluoroquinoxazin-2-yl, 7-fluoroquinoxalin-2-yl, 6-chloroquinoxalin-2-yl, 7-chloroquinoxalin-2-yl, 6-bromoquinoxalin-2-yl, 7-bromoquinoxalin-2-yl, 6-trifluoromethylquinoxalin-2-yl, 7-trifluoromethylquinoxalin-2-yl, quinazolin-2-yl, 6-fluoroquinazolin-2-yl, 7-fluoroquinazolin-2-yl, 6-chloroquinazolin-2-yl, 7-chloroquinazolin-2-yl, 6-bromoquinazolin-2-yl, 7-bromoquinazolin-2-yl, benzoxazol-2-yl, 5-fluorobenzoxazol-2-yl, 6-fluorobenzoxazol-2-yl, 5-chlorobenzoxazol-2-yl, 6-chlorobenzoxazol-2-yl, 5-bromobenzoxazol-2-yl, 6-bromobenzoxazol-2-yl, 5-trifluoromethylbenzoxazol-2-yl, 6-trifluoromethylbenzoxazol-2-yl, benzothiazol-2-yl, 5-fluorobenzothiazol-2-yl, 6-fluorobenzothiazol-2-yl, 5-chlorobenzothiazol-2-yl, 6-chlorobenzothiazol-2-yl, 5-bromobenzothiazol-2-yl, 6-bromobenzothiazol-2-yl, 5-trifluoromethylbenzothiazol-2-yl, 6-trifluoromethylbenzothiazol-2-yl, benzo[1,2,4]triazin-3-yl, 6-fluorobenzo[1,2,4]triazin-3-yl, 7-fluorobenzo[1,2,4]triazin-3-yl, 6-chlorobenzo[1,2,4]triazin-3-yl, 7-chlorobenzo[1,2,4]triazin-3-yl, 6-bromobenzo[1,2,4]triazin-3-yl, or 7-bromobenzo[1,2,4]triazin-3-yl.

25. A compound of the following formula:

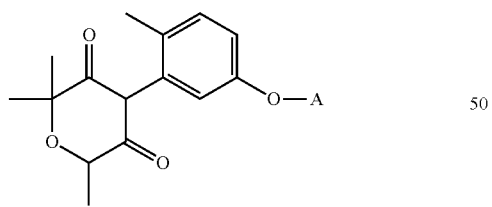

wherein A is 3-chloropyridin-2-yl, 4-chloropyridin-2-yl, 5-chloropyridin-2-yl, 6-chloropyridin-2-yl, 2-chloropyridin-3-yl, 4-chloropyridin-3-yl, 5-chloropyridin-3-yl, 6-chloropyridin-3-yl, 2-chloropyridin-4-yl, 3-chloropyridin-4-yl, 3,4-dichloropyridin-2-yl, 3,5-dichloropyridin-2-yl, 3,6-dichloropyridin-2-yl, 2,5-dichloropyridin-3-yl, 2,6-dichloropyridin-3-yl, 2,3-dichloropyridin-4-yl, 2,5-dichloropyridin-4-yl, 3,5,6-trichloropyridin-2-yl, 3-fluoropyridin-2-yl, 4-fluoropyridin-2-yl, 5-fluoropyridin-2-yl, 6-fluoropyridin-2-yl, 2-fluoropyridin-3-yl, 4-fluoropyridin-3-yl, 5-fluoropyridin-3-yl, 6-fluoropyridin-3-yl, 2-fluoropyridin-4-yl, 3-fluoropyridin-4-yl, 3,4-difluoropyridin-2-yl, 3,5-difluoropyridin-2-yl, 3,6-difluoropyridin-2-yl, 2,5-difluoropyridin-3-yl, 2,6-difluoropyridin-3-yl, 2,3-difluoropyridin-4-yl, 2,5-difluoropyridin-4-yl, 3,5,6-trifluoropyridin-2-yl, 3-trifluoromethylpyridin-2-yl, 4-trifluoromethylpyridin-2-yl, 5-trifluoromethylpyridin-2-yl, 6-trifluoromethylpyridin-2-yl, 2-trifluoromethylpyridin-3-yl, 4-trifluoromethylpyridin-3-yl, 5-trifluoromethylpyridin-3-yl, 6-trifluoromethylpyridin-3-yl, 2-trifluoromethylpyridin-4-yl, 3-trifluoromethylpyridin-4-yl, 4-chloro-3-fluoropyridin-2-yl, 5-chloro-3-fluoropyridin-2-yl, 6-chloro-3-fluoropyridin-2-yl, 3-chloro-4-fluoropyridin-2-yl, 3-chloro-5-fluoropyridin-2-yl, 3-chloro-6-fluoropyridin-2-yl, 3-chloro-5-trifluoromethylpyridin-2-yl, 3-fluoro-5-trifluoromethylpyridin-2-yl, 6-fluoro-3,4,5-trichloropyridin-2-yl, 4-methyl-3,5,6-trifluoropyridin-2-yl, pyrimidin-2-yl, 5-fluoropyrimidin-2-yl, 5-chloropyrimidin-2-yl, 5-bromopyrimidin-2-yl, 6-chloropyridazin-3-yl, 6-bromopyridazin-3-yl, quinoline-2-yl, 6-fluoroquinolin-2-yl, 7-fluoroquinolin-2-yl, 6-chloroquinolin-2-yl, 7-chloroquinolin-2-yl, 6-bromoquinolin-2-yl, 7-bromoquinolin-2-yl, 6-trifluoromethylquinolin-2-yl, 7-trifluoromethylquinolin-2-yl, quinoxalin-2-yl, 6-fluoroquinoxazin-2-yl, 7-fluoroquinoxalin-2-yl, 6-chloroquinoxalin-2-yl, 7-chloroquinoxalin-2-yl, 6-bromoquinoxalin-2-yl, 7-bromoquinoxalin-2-yl, 6-trifluoromethylquinoxalin-2-yl, 7-trifluoromethylquinoxalin-2-yl, quinazolin-2-yl, 6-fluoroquinazolin-2-yl, 7-fluoroquinazolin-2-yl, 6-chloroquinazolin-2-yl, 7-chloroquinazolin-2-yl, 6-bromoquinazolin-2-yl, 7-bromoquinazolin-2-yl, benzoxazol-2-yl, 5-fluorobenzoxazol-2-yl, 6-fluorobenzoxazol-2-yl, 5-chlorobenzoxazol-2-yl, 6-chlorobenzoxazol-2-yl, 5-bromobenzoxazol-2-yl, 6-bromobenzoxazol-2-yl, 5-trifluoromethylbenzoxazol-2-yl, 6-trifluoromethylbenzoxazol-2-yl, benzothiazol-2-yl, 5-fluorobenzothiazol-2-yl, 6-fluorobenzothiazol-2-yl, 5-chlorobenzothiazol-2-yl, 6-chlorobenzothiazol-2-yl, 5-bromobenzothiazol-2-yl, 6-bromobenzothiazol-2-yl, 5-trifluoromethylbenzothiazol-2-yl, 6-trifluoromethylbenzothiazol-2-yl, benzo[1,2,4]triazin-3-yl, 6-fluorobenzo[1,2,4]triazin-3-yl, 7-fluorobenzo[1,2,4]triazin-3-yl, 6-chlorobenzo[1,2,4]triazin-3-yl, 7-chlorobenzo[1,2,4]triazin-3-yl, 6-bromobenzo[1,2,4]triazin-3-yl, or 7-bromobenzo[1,2,4]triazin-3-yl.

26. A compound of the following formula:

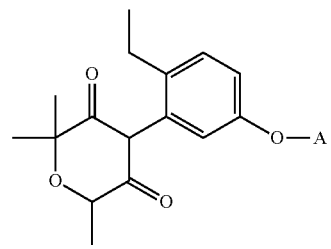

wherein A is 3-chloropyridin-2-yl, 4-chloropyridin-2-yl, 5-chloropyridin-2-yl, 6-chloropyridin-2-yl, 2-chloropyridin-3-yl, 4-chloropyridin-3-yl, 5-chloropyridin-3-yl, 6-chloropyridin-3-yl, 2-chloropyridin-4-yl, 3-chloropyridin-4-yl, 3,4-dichloropyridin-2-yl, 3,5-dichloropyridin-2-yl, 3,6-dichloropyridin-2-yl, 2,5-dichloropyridin-3-yl, 2,6-dichloropyridin-3-yl, 2,3-dichloropyridin-4- yl, 2,5-dichloropyridin-4-yl, 3,5,6-trichloropyridin-2-yl, 3-fluoropyridin-2-yl, 4-fluoropyridin-2-yl, 5-fluoropyridin-2-yl, 6-fluoropyridin-2-yl, 2-fluoropyridin-3-yl, 4-fluoropyridin-3-yl, 5-fluoropyridin-3-yl, 6-fluoropyridin-3-yl, 2-fluoropyridin-4-yl, 3-fluoropyridin-4-yl, 3,4-difluoropyridin-2-yl, 3,5-difluoropyridin-2-yl, 3,6-difluoropyridin-2-yl, 2,5-difluoropyridin-3-yl, 2,6-difluoropyridin-3-yl, 2,3-difluoropyridin-4-yl, 2,5-difluoropyridin-4-yl, 3,5,6-trifluoropyridin-2-yl, 3-trifluoromethylpyridin-2-yl, 4-trifluoromethylpyridin-2-yl, 5-trifluoromethylpyridin-2-yl, 6-trifluoromethylpyridin-2-yl, 2-trifluoromethylpyridin-3-yl, 4-trifluoromethylpyridin-3-yl, 5-trifluoromethylpyridin-3-yl, 6-trifluoromethylpyridin-3-yl, 2-trifluoromethylpyridin-4-yl, 3-trifluoromethylpyridin-4-yl, 4-chloro-3-fluoropyridin-2-yl, 5-chloro-3-fluoropyridin-2-yl, 6-chloro-3-fluoropyridin-2-yl, 3-chloro-4-fluoropyridin-2-yl, 3-chloro-5-fluoropyridin-2-yl, 3-chloro-6-fluoropyridin-2-yl, 3-chloro-5-trifluoromethylpyridin-2-yl, 3-fluoro-5-trifluoromethylpyridin-2-yl, 6-fluoro-3,4,5-trichloropyridin-2-yl, 4-methyl-3,5,6-trifluoropyridin-2-yl, pyrimidin-2-yl, 5-fluoropyrimidin-2-yl, 5-chloropyrimidin-2-yl, 5-bromopyrimidin-2-yl, 6-chloropyridazin-3-yl, 6-bromopyridazin-3-yl, quinoline-2-yl, 6-fluoroquinolin-2-yl, 7-fluoroquinolin-2-yl, 6-chloroquinolin-2-yl, 7-chloroquinolin-2-yl, 6-bromoquinolin-2-yl, 7-bromoquinolin-2-yl, 6-trifluoromethylquinolin-2-yl, 7-trifluoromethylquinolin-2-yl, quinoxalin-2-yl, 6-fluoroquinoxazin-2-yl, 7-fluoroquinoxalin-2-yl, 6-chloroquinoxalin-2-yl, 7-chloroquinoxalin-2-yl, 6-bromoquinoxalin-2-yl, 7-bromoquinoxalin-2-yl, 6-trifluoromethylquinoxalin-2-yl, 7-trifluoromethylquinoxalin-2-yl, quinazolin-2-yl, 6-fluoroquinazolin-2-yl, 7-fluoroquinazolin-2-yl, 6-chloroquinazolin-2-yl, 7-chloroquinazolin-2-yl, 6-bromoquinazolin-2-yl, 7-bromoquinazolin-2-yl, benzoxazol-2-yl, 5-fluorobenzoxazol-2-yl, 6-fluorobenzoxazol-2-yl, 5-chlorobenzoxazol-2-yl, 6-chlorobenzoxazol-2-yl, 5-bromobenzoxazol-2-yl, 6-bromobenzoxazol-2-yl, 5-trifluoromethylbenzoxazol-2-yl, 6-trifluoromethylbenzoxazol-2-yl, benzothiazol-2-yl, 5-fluorobenzothiazol-2-yl, 6-fluorobenzothiazol-2-yl, 5-chlorobenzothiazol-2-yl, 6-chlorobenzothiazol-2-yl, 5-bromobenzothiazol-2-yl, 6-bromobenzothiazol-2-yl, 5-trifluoromethylbenzothiazol-2-yl, 6-trifluoromethylbenzothiazol-2-yl, benzo[1,2,4]triazin-3-yl, 6-fluorobenzo[1,2,4]triazin-3-yl, 7-fluorobenzo[1,2,4]triazin-3-yl, 6-chlorobenzo[1,2,4]triazin-3-yl, 7-chlorobenzo[1,2,4]triazin-3-yl, 6-bromobenzo[1,2,4]triazin-3-yl, or 7-bromobenzo[1,2,4]triazin-3-yl.

27. A compound of the following formula:

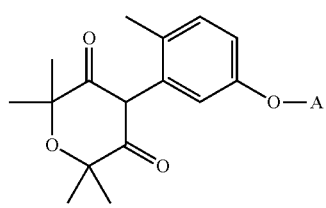

wherein A is 3-chloropyridin-2-yl, 4-chloropyridin-2-yl, 5-chloropyridin-2-yl, 6-chloropyridin-2-yl, 2-chloropyridin-3-yl, 4-chloropyridin-3-yl, 5-chloropyridin-3-yl, 6-chloropyridin-3-yl, 2-chloropyridin-4-yl, 3-chloropyridin-4-yl, 3,4-dichloropyridin-2-yl, 3,5-dichloropyridin-2-yl, 3,6-dichloropyridin-2-yl, 2,5-dichloropyridin-3-yl, 2,6-dichloropyridin-3-yl, 2,3-dichloropyridin-4-yl, 2,5-dichloropyridin-4-yl, 3,5,6-trichloropyridin-2-yl, 3-fluoropyridin-2-yl, 4-fluoropyridin-2-yl, 5-fluoropyridin-2-yl, 6-fluoropyridin-2-yl, 2-fluoropyridin-3-yl, 4-fluoropyridin-3-yl, 5-fluoropyridin-3-yl, 6-fluoropyridin-3-yl, 2-fluoropyridin-4-yl, 3-fluoropyridin-4-yl, 3,4-difluoropyridin-2-yl, 3,5-difluoropyridin-2-yl, 3,6-difluoropyridin-2-yl, 2,5-difluoropyridin-3-yl, 2,6-difluoropyridin-3-yl, 2,3-difluoropyridin-4-yl, 2,5-difluoropyridin-4-yl, 3,5,6-trifluoropyridin-2-yl, 3-trifluoromethylpyridin-2-yl, 4-trifluoromethylpyridin-2-yl, 5-trifluoromethylpyridin-2-yl, 6-trifluoromethylpyridin-2-yl, 2-trifluoromethylpyridin-3-yl, 4-trifluoromethylpyridin-3-yl, 5-trifluoromethylpyridin-3-yl, 6-trifluoromethylpyridin-3-yl, 2-trifluoromethylpyridin-4-yl, 3-trifluoromethylpyridin-4-yl, 4-chloro-3-fluoropyridin-2-yl, 5-chloro-3-fluoropyridin-2-yl, 6-chloro-3-fluoropyridin-2-yl, 3-chloro-4-fluoropyridin-2-yl, 3-chloro-5-fluoropyridin-2-yl, 3-chloro-6-fluoropyridin-2-yl, 3-chloro-5-trifluoromethylpyridin-2-yl, 3-fluoro-5-trifluoromethylpyridin-2-yl, 6-fluoro-3,4,5-trichloropyridin-2-yl, 4-methyl-3,5,6-trifluoropyridin-2-yl, pyrimidin-2-yl, 5-fluoropyrimidin-2-yl, 5-chloropyrimidin-2-yl, 5-bromopyrimidin-2-yl, 6-chloropyridazin-3-yl, 6-bromopyridazin-3-yl, quinoline-2-yl, 6-fluoroquinolin-2-yl, 7-fluoroquinolin-2-yl, 6-chloroquinolin-2-yl, 7-chloroquinolin-2-yl, 6-bromoquinolin-2-yl, 7-bromoquinolin-2-yl, 6-trifluoromethylquinolin-2-yl, 7-trifluoromethylquinolin-2-yl, quinoxalin-2-yl, 6-fluoroquinoxazin-2-yl, 7-fluoroquinoxalin-2-yl, 6-chloroquinoxalin-2-yl, 7-chloroquinoxalin-2-yl, 6-bromoquinoxalin-2-yl, 7-bromoquinoxalin-2-yl, 6-trifluoromethylquinoxalin-2-yl, 7-trifluoromethylquinoxalin-2-yl, quinazolin-2-yl, 6-fluoroquinazolin-2-yl, 7-fluoroquinazolin-2-yl, 6-chloroquinazolin-2-yl, 7-chloroquinazolin-2-yl, 6-bromoquinazolin-2-yl, 7-bromoquinazolin-2-yl, benzoxazol-2-yl, 5-fluorobenzoxazol-2-yl, 6-fluorobenzoxazol-2-yl, 5-chlorobenzoxazol-2-yl, 6-chlorobenzoxazol-2-yl, 5-bromobenzoxazol-2-yl, 6-bromobenzoxazol-2-yl, 5-trifluoromethylbenzoxazol-2-yl, 6-trifluoromethylbenzoxazol-2-yl, benzothiazol-2-yl, 5-fluorobenzothiazol-2-yl, 6-fluorobenzothiazol-2-yl, 5-chlorobenzothiazol-2-yl, 6-chlorobenzothiazol-2-yl, 5-bromobenzothiazol-2-yl, 6-bromobenzothiazol-2-yl, 5-trifluoromethylbenzothiazol-2-yl, 6-trifluoromethylbenzothiazol-2-yl, benzo[1,2,4]triazin-3-yl, 6-fluorobenzo[1,2,4]triazin-3-yl, 7-fluorobenzo[1,2,4]triazin-3-yl, 6-chlorobenzo[1,2,4]triazin-3-yl, 7-chlorobenzo[1,2,4]triazin-3-yl, 6-bromobenzo[1,2,4]triazin-3-yl, or 7-bromobenzo[1,2,4]triazin-3-yl.

28. A compound of the following formula:

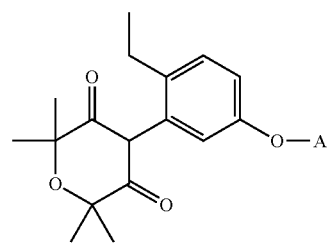

wherein A is 3-chloropyridin-2-yl, 4-chloropyridin-2-yl, 5-chloropyridin-2-yl, 6-chloropyridin-2-yl, 2-chloropyridin-3-yl, 4-chloropyridin-3-yl, 5-chloropyridin-3-yl, 6-chloropyridin-3-yl, 2-chloropyridin-4-yl, 3-chloropyridin-4-yl, 3,4-dichloropyridin-2-yl, 3,5-dichloropyridin-2-yl, 3,6-dichloropyridin-2-yl, 2,5-dichloropyridin-3-yl, 2,6-dichloropyridin-3-yl, 2,3-dichloropyridin-4-yl, 2,5-dichloropyridin-4-yl, 3,5,6-trichloropyridin-2-yl, 3-fluoropyridin-2-yl, 4-fluoropyridin-2-yl, 5-fluoropyridin-2-yl, 6-fluoropyridin-2-yl, 2-fluoropyridin-3-yl, 4-fluoropyridin-3-yl, 5-fluoropyridin-3-yl, 6-fluoropyridin-3-yl, 2-fluoropyridin-4-yl, 3-fluoropyridin-4-yl, 3,4-difluoropyridin-2-yl, 3,5-difluoropyridin-2-yl, 3,6-difluoropyridin-2-yl, 2,5-difluoropyridin-3-yl, 2,6-difluoropyridin-3-yl, 2,3-difluoropyridin-4-yl, 2,5-difluoropyridin-4-yl, 3,5,6-trifluoropyridin-2-yl, 3-trifluoromethylpyridin-2-yl, 4-trifluoromethylpyridin-2-yl, 5-trifluoromethylpyridin-2-yl, 6-trifluoromethylpyridin-2-yl, 2-trifluoromethylpyridin-3-yl, 4-trifluoromethylpyridin-3-yl, 5-trifluoromethylpyridin-3-yl, 6-trifluoromethylpyridin-3-yl, 2-trifluoromethylpyridin-4-yl, 3-trifluoromethylpyridin-4-yl, 4-chloro-3-fluoropyridin-2-yl, 5-chloro-3-fluoropyridin-2-yl, 6-chloro-3-fluoropyridin-2-yl, 3-chloro-4-fluoropyridin-2-yl, 3-chloro-5-fluoropyridin-2-yl, 3-chloro-6-fluoropyridin-2-yl, 3-chloro-5-trifluoromethylpyridin-2-yl, 3-fluoro-5-trifluoromethylpyridin-2-yl, 6-fluoro-3,4,5-trichloropyridin-2-yl, 4-methyl-3,5,6-trifluoropyridin-2-yl, pyrimidin-2-yl, 5-fluoropyrimidin-2-yl, 5-chloropyrimidin-2-yl, 5-bromopyrimidin-2-yl, 6-chloropyridazin-3-yl, 6-bromopyridazin-3-yl, quinoline-2-yl, 6-fluoroquinolin-2-yl, 7-fluoroquinolin-2-yl, 6-chloroquinolin-2-yl, 7-chloroquinolin-2-yl, 6-bromoquinolin-2-yl, 7-bromoquinolin-2-yl, 6-trifluoromethylquinolin-2-yl, 7-trifluoromethylquinolin-2-yl, quinoxalin-2-yl, 6-fluoroquinoxazin-2-yl, 7-fluoroquinoxalin-2-yl, 6-chloroquinoxalin-2-yl, 7-chloroquinoxalin-2-yl, 6-bromoquinoxalin-2-yl, 7-bromoquinoxalin-2-yl, 6-trifluoromethylquinoxalin-2-yl, 7-trifluoromethylquinoxalin-2-yl, quinazolin-2-yl, 6-fluoroquinazolin-2-yl, 7-fluoroquinazolin-2-yl, 6-chloroquinazolin-2-yl, 7-chloroquinazolin-2-yl, 6-bromoquinazolin-2-yl, 7-bromoquinazolin-2-yl, benzoxazol-2-yl, 5-fluorobenzoxazol-2-yl, 6-fluorobenzoxazol-2-yl, 5-chlorobenzoxazol-2-yl, 6-chlorobenzoxazol-2-yl, 5-bromobenzoxazol-2-yl, 6-bromobenzoxazol-2-yl, 5-trifluoromethylbenzoxazol-2-yl, 6-trifluoromethylbenzoxazol-2-yl, benzothiazol-2-yl, 5-fluorobenzothiazol-2-yl, 6-fluorobenzothiazol-2-yl, 5-chlorobenzothiazol-2-yl, 6-chlorobenzothiazol-2-yl, 5-bromobenzothiazol-2-yl, 6-bromobenzothiazol-2-yl, 5-trifluoromethylbenzothiazol-2-yl, 6-trifluoromethylbenzothiazol-2-yl, benzo[1,2,4]triazin-3-yl, 6-fluorobenzo[1,2,4]triazin-3-yl, 7-fluorobenzo[1,2,4]triazin-3-yl, 6-chlorobenzo[1,2,4]triazin-3-yl, 7-chlorobenzo[1,2,4]triazin-3-yl, 6-bromobenzo[1,2,4]triazin-3-yl, or 7-bromobenzo[1,2,4]triazin-3-yl.

29. The compound according to claim 1, which is compound number A-45, having the following structure:

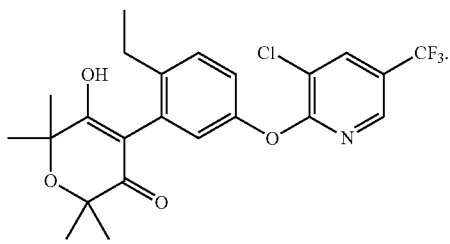 [SMILES: CCc1ccc(Oc2ncc(C(F)(F)F)cc2Cl)cc1C1=C(O)C(C)(C)OC(C)(C)C1=O]

30. The compound according to claim 1, which is compound number A-55, having the following structure:

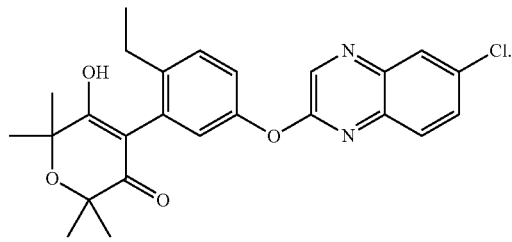 [SMILES: CCc1ccc(Oc2cnc3cc(Cl)ccc3n2)cc1C1=C(O)C(C)(C)OC(C)(C)C1=O]

31. The compound according to claim 1, which is compound number A-82, having the following structure:

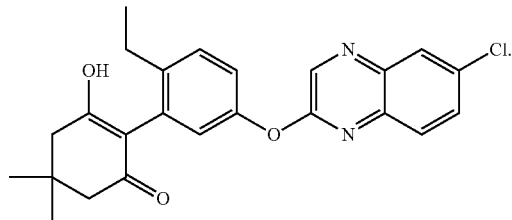 [SMILES: CCc1ccc(Oc2cnc3cc(Cl)ccc3n2)cc1C1=C(O)CC(C)(C)CC1=O]

32. The compound according to claim 1, which is compound number A-86, having the following structure:

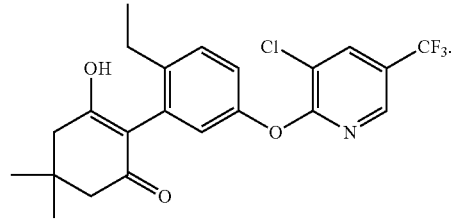 [SMILES: CCc1ccc(Oc2ncc(C(F)(F)F)cc2Cl)cc1C1=C(O)CC(C)(C)CC1=O]

33. The compound according to claim 1, which is compound number A-148, having the following structure:

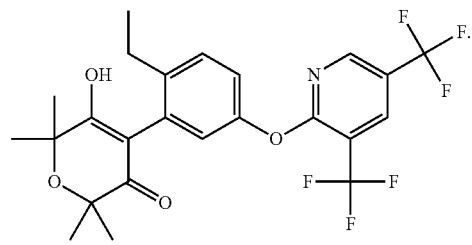 [SMILES: CCc1ccc(Oc2ncc(C(F)(F)F)cc2C(F)(F)F)cc1C1=C(O)C(C)(C)OC(C)(C)C1=O]

34. The compound according to claim 1, which is compound number A-161, having the following structure:

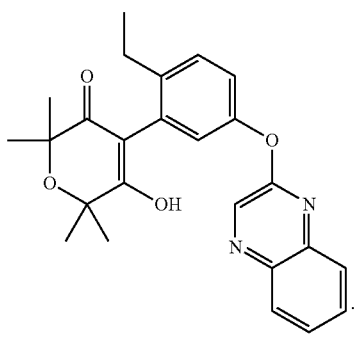 [SMILES: CCc1ccc(Oc2cnc3ccccc3n2)cc1C1=C(O)C(C)(C)OC(C)(C)C1=O]

35. The compound according to claim 1, which is compound number A-172, having the following structure:

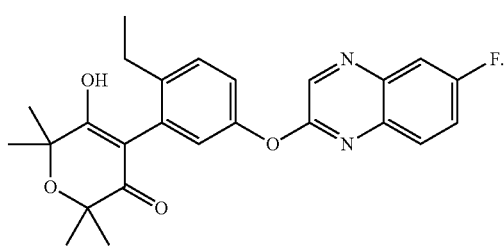 [SMILES: CCc1ccc(Oc2cnc3cc(F)ccc3n2)cc1C1=C(O)C(C)(C)OC(C)(C)C1=O]

36. The compound according to claim 1, which is compound number A-188, having the following structure:

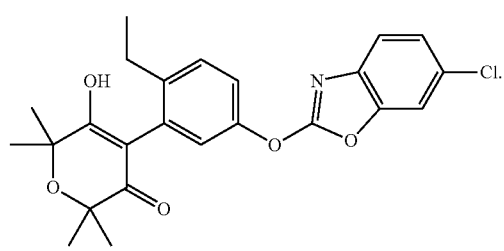 [SMILES: CCc1ccc(Oc2nc3ccc(Cl)cc3o2)cc1C1=C(O)C(C)(C)OC(C)(C)C1=O]

37. The compound according to claim 1, which is compound number A-233, having the following structure:

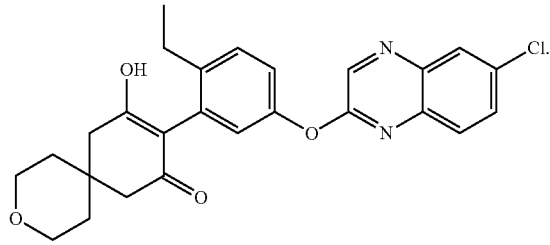 [SMILES: CCc1ccc(Oc2cnc3cc(Cl)ccc3n2)cc1C1=C(O)CC2(CCOCC2)CC1=O]

38. The compound according to claim 1, which is compound number A-269, having the following structure:

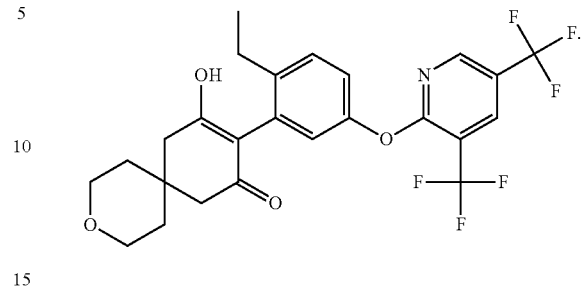

39. The compound according to claim 1, which is compound number A-272, having the following structure:

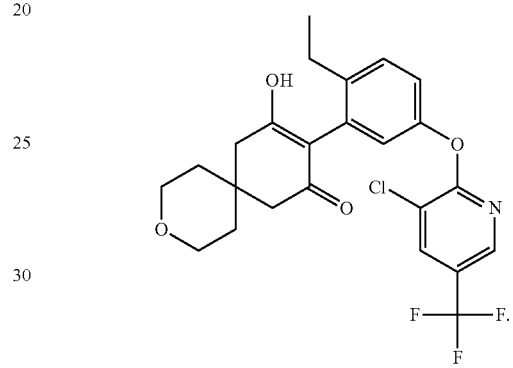

40. The compound according to claim 1, which is compound number A-296, having the following structure:

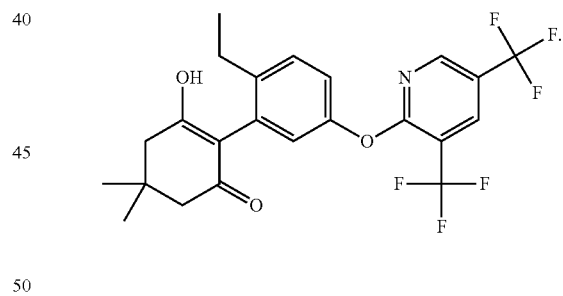

41. The compound according to claim 1, which is compound number A-311, having the following structure:

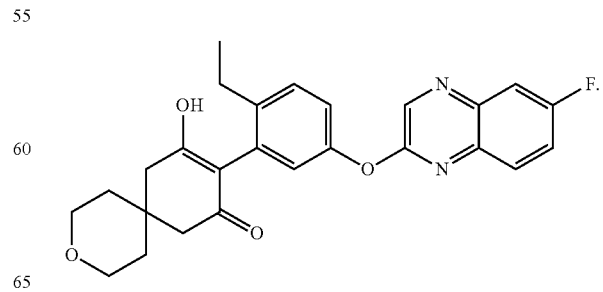

42. The compound according to claim 28, which is a compound of the following formula:

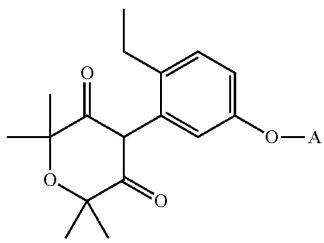

wherein A is 6-trifluoromethylquinoxalin-2-yl.

43. The compound according to claim 27, which is a compound of the following formula:

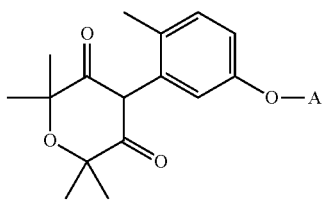

wherein A is 3-chloro-5-trifluoromethylpyridin-2-yl.

44. The compound according to claim 27, which is a compound of the following formula:

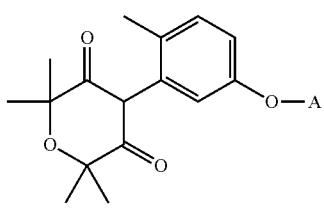

wherein A is 6-chloroquinoxalin-2-yl.

45. The compound according to claim 27, which is a compound of the following formula:

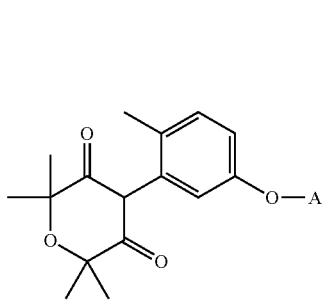

wherein A is 6-trifluoromethylquinoxalin-2-yl.

46. The compound according to claim 27, which is a compound of the following formula:

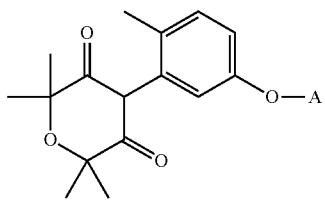

wherein A is 6-chlorobenzoxazol-2-yl.

* * * * *